(12) United States Patent
Keasling et al.

(10) Patent No.: US 7,183,089 B2
(45) Date of Patent: Feb. 27, 2007

(54) METHOD FOR ENHANCING PRODUCTION OF ISOPRENOID COMPOUNDS

(75) Inventors: Jay D. Keasling, Berkeley, CA (US);
Jack D. Newman, Berkeley, CA (US);
Douglas J. Pitera, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/134,705

(22) Filed: May 20, 2005

(65) Prior Publication Data

US 2006/0079476 A1 Apr. 13, 2006

Related U.S. Application Data

(60) Provisional application No. 60/573,492, filed on May 21, 2004.

(51) Int. Cl.
*C12N 15/64* (2006.01)
*C12N 15/00* (2006.01)
*C12N 15/74* (2006.01)
*C12P 13/00* (2006.01)
*A61K 48/00* (2006.01)

(52) U.S. Cl. .................. 435/167; 435/67; 435/128; 435/320.1; 435/488; 435/166; 514/44

(58) Field of Classification Search .............. 435/189, 435/252.3, 252.8, 466, 69.1, 170, 91.4, 320.1, 435/488, 128; 514/44
See application file for complete search history.

(56) References Cited

U.S. PATENT DOCUMENTS

| | | | |
|---|---|---|---|
| 5,460,949 A | 10/1995 | Saunders et al. | |
| 6,495,354 B2 | 12/2002 | Chappell et al. | |
| 6,531,303 B1 | 3/2003 | Millis et al. | |
| 6,689,593 B2 | 2/2004 | Millis et al. | |
| 2003/0148416 A1* | 8/2003 | Berry et al. ................. | 435/67 |
| 2003/0148479 A1 | 8/2003 | Keasling et al. | |
| 2004/0005678 A1 | 1/2004 | Keasling et al. | |
| 2004/0029239 A1 | 2/2004 | Ohto et al. | |
| 2004/0063182 A1 | 4/2004 | Ohto et al. | |
| 2004/0072323 A1 | 4/2004 | Matsuda et al. | |
| 2004/0077039 A1 | 4/2004 | Holtzman | |
| 2004/0110259 A1 | 6/2004 | Baugh et al. | |
| 2004/0194162 A1 | 9/2004 | Hahn et al. | |

FOREIGN PATENT DOCUMENTS

WO     WO 00/01650     1/2003

OTHER PUBLICATIONS

Martin et al., Engineering a mevalonate pathway in *Escherichia coli* for production of terpenoids. Nature Biotechnology 2003, vol. 21 (7); 796-802.*
Jackson et al., Metabolic engineering to produce sesquiterpenes in yeast. Organic Letters 2003, vol. 5 (10): 1629-1632.*
Martin et al. (2003) *Nat. Biotech.* 21(7):796-802.
Donald et al. (1997) *Appl. Env. Microbiol.* 63:3341-3344.
Jackson et al. (2003) *Organ. Lett.* 5:1629-1632.
Hamano et al. (2001) *Biosci. Biotechnol. Biochem.* 65:1627-1635.
T. Kuzuyama. (2004) *Biosci. Biotechnol. Biochem.* 68(4): 931-934.
T. Kazuhiko. (2004) *Biotechnology Letters.* 26: 1487-1491.
Brock et al. (2004) *Eur J. Biochem.* 271: 3227-3241.
Choi, et al. (1999) *Appl. Environ. Microbio.* 65 4363-4368.
Parke et al., (2004) *Appl. Environ. Microbio.* 70:2974-.
Subrahmanyam et al. (1998) *J. Bact.* 180: 4596-4602.
Murli et al. (2003) *J. Ind. Microbiol. Biotechnol.* 30:500-509.
Polakowski et al. (1998) *Appl. Microbiol. Biotechnol.* 49: 67-71.
Wilding et al. (2000) *J Bacteriol* 182(15): 4319-27.

* cited by examiner

*Primary Examiner*—Rebecca E. Prouty
*Assistant Examiner*—Ganapathirama Raghu
(74) *Attorney, Agent, or Firm*—Paula A. Borden; Bozicevic, Field & Francis LLP

(57) ABSTRACT

The present invention provides methods of producing an isoprenoid or an isoprenoid precursor in a genetically modified host cell. The methods generally involve modulating the level of hydroxymethylglutaryl-CoA (HMG-CoA) in the cell, such that the level of HMG-CoA is not toxic to the cell and/or does not substantially inhibit cell growth, but is maintained at a level that provides for high-level production of mevalonate, IPP, and other downstream products of an isoprenoid or isoprenoid pathway, e.g., polyprenyl diphosphates and isoprenoid compounds. The present invention further provides genetically modified host cells that are suitable for use in a subject method. The present invention further provides recombinant nucleic acid constructs for use in generating a subject genetically modified host cell, including recombinant nucleic acid constructs comprising nucleotide sequences encoding one or more mevalonate pathway enzymes, and recombinant vectors (e.g., recombinant expression vectors) comprising same. The present invention further provides methods for identifying nucleic acids that encode HMG-CoA reductase (HMGR) variants that provide for relief of HMG-CoA accumulation-induced toxicity. The present invention further provides methods for identifying agents that reduce intracellular accumulation of HMG-CoA.

16 Claims, 46 Drawing Sheets

Isoprenoid metabolic pathways

Mevalonate pathway

DXP pathway

FIG. 13A pBAD24MevT plasmid sequence

```
ATCGATGCATAATGTGCCTGTCAAATGGACGAAGCAGGGATTCTGCAAACCCTATGCTACTCCGTCAAGCCGTCA
ATTGT
```

├▶                                             *araC*

```
CTGATTCGTTACCAATTATGACAACTTGACGGCTACATCATTCACTTTTTCTTCACAACCGGCACGGAACTCGCT
CGGGCTGGCCCCGGTGCATTTTTTAAATACCCGCGAGAAATAGAGTTGATCGTCAAAACCAACATTGCGACCGAC
GGTGGCGATAGGCATCCGGGTGGTGCTCAAAAGCAGCTTCGCCTGGCTGATACGTTGGTCCTCGCGCCAGCTTAA
GACGCTAATCCCTAACTGCTGGCGGAAAAGATGTGACAGACGCGACGGCGACAAGCAAACATGCTGTGCGACGCT
GGCGATATCAAAATTGCTGTCTGCCAGGTGATCGCTGATGTACTGACAAGCCTCGCGTACCCGATTATCCATCGG
TGGATGGAGCGACTCGTTAATCGCTTCCATGCGCCGCAGTAACAATTGCTCAAGCAGATTTATCGCCAGCAGCTC
CGAATAGCGCCCTTCCCCTTGCCCGGCGTTAATGATTTGCCCAAACAGGTCGCTGAAATGCGGCTGGTGCGCTTC
ATCCGGGCGAAAGAACCCCGTATTGGCAAATATTGACGGCCAGTTAAGCCATTCATGCCAGTAGGCGCGCGGACG
AAAGTAAACCCACTGGTGATACCATTCGCGAGCCTCCGGATGACGACCGTAGTGATGAATCTCTCCTGGCGGGAA
CAGCAAAATATCACCCGGTCGGCAAACAAATTCTCGTCCCTGATTTTTCACCACCCCCTGACCGCGAATGGTGAG
ATTGAGAATATAACCTTTCATTCCCAGCGGTCGGTCGATAAAAAAATCGAGATAACCGTTGGCCTCAATCGGCGT
TAAACCCGCCACCAGATGGGCATTAAACGAGTATCCCGGCAGCAGGGGATCATTT
```

*araC*    ◀┤

```
TGCGCTTCAGCCATACTTTTCATACTCCCGCCATTCAGAGAAGAAACCAATTGTCCATATTGCATCAGACATTGC
CGTCACTGCGTCTTTTACTGGCTCTTCTCGCTAACCAAACCGGTAACCCCGCTTATTAAAAGCATTCTGTAACAA
AGCGGGACCAAAGCCATGACAAAAACGCGTAACAAAAGTGTCTATAATCACGGCAGAAAAGTCCACATTGATTAT
TTGCACGGCGTCACA
```

├▶    $P_{BAD}$ Promoter

```
CTTTGCTATGCCATAGCATTTTTATCCATAAGATTAGCGGATCCTACCT GACGCTTTTTATCGCAACTCTCTACT
GT TTCTCCATACCCGTTTTTTTGGGCTAGCAGGAGGAATTCACCATGGTACCCGGGGATCCTCTAGAGTCGACTA
GGAGGAATAT
```

├▶                                                                                  *atoB*

```
AAAATGAAAAATTGTGTCATCGTCAGTGCGGTACGTACTGCTATCGGTAGTTTTAACGGTTCACTCGCTTCCACC
AGCGCCATCGACCTGGGGGCGACAGTAATTAAAGCCGCCATTGAACGTGCAAAAATCGATTCACAACACGTTGAT
GAAGTGATTATGGGTAACGTGTTACAAGCCGGGCTGGGGCAAAATCCGGCGCGTCAGGCACTGTTAAAAAGCGGG
CTGGCAGAAACGGTGTGCGGATTCACGGTCAATAAAGTATGTGGTTCGGGTCTTAAAAGTGTGGCGCTTGCCGCC
CAGGCCATTCAGGCAGGTCAGGCGCAGAGCATTGTGGCGGGGGGTATGGAAAATATGAGTTTAGCCCCCTACTTA
CTCGATGCAAAAGCACGCTCTGGTTATCGTCTTGGAGACGGACAGGTTTATGACGTAATCCTGCGCGATGGCCTG
ATGTGCGCCACCCATGGTTATCATATGGGGATTACCGCCGAAAACGTGGCTAAAGAGTACGGAATTACCCGTGAA
ATGCAGGATGAACTGGCGCTACATTCACAGCGTAAAGCGGCAGCCGCAATTGAGTCCGGTGCTTTTACAGCCGAA
ATCGTCCCGGTAAATGTTGTCACTCGAAAGAAAACCTTCGTCTTCAGTCAAGACGAATTCCCGAAAGCGAATTCA
ACGGCTGAAGCGTTAGGTGCATTGCGCCCGGCCTTCGATAAAGCAGGAACAGTCACCGCTGGGAACGCGTCTGGT
ATTAACGACGGTGCTGCCGCTCTGGTGATTATGGAAGAATCTGCGGCGCTGGCAGCAGGCCTTACCCCCCTGGCT
CGCATTAAAAGTTATGCCAGCGGTGGCGTGCCCCCCGCATTGATGGGTATGGGGCCAGTACCTGCCACGCAAAAA
GCGTTACAACTGGCGGGGCTGCAACTGGCGGATATTGATCTCATTGAGGCTAATGAAGCATTTGCTGCACAGTTC
CTTGCCGTTGGGAAAAACCTGGGCTTTGATTCTGAGAAAGTGAATGTCAACGGCGGGGCCATCGCGCTCGGGCAT
CCTATCGGTGCCAGTGGTGCTCGTATTCTGGTCACACTATTACATGCCATGCAGGCACGCGATAAAACGC
TGGGGCTGGCAACACTGTGCATTGGCGGCGGTCAGGGAATTGCGATGGTGATTGAACGGTTGAATTAAGGAGGAC
AGCTA                                                                 ◀┤
```

├▶                               *HMGS*

```
AATGAAACTCTCAACTAAACTTTGTTGGTGTGGTATTAAAGGAAGACTTAGGCCGCAAAAGCAACAACAATTACA
CAATACAAACTTGCAAATGACTGAACTAAAAAAACAAAAGACCGCTGAACAAAAAACCAGACCTCAAATGTCGG
TATTAAAGGTATCCAAATTTACATCCCAACTCAATGTGTCAACCAATCTGAGCTAGAGAAATTTGATGGCGTTTC
TCAAGGTAAATACACAATTGGTCTGGGCCAAACCAACATGTCTTTTGTCAATGACAGAGAAGATATCTACTCGAT
GTCCCTAA
```

FIG. 13B

```
CTGTTTTGTCTAAGTTGATCAAGAGTTACAACATCGACACCAACAAAATTGGTAGATTAGAAGTCGGTACTGAAA
CTCTGATTGACAAGTCCAAGTCTGTCAAGTCTGTCTTGATGCAATTGTTTGGTGAAAACACTGACGTCGAAGGTA
TTGACACGCTTAATGCCTGTTACGGTGGTACCAACGCGTTGTTCAACTCTTTGAACTGGATTGAATCTAACGCAT
GGGATGGTAGAGACGCCATTGTAGTTTGCGGTGATATTGCCATCTACGATAAGGGTGCCGCAAGACCAACCGGTG
GTGCCGGTACTGTTGCTATGTGGATCGGTCCTGATGCTCCAATTGTATTTGACTCTGTAAGAGCTTCTTACATGG
AACACGCCTACGATTTTACAAGCCAGATTTCACCAGCGAATATCCTTACGTCGATGGTCATTTTTCATTAACTT
GTTACGTCAAGGCTCTTGATCAAGTTTACAAGAGTTATTCCAAGAAGGCTATTTCTAAAGGGTTGGTTAGCGATC
CCGCTGGTTCGGATGCTTTGAACGTTTTGAAATATTTCGACTACAACGTTTTCCATGTTCCAACCTGTAAATTGG
TCACAAAATCATACGGTAGATTACTATATAACGATTTCAGAGCCAATCCTCAATTGTTCCCAGAAGTTGACGCCG
AATTAGCTACTCGCGATTATGACGAATCTTTAACCGATAAGAACATTGAAAAACTTTTGTTAATGTTGCTAAGC
CATTCCACAAAGAGAGTTGCCCAATCTTTGATTGTTCCAACAAACACAGGTAACATGTACACCGCATCTGTTT
ATGCCGCCTTTGCATCTCTATTAAACTATGTTGGATCTGACGACTTACAAGGCAAGCGTGTTGGTTTATTTCTT
ACGGTTCCGGTTTAGCTGCATCTCTATATTCTTGCAAAATTGTTGGTGACGTCCAACATATTATCAAGGAATTAG
ATATTACTAACAAATTAGCCAAGAGAATCACCGAAACTCCAAAGGATTACGAAGCTGCCATCGAATTGAGAGAAA
ATGCCCATTTGAAGAAGAACTTCAAACCTCAAGGTTCCATTGAGCATTTGCAAAGTGGTGTTTACTACTTGACCA
ACATCGA
```

*HMGS*                                  truncated *HMGR*

```
TGACAAATTTAGAAGATCTTACGATGTTAAAAAATAAGGAGGATTACACTATGGTTTTAACCAATAAAACAGTCA
TTTCTGGATCGAAAGTCAAAAGTTTATCATCTGCGCAATCGAGCTCATCAGGACCTTCATCATCTAGTGAGGAAG
ATGATTCCCGCGATATTGAAAGCTTGGATAAGAAAATACGTCCTTTAGAAGAATTAGAAGCATTATTAAGTAGTG
GAAATACAAAACAATTGAAGAACAAAGAGGTCGCTGCCTTGGTTATTCACGGTAAGTTACCTTTGTACGCTTTGG
AGAAAAAATTAGGTGATACTACGAGAGCGGTTGCGGTACGTAGGAAGGCTCTTTCAATTTTGGCAGAAGCTCCTG
TATTAGCATCTGATCGTTTACCATATAAAAATTATGACTACGACCGCGTATTTGGCGCTTGTTGTGAAAATGTTA
TAGGTTACATGCCTTTGCCCGTTGGTGTTATAGGCCCCTTGGTTATCGATGGTACATCTTATCATATACCAATGG
CAACTACAGAGGGTTGTTTGGTAGCTTCTGCCATGCGTGGCTGTAAGGCAATCAATGCTGGCGGTGGTGCAACAA
CTGTTTTAACTAAGGATGGTATGACAAGAGGCCCAGTAGTCCGTTTCCCAACTTTGAAAAGATCTGGTGCCTGTA
AGATATGGTTAGACTCAGAAGAGGGACAAAACGCAATTAAAAAAGCTTTTAACTCTACATCAAGATTTGCACGTC
TGCAACATATTCAAACTTGTCTAGCAGGAGATTTACTCTTCATGAGATTTAGAACAACTACTGGTGACGCAATGG
GTATGAATATGATTTCTAAAGGTGTCGAATACTCATTAAAGCAAATGGTAGAAGAGTATGGCTGGGAAGATATGG
AGGTTGTCTCCGTTTCTGGTAACTACTGTACCGACAAAAAACCAGCTGCCATCAACTGGATCGAAGGTCGTGGTA
AGAGTGTCGTCGCAGAAGCTACTATTCCTGGTGATGTTGTCAGAAAAGTGTTAAAAAGTGATGTTTCCGCATTGG
TTGAGTTGAACATTGCTAAGAATTTGGTTGGATCTGCAATGGCTGGGTCTGTTGGTGGATTTAACGCACATGCAG
CTAAATTTAGTGACAGCTGTTTTCTTGGCATTAGGACAAGATCCTGCACAAAATGTTGAAAGTTCCAACTGTATAA
CATTGATGAAAGAAGTGGACGGTGATTTGAGAATTTCCGTATCCATGCCATCCATCGAAGTAGGTACCATCGGTG
GTGGTACTGTTCTAGAACCACAAGGTGCCATGTTGGACTTATTAGGTGTAAGAGGCCCGCATGCTACCGCTCCTG
GTACCAACGCACGTCAATTAGCAAGAATAGTTGCCTGTGCCGTCTTGGCAGGTGAATTATCCTTATGTGCTGCCC
TAGCAGCCGGCCATTTGGTTCAAAGTCATATGACCCACAACAGGAAACCTGCTGAACCAACAAAACCTAACAATT
TGGACGCCACTGATATAAAT
``` truncated *HMGR*                                              rrnB terminator<br>

```
CGTTTGAAAGATGGGTCCGTCACCTGCATTAAATCCTAAGTCGACCTGCAGGCATGCAAGCTTGGCTGTTTTGGC
GGATGAGAGAAGATTTTCAGCCTGATACAGATTAAATCAGAACGCAGAAGCGGTCTGATAAAACAGAATTTGCCT
GGCGGCAGTAGCGCGGTGGTCCCACCTGACCCCATGCCGAACTCAGAAGTGAAACGCCGTAGCGCCGATGGTAGT
GTGGGGTCTCCCCATGCGAGAGTAGGGAACTGCCAGGCATCAAATAAAACGAAAGGCTCAGTCGAAAGACTGGGC
CTTTCGTTTTATCTGTTGTTTGTCGGTGAACGCTCTCCTGAGTAGGACAAATCCGCCGGGAGCGGATTTGAACGT
TGCGAAGCAACGGCCCGGAGGGTGGCGGGCAGGACGCCCGCCATAAACTGCCAGGCATCAAATTAAGCAGAAGGC
CATCCTGACGGATGGCCTTTTTGCGTTTCT
```

Ampicillin resistance cassette<br>
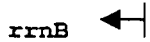                                                                                               

```
ACAAACTCTTTTGTTTATTTTTCTAAATACATTCAAATATGTATCCGCTCATGAGACAATAACCCTGATAAATGC
TTCAA
```

FIG. 13C

TAATATTGAAAAAGGAAGAGTATGAGTATTCAACATTTCCGTGTCGCCCTTATTCCCTTTTTTGCGGCATTTTGC
CTTCCTGTTTTTGCTCACCCAGAAACGCTGGTGAAAGTAAAAGATGCTGAAGATCAGTTGGGTGCACGAGTGGGT
TACATCGAACTGGATCTCAACAGCGGTAAGATCCTTGAGAGTTTTCGCCCCGAAGAACGTTTTCCAATGATGAGC
ACTTTTAAAGTTCTGCTATGTGGCGCGGTATTATCCCGTGTTGACGCCGGGCAAGAGCAACTCGGTCGCCGCATA
CACTATTCTCAGAATGACTTGGTTGAGTACTCACCAGTCACAGAAAAGCATCTTACGGATGGCATGACAGTAAGA
GAATTATGCAGTGCTGCCATAACCATGAGTGATAACACTGCGGCCAACTTACTTCTGACAACGATCGGAGGACCG
AAGGAGCTAACCGCTTTTTTGCACAACATGGGGGATCATGTAACTCGCCTTGATCGTTGGGAACCGGAGCTGAAT
GAAGCCATACCAAACGACGAGCGTGACACCACGATGCCTGTAGCAATGGCAACAACGTTGCGCAAACTATTAACT
GGCGAACTACTTACTCTAGCTTCCCGGCAACAATTAATAGACTGGATGGAGGCGGATAAAGTTGCAGGACCACTT
CTGCGCTCGGCCCTTCCGGCTGGCTGGTTTATTGCTGATAAATCTGGAGCCGGTGAGCGTGGGTCTCGCGGTATC
ATTGCAGCACTGGGGCCAGATGGTAAGCCCTCCCGTATCGTAGTTATCTACACGACGGGGAGTCAGGCAACTATG
GATGAACGAAATAGACAGATCGCTGAGATAGGTGCCTCACTGATTAAGCATTGGT
AACTGTCAGACCAAGTTTACTCATATATACTTTAGATTGATTTACGCGCCCTGTAGCGGCGCATTAAGCGCGGCG
GGTGTGGTGGTTACGCGCAGCGTGACCGCTACACTTGCCAGCGCCCTAGCGCCCGCTCCTTTCGCTTTCTTCCCT
TCCTTTCTCGCCACGTTCGCCGGCTTTCCCCGTCAAGCTCTAAATCGGGGGCTCCCTTTAGGGTTCCGATTTAGT
GCTTTACGGCACCTCGACCCCAAAAAACTTGATTTGGGTGATGGTTCACGTAGTGGGCCATCGCCCTGATAGACG
GTTTTTCGCCCTTTGACGTTGGAGTCCACGTTCTTTAATAGTGGACTCTTGTTCCAAACTTGAACAACACTCAAC
CCTATCTCGGGCTATTCTTTTGATTTATAAGGGATTTTGCCGATTTCGGCCTATTGGTTAAAAAATGAGCTGATT
TAACAAAAATTTAACGCGAATTTTAACAAA modified pBR322 origin
ATATTAACGTTTACAATTTAAAAGGATCTAGGTGAAGATCCTTTTTGATAATCTCATGACCAAAATCCCTTAACG
TGAGTTTTCGTTCCACTGAGCGTCAGACCCCGTAGAAAAGATCAAAGGATCTTCTTGAGATCCTTTTTTTCTGCG
CGTAATCTGCTGCTTGCAAACAAAAAAACCACCGCTACCAGCGGTGGTTTGTTTGCCGGATCAAGAGCTACCAAC
TCTTTTTCCGAAGGTAACTGGCTTCAGCAGAGCGCAGATACCAAATACTGTCCTTCTAGTGTAGCCGTAGTTAGG
CCACCACTTCAAGAACTCTGTAGCACCGCCTACATACCTCGCTCTGCTAATCCTGTTACCAGTGGCTGCTGCCAG
TGGCGATAAGTCGTGTCTTACCGGGTTGGACTCAAGACGATAGTTACCGGATAAGGCGCAGCGGTCGGGCTGAAC
GGGGGGTTCGTGCACACAGCCCAGCTTGGAGCGAACGACCTACACCGAACTGAGATACCTACAGCGTGAGCTATG
AGAAAGCGCCACGCTTCCCGAAGGGAGAAAGGCGGACAGGTATCCGGTAAGCGGCAGGGTCGGAACAGGAGAGCG
CACGAGGGAGCTTCCAGGGGGAAACGCCTGGTATCTTTATAGTCCTGTCGGGTTTCGCCACCTCTGACTTGAGCG
TCGATTTTTGTGATGCTCGTCAGGGGGCGGAGCCTATGGAAAAACGCCAGCAACGCGGCCTTTTTACGGTTCCT
GGCCTTTTGCTGGCCTTTTGCTCACATGTTCTTTCCTGCGTTATCCCCTGATTCTGTGGATAACCGTATTACCGC
CTTTGAGTGAGCTGATACCGCTCGCCGCAGCCGAACGACCGAGCGCAGCGAGTCAGTGAGCGAGGAAGCGGAAGA
GCGCCTGATGCGGTATTTTCTCCTTACGCATCTGTGCGGTATTTCACACCGCATAGGGTCATGGCTGCGCCCCGA
CACCCGCCAACACCCGCTGACGCGCCCTGACGGGCTTGTCTGCTCCCGGCATCCGCTTACAGACAAGCTGTGACC
GTCTCCGGGAGCTGCATGTGTCAGAGGTTTTCACCGTCATCACCGAAACGCGCGAGGCAGCAAGGAGATGGCGCC
CAACAGTCCCCCGGCCACGGGGCCTGCCACCATACCCACGCCGAAACAAGCGCTCATGAGCCCGAAGTGGCGAGC
CCGATCTTCCCCATCGGTGATGTCGGCGATATAGGCGCCAGCAACCGCACCTGTGGCGCCGGTGATGCCGGCCAC
GATGCGTCCGGCGTAGAGGATCTGCTCATGTTTGACAGCTTATC (SEQ ID NO:1)

FIG. 14A pBAD33MevT plasmid sequence

```
ATCGATGCATAATGTGCCTGTCAAATGGACGAAGCAGGGATTCTGCAAACCCTATGCTACTCCGTCAAGCCGTCA
ATTGT
```
→ araC
```
CTGATTCGTTACCAATTATGACAACTTGACGGCTACATCATTCACTTTTTCTTCACAACCGGCACGGAACTCGCT
CGGGCTGGCCCCGGTGCATTTTTTAAATACCCGCGAGAAATAGAGTTGATCGTCAAAACCAACATTGCGACCGAC
GGTGGCGATAGGCATCCGGGTGGTGCTCAAAAGCAGCTTCGCCTGGCTGATACGTTGGTCCTCGCGCCAGCTTAA
GACGCTAATCCCTAACTGCTGGCGGAAAAGATGTGACAGACGCGACGGCGACAAGCAAACATGCTGTGCGACGCT
GGCGATATCAAAATTGCTGTCTGCCAGGTGATCGCTGATGTACTGACAAGCCTCGCGTACCCGATTATCCATCGG
TGGATGGAGCGACTCGTTAATCGCTTCCATGCGCCGCAGTAACAATTGCTCAAGCAGATTTATCGCCAGCAGCTC
CGAATAGCGCCCTTCCCCTTGCCCGGCGTTAATGATTTGCCCAAACAGGTCGCTGAAATGCGGCTGGTGCGCTTC
ATCCGGGCGAAAGAACCCCGTATTGGCAAATATTGACGGCCAGTTAAGCCATTCATGCCAGTAGGCGCGCGGACG
AAAGTAAACCCACTGGTGATACCATTCGCGAGCCTCCGGATGACGACCGTAGTGATGAATCTCTCCTGGCGGGAA
CAGCAAAATATCACCCGGTCGGCAAACAAATTCTCGTCCCTGATTTTTCACCACCCCCTGACCGCGAATGGTGAG
ATTGAGAATATAACCTTTCATTCCCAGCGGTCGGTCGATAAAAAAATCGAGATAACCGTTGGCCTCAATCGGCGT
TAAACCCGCCACCAGATGGGCATTAAACGAGTATCCCGGCAGCAGGGGATCATTT
```
araC ←
```
TGCGCTTCAGCCATACTTTTCATACTCCCGCCATTCAGAGAAGAAACCAATTGTCCATATTGCATCAGACATTGC
CGTCACTGCGTCTTTTACTGGCTCTTCTCGCTAACCAAACCGGTAACCCCGCTTATTAAAGCATTCTGTAACAA
AGCGGGACCAAAGCCATGACAAAAACGCGTAACAAAAGTGTCTATAATCACGGCAGAAAAGTCCACATTGATTAT
TTGCACGGCGTCACA
```
→ P_BAD Promoter
```
CTTTGCTATGCCATAGCATTTTTATCCATAAGATTAGCGGATCCTACCT GACGCTTTTTATCGCAACTCTCTACT
GT TTC
```
atoB
```
TCCATACCCGTTTTTTTGGGCTAGCGAATTCGAGCTCGGTACCCGGGGATCCTCTAGAGTCGACTAGGAGGAATA
```
→
```
TAAAATGAAAAATTGTGTCATCGTCAGTGCGGTACGTACTGCTATCGGTAGTTTTAACGGTTCACTCGCTTCCAC
CAGCGCCATCGACCTGGGGGCGACAGTAATTAAAGCCGCCATTGAACGTGCAAAAATCGATTCACAACACGTTGA
TGAAGTGATTATGGGTAACGTGTTACAAGCCGGGCTGGGGCAAAATCCGGCGCGTCAGGCACTGTTAAAAGCGG
GCTGGCAGAAACGGTGTGCGGATTCACGGTCAATAAAGTATGTGGTTCGGGTCTTAAAAGTGTGGCGCTTGCCGC
CCAGGCCATTCAGGCAGGTCAGGCGCAGAGCATTGTGGCGGGGGGTATGGAAAATATGAGTTTAGCCCCCTACTT
ACTCGATGCAAAAGCACGCTCTGGTTATCGTCTTGGAGACGGACAGGTTTATGACGTAATCCTGCGCGATGGCCT
GATGTGCGCCACCCATGGTTATCATATGGGGATTACCGCCGAAAACGTGGCTAAAGAGTACGGAATTACCCGTGA
AATGCAGGATGAACTGGCGCTACATTCACAGCGTAAAGCGGCAGCCGCAATTGAGTCCGGTGCTTTTACAGCCGA
AATCGTCCCGGTAAATGTTGTCACTCGAAAGAAAACCTTCGTCTTCAGTCAAGACGAATTCCCGAAAGCGAATTC
AACGGCTGAAGCGTTAGGTGCATTGCGCCCGGCCTTCGATAAAGCAGGAACAGTCACCGCTGGGAACGCGTCTGG
TATTAACGACGGTGCTGCCGCTCTGGTGATTATGGAAGAATCTGCGGCGCTGGCAGCAGGCCTTACCCCCCTGGC
TCGCATTAAAAGTTATGCCAGCGGTGGCGTGCCCCCGCATTGATGGGTATGGGGCCAGTACCTGCCACGCAAAA
AGCGTTACAACTGGCGGGGCTGCAACTGGCGGATATTGATCTCATTGAGGCTAATGAAGCATTTGCTGCACAGTT
CCTTGCCGTTGGGAAAAACCTGGGCTTTGATTCTGAGAAAGTGAATGTCAACGGCGGGGCCATCGCGCTCGGGCA
TCCTATCGGTGCCAGTGGTGCTCGTATTCTGGTCACACTATTACATGCCATGCAGGCACGCGATAAAACGCTGGG
```
atoB ←
```
GCTGGCAACACTGTGCATTGGCGGCGGTCAGGGAATTGCGATGGTGATTGAACGGTTGAATTAAGGAGGACAGCT
```
→ HMGS
```
AAATGAAACTCTCAACTAAACTTTGTTGGTGTGGTATTAAAGGAAGACTTAGGCCGCAAAAGCAACAACAATTAC
ACAATACAAACTTGCAAATGACTGAACTAAAAAAACAAAAGACCGCTGAACAAAAAACCAGACCTCAAAATGTCG
GTATTAAAGGTATCC
```

FIG. 14B

AAATTTACATCCCAACTCAATGTGTCAACCAATCTGAGCTAGAGAAATTTGATGGCGTTTCTCAAGGTAAATACA
CAATTGGTCTGGGCCAAACCAACATGTCTTTTGTCAATGACAGAGAAGATATCTACTCGATGTCCCTAACTGTTT
TGTCTAAGTTGATCAAGAGTTACAACATCGACACCAACAAAATTGGTAGATTAGAAGTCGGTACTGAAACTCTGA
TTGACAAGTCCAAGTCTGTCAAGTCTGTCTTGATGCAATTGTTTGGTGAAAACACTGACGTCGAAGGTATTGACA
CGCTTAATGCCTGTTACGGTGGTACCAACGCGTTGTTCAACTCTTTGAACTGGATTGAATCTAACGCATGGGATG
GTAGAGACGCCATTGTAGTTTGCGGTGATATTGCCATCTACGATAAGGGTGCCGCAAGACCAACCGGTGGTGCCG
GTACTGTTGCTATGTGGATCGGTCCTGATGCTCCAATTGTATTTGACTCTGTAAGAGCTTCTTACATGGAACACG
CCTACGATTTTTACAAGCCAGATTTCACCAGCGAATATCCTTACGTCGATGGTCATTTTCATTAACTTGTTACG
TCAAGGCTCTTGATCAAGTTTACAAGAGTTATTCCAAGAAGGCTATTTCTAAAGGGTTGGTTAGCGATCCCGCTG
GTTCGGATGCTTTGAACGTTTTGAAATATTTCGACTACAACGTTTTCCATGTTCCAACCTGTAAATTGGTCACAA
AATCATACGGTAGATTACTATATAACGATTTCAGAGCCAATCCTCAATTGTTCCCAGAAGTTGACGCCGAATTAG
CTACTCGCGATTATGACGAATCTTTAACCGATAAGAACATTGAAAAAACTTTTGTTAATGTTGCTAAGCCATTCC
ACAAAGAGAGAGTTGCCCAATCTTTGATTGTTCCAACAAACACAGGTAACATGTACACCGCATCTGTTTATGCCG
CCTTTGCATCTCTATTAAACTATGTTGGATCTGACGACTTACAAGGCAAGCGTGTTGGTTTATTTTCTTACGGTT
CCGGTTTAGCTGCATCTCTATATTCTTGCAAAATTGTTGGTGACGTCCAACATATTATCAAGGAATTAGATATTA
CTAACAAATTAGCCAAGAGAATCACCGAAACTCCAAAGGATTACGAAGCTGCCATCGAATTGAGAGAAAATGCCC
ATTTGAAGAAGAACTTCAAACCTCAAGGTTCCATTGAGCATTTGCAAAGTGGTGTTTACTACTTGACCAACATCG
ATGAC

*HMGS* ◄┤ ├► truncated *HMGR*
AAATTTAGAAGATCTTACGATGTTAAAAAATAAGGAGGATTACACTATGGTTTTAACCAATAAAACAGTCATTTC
TGGATCGAAAGTCAAAAGTTTATCATCTGCGCAATCGAGCTCATCAGGACCTTCATCATCTAGTGAGGAAGATGA
TTCCCGCGATATTGAAAGCTTGGATAAGAAAATACGTCCTTTAGAAGAATTAGAAGCATTATTAAGTAGTGGAAA
TACAAAACAATTGAAGAACAAAGAGGTCGCTGCCTTGGTTATTCACGGTAAGTTACCTTTGTACGCTTTGGAGAA
AAAATTAGGTGATACTACGAGAGCGGTTGCGGTACGTAGGAAGGCTCTTTCAATTTTGGCAGAAGCTCCTGTATT
AGCATCTGATCGTTTACCATATAAAAATTATGACTACGACCGCGTATTTGGCGCTTGTTGTGAAAATGTTATAGG
TTACATGCCTTTGCCCGTTGGTGTTATAGGCCCCTTGGTTATCGATGGTACATCTTATCATATACCAATGGCAAC
TACAGAGGGTTGTTTGGTAGCTTCTGCCATGCGTGGCTGTAAGGCAATCAATGCTGGCGGTGGTGCAACAACTGT
TTTAACTAAGGATGGTATGACAAGAGGCCCAGTAGTCCGTTTCCCAACTTTGAAAAGATCTGGTGCCTGTAAGAT
ATGGTTAGACTCAGAAGAGGGACAAAACGCAATTAAAAAAGCTTTTAACTCTACATCAAGATTTGCACGTCTGCA
ACATATTCAAACTTGTCTAGCAGGAGATTTACTCTTCATGAGATTTAGAACAACTACTGGTGACGCAATGGGTAT
GAATATGATTTCTAAAGGTGTCGAATACTCATTAAAGCAAATGGTAGAAGAGTATGGCTGGGAAGATATGGAGGT
TGTCTCCGTTTCTGGTAACTACTGTACCGACAAAAAACCAGCTGCCATCAACTGGATCGAAGGTCGTGGTAAGAG
TGTCGTCGCAGAAGCTACTATTCCTGGTGATGTTGTCAGAAAAGTGTTAAAAAGTGATGTTTCCGCATTGGTTGA
GTTGAACATTGCTAAGAATTTGGTTGGATCTGCAATGGCTGGGTCTGTTGGTGGATTTAACGCACATGCAGCTAA
TTTAGTGACAGCTGTTTTCTTGGCATTAGGACAAGATCCTGCACAAAATGTTGAAAGTTCCAACTGTATAACATT
GATGAAAGAAGTGGACGGTGATTTGAGAATTTCCGTATCCATGCCATCCATCGAAGTAGGTACCATCGGTGGTGG
TACTGTTCTAGAACCACAAGGTGCCATGTTGGACTTATTAGGTGTAAGAGGCCCGCATGCTACCGCTCCTGGTAC
CAACGCACGTCAATTAGCAAGAATAGTTGCCTGTGCCGTCTTGGCAGGTGAATTATCCTTATGTGCTGCCCTAGC
AGCCGGCCATTTGGTTCAAAGTCATATGACCCACAACAGGAAACCTGCTGAACCAACAAAACCTAACAATTTGGA
CGCCACTGATATAAATCGTT truncated *HMGR* ◄┤ rrnB terminator
TGAAAGATGGGTCCGTCACCTGCATTAAATCCTAAGTCGACCTGCAGGCATGCAAGCTTGGCTGTTTTGGCGGAT
GAGAGAAGATTTTCAGCCTGATACAGATTAAATCAGAACGCAGAAGCGGTCTGATAAAACAGAATTTGCCTGGCG
GCAGTAGCGCGGTGGTCCCACCTGACCCCATGCCGAACTCAGAAGTGAAACGCCGTAGCGCCGATGGTAGTGTGG
GGTCTCCCCATGCGAGAGTAGGGAACTGCCAGGCATCAAATAAAACGAAAGGCTCAGTCGAAAGACTGGGCCTTT
CGTTTTATCTGTTGTTTGTCGGTGAACGCTCTCCTGAGTAGGACAAATCCGCCGGGAGCGGATTTGAACGTTGCG
AAGCAACGGCCCGGAGGGTGGCGGGCAGGACGCCCGCCATAAACTGCCAGGCATCAAATTAAGCAGAAGGCCATC
CTGACGGATGGCCTTTTTGCGTTTCTACAAACTCTTTTGTTTATTTTTCTAAATACATTCAAATATGTATCCGCT
CATGAGACAATAACCCTGATAAATGCTTCAATAATATTGAAAAGGAAGAGTATGAGTATTCAACATTTCCGTGT
CGCCCTTATTCCCTTTTTGCGGCATTTTGCCTTCCTGTTTTTGCTCACCCAGAAACGCTGGTGAAAGTAAAAGA
TGCTGAAGATCAGTTGGGTGCAGCAAACTATTAACTGGCGAACTACTTACTCTAGCTTCCCGGCAACAATTAATA
GACTGGATGGAGGCGGATAAAGTTGCAGGACCACTTCTGCGCTCGGCCCTTCCGGCTGGCTGGTTTATTGCTGAT
AAATCTGGAGCCGGTGAGCGTGGGTCTCGCGGTATCATTGCAGCACTGGGGCCAGATGGTAAGCCCTCCCGTATC
GTAGTTATCTACACGACGGGGAGTCAGGCAACTATGGATGAACGAAATAGACAGATCGCTGAGATAGGTGCCTCA
CTGATTAAGCATTGGTAACTGTCAGACCAAGTTTACTCATATATACTTTAGATTGATTTACGCGC

FIG. 14C

CCTGTAGCGGCGCATTAAGCGCGGCGGGTGTGGTGGTTACGCGCAGCGTGACCGCTACACTTGCCAGCGCCCTAG
CGCCCGCTCCTTTCGCTTTCTTCCCTTCCTTTCTCGCCACGTTCGCCGGCTTTCCCCGTCAAGCTCTAAATCGGG
GGCTCCCTTTAGGGTTCCGATTTAGTGCTTTACGGCACCTCGACCCCAAAAAACTTGATTTGGGTGATGGTTCAC
GTAGTGGGCCATCGCCCTGATAGACGGTTTTTCGCCCTTTGACGTTGGAGTCCACGTTCTTTAATAGTGGACTCT
TGTTCCAAACTTGAACAACACTCAACCCTATCTCGGGCTATTCTTTTGATTTATAAGGGATTTTGCCGATTTCGG
CCTATTGGTTAAAAAATGAGCTGATTTAACAAAAATTTAACGCGAATTTTAACAAAATATTAACGTTTACAATTT
AAAAGGATCTAGGTGAAGATCCTTTTTGATAATCTCATGACCAAAATCCCTTAACGTGAGTTTTCGTTCCACTGA
GCGTCAGACCCCGTAGAAAAGATCAAAGGATCTTCTTGAGATCCTTTTTTTCTGCGCGTAATCTGCTGCTTGCAA
ACAAAAAAACCACCGCTACCAGCGGTGGTTTGTTTGCCGGATCAAGAGCTACCAACTCTTTTTCCGAAGGTAACT
GGCTTCAGCAGAGCGCAGATACCAAATACTGTCCTTCTAGTGTAGCCGTAGTTAGGCCACCACTTCAAGAACTCT
GTAGCACCGCCTACATACCTCGCTCTGCTAATCCTGTTACCAGTGGGGCATTTGAGAAGCACACGGTCACACTGC
TTCCGGTAGTCAATAAACCGGTAAACCAGCAATAGACATAAGCGGCTATTTAACGACCCTGCCCTGAACCGACGA
CCGGGTCGAATTTGCTTTCGAATTTCTGCCATTCATCCGCTTATTATCACTTATTCAGGC

Chloramphenicol resistance gene
                                  ⊢▶

GTAGCACCAGGCGTTTAAGGGCACCAATAACTGCCTTAAAAAAATTACGCCCCGCCCTGCCACTCATCGCAGTAC
TGTTGTAATTCATTAAGCATTCTGCCGACATGGAAGCCATCACAGACGGCATGATGAACCTGAATCGCCAGCGGC
ATCAGCACCTTGTCGCCTTGCGTATAATATTTGCCCATGGTGAAAACGGGGGCGAAGAAGTTGTCCATATTGGCC
ACGTTTAAATCAAAACTGGTGAAACTCACCCAGGGATTGGCTGAGACGAAAAACATATTCTCAATAAACCCTTTA
GGGAAATAGGCCAGGTTTTCACCGTAACACGCCACATCTTGCGAATATATGTGTAGAAACTGCCGGAAATCGTCG
TGGTATTCACTCCAGAGCGATGAAAACGTTTCAGTTTGCTCATGGAAAACGGTGTAACAAGGGTGAACACTATCC
CATATCACCAGCTCACCGTCTTTCATTGCCATACGGAATTCCGGATGAGCATTCATCAGGCGGGCAAGAATGTGA
ATAAAGGCCGGATAAAACTTGTGCTTATTTTTCTTTACGGTCTTTAAAAAGGCCGTAATATCCAGCTGAACGGTC
TGGTTATAGGTACATTGAGCAACTGACTGAAATGCCTCAA

◀⊣

AATGTTCTTTACGATGCCATTGGGATATATCAACGGTGGTATATCCAGTGATTTTTTTCTCCATTTTAGCTTCCT
TAGCTCCTGAAAATCTCGATAACTCAAAAAATACGCCCGGTAGTGATCTTATTTCATTATGGTGAAAGTTGGAAC
CTCTTACGTGCCGATCAACGTCTCATTTTCGCCAAAAGTTGGCCCAGGGCTTCCCGGTATCAACAGGGACACCAG
GATTTATTTATTCTGCGAAGTGATCTTCCGTCACAGGTATTTATTCGGCGCAAAGTGCGTCGGGTGATGCTGCCA
ACTTACTGATTTAGTGTATGATGGTGTTTTTGAGGTGCTCCAGTGGCTTCTGTTTCTATCAGCTGTCCCTCCTGT
TCAGCTACTGACGGGGTGGTGCGTA pACYC184 origin
ACGGCAAAAGCACCGCCGGACATCA<u>GCGCTAGCGGAGTGTATACTGGCTTACTATGTTGGCACTGATGAGGGTGT</u>
<u>CAGTGAAGTGCTTCATGTGGCAGGAGAAAAAAGGCTGCACCGGTGCGTCAGCAGAATATGTGATACAGGATATAT</u>
<u>TCCGCTTCCTCGCTCACTGACTCGCTACGCTCGGTCGTTCGACTGCGGCGAGCGGAAATGGCTTACGAACGGGGC</u>
<u>GGAGATTTCCTGGAAGATGCCAGGAAGATACTTAACAGGGAAGTGAGAGGGCCGCGGCAAAGCCGTTTTTCCATA</u>
<u>GGCTCCGCCCCCCTGACAAGCATCACGAAATCTGACGCTCAAATCAGTGGTGGCGAAACCCGACAGGACTATAAA</u>
<u>GATACCAGGCGTTTCCCCCTGGCGGCTCCCTCGTGCGCTCTCCTGTTCCTGCCTTTCGGTTTACCGGTGTCATTC</u>
<u>CGCTGTTATGGCCGCGTTTGTCTCATTCCACGCCTGACACTCAGTTCCGGGTAGGCAGTTCGCTCCAAGCTGGAC</u>
<u>TGTATGCACGAACCCCCCGTTCAGTCCGACCGCTGCGCCTTATCCGGTAACTATCGTCTTGAGTCCAACCCGGAA</u>
<u>AGACATGCAAAAGCACCACTGGCAGCAGCCACTGGTAATTGATTTAGAGGAGTTAGTCTTGAAGTCATGCGCCGG</u>
<u>TTAAGGCTAAACTGAAGGACAAGTTTTGGTGACTGCGCTCCTCCAAGCCAGTTACCTCGGTTCAAAGAGTTGGT</u>
<u>AGCTCAGAGAACCTTCGAAAAACCGCCCTGCAAGGCGGTTTTTTCGTTTTCAGAGCAAGAGATTACGCGCAGACC</u>
<u>AAAACGATCTCAAGAAGATCATCTTATTAATCAGATAAAATATTT</u>GCTCATGAGCCCGAAGTGGCGAGCCCGATC
TTCCCCATCGGTGATGTCGGCGATATAGGCGCCAGCAACCGCACCTGTGGCGCCGGTGATGCCGGCCACGATGCG
TCCGGCGTAGAGGATCTGCTCATGTTTGACAGCTTATC (SEQ ID NO:2)

FIG. 15A pMevT plasmid sequence

ATCGATGCATGCGCCCAATACGCAAACCGCCTCTCCCCGCGCGTTGGCCGATTCATTAATGCAGCTGGCACGACA
GGTTT

Modified P$_{LAC}$ promoter
CCCGACTGGAAAGCGGGCAGTGAGCG|CAACGCAATTAATGTGAGTTAGCTCACTCATTAGGCACCCCAGGCTTTA
CACTTTATGCTTCCGGCTCGTATGTTGTGTGGAATTGTGAGCGG|ATAACAATTTCACACAGGAAACAGCTATGAC
CATGATTACGCCAAGCGCGCAATTAACCCTCACTAAAGGGAACAAAAGCTGGGTACCGGGCCCCCCCTCGAGGTC
GACGGTATCGATAAG atoB
CTTGATATCGAATTCCTGCAGCCCGGGGATCCTCTAGAGTCGACTAGGAGGAATATAAAATGAAAAATTGTGTCA
TCGTCAGTGCGGTACGTACTGCTATCGGTAGTTTTAACGGTTCACTCGCTTCCACCAGCGCCATCGACCTGGGGG
CGACAGTAATTAAAGCCGCCATTGAACGTGCAAAAATCGATTCACAACACGTTGATGAAGTGATTATGGGTAACG
TGTTACAAGCCGGGCTGGGGCAAAATCCGGCGCGTCAGGCACTGTTAAAAGCGGGCTGGCAGAAACGGTGTGCG
GATTCACGGTCAATAAAGTATGTGGTTCGGGTCTTAAAAGTGTGGCGCTTGCCGCCCAGGCCATTCAGGCAGGTC
AGGCGCAGAGCATTGTGGCGGGGGGTATGGAAAATATGAGTTTAGCCCCCTACTTACTCGATGCAAAAGCACGCT
CTGGTTATCGTCTTGGAGACGGACAGGTTTATGACGTAATCCTGCGCGATGGCCTGATGTGCGCCACCCATGGTT
ATCATATGGGGATTACCGCCGAAAACGTGGCTAAAGAGTACGGAATTACCCGTGAAATGCAGGATGAACTGGCGC
TACATTCACAGCGTAAAGCGGCAGCCGCAATTGAGTCCGGTGCTTTTACAGCCGAAATCGTCCCGGTAAATGTTG
TCACTCGAAAGAAAACCTTCGTCTTCAGTCAAGACGAATTCCCGAAAGCGAATTCAACGGCTGAAGCGTTAGGTG
CATTGCGCCCGGCCTTCGATAAAGCAGGAACAGTCACCGCTGGGAACGCGTCTGGTATTAACGACGGTGCTGCCG
CTCTGGTGATTATGGAAGAATCTGCGGCGCTGGCAGCAGGCCTTACCCCCCTGGCTCGCATTAAAAGTTATGCCA
GCGGTGGCGTGCCCCCCGCATTGATGGGTATGGGGCCAGTACCTGCCACGCAAAAAGCGTTACAACTGGCGGGGC
TGCAACTGGCGGATATTGATCTCATTGAGGCTAATGAAGCATTTGCTGCACAGTTCCTTGCCGTTGGGAAAAACC
TGGGCTTTGATTCTGAGAAAGTGAATGTCAACGGCGGGGCCATCGCGCTCGGGCATCCTATCGGTGCCAGTGGTG
CTCGTATTCTGGTCACACTATTACATGCCATGCAGGCACGCGATAAAACGCTGGGCTGGCAACACTGTGCATTG atoB                                                                              HMGS
GCGGCGGTCAGGGAATTGCGATGGTGATTGAACGGTTGAATTAAGGAGGACAGCTAAATGAAACTCTCAACTAAA
CTTTGTTGGTGTGGTATTAAAGGAAGACTTAGGCCGCAAAAGCAACAACAATTACACAATACAAACTTGCAAATG
ACTGAACTAAAAAAACAAAAGACCGCTGAACAAAAAACCAGACCTCAAAATGTCGGTATTAAAGGTATCCAAATT
TACATCCCAACTCAATGTGTCAACCAATCTGAGCTAGAGAAATTTGATGGCGTTTCTCAAGGTAAATACACAATT
GGTCTGGGCCAAACCAACATGTCTTTTGTCAATGACAGAGAAGATATCTACTCGATGTCCCTAACTGTTTTGTCT
AAGTTGATCAAGAGTTACAACATCGACACCAACAAAATTGGTAGATTAGAAGTCGGTACTGAAACTCTGATTGAC
AAGTCCAAGTCTGTCAAGTCTGTCTTGATGCAATTGTTTGGTGAAAACACTGACGTCGAAGGTATTGACACGCTT
AATGCCTGTTACGGTGGTACCAACGCGTTGTTCAACTCTTTGAACTGGATTGAATCTAACGCATGGGATGGTAGA
GACGCCATTGTAGTTTGCGGTGATATTGCCATCTACGATAAGGGTGCCGCAAGACCAACCGGTGGTGCCGGTACT
GTTGCTATGTGGATCGGTCCTGATGCTCCAATTGTATTTGACTCTGTAAGAGCTTCTTACATGGAACACGCCTAC
GATTTTTACAAGCCAGATTTCACCAGCGAATATCCTTACGTCGATGGTCATTTTTCATTAACTTGTTACGTCAAG
GCTCTTGATCAAGTTTACAAGAGTTATTCCAAGAAGGCTATTTCTAAAGGGTTGGTTAGCGATCCCGCTGGTTCG
GATGCTTTGAACGTTTTGAAATATTTCGACTACAACGTTTTCCATGTTCCAACCTGTAAATTGGTCACAAAATCA
TACGGTAGATTACTATATAACGATTTCAGAGCCAATCCTCAATTGTTCCCAGAAGTTGACGCCGAATTAGCTACT
CGCGATTATGACGAATCTTTAACCGATAAGAACATTGAAAAAACTTTTGTTAATGTTGCTAAGCCATTCCACAAA
GAGAGAGTTGCCCAATCTTTGATTGTTCCAACAAACACAGGTAACATGTACACCGCATCTGTTTATGCCGCCTTT
GCATCTCTATTAAACTATGTTGGATCTGACGACTTACAAGGCAAGCGTGTTGGTTTATTTTCTTACGGTTCCGGT
TTAGCTGCATCTCTATATTCTTGCAAAATTGTTGGTGACGTCCAACATATTATCAAGGAATTAGATATTACTAAC
AAATTAGCCAAGAGAATCACCGAAACTCCAAAGGATTACGAAGCTGCCATCGAATTGAGAGAAAATGCCCATTTG
AAGAAGAACTTCAAACCTCAAGGTTCCATTGAGCATTTGCAAAGTGGTGTTTACTACTTGACCAACATCGATGAC
AAATTTAGAAGATCTTACGA HMGS                                                                 truncated HMGR
TGTTAAAAAATAAGGAGGATTACACTATGGTTTTAACCAATAAAACAGTCATTTCTGGATCGAAAGTCAAAAGTT
TATCATCTGCGCAATCGAGCTCATCAGGACCTTCATCATCTAGTGAGGAAGATGATTCCCGCGATATTGAAAGCT
TGGATAAGAAAATACGTCCTTTAGAAGAATTAGAAGCATTATTAAGTAGTGGAAATACAAAACAATTGAAGAACA
AAGAGGTCGCTGCCT

FIG. 15B

```
TGGTTATTCACGGTAAGTTACCTTTGTACGCTTTGGAGAAAAAATTAGGTGATACTACGAGAGCGGTTGCGGTAC
GTAGGAAGGCTCTTTCAATTTTGGCAGAAGCTCCTGTATTAGCATCTGATCGTTTACCATATAAAAATTATGACT
ACGACCGCGTATTTGGCGCTTGTTGTGAAAATGTTATAGGTTACATGCCTTTGCCCGTTGGTGTTATAGGCCCCT
TGGTTATCGATGGTACATCTTATCATATACCAATGGCAACTACAGAGGGTTGTTTGGTAGCTTCTGCCATGCGTG
GCTGTAAGGCAATCAATGCTGGCGGTGGTGCAACAACTGTTTTAACTAAGGATGGTATGACAAGAGGCCCAGTAG
TCCGTTTCCCAACTTTGAAAAGATCTGGTGCCTGTAAGATATGGTTAGACTCAGAAGAGGGACAAAACGCAATTA
AAAAAGCTTTTAACTCTACATCAAGATTTGCACGTCTGCAACATATTCAAACTTGTCTAGCAGGAGATTTACTCT
TCATGAGATTTAGAACAACTACTGGTGACGCAATGGGTATGAATATGATTTCTAAAGGTGTCGAATACTCATTAA
AGCAAATGGTAGAAGAGTATGGCTGGGAAGATATGGAGGTTGTCTCCGTTTCTGGTAACTACTGTACCGACAAAA
AACCAGCTGCCATCAACTGGATCGAAGGTCGTGGTAAGAGTGTCGTCGCAGAAGCTACTATTCCTGGTGATGTTG
TCAGAAAAGTGTTAAAAAGTGATGTTTCCGCATTGGTTGAGTTGAACATTGCTAAGAATTTGGTTGGATCTGCAA
TGGCTGGGTCTGTTGGTGGATTTAACGCACATGCAGCTAATTTAGTGACAGCTGTTTTCTTGGCATTAGGACAAG
ATCCTGCACAAAATGTTGAAAGTTCCAACTGTATAACATTGATGAAAGAAGTGGACGGTGATTTGAGAATTTCCG
TATCCATGCCATCCATCGAAGTAGGTACCATCGGTGGTGGTACTGTTCTAGAACCACAAGGTGCCATGTTGGACT
TATTAGGTGTAAGAGGCCCGCATGCTACCGCTCCTGGTACCAACGCACGTCAATTAGCAAGAATAGTTGCCTGTG
CCGTCTTGGCAGGTGAATTATCCTTATGTGCTGCCCTAGCAGCCGGCCATTTGGTTCAAAGTCATATGACCCACA
ACAGGAAACCTGCTGAACCAACAAAACCTAACAATTTGGACGCCACTGATATAAATCGTTTGAAAGATGGGTCCG
TCACC
``` truncated *HMGR*
◄—┤                                                                   *rrnB terminator*
```
TGCATTAAATCCTAAGTCGACCTGCAGGCATGCAAGCTTGGCTGTTTTGGCGGATGAGAGAAGATTTTCAGCCTG
ATACAGATTAAATCAGAACGCAGAAGCGGTCTGATAAAACAGAATTTGCCTGGCGGCAGTAGCGCGGTGGTCCCA
CCTGACCCCATGCCGAACTCAGAAGTGAAAACGCCGTAGCGCCGATGGTAGTGTGGGGTCTCCCCATGCGAGAGTA
GGGAACTGCCAGGCATCAAATAAAACGAAAGGCTCAGTCGAAAGACTGGGCCTTTCGTTTTATCTGTTGTTTGTC
GGTGAACGCTCTCCTGAGTAGGACAAATCCGCCGGGAGCGGATTTGAACGTTGCGAAGCAACGGCCCGGAGGGTG
GCGGGCAGGACGCCCGCCATAAACTGCCAGGCATCAAATTAAGCAGAAGGCCATCCTGACGGATGGCCTTTTTGC
GTTTCTACAAACTCTTTTGTTTATTTTTCTAAATACATTCAAATATGTATCCGCTCATGAGACAATAACCCTGAT
AAATGCTTCAATAATATTGAAAAAGGAAGAGTATGAGTATTCAACATTTCCGTGTCGCCCTTATTCCCTTTTTTG
CGGCATTTTGCCTTCCTGTTTTTGCTCACCCAGAAACGCTGGTGAAAGTAAAAGATGCTGAAGATCAGTTGGGTG
CAGCAAACTATTAACTGGCGAACTACTTACTCTAGCTTCCCGGCAACAATTAATAGACTGGATGGAGGCGGATAA
AGTTGCAGGACCACTTCTGCGCTCGGCCCTTCCGGCTGGCTGGTTTATTGCTGATAAATCTGGAGCCGGTGAGCG
TGGGTCTCGCGGTATCATTGCAGCACTGGGGCCAGATGGTAAGCCCTCCCGTATCGTAGTTATCTACACGACGGG
GAGTCAGGCAACTATGGATGAACGAAATAGACAGATCGCTGAGATAGGTGCCTCACTGATTAAGCATTGGTAACT
GTCAGACCAAGTTTACTCATATATACTTTAGATTGATTTACGCGCCCTGTAGCGGCGCATTAAGCGCGGCGGGTG
TGGTGGTTACGCGCAGCGTGACCGCTACACTTGCCAGCGCCCTAGCGCCCGCTCCTTTCGCTTTCTTCCCTTCCT
TTCTCGCCACGTTCGCCGGCTTTCCCCGTCAAGCTCTAAATCGGGGGCTCCCTTTAGGGTTCCGATTTAGTGCTT
TACGGCACCTCGACCCCAAAAAACTTGATTTGGGTGATGGTTCACGTAGTGGGCCATCGCCCTGATAGACGGTTT
TTCGCCCTTTGACGTTGGAGTCCACGTTCTTTAATAGTGGACTCTTGTTCCAAACTTGAACAACACTCAACCCTA
TCTCGGGCTATTCTTTTGATTTATAAGGGATTTTGCCGATTTCGGCCTATTGGTTAAAAAATGAGCTGATTTAAC
AAAAATTTAACGCGAATTTTAACAAAATATTAACGTTTACAATTTAAAAGGATCTAGGTGAAGATCCTTTTTGAT
AATCTCATGACCAAAATCCCTTAACGTGAGTTTTCGTTCCACTGAGCGTCAGACCCCGTAGAAAAGATCAAAGGA
TCTTCTTGAGATCCTTTTTTTCTGCGCGTAATCTGCTGCTTGCAAACAAAAAAACCACCGCTACCAGCGGTGGTT
TGTTTGCCGGATCAAGAGCTACCAACTCTTTTTCCGAAGGTAACTGGCTTCAGCAGAGCGCAGATACCAAATACT
GTCCTTCTAGTGTAGCCGTAGTTAGGCCACCACTTCAAGAACTCTGTAGCACCGCCTACATACCTCGCTCTGCTA
ATCCTGTTACCAGTGGGGCATTTGAGAAGCACACGGTCACACTGCTTCCGGTAGTCAATAAACCGGTAAACCAGC
AATAGACATAAGCGGCTATTTAACGACCCTGCCCTGAACCGACGACCGGGTCGAATTTGCTTTCGAATTTCTGCC
ATTCATCCGCTTATTATCACTTATTCAGGCGTAGCACCAGGCGTTTAAGG
```

├—►          Chloramphenicol resistance gene
```
GCACCAATAACTGCCTTAAAAAAATTACGCCCCGCCCTGCCACTCATCGCAGTACTGTTGTAATTCATTAAGCAT
TCTGCCGACATGGAAGCCATCACAGACGGCATGATGAACCTGAATCGCCAGCGGCATCAGCACCTTGTCGCCTTG
CGTATAATATTTGCCCATGGTGAAAACGGGGGCGAAGAAGTTGTCCATATTGGCCACGTTTAAATCAAAACTGGT
GAAACTCACCCAGGGATTGGCTGAGACGAAAAACATATTCTCAATAAACCCTTTAGGGAAATAGGCCAGGTTTTC
ACCGTAACACGCCACATCTTGCGAATATATGTGTAGAAACTGCCGGAAATCGTCGTGGTATTCACTCCAGAGCGA
TGAAAACGTTTCAGTTTGCTCATGGAAAACGGTGTAACAAGGGTGAACACTATCCCATATCACCAGCTCACCGTC
TTTCATTGCCATACGGAATTCCGGATGAGCATTCATCAGGCGGGCAAGAATGTGAATAAAGGCCGGATAAAACTT
GTGCTTATTTTTCTTTACGGTCTTTAAAAAGGCCGTAATATCCAGCTGAACGGTCTGGTTATAGGTACATTGAGC
AACTGACTGAAATGCCTCAAAATGTTCTTTACGATGCCAT
```

FIG. 15C

TGGGATATATCAACGGTGGTATATCCAGTGATTTTTTTCTCCATTTTAGCTTCCTTAGCTCCTGAAAATCTCGAT
AACTCAAAAAATACGCCCGGTAGTGATCTTATTTCATTATGGTGAAAGTTGGAACCTCTTACGTGCCGATCAACG
TCTCATTTTCGCCAAAAGTTGGCCCAGGGCTTCCCGGTATCAACAGGGACACCAGGATTTATTTATTCTGCGAAG
TGATCTTCCGTCACAGGTATTTATTCGGCGCAAAGTGCGTCGGGTGATGCTGCCAACTTACTGATTTAGTGTATG
ATGGTGTTTTTGAGGTGCTCCAGTGGCTTCTGTTTCTATCAGCTGTCCCTCCTGTTCAGCTACTGACGGGGTGGT
GCGTAACGGCAAAAGCACCGCCGGA pACYC184 origin
CATCA<u>GCGCTAGCGGAGTGTATACTGGCTTACTATGTTGGCACTGATGAGGGTGTCAGTGAAGTGCTTCATGTGG
CAGGAGAAAAAAGGCTGCACCGGTGCGTCAGCAGAATATGTGATACAGGATATATTCCGCTTCCTCGCTCACTGA
CTCGCTACGCTCGGTCGTTCGACTGCGGCGAGCGGAAATGGCTTACGAACGGGGCGGAGATTTCCTGGAAGATGC
CAGGAAGATACTTAACAGGGAAGTGAGAGGGCCGCGGCAAAGCCGTTTTTCCATAGGCTCCGCCCCCCTGACAAG
CATCACGAAATCTGACGCTCAAATCAGTGGTGGCGAAACCCGACAGGACTATAAAGATACCAGGCGTTTCCCCCT
GGCGGCTCCCTCGTGCGCTCTCCTGTTCCTGCCTTTCGGTTTACCGGTGTCATTCCGCTGTTATGGCCGCGTTTG
TCTCATTCCACGCCTGACACTCAGTTCCGGGTAGGCAGTTCGCTCCAAGCTGGACTGTATGCACGAACCCCCCGT
TCAGTCCGACCGCTGCGCCTTATCCGGTAACTATCGTCTTGAGTCCAACCCGGAAAGACATGCAAAAGCACCACT
GGCAGCAGCCACTGGTAATTGATTTAGAGGAGTTAGTCTTGAAGTCATGCGCCGGTTAAGGCTAAACTGAAAGGA
CAAGTTTTGGTGACTGCGCTCCTCCAAGCCAGTTACCTCGGTTCAAAGAGTTGGTAGCTCAGAGAACCTTCGAAA
AACCGCCCTGCAAGGCGGTTTTTTCGTTTTCAGAGCAAGAGATTACGCGCAGACCAAAACGATCTCAAGAAGATC
ATCTTATTAATCAGATAAAATATTT</u>GCTCATGAGCCCGAAGTGGCGAGCCCGATCTTCCCCATCGGTGATGTCGG
CGATATAGGCGCCAGCAACCGCACCTGTGGCGCCGGTGATGCCGGCCACGATGCGTCCGGCGTAGAGGATCTGCT
CATGTTTGACAGCTTATC (SEQ ID NO:3)

FIG. 16A pMBIS plasmid sequence

ACCTTCGGGAGCGCCTGAAGCCCGTTCTGGACGCCCTGGGGCCGTTGAATCGGGATATGCAGGCCAAGGCCGCCG
CGATCATCAAGGCCGTGGGCGAAAAGCTGCTGACGGAACAGCGGGAAGTCCAGCGCCAGAAACAGGCCCAGCGCC
AGCAGGAACGCGGGCGCGCACATTTCCCCGAAAAGTGCCACCTGACGTCTAAGAAACCATTATTATCATGACATT
AACCTATAAAAATAGGCGTATCACGAGGCCCTTTCGTCTTCAAGAATTCTCATGTTTGACAGCTTATCATCGATA
AGCTTTAATGCGGTAGTTTA

⟶ Tetracycline resistance gene
TCACAGTTAAATTGCTAACGCAGTCAGGCACCGTGT<u>ATGAAATCTAACAATGCGCTCATCGTCATCCTCGGCACC
GTCACCCTGGATGCTGTAGGCATAGGCTTGGTTATGCCGGTACTGCCGGGCCTCTTGCGGGATATCGTCCATTCC
GACAGCATCGCCAGTCACTATGGCGTGCTGCTAGCGCTATATGCGTTGATGCAATTTCTATGCGCACCCGTTCTC
GGAGCACTGTCCGACCGCTTTGGCCGCCGCCCAGTCCTGCTCGCTTCGCTACTTGGAGCCACTATCGACTACGCG
ATCATGGCGACCACACCCGTCCTGTGGATCCTCTACGCCGGACGCATCGTGGCCGGCATCACCGGCGCCACAGGT
GCGGTTGCTGGCGCCTATATCGCCGACATCACCGATGGGGAAGATCGGGCTCGCCACTTCGGGCTCATGAGCGCT
TGTTTCGGCGTGGGTATGGTGGCAGGCCCCGTGGCCGGGGACTGTTGGGCGCCATCTCCTTGCATGCACCATTC
CTTGCGGCGGCGGTGCTCAACGGCCTCAACCTACTACTGGGCTGCTTCCTAATGCAGGAGTCGCATAAGGGAGAG
CGTCGACCGATGCCCTTGAGAGCCTTCAACCCAGTCAGCTCCTTCCGGTGGGCGCGGGGCATGACTATCGTCGCC
GCACTTATGACTGTCTTCTTTATCATGCAACTCGTAGGACAGGTGCCGGCAGCGCTCTGGGTCATTTTCGGCGAG
GACCGCTTTCGCTGGAGCGCGACGATGATCGGCCTGTCGCTTGCGGTATTCGGAATCTTGCACGCCCTCGCTCAA
GCCTTCGTCACTGGTCCCGCCACCAAACGTTTCGGCGAGAAGCAGGCCATTATCGCCGGCATGGCGGCCGACGCG
CTGGGCTACGTCTTGCTGGCGTTCGCGACGCGAGGCTGGATGGCCTTCCCCATTATGATTCTTCTCGCTTCCGGC
GGCATCGGGATGCCCGCGTTGCAGGCCATGCTGTCCAGGCAGGTAGATGACGACCATCAGGGACAGCTTCAAGGA
TCGCTCGCGGCTCTTACCAGCCTAACTTCGATCACTGGACCGCTGATCGTCACGGCGATTTATGCCGCCTCGGCG
AGCACATGGAACGGGTTGGCATGGATTGTAGGCGCCGCCCTATACCTTGTCTGCCTCCCCGCGTTGCGTCGCGGT
GCATGGAGCCGGGCCACCTCGACCTGA</u>ATGGAAGCCGGCGGCACCTCGCTAACGGATTCACCACTCCAAGAATTG
GAGCCAATCAATTCTTGCGGAGAACTGTGAATGCGCAAATGCGCCCAATACGCAAACCGCCTCTCCCCGCGCGTT
GGCCGATTCA ⟶ Modified $P_{LAC}$ promoter
TTAATGCAGCTGGCACGACAGGTTTCCCGACTGGAAAGCGGGCAGTGAGCG CAACGCAATTAATGTGAGTTAGCT
CACTCATTAGGCACCCCAGGCTTTACACTTTATGCTTCCGGCTCGTATGTTGTGTGGAATTGTGAGCGG ATAACA
ATTTCACACAGGAAACAGCTATGACCATGATTACGCCAAGCGCGCAATTAACCCTCACTAAAGGGAACAAAAGCT
GGGTACCGGGCCCC ⟶ MK
CCTCGAGGTCGACGGTATCGATAAGCTTGATATCGAATTCCTGCAGTAGGAGGAATTAACCATGTCATTACCGTT
CTTAACTTCTGCACCGGGAAAGGTTATTATTTTTGGTGAACACTCTGCTGTGTACAACAAGCCTGCCGTCGCTGC
TAGTGTGTCTGCGTTGAGAACCTACCTGCTAATAAGCGAGTCATCTGCACCAGATACTATTGAATTGGACTTCCC
GGACATTAGCTTTAATCATAAGTGGTCCATCAATGATTTCAATGCCATCACCGAGGATCAAGTAAACTCCCAAAA
ATTGGCCAAGGCTCAACAAGCCACCGATGGCTTGTCTCAGGAACTCGTTAGTCTTTTGGATCCGTTGTTAGCTCA
ACTATCCGAATCCTTCCACTACCATGCAGCGTTTTGTTTCCTGTATATGTTTGTTTGCCTATGCCCCCATGCCAA
GAATATTAAGTTTTCTTTAAAGTCTACTTTACCCATCGGTGCTGGGTTGGGCTCAAGCGCCTCTATTTCTGTATC
ACTGGCCTTAGCTATGGCCTACTTGGGGGGGTTAATAGGATCTAATGACTTGGAAAAGCTGTCAGAAAACGATAA
GCATATAGTGAATCAATGGGCCTTCATAGGTGAAAAGTGTATTCACGGTACCCCTTCAGGAATAGATAACGCTGT
GGCCACTTATGGTAATGCCCTGCTATTTGAAAAAGACTCACATAATGGAACAATAAACACAAACAATTTTAAGTT
CTTAGATGATTTCCCAGCCATTCCAATGATCCTAACCTATACTAGAATTCCAAGGTCTACAAAAGATCTTGTTGC
TCGCGTTCGTGTGTTGGTCACCGAGAAATTTCCTGAAGTTATGAAGCCAATTCTAGATGCCATGGGTGAATGTGC
CCTACAAGGCTTAGAGATCATGACTAAGTTAAGTAAATGTAAAGGCACCGATGACGAGGCTGTAGAAACTAATAA
TGAACTGTATGAACAACTATTGGAATTGATAAGAATAAATCATGGACTGCTTGTCTCAATCGGTGTTTCTCATCC
TGGATTAGAACTTATTAAAAATCTGAGCGATGATTTGAGAATTGGCTCCACAAAACTTACCGGTGCTGGTGGCGG
CGGTTGCTCTTTGACTTTGTTACGAAGAGACATTACTCAAGAGCAAATTGACAGCTTCAAAAGAAATTGCAAGA
TGATTTTAGTTACGAGACATTTGAAACAGACTTGGGTGGGACTGGCTGCTGTTTGTTAAGCGCAAAAAATTTGAA
TAAAGATCTTAAAATCAAATCCCTAGTATTCCAATTATTTGAAAATAAAACTACCACAAAGCAACAAATTGACGA
TCTATTATTG

FIG. 16B

```
       MK                ◄┤       ├►         PMK
CCAGGAAACACGAATTTACCATGGACTTCATAGGAGGCAGATCAAATGTCAGAGTTGAGAGCCTTCAGTGCCCCA
GGGAAAGCGTTACTAGCTGGTGGATATTTAGTTTTAGATACAAAATATGAAGCATTTGTAGTCGGATTATCGGCA
AGAATGCATGCTGTAGCCCATCCTTACGGTTCATTGCAAGGGTCTGATAAGTTTGAAGTGCGTGTGAAAAGTAAA
CAATTTAAAGATGGGGAGTGGCTGTACCATATAAGTCCTAAAAGTGGCTTCATTCCTGTTTCGATAGGCGGATCT
AAGAACCCTTTCATTGAAAAAGTTATCGCTAACGTATTTAGCTACTTTAAACCTAACATGGACGACTACTGCAAT
AGAAACTTGTTCGTTATTGATATTTTCTCTGATGATGCCTACCATTCTCAGGAGGATAGCGTTACCGAACATCGT
GGCAACAGAAGATTGAGTTTTCATTCGCACAGAATTGAAGAAGTTCCCAAAACAGGGCTGGGCTCCTCGGCAGGT
TTAGTCACAGTTTTAACTACAGCTTTGGCCTCCTTTTTTGTATCGGACCTGGAAAATAATGTAGACAAATATAGA
GAAGTTATTCATAATTTAGCACAAGTTGCTCATTGTCAAGCTCAGGGTAAAATTGGAAGCGGGTTTGATGTAGCG
GCGGCAGCATATGGATCTATCAGATATAGAAGATTCCCACCCGCATTAATCTCTAATTTGCCAGATATTGGAAGT
GCTACTTACGGCAGTAAACTGGCGCATTTGGTTGATGAAGAAGACTGGAATATTACGATTAAAAGTAACCATTTA
CCTTCGGGATTAACTTTATGGATGGGCGATATTAAGAATGGTTCAGAAACAGTAAAACTGGTCCAGAAGGTAAAA
AATTGGTATGATTCGCATATGCCAGAAAGCTTGAAAATATATACAGAACTCGATCATGCAAATTCTAGATTTATG
GATGGACTATCTAAACTAGATCGCTTACACGAGACTCATGACGATTACAGCGATCAGATATTTGAGTCTCTTGAG
AGGAATGACTGTACCTGTCAAAAGTATCCTGAAATCACAGAAGTTAGAGATGCAGTTGCCACAATTAGACGTTCC
TTTAGAAAAATAACTAAAGAATCTGGTGCCGATATCGAACCTCCCGTACAAACTAGCTTATTGGATGATTGCCAG
ACCTTAAAAGGAGTTCTTACTTGCTTAATACCTGGTGCTGGTGGTTATGACGCCATTGCAGTGATTACTAAGCAA
GATGTTGATCTTAGGGCTCAAACCGCTAATGACAAAAGATTTTCTAAGGTTCAATGGCTGGATGTAACTCAGGCT
GACTGGGGTG

PMK                    ◄┤         ├►            MPD
TTAGGAAAGAAAAAGATCCGGAAACTTATCTTGATAAATAGGAGGTAATACTCATGACCGTTTACACAGCATCCG
TTACCGCACCCGTCAACATCGCAACCCTTAAGTATTGGGGGAAAAGGGACACGAAGTTGAATCTGCCCACCAATT
CGTCCATATCAGTGACTTTATCGCAAGATGACCTCAGAACGTTGACCTCTGCGGCTACTGCACCTGAGTTTGAAC
GCGACACTTTGTGGTTAAATGGAGAACCACACAGCATCGACAATGAAAGAACTCAAAATTGTCTGCGCGACCTAC
GCCAATTAAGAAAGGAAATGGAATCGAAGGACGCCTCATTGCCCACATTATCTCAATGGAAACTCCACATTGTCT
CCGAAAATAACTTTCCTACAGCAGCTGGTTTAGCTTCCTCCGCTGCTGGCTTTGCTGCATTGGTCTCTGCAATTG
CTAAGTTATACCAATTACCACAGTCAACTTCAGAAATATCTAGAATAGCAAGAAAGGGGTCTGGTTCAGCTTGTA
GATCGTTGTTTGGCGGATACGTGGCCTGGGAAATGGGAAAAGCTGAAGATGGTCATGATTCCATGGCAGTACAAA
TCGCAGACAGCTCTGACTGGCCTCAGATGAAAGCTTGTGTCCTAGTTGTCAGCGATATTAAAAAGGATGTGAGTT
CCACTCAGGGTATGCAATTGACCGTGGCAACCTCCGAACTATTTAAAGAAAGAATTGAACATGTCGTACCAAAGA
GATTTGAAGTCATGCGTAAAGCCATTGTTGAAAAGATTTCGCCACCTTTGCAAAGGAAACAATGATGGATTCCA
ACTCTTTCCATGCCACATGTTTGGACTCTTTCCCTCCAATATTCTACATGAATGACACTTCCAAGCGTATCATCA
GTTGGTGCCACACCATTAATCAGTTTTACGGAGAAACAATCGTTGCATACACGTTTGATGCAGGTCCAAATGCTG
TGTTGTACTACTTAGCTGAAAATGAGTCGAAACTCTTTGCATTTATCTATAAATTGTTTGGCTCTGTTCCTGGAT
GGGACAAGAAATTTACTACTGAGCAGCTTGAGGCTTTCAACCATCAATTTGAATCATCTAACTTTACTGCACGTG
AATTGGATCTTGAGTTGCAAAAGGATGTTGCCAGAGTGATTTTAACTCAAGTCGGTTCAGGCCCACAAGAAACAA

MPD              ◄┤                 ├►  idi
ACGAATCTTTGATTGACGCAAAGACTGGTCTACCAAAGGAATAACTGCAGCCCGGGAGGAGGATTACTATATGCA
AACGGAACACGTCATTTTATTGAATGCACAGGGAGTTCCCACGGGTACGCTGGAAAAGTATGCCGCACACACGGC
AGACACCCGCTTACATCTCGCGTTCTCCAGTTGGCTGTTTAATGCCAAAGGACAATTATTAGTTACCCGCCGCGC
ACTGAGCAAAAAGCATGGCCTGGCGTGTGGACTAACTCGGTTTGTGGGCACCCACAACTGGGAGAAAGCAACGA
AGACGCAGTGATCCGCCGTTGCCGTTATGAGCTTGGCGTGGAAATTACGCCTCCTGAATCTATCTATCCTGACTT
TCGCTACCGCGCCACCGATCCGAGTGGCATTGTGGAAAATGAAGTGTGTCCGGTATTTGCCGCACGCACCACTAG
TGCGTTACAGATCAATGATGATGAAGTGATGGATTATCAATGGTGTGATTTAGCAGATGTATTACACGGTATTGA
TGCCACGCCGTGGGCGTTCAGTCCGTGGATGGTGATGCAGGCGACAAATCGCGAAGCCAGAAAACGATTATCTGC
ATTTACCCAGCTTAAATAACCCGGGGGATCCACTAGTTCT
               ◄┤
```

FIG. 16C

```
                                                        ispA
AGAGCGGCCGCCACCGCGGAGGAGGAATGAGTAATGGACTTTCCGCAGCAACTCGAAGCCTGCGTTAAGCAGGCC
AACCAGGCGCTGAGCCGTTTTATCGCCCCACTGCCCTTTCAGAACACTCCCGTGGTCGAAACCATGCAGTATGGC
GCATTATTAGGTGGTAAGCGCCTGCGACCTTTCCTGGTTTATGCCACCGGTCATATGTTCGGCGTTAGCACAAAC
ACGCTGGACGCACCCGCTGCCGCCGTTGAGTGTATCCACGCTTACTCATTAATTCATGATGATTTACCGGCAATG
GATGATGACGATCTGCGTCGCGGTTTGCCAACCTGCCATGTGAAGTTTGGCGAAGCAAACGCGATTCTCGCTGGC
GACGCTTTACAAACGCTGGCGTTCTCGATTTTAAGCGATGCCGATATGCCGGAAGTGTCGGACCGCGACAGAATT
TCGATGATTTCTGAACTGGCGAGCGCCAGTGGTATTGCCGGAATGTGCGGTGGTCAGGCATTAGATTTAGACGCG
GAAGGCAAACACGTACCTCTGGACGCGCTTGAGCGTATTCATCGTCATAAAACCGGCGCATTGATTCGCGCCGCC
GTTCGCCTTGGTGCATTAAGCGCCGGAGATAAAGGACGTCGTGCTCTGCCGGTACTCGACAAGTATGCAGAGAGC
ATCGGCCTTGCCTTCCAGGTTCAGGATGACATCCTGGATGTGGTGGGAGATACTGCAACGTTGGGAAAACGCCAG
GGTGCCGACCAGCAACTTGGTAAAAGTACCTACCCTGCACTTCTGGGTCTTGAGCAAGCCCGGAAGAAAGCCCGG
GATCTGATCGACGATGCCCGTCAGTCGCTGAAACAACTGGCTGAACAGTCACTCGATACCTCGGCACTGGAAGCG
CTAGCGGACTACATCATCCAGCGTAATAAATAA GAGCTCCAATTCGCCCTATAGTGAGTCGTATTACGCGCGCTCACTGGCCGTCGTTTTACAACGTCGTGACTGGGA
AAACCCTGGCGTTACCCAACTTAATCGCCTTGCAGCACATCCCCCTTTCGCCAGCTGGCGTAATAGCGAAGAGGC
CCGCACCGATCGCCCTTCCCAACAGTTGCGCAGCCTGAATGGCGAATGGAAATTGTAAGCGTTAATATTTTGTTA
AAATTCGCGTTAAATTTTTGTTAAATCAGCTCATTTTTTAACCAATAGGCCGACTGCGATGAGTGGCAGGGCGGG
GCGTAATTTTTTTAAGGCAGTTATTGGTGCCCTTAAACGCCTGGTGCTACGCCTGAATAAGTGATAATAAGCGGA
TGAATGGCAGAAATTCGAAAGCAAATTCGACCCGGTCGTCGGTTCAGGGCAGGGTCGTTAAATAGCCGCTTATGT
CTATTGCTGGTTTACCGGTTTATTGACTACCGGAAGCAGTGTGACCGTGTGCTTCTCAAATGCCTGAGGCCAGTT
TGCTCAGGCTCTCCCCGTGGAGGTAATAATTGACGATATGATCATTTATTCTGCCTCCCAGAGCCTGATAAAAAC
GGTGAATCCGTTAGCGAGGTGCCGCCGGCTTCCATTCAGGTCGAGGTGGCCCGGCTCCATGCACCGCGACGCAAC
GCGGGGAGGCAGACAAGGTATAGGGCGGCGAGGCGGCTACAGCCGATAGTCTGGAACAGCGCACTTACGGGT Origin of replication
TGCTGCGCAACCCAAGTGCTACCGGCGCGGCAGCGTGACCCGTGTCGGCGGCTCCAACGGCTCGCCATCGTCCAG
AAAACACGGCTCATCGGGCATCGGCAGGCGCTGCTGCCCGCGCCGTTCCCATTCCTCCGTTTCGGTCAAGGCTGG
CAGGTCTGGTTCCATGCCCGGAATGCCGGGCTGGCTGGGCGGCTCCTCGCCGGGGCCGGTCGGTAGTTGCTGCTC
GCCCGGATACAGGGTCGGGATGCGGCGCAGGTCGCCATGCCCCAACAGCGATTCGTCCTGGTCGTCGTGATCAAC
CACCACGGCGGCACTGAACACCGACAGGCGCAACTGGTCGCGGGGCTGGCCCCACGCCACGCGGTCATTGACCAC
GTAGGCCGACACGGTGCCGGGGCCGTTGAGCTTCACGACGGAGATCCAGCGCTCGGCCACCAAGTCCTTGACTGC
GTATTGGACCGTCCGCAAAGAACGTCCGATGAGCTTGGAAAGTGTCTTCTGGCTGACCACCACGGCGTTCTGGTG
GCCCATCTGCGCCACGAGGTGATGCAGCAGCATTGCCGCCGTGGGTTTCCTCGCAATAAGCCCGGCCCACGCCTC
ATGCGCTTTGCGTTCCGTTTGCACCCAGTGACCGGGCTTGTTCTTGGCTTGAATGCCGATTTCTCTGGACTGCGT
GGCCATGCTTATCTCCATGCGGTAGGGTGCCGCACGGTTGCGGCACCATGCGCAATCAGCTGCAACTTTTCGGCA
GCGCGACAACAATTATGCGTTGCGTAAAAGTGGCAGTCAATTACAGATTTTCTTTAACCTACGCAATGAGCTATT
GCGGGGGGTGCCGCAATGAGCTGTTGCGTACCCCCCTTTTTAAGTTGTTGATTTTTAAGTCTTTCGCATTTCGC
CCTATATCTAGTTCTTTGGTGCCCAAAGAAGGGCACCCCTGCGGGGTTCCCCACGCCTTCGGCGCGGCTCCCCC
TCCGGCAAAAAGTGGCCCCTCCGGGGCTTGTTGATCGACTGCGCGGCCTTCGGCCTTGCCCAAGGTGGCGCTGCC
CCCTTGGAACCCCGCACTCGCCGCCGTGAGGCTCGGGGGGCAGGCGGGCGGGCTTCGCCTTCGACTGCCCCCAC
TCGCATAGGCTTGGGTCGTTCCAGGCGCGTCAAGGCCAAGCCGCTGCGCGGTCGCTGCGCGAGCCTTGACCCGCC
TTCCACTTGGTGTCCAACCGGCAAGCGAAGCGCGCAGGCCGCAGGCCGGAGGCTTTTCCCCAGAGAAATTAAAA
AAATTGATGGGGCAAGGCCGCAGGCCGCGCAGTTGGAGCCGGTGGGTATGTGGTCGAAGGCTGGGTAGCCGGTGG
GCAATCCCTGTGGTCAAGCTCGTGGGCAGGCGCAGCCTGTCCATCAGCTTGTCCAGCAGGGTTGTCCACGGGCCG
AGCGAAGCGAGCCAGCCGGTGGCCGCTCGCGGCCATCGTCCACATATCCACGGGCTGGCAAGGGAGCGCAGCGAC
CGCGCAGGGCGAAGCCCGGAGAGCAAGCCCGTAGGGCGCCGCAGCCGCCGTAGGCGGTCACGACTTTGCGAAGCA
AAGTCTAGTGAGTATACTCAAGCATTGAGTGGCCCGCCGGAGGCACCGCCTTGCGCTGCCCCGTCGAGCCGGTT
GGACACCAAAAGGGAGGGGCAGGCATGGCGGCATACGCGATCATGCGATGCAAGAAGCTGGCGAAAATGGGCAAC
GTGGCGGCCAGTCTCAAGCACGCCTACCGCGAGCGCGAGACGCCCAACGCTGACGCCAGCAGGACGCCAGAGAAC
GAGCACTGGGCGGCCAGCAGCACCGATGAAGCGATGGGCCGACTGCGCGAGTTGCTGCCAGAGAAGCGGCGCAAG
GACGCTGTGTTGGCGGTCGAGTACGTCATGACGGCCAGCCCGGAATGGTGGAAGTCGGCCAGCCAAGAACAGCAG
GCGGCGTTCTTCGAGAAGGCGCACAAGTGGCTGGCGGACAAGTACGGGCGGATCGCATCGTGACGGCCAGCATC
CACCGTGACGAAACCAGCCCGCACATGACCGCGTTCGTGGTGCCGCTGACGCAGGACGGCAGGCTGTCGGCCAAG
```

FIG. 16D

```
GAGTTCATCGGCAACAAAGCGCAGATGACCCGCGACCAGACCACGTTTGCGGCCGCTGTGGCCGATCTAGGGCTG
CAACGGGGCATCGAGGGCAGCAAGGCACGTCACACGCGCATTCAGGCGTTCTACGAGGCCCTGGAGCGGCCACCA
GTGGGCCACGTCACCATCAGCCCGCAAGCGGTCGAGCCACGCGCCTATGCACCGCAGGGATTGGCCGAAAAGCTG
GGAATCTCAAAGCGCGTTGAGACGCCGGAAGCCGTGGCCGACCGGCTGACAAAAGCGGTTCGGCAGGGGTATGAG
CCTGCCCTACAGGCCGCCGCAGGAGCGCGTGAGATGCGCAAGAAGGCCGATCAAGCCCAAGAGACGGCCCGAG
(SEQ ID NO:4)
```

FIG. 17A pADS plasmid sequence

▶                        *LacI$^Q$*

```
CAATTCGCGCGCGAAGGCGAAGCGGCATGCATTTACGTTGACACCATCGAATGGTGCAAAACCTTTCGCGGTATG
GCATGATAGCGCCCGGAAGAGAGTCAATTCAGGGTGGTGAATGTGAAACCAGTAACGTTATACGATGTCGCAGAG
TATGCCGGTGTCTCTTATCAGACCGTTTCCCGCGTGGTGAACCAGGCCAGCCACGTTTCTGCGAAAACGCGGGAA
AAAGTGGAAGCGGCGATGGCGGAGCTGAATTACATTCCCAACCGCGTGGCACAACAACTGGCGGGCAAACAGTCG
TTGCTGATTGGCGTTGCCACCTCCAGTCTGGCCCTGCACGCGCCGTCGCAAATTGTCGCGGCGATTAAATCTCGC
GCCGATCAACTGGGTGCCAGCGTGGTGGTGTCGATGGTAGAACGAAGCGGCGTCGAAGCCTGTAAAGCGGCGGTG
CACAATCTTCTCGCGCAACGCGTCAGTGGGCTGATCATTAACTATCCGCTGGATGACCAGGATGCCATTGCTGTG
GAAGCTGCCTGCACTAATGTTCCGGCGTTATTTCTTGATGTCTCTGACCAGACACCCATCAACAGTATTATTTTC
TCCCATGAAGACGGTACGCGACTGGGCGTGGAGCATCTGGTCGCATTGGGTCACCAGCAAATCGCGCTGTTAGCG
GGCCCATTAAGTTCTGTCTCGGCGCGTCTGCGTCTGGCTGGCTGGCATAAATATCTCACTCGCAATCAAATTCAG
CCGATAGCGGAACGGGAAGGCGACTGGAGTGCCATGTCCGGTTTTCAACAAACCATGCAAATGCTGAATGAGGGC
ATCGTTCCCACTGCGATGCTGGTTGCCAACGATCAGATGGCGCTGGGCGCAATGCGCGCCATTACCGAGTCCGGG
CTGCGCGTTGGTGCGGATATCTCGGTAGTGGGATACGACGATACCGAAGACAGCTCATGTTATATCCCGCCGTCA
ACCACCATCAAACAGGATTTTCGCCTGCTGGGGCAAACCAGCGTGGACCGCTTGCTGCAACTCTCTCAGGGCCAG
GCGGTGAAGGGCAATCAGCTGTTGCCCGTCTCACTGGTGAAAAGAAAAACCACCCTGGCGCCCAATACGCAAACC
GCCTCTCCCCGCGCGTTGGCCGATTCATTAATGCAGCTGGCACGACAGGTTTCCCGACTGGAAAGCGGGCAGTGA
```

*LacI$^Q$*    ◀                                                          ▶  P$_{TRC}$ Promoter

```
GCGCAACGCAATTAATGTGAGTTAGCGCGAATTGATCTGGTTTGACAGCTTATCAT CGACTGCACGGTGCACCAA
TGCTTCTGGCGTCAGGCAGCCATCGGAAGCTGTGGTATGGCTGTGCAGGTCGTAAATCACTGCATAATTCGTGTC
GCTCAAGGCGCACTCCCGTTCTGGATAATGTTTTTTGCGCCGACATCATAACGGTTCTGGCAAATATTCTGAAAT
GAGCTGTTGACAATT
```

P$_{TRC}$ Promoter                                                ▶    *ADS*

```
AATCATCCGGCTCGTATAATGTGTGGAATTGTGAGCGGATAACAATTTCACACAGGAAACAG ACCATGGCCCTGA
CCGAAGAGAAACCGATCCGCCCGATCGCTAACTTCCCGCCGTCTATCTGGGGTGACCAGTTCCTGATCTACGAAA
AGCAGGTTGAGCAGGGTGTTGAACAGATCGTAAACGACCTGAAGAAAGAAGTTCGTCAGCTGCTGAAAGAAGCTC
TGGACATCCCGATGAAACACGCTAACCTGCTGAAACTGATCGACGAGATCCAGCGTCTGGGTATCCCGTACCACT
TCGAACGCGAAATCGACCACGCACTGCAGTGCATCTACGAAACCTACGGCGACAACTGGAACGGCGACCGTTCTT
CTCTGTGGTTTCGTCTGATGCGTAAACAGGGCTACTACGTTACCTGTGACGTTTTTAACAACTACAAGGACAAGA
ACGGTGCTTTCAAACAGTCTCTGGCTAACGACGTTGAAGGCCTGCTGGAACTGTACGAAGCGACCTCCATGCGTG
TACCGGGTGAAATCATCCTGGAGGACGCGCTGGGTTTCACCCGTTCTCGTCTGTCCATTATGACTAAAGACGCTT
TCTCTACTAACCCGGCTCTGTTCACCGAAATCCAGCGTGCTCTGAAACAGCCGCTGTGGAAACGTCTGCCGCGTA
TCGAAGCAGCACAGTACATTCCGTTTTACCAGCAGCAGGACTCTCACAACAAGACCCTGCTGAAACTGGCTAAGC
TGGAATTCAACCTGCTGCAGTCTCTGCACAAAGAAGAACTGTCTCACGTTTGTAAGTGGTGGAAGGCATTTGACA
TCAAGAAAAACGCGCCGTGCCTGCGTGACCGTATCGTTGAATGTTACTTCTGGGGTCTGGGTTCTGGTTATGAAC
CACAGTACTCCCGTGCACGTGTGTTCTTCACTAAAGCTGTAGCTGTTATCACCCTGATCGATGACACTTACGATG
CTTACGGCACCTACGAAGAACTGAAGATCTTTACTGAAGCTGTAGAACGCTGGTCTATCACTTGCCTGGACACTC
TGCCGGAGTACATGAAACCGATCTACAAACTGTTCATGGATACCTACACCGAAATGGAGGAATTCCTGGCAAAAG
AAGGCCGTACCGACCTGTTCAACTGCGGTAAAGAGTTTGTTAAAGAATTCGTACGTAACCTGATGGTTGAAGCTA
AATGGGCTAACGAAGGCCATATCCCGACTACCGAAGAACATGACCCGGTTGTTATCATCACCGGCGGTGCAAACC
TGCTGACCACCACTTGCTATCTGGGTATGTCCGACATCTTTACCAAGGAATCTGTTGAATGGGCTGTTTCTGCAC
CGCCGCTGTTCCGTTACTCCGGTATTCTGGGTCGTCGTCTGAACGACCTGATGACCCACAAAGCAGAGCAGGAAC
GTAAACACTCTTCCTCCTCTCTGGAATCCTACATGAAGGAATATAACGTTAACGAGGAGTACGCACAGACTCTGA
TCTATAAAGAAGTTGAAGACGTATGGAAAGACATCAACCGTGAATACCTGACTACTAAAAACATCCCGCGCCCGC
TGCTGATGGCAGTAATCTACCTGTGCCAGTTCCTGGAAGTACAGTACGCTGGTAAAGATAACTTCACTCGCATGG
GCGACGAATACAAACACCTGATCAAATCCC
```

FIG. 17B

```
ADS                          ←|                                    rrnB terminator
TGCTGGTTTACCCGATGTCCATCTGATCCCGGGGATCCTCTAGAGTCGACCTGCAGGCATGCAAGCTTGGCTGTT
TTGGCGGATGAGAGAAGATTTTCAGCCTGATACAGATTAAATCAGAACGCAGAAGCGGTCTGATAAAACAGAATT
TGCCTGGCGGCAGTAGCGCGGTGGTCCCACCTGACCCCATGCCGAACTCAGAAGTGAAACGCCGTAGCGCCGATG
GTAGTGTGGGGTCTCCCCATGCGAGAGTAGGGAACTGCCAGGCATCAAATAAAACGAAAGGCTCAGTCGAAAGAC
TGGGCCTTTCGTTTTATCTGTTGTTTGTCGGTGAACGCTCTCCTGAGTAGGACAAATCCGCCGGGAGCGGATTTG
AACGTTGCGAAGCAACGGCCCGGAGGGTGGCGGGCAGGACGCCCGCCATAAACTGCCAGGCATCAAATTAAGCAG
AAGGCCATCCTGACGGATGGCCTTTTTGCGTTTCTACAAACTCTTTTTGTTTATTTTTCTAAATACATTCAAATA
TGTATCCGCTCATGAGACAATAACCCTGATAAATG

|→                    Ampicillin resistance gene
CTTCAATAATATTGAAAAAGGAAGAGTATGAGTATTCAACATTTCCGTGTCGCCCTTATTCCCTTTTTTGCGGCA
TTTTGCCTTCCTGTTTTTGCTCACCCAGAAACGCTGGTGAAAGTAAAAGATGCTGAAGATCAGTTGGGTGCACGA
GTGGGTTACATCGAACTGGATCTCAACAGCGGTAAGATCCTTGAGAGTTTTCGCCCCGAAGAACGTTTTCCAATG
ATGAGCACTTTTAAAGTTCTGCTATGTGGCGCGGTATTATCCCGTGTTGACGCCGGGCAAGAGCAACTCGGTCGC
CGCATACACTATTCTCAGAATGACTTGGTTGAGTACTCACCAGTCACAGAAAAGCATCTTACGGATGGCATGACA
GTAAGAGAATTATGCAGTGCTGCCATAACCATGAGTGATAACACTGCGGCCAACTTACTTCTGACAACGATCGGA
GGACCGAAGGAGCTAACCGCTTTTTTGCACAACATGGGGGATCATGTAACTCGCCTTGATCGTTGGGAACCGGAG
CTGAATGAAGCCATACCAAACGACGAGCGTGACACCACGATGCCTACAGCAATGGCAACAACGTTGCGCAAACTA
TTAACTGGCGAACTACTTACTCTAGCTTCCCGGCAACAATTAATAGACTGGATGGAGGCGGATAAAGTTGCAGGA
CCACTTCTGCGCTCGGCCCTTCCGGCTGGCTGGTTTATTGCTGATAAATCTGGAGCCGGTGAGCGTGGGTCTCGC
GGTATCATTGCAGCACTGGGGCCAGATGGTAAGCCCTCCCGTATCGTAGTTATCTACACGACGGGGAGTCAGGCA
ACTATGGATGAACGAAATAGACAGATCGCTGAGATAGGTGCCTCACTGATTAAGCATTGGTAACTGTCAGACCAA
GTTTACTCATATATACTTTAGATTGATTTAAAACTTCATTTTTAATTTAAAAGGATCTAGGTGAAGATCCTTTTT
GATAATCTCATGACCAAAATCCCTTAACGTGAGTTTTCGTTCCACTGAGCGTCAGACCCCGTAGAAAAGATCAAA
GGATCTTCTTGAGATCCTTTTTTTCTGCGCGTAATCTGCTGCTTGCAAACAAAAAAACCACCGCTACCAGCGGTG
GTTTGTTTGCCGGATCAAGAGCTACCAACTCTTTTTCCGAAGGTAACTGGCTTCAGCAGAGCGCAGATACCAAAT
ACTGTCCTTCTAGTGTAGCCGTAGTTAGGCCACCACTTCAAGAACTCTGTAGCACCGCCTACATACCTCGCTCTG
CTAATCCTGTTACCAGTGGCTGCTGCCAGTGGCGATAAGTCGTGTCTTACCGGGTTGGACTCAAGACGATAGTTA
CCGGATAAGGCGCAGCGGTCGGGCTGAACGGGGGGTTCGTGCACACAGCCCAGCTTGGAGCGAACGACCTACACC
GAACTGAGATACCTACAGCGTGAGCTATGAGAAAGCGCCACGCTTCCCGAAGGGAGAAAGGCGGACAGGTATCCG
GTAAGCGGCAGGGTCGGAACAGGAGAGCGCACGAGGGAGCTTCCAGGGGGAAACGCCTGGTATCTTTATAGTCCT
GTCGGGTTTCGCCACCTCTGACTTGAGCGTCGATTTTTGTGATGCTCGTCAGGGGGCGGAGCCTATGGAAAAAC
GCCAGCAACGCGGCCTTTTTACGGTTCCTGGCCTTTTGCTGGCCTTTTGCTCACATGTTCTTTCCTGCGTTATCC
CCTGATTCTGTGGATAACCGTATTACCGCCTTTGAGTGAGCTGATACCGCTCGCCGCAGCCGAACGACCGAGCGC
AGCGAGTCAGTGAGCGAGGAAGCGGAAGAGCGCCTGATGCGGTATTTTCTCCTTACGCATCTGTGCGGTATTTCA
CACCGCATATGGTGCACTCTCAGTACAATCTGCTCTGATGCCGCATAGTTAAGCCAGTATACACTCCGCTATCGC
TACGTGACTGGGTCATGGCTGCGCCCCGACACCCGCCAACACCCGCTGACGCGCCCTGACGGGCTTGTCTGCTCC
CGGCATCCGCTTACAGACAAGCTGTGACCGTCTCCGGGAGCTGCATGTGTCAGAGGTTTTCACCGTCATCACCGA
AACGCGCGAGGCAGCAGAT (SEQ ID NO:5)
```

FIG. 18A pAtoB plasmid sequence

```
ATCGATGCATAATGTGCCTGTCAAATGGACGAAGCAGGGATTCTGCAAACCCTATGCTACTCCGTCAAGCCGTCA
ATTGT
```
     araC
```
CTGATTCGTTACCAATTATGACAACTTGACGGCTACATCATTCACTTTTTCTTCACAACCGGCACGGAACTCGCT
CGGGCTGGCCCCGGTGCATTTTTTAAATACCCGCGAGAAATAGAGTTGATCGTCAAAACCAACATTGCGACCGAC
GGTGGCGATAGGCATCCGGGTGGTGCTCAAAAGCAGCTTCGCCTGGCTGATACGTTGGTCCTCGCGCCAGCTTAA
GACGCTAATCCCTAACTGCTGGCGGAAAAGATGTGACAGACGCGACGGCGACAAGCAAACATGCTGTGCGACGCT
GGCGATATCAAAATTGCTGTCTGCCAGGTGATCGCTGATGTACTGACAAGCCTCGCGTACCCGATTATCCATCGG
TGGATGGAGCGACTCGTTAATCGCTTCCATGCGCCGCAGTAACAATTGCTCAAGCAGATTTATCGCCAGCAGCTC
CGAATAGCGCCCTTCCCCTTGCCCGGCGTTAATGATTTGCCCAAACAGGTCGCTGAAATGCGGCTGGTGCGCTTC
ATCCGGGCGAAAGAACCCCGTATTGGCAAATATTGACGGCCAGTTAAGCCATTCATGCCAGTAGGCGCGCGGACG
AAAGTAAACCCACTGGTGATACCATTCGCGAGCCTCCGGATGACGACCGTAGTGATGAATCTCTCCTGGCGGGAA
CAGCAAAATATCACCCGGTCGGCAAACAAATTCTCGTCCCTGATTTTTCACCACCCCCTGACCGCGAATGGTGAG
ATTGAGAATATAACCTTTCATTCCCAGCGGTCGGTCGATAAAAAAATCGAGATAACCGTTGGCCTCAATCGGCGT
TAAACCCGCCACCAGATGGGCATTAAACGAGTATCCCGGCAGCAGGGGATCATTT
```
  araC  
```
TGCGCTTCAGCCATACTTTTCATACTCCCGCCATTCAGAGAAGAAACCAATTGTCCATATTGCATCAGACATTGC
CGTCACTGCGTCTTTTACTGGCTCTTCTCGCTAACCAAACCGGTAACCCCGCTTATTAAAAGCATTCTGTAACAA
AGCGGGACCAAAGCCATGACAAAAACGCGTAACAAAAGTGTCTATAATCACGGCAGAAAAGTCCACATTGATTAT
TTGCACGGCGTCACA
```
                                                          ⊢→  P<sub>BAD</sub> Promoter
```
CTTTGCTATGCCATAGCATTTTTATCCATAAGATTAGCGGATCCTACCT GACGCTTTTTATCGCAACTCTCTACT
GT TTC
```
                                                                 ⊢→  atoB
```
TCCATACCCGTTTTTTTGGGCTAGCGAATTCGAGCTCGGTACCCGGGTAGGAGGAATATAAAATGAAAAATTGTG
TCATCGTCAGTGCGGTACGTACTGCTATCGGTAGTTTTAACGGTTCACTCGCTTCCACCAGCGCCATCGACCTGG
GGGCGACAGTAATTAAAGCCGCCATTGAACGTGCAAAAATCGATTCACAACACGTTGATGAAGTGATTATGGGTA
ACGTGTTACAAGCCGGGCTGGGGCAAAATCCGGCGCGTCAGGCACTGTTAAAAAGCGGGCTGGCAGAAACGGTGT
GCGGATTCACGGTCAATAAAGTATGTGGTTCGGGTCTTAAAAGTGTGGCGCTTGCCGCCCAGGCCATTCAGGCAG
GTCAGGCGCAGAGCATTGTGGCGGGGGGTATGGAAAATATGAGTTTAGCCCCCTACTTACTCGATGCAAAAGCAC
GCTCTGGTTATCGTCTTGGAGACGGACAGGTTTATGACGTAATCCTGCGCGATGGCCTGATGTGCGCCACCCATG
GTTATCATATGGGGATTACCGCCGAAAACGTGGCTAAAGAGTACGGAATTACCCGTGAAATGCAGGATGAACTGG
CGCTACATTCACAGCGTAAAGCGGCAGCCGCAATTGAGTCCGGTGCTTTTACAGCCGAAATCGTCCCGGTAAATG
TTGTCACTCGAAAGAAACCTTCGTCTTCAGTCAAGACGAATTCCCGAAAGCGAATTCAACGGCTGAAGCGTTAG
GTGCATTGCGCCCGGCCTTCGATAAAGCAGGAACAGTCACCGCTGGGAACGCGTCTGGTATTAACGACGGTGCTG
CCGCTCTGGTGATTATGGAAGAATCTGCGGCGCTGGCAGCAGGCCTTACCCCCCTGGCTCGCATTAAAAGTTATG
CCAGCGGTGGCGTGCCCCCGCATTGATGGGTATGGGGCCAGTACCTGCCACGCAAAAAGCGTTACAACTGGCGG
GGCTGCAACTGGCGGATATTGATCTCATTGAGGCTAATGAAGCATTTGCTGCACAGTTCCTTGCCGTTGGGAAAA
ACCTGGGCTTTGATTCTGAGAAAGTGAATGTCAACGGCGGGGCCATCGCGCTCGGGCATCCTATCGGTGCCAGTG
GTGCTCGTATTCTGGTCACACTATTACATGCCATGCAGGCACGCGATAAAACGCTGGGGCTGGCAACACTGTGCA
```
       atoB                                
```
TTGGCGGCGGTCAGGGAATTGCGATGGTGATTGAACGGTTGAATTAAGTCGACCTGCAGGCATGCAAGCTT
rrnB terminator
GGCTGTTTTGGCGGATGAGAGAAGATTTTCAGCCTGATACAGATTAAATCAGAACGCAGAAGCGGTCTGATAAAA
CAGAATTTGCCTGGCGGCAGTAGCGCGGTGGTCCCACCTGACCCCATGCCGAACTCAGAAGTGAAACGCCGTAGC
GCCGATGGTAGTGTGGGGTCTCCCCATGCGAGAGTAGGGAACTGCCAGGCATCAAATAAAACGAAAGGCTCAGTC
GAAAGACTGGGC
```

FIG. 18B

CTTTCGTTTTATCTGTTGTTTGTCGGTGAACGCTCTCCTGAGTAGGACAAATCCGCCGGGAGCGGATTTGAACGT
TGCGAAGCAACGGCCCGGAGGGTGGCGGGCAGGACGCCCGCCATAAACTGCCAGGCATCAAATTAAGCAGAAGGC
CATCCTGACGGATGGCCTTTTTGCGTTTCTACAAACTCTTTTGTTTATTTTTCTAAATACATTCAAATATGTATC
CGCTCATGAGACAATAACCCTGATAAATGCTTCAATAATATTGAAAAAGGAAGAGTATGAGTATTCAACATTTCC
GTGTCGCCCTTATTCCCTTTTTTGCGGCATTTTGCCTTCCTGTTTTTGCTCACCCAGAAACGCTGGTGAAAGTAA
AAGATGCTGAAGATCAGTTGGGTGCAGCAAACTATTAACTGGCGAACTACTTACTCTAGCTTCCCGGCAACAATT
AATAGACTGGATGGAGGCGGATAAAGTTGCAGGACCACTTCTGCGCTCGGCCCTTCCGGCTGGCTGGTTTATTGC
TGATAAATCTGGAGCCGGTGAGCGTGGGTCTCGCGGTATCATTGCAGCACTGGGGCCAGATGGTAAGCCCTCCCG
TATCGTAGTTATCTACACGACGGGGAGTCAGGCAACTATGGATGAACGAAATAGACAGATCGCTGAGATAGGTGC
CTCACTGATTAAGCATTGGTAACTGTCAGACCAAGTTTACTCATATATACTTTAGATTGATTTACGCGCCCTGTA
GCGGCGCATTAAGCGCGGCGGGTGTGGTGGTTACGCGCAGCGTGACCGCTACACTTGCCAGCGCCCTAGCGCCCG
CTCCTTTCGCTTTCTTCCCTTCCTTTCTCGCCACGTTCGCCGGCTTTCCCCGTCAAGCTCTAAATCGGGGGCTCC
CTTTAGGGTTCCGATTTAGTGCTTTACGGCACCTCGACCCCAAAAAACTTGATTTGGGTGATGGTTCACGTAGTG
GGCCATCGCCCTGATAGACGGTTTTTCGCCCTTTGACGTTGGAGTCCACGTTCTTTAATAGTGGACTCTTGTTCC
AAACTTGAACAACACTCAACCCTATCTCGGGCTATTCTTTTGATTTATAAGGGATTTTGCCGATTTCGGCCTATT
GGTTAAAAAATGAGCTGATTTAACAAAAATTTAACGCGAATTTTAACAAAATATTAACGTTTACAATTTAAAAGG
ATCTAGGTGAAGATCCTTTTTGATAATCTCATGACCAAAATCCCTTAACGTGAGTTTTCGTTCCACTGAGCGTCA
GACCCCGTAGAAAAGATCAAAGGATCTTCTTGAGATCCTTTTTTTCTGCGCGTAATCTGCTGCTTGCAAACAAAA
AAACCACCGCTACCAGCGGTGGTTTGTTTGCCGGATCAAGAGCTACCAACTCTTTTTCCGAAGGTAACTGGCTTC
AGCAGAGCGCAGATACCAAATACTGTCCTTCTAGTGTAGCCGTAGTTAGGCCACCACTTCAAGAACTCTGTAGCA
CCGCCTACATACCTCGCTCTGCTAATCCTGTTACCAGTGGGGCATTTGAGAAGCACACGGTCACACTGCTTCCGG
TAGTCAATAAACCGGTAAACCAGCAATAGACATAAGCGGCTATTTAACGACCCTGCCCTGAACCGACGACCGGGT
CGAATTTGCTTTCGAATTTCTGCCATTCATCCGCTTATTATCACTTATTCAGGC

<span style="margin-left:60%">Chloramphenicol resistance gene →</span>

GTAGCACCAGGCGTTTAAGGGCACCAATAACTGCCTTAAAAAATTACGCCCCGCCCTGCCACTCATCGCAGTAC
TGTTGTAATTCATTAAGCATTCTGCCGACATGGAAGCCATCACAGACGGCATGATGAACCTGAATCGCCAGCGGC
ATCAGCACCTTGTCGCCTTGCGTATAATATTTGCCCATGGTGAAAACGGGGGCGAAGAAGTTGTCCATATTGGCC
ACGTTTAAATCAAAACTGGTGAAACTCACCCAGGGATTGGCTGAGACGAAAAACATATTCTCAATAAACCCTTTA
GGGAAATAGGCCAGGTTTTCACCGTAACACGCCACATCTTGCGAATATATGTGTAGAAACTGCCGGAAATCGTCG
TGGTATTCACTCCAGAGCGATGAAAACGTTTCAGTTTGCTCATGGAAAACGGTGTAACAAGGGTGAACACTATCC
CATATCACCAGCTCACCGTCTTTCATTGCCATACGGAATTCCGGATGAGCATTCATCAGGCGGGCAAGAATGTGA
ATAAAGGCCGGATAAAACTTGTGCTTATTTTTCTTTACGGTCTTTAAAAAGGCCGTAATATCCAGCTGAACGGTC
TGGTTATAGGTACATTGAGCAACTGACTGAAATGCCTCAAAATGTTCTTTACGATGCCATTGGGATATATCAACG
GTGGTATATCCAGTGATTTTTTTCTCCAT ←

TTTAGCTTCCTTAGCTCCTGAAAATCTCGATAACTCAAAAAATACGCCCGGTAGTGATCTTATTTCATTATGGTG
AAAGTTGGAACCTCTTACGTGCCGATCAACGTCTCATTTTCGCCAAAAGTTGGCCCAGGGCTTCCCGGTATCAAC
AGGGACACCAGGATTTATTTATTCTGCGAAGTGATCTTCCGTCACAGGTATTTATTCGGCGCAAAGTGCGTCGGG
TGATGCTGCCAACTTACTGATTTAGTGTATGATGGTGTTTTTGAGGTGCTCCAGTGGCTTCTGTTTCTATCAGCT
GTCCCTCCTGTTCAGCTACTGACGGGGTGGTGCGTA

<span style="margin-left:45%">pACYC184 origin</span>

ACGGCAAAAGCACCGCCGGACATCAGCGCTAGCGGAGTGTATACTGGCTTACTATGTTGGCACTGATGAGGGTGT
CAGTGAAGTGCTTCATGTGGCAGGAGAAAAAAGGCTGCACCGGTGCGTCAGCAGAATATGTGATACAGGATATAT
TCCGCTTCCTCGCTCACTGACTCGCTACGCTCGGTCGTTCGACTGCGGCGAGCGGAAATGGCTTACGAACGGGGC
GGAGATTTCCTGGAAGATGCCAGGAAGATACTTAACAGGGAAGTGAGAGGGCCGCGGCAAAGCCGTTTTTCCATA
GGCTCCGCCCCCCTGACAAGCATCACGAAATCTGACGCTCAAATCAGTGGTGGCGAAACCCGACAGGACTATAAA
GATACCAGGCGTTTCCCCCTGGCGGCTCCCTCGTGCGCTCTCCTGTTCCTGCCTTTCGGTTTACCGGTGTCATTC
CGCTGTTATGGCCGCGTTTGTCTCATTCCACGCCTGACACTCAGTTCCGGGTAGGCAGTTCGCTCCAAGCTGGAC
TGTATGCACGAACCCCCGTTCAGTCCGACCGCTGCGCCTTATCCGGTAACTATCGTCTTGAGTCCAACCCGGAA
AGACATGCAAAAGCACCACTGGCAGCAGCCACTGGTAATTGATTTAGAGGAGTTAGTCTTGAAGTCATGCGCCGG
TTAAGGCTAAACTGAAAGGACAAGTTTTGGTGACTGCGCTCCTCCAAGCCAGTTACCTCGGTTCAAAGAGTTGGT
AGCTCAGAGAACCTTCGAAAAACCGCCCTGCAAGGCGGTTTTTTCGTTTTCAGAGCAAGAGATTACGCGCAGACC
AAAACGATCTCAAGAAGATCATCTTATTAATCAGATAAAATATTTGCTCATGAGCCCGAAGTGGCGAGCCCGATC
TTCCCCATCGGTGATGTCGGCGATATAGGCGCCAGCAACCGCACCTGTGGCGCCGGTGATGCCGGCCACGATGCG
TCCGGCGTAGAGGATCTGCTCATGTTTGACAGCTTATC (SEQ ID NO:6)

FIG. 19A pHMGS plasmid sequence

```
ATCGATGCATAATGTGCCTGTCAAATGGACGAAGCAGGGATTCTGCAAACCCTATGCTACTCCGTCAAGCCGTCA
ATTGT
```

⊢▶                                        *araC*

```
CTGATTCGTTACCAATTATGACAACTTGACGGCTACATCATTCACTTTTTCTTCACAACCGGCACGGAACTCGCT
CGGGCTGGCCCCGGTGCATTTTTTAAATACCCGCGAGAAATAGAGTTGATCGTCAAAACCAACATTGCGACCGAC
GGTGGCGATAGGCATCCGGGTGGTGCTCAAAAGCAGCTTCGCCTGGCTGATACGTTGGTCCTCGCGCCAGCTTAA
GACGCTAATCCCTAACTGCTGGCGGAAAAGATGTGACAGACGCGACGGCGACAAGCAAACATGCTGTGCGACGCT
GGCGATATCAAAATTGCTGTCTGCCAGGTGATCGCTGATGTACTGACAAGCCTCGCGTACCCGATTATCCATCGG
TGGATGGAGCGACTCGTTAATCGCTTCCATGCGCCGCAGTAACAATTGCTCAAGCAGATTTATCGCCAGCAGCTC
CGAATAGCGCCCTTCCCCTTGCCCGGCGTTAATGATTTGCCCAAACAGGTCGCTGAAATGCGGCTGGTGCGCTTC
ATCCGGGCGAAAGAACCCCGTATTGGCAAATATTGACGGCCAGTTAAGCCATTCATGCCAGTAGGCGCGCGGACG
AAAGTAAACCCACTGGTGATACCATTCGCGAGCCTCCGGATGACGACCGTAGTGATGAATCTCTCCTGGCGGGAA
CAGCAAAATATCACCCGGTCGGCAAACAAATTCTCGTCCTGATTTTTCACCACCCCTGACCGCGAATGGTGAG
ATTGAGAATATAACCTTTCATTCCCAGCGGTCGGTCGATAAAAAAATCGAGATAACCGTTGGCCTCAATCGGCGT
TAAACCCGCCACCAGATGGGCATTAAACGAGTATCCCGGCAGCAGGGGATCATTT
```

*araC* ◀⊣

```
TGCGCTTCAGCCATACTTTTCATACTCCCGCCATTCAGAGAAGAAACCAATTGTCCATATTGCATCAGACATTGC
CGTCACTGCGTCTTTTACTGGCTCTTCTCGCTAACCAAACCGGTAACCCCGCTTATTAAAAGCATTCTGTAACAA
AGCGGGACCAAAGCCATGACAAAAACGCGTAACAAAAGTGTCTATAATCACGGCAGAAAAGTCCACATTGATTAT
TTGCACGGCGTCACA
```

⊢▶ $P_{BAD}$ Promoter

```
CTTTGCTATGCCATAGCATTTTTATCCATAAGATTAGCGGATCCTACCT GACGCTTTTTATCGCAACTCTCTACT
GT TTC
```

⊢▶ *HMGS*

```
TCCATACCCGTTTTTTTGGGCTAGCGAATTCGAGCTCGGTACCCGGGAGGAGGACAGCTAAATGAAACTCTCAAC
TAAACTTTGTTGGTGTGGTATTAAAGGAAGACTTAGGCCGCAAAAGCAACAACAATTACACAATACAAACTTGCA
AATGACTGAACTAAAAAAACAAAAGACCGCTGAACAAAAAACCAGACCTCAAAATGTCGGTATTAAAGGTATCCA
AATTTACATCCCAACTCAATGTGTCAACCAATCTGAGCTAGAGAAATTTGATGGCGTTTCTCAAGGTAAATACAC
AATTGGTCTGGGCCAAACCAACATGTCTTTTGTCAATGACAGAGAAGATATCTACTCGATGTCCCTAACTGTTTT
GTCTAAGTTGATCAAGAGTTACAACATCGACACCAACAAAATTGGTAGATTAGAAGTCGGTACTGAAACTCTGAT
TGACAAGTCCAAGTCTGTCAAGTCTGTCTTGATGCAATTGTTTGGTGAAAACACTGACGTCGAAGGTATTGACAC
GCTTAATGCCTGTTACGGTGGTACCAACGCGTTGTTCAACTCTTTGAACTGGATTGAATCTAACGCATGGGATGG
TAGAGACGCCATTGTAGTTTGCGGTGATATTGCCATCTACGATAAGGGTGCCGCAAGACCAACCGGTGGTGCCGG
TACTGTTGCTATGTGGATCGGTCCTGATGCTCCAATTGTATTTGACTCTGTAAGAGCTTCTTACATGGAACACGC
CTACGATTTTTACAAGCCAGATTTCACCAGCGAATATCCTTACGTCGATGGTCATTTTTCATTAACTTGTTACGT
CAAGGCTCTTGATCAAGTTTACAAGAGTTATTCCAAGAAGGCTATTTCTAAAGGGTTGGTTAGCGATCCCGCTGG
TTCGGATGCTTTGAACGTTTTGAAATATTTCGACTACAACGTTTTCCATGTTCCAACCTGTAAATTGGTCACAAA
ATCATACGGTAGATTACTATATAACGATTTCAGAGCCAATCCTCAATTGTTCCCAGAAGTTGACGCCGAATTAGC
TACTCGCGATTATGACGAATCTTTAACCGATAAGAACATTGAAAAAACTTTTGTTAATGTTGCTAAGCCATTCCA
CAAAGAGAGTTGCCCAATCTTTGATTGTTCCAACAAACACAGGTAACATGTACACCGCATCTGTTTATGCCGC
CTTTGCATCTCTATTAAACTATGTTGGATCTGACGACTTACAAGGCAAGCGTGTTGGTTTATTTTCTTACGGTTC
CGGTTTAGCTGCATCTCTATATTCTTGCAAAATTGTTGGTGACGTCCAACATATTATCAAGGAATTAGATATTAC
TAACAAATTAGCCAAGAGAATCACCGAAACTCCAAAGGATTACGAAGCTGCCATCGAATTGAGAGAAAATGCCCA
TTTGAAGAAGAACTTCAAACCTCAAGGTTCCATTGAGCATTTGCAAAGTGGTGTTTACTACTTGACCAACATCGA
TGACAAATTTAGAAGATCTT
```

*HMGS* ◀⊣                                                             *rrnB* terminator

```
ACGATGTTAAAAAATAAGTCGACCTGCAGGCATGCAAGCTTGGCTGTTTTGGCGGATGAGAGAAGATTTTCAGCC
TGATACAGATTAAATCGAACGCAGAAGCGGTCTGATAAAACAGAATTTGCCTGGCGGCAGTAGCGCGGTGGTCC
CACCTGACCCCATGCCGAACTCAGAAGTGAAACGCCGTAGCGCCGATGGTAGTGTGGGGTCTCCCCATGCGAGAG
TAGGGA
```

FIG. 19B

```
ACTGCCAGGCATCAAATAAAACGAAAGGCTCAGTCGAAAGACTGGGCCTTTCGTTTTATCTGTTGTTTGTCGGTG
AACGCTCTCCTGAGTAGGACAAATCCGCCGGGAGCGGATTTGAACGTTGCGAAGCAACGGCCCGGAGGGTGGCGG
GCAGGACGCCCGCCATAAACTGCCAGGCATCAAATTAAGCAGAAGGCCATCCTGACGGATGGCCTTTTTGCGTTT
CTACAAACTCTTTTGTTTATTTTTCTAAATACATTCAAATATGTATCCGCTCATGAGACAATAACCCTGATAAAT
GCTTCAATAATATTGAAAAAGGAAGAGTATGAGTATTCAACATTTCCGTGTCGCCCTTATTCCCTTTTTTGCGGC
ATTTTGCCTTCCTGTTTTTGCTCACCCAGAAACGCTGGTGAAAGTAAAAGATGCTGAAGATCAGTTGGGTGCAGC
AAACTATTAACTGGCGAACTACTTACTCTAGCTTCCCGGCAACAATTAATAGACTGGATGGAGGCGGATAAAGTT
GCAGGACCACTTCTGCGCTCGGCCCTTCCGGCTGGCTGGTTTATTGCTGATAAATCTGGAGCCGGTGAGCGTGGG
TCTCGCGGTATCATTGCAGCACTGGGGCCAGATGGTAAGCCCTCCCGTATCGTAGTTATCTACACGACGGGGAGT
CAGGCAACTATGGATGAACGAAATAGACAGATCGCTGAGATAGGTGCCTCACTGATTAAGCATTGGTAACTGTCA
GACCAAGTTTACTCATATATACTTTAGATTGATTTACGCGCCCTGTAGCGGCGCATTAAGCGCGGCGGGTGTGGT
GGTTACGCGCAGCGTGACCGCTACACTTGCCAGCGCCCTAGCGCCCGCTCCTTTCGCTTTCTTCCCTTCCTTTCT
CGCCACGTTCGCCGGCTTTCCCCGTCAAGCTCTAAATCGGGGGCTCCCTTTAGGGTTCCGATTTAGTGCTTTACG
GCACCTCGACCCCAAAAAACTTGATTTGGGTGATGGTTCACGTAGTGGGCCATCGCCCTGATAGACGGTTTTTCG
CCCTTTGACGTTGGAGTCCACGTTCTTTAATAGTGGACTCTTGTTCCAAACTTGAACAACACTCAACCCTATCTC
GGGCTATTCTTTTGATTTATAAGGGATTTTGCCGATTTCGGCCTATTGGTTAAAAAATGAGCTGATTTAACAAAA
ATTTAACGCGAATTTTAACAAAATATTAACGTTTACAATTTAAAAGGATCTAGGTGAAGATCCTTTTTGATAATC
TCATGACCAAATCCCTTAACGTGAGTTTTCGTTCCACTGAGCGTCAGACCCCGTAGAAAAGATCAAAGGATCTT
CTTGAGATCCTTTTTTTCTGCGCGTAATCTGCTGCTTGCAAACAAAAAAACCACCGCTACCAGCGGTGGTTTGTT
TGCCGGATCAAGAGCTACCAACTCTTTTTCCGAAGGTAACTGGCTTCAGCAGAGCGCAGATACCAAATACTGTCC
TTCTAGTGTAGCCGTAGTTAGGCCACCACTTCAAGAACTCTGTAGCACCGCCTACATACCTCGCTCTGCTAATCC
TGTTACCAGTGGGGCATTTGAGAAGCACACGGTCACACTGCTTCCGGTAGTCAATAAACCGGTAAACCAGCAATA
GACATAAGCGGCTATTTAACGACCCTGCCCTGAACCGACGACCGGGTCGAATTTGCTTTCGAATTTCTGCCATTC
ATCCGCTTATTATCACTTATTCAGGC
```

Chloramphenicol resistance gene →

```
GTAGCACCAGGCGTTTAAGGGCACCAATAACTGCCTTAAAAAAATTACGCCCCGCCCTGCCACTCATCGCAGTAC
TGTTGTAATTCATTAAGCATTCTGCCGACATGGAAGCCATCACAGACGGCATGATGAACCTGAATCGCCAGCGGC
ATCAGCACCTTGTCGCCTTGCGTATAATATTTGCCCATGGTGAAAACGGGGGCGAAGAAGTTGTCCATATTGGCC
ACGTTTAAATCAAAACTGGTGAAACTCACCCAGGGATTGGCTGAGACGAAAAACATATTCTCAATAAACCCTTTA
GGGAAATAGGCCAGGTTTTCACCGTAACACGCCACATCTTGCGAATATATGTGTAGAAACTGCCGGAAATCGTCG
TGGTATTCACTCCAGAGCGATGAAAACGTTTCAGTTTGCTCATGGAAAACGGTGTAACAAGGGTGAACACTATCC
CATATCACCAGCTCACCGTCTTTCATTGCCATACGGAATTCCGGATGAGCATTCATCAGGCGGGCAAGAATGTGA
ATAAAGGCCGGATAAAACTTGTGCTTATTTTTCTTTACGGTCTTTAAAAAGGCCGTAATATCCAGCTGAACGGTC
TGGTTATAGGTACATTGAGCAACTGACTGAAATGCCTCAAAATGTTCTTTACGATGCCATTGGGATATATCAACG
GTGGTATATCCAGTGATTTTTTTCTCCAT
```
←

```
TTTAGCTTCCTTAGCTCCTGAAAATCTCGATAACTCAAAAAATACGCCCGGTAGTGATCTTATTTCATTATGGTG
AAAGTTGGAACCTCTTACGTGCCGATCAACGTCTCATTTTCGCCAAAAGTTGGCCCAGGGCTTCCCGGTATCAAC
AGGGACACCAGGATTTATTTATTCTGCGAAGTGATCTTCCGTCACAGGTATTTATTCGGCGCAAAGTGCGTCGGG
TGATGCTGCCAACTTACTGATTTAGTGTATGATGGTGTTTTTGAGGTGCTCCAGTGGCTTCTGTTTCTATCAGCT
GTCCCTCCTGTTCAGCTACTGACGGGGTGGTGCGTA
``` pACYC184 origin

```
ACGGCAAAAGCACCGCCGGACATCAGCGCTAGCGGAGTGTATACTGGCTTACTATGTTGGCACTGATGAGGGTGT
CAGTGAAGTGCTTCATGTGGCAGGAGAAAAAAGGCTGCACCGGTGCGTCAGCAGAATATGTGATACAGGATATAT
TCCGCTTCCTCGCTCACTGACTCGCTACGCTCGGTCGTTCGACTGCGGCGAGCGGAAATGGCTTACGAACGGGGC
GGAGATTTCCTGGAAGATGCCAGGAAGATACTTAACAGGGAAGTGAGAGGGCCGCGGCAAAGCCGTTTTTCCATA
GGCTCCGCCCCCCTGACAAGCATCACGAAATCTGACGCTCAAATCAGTGGTGGCGAAACCCGACAGGACTATAA
AGATACCAGGCGTTTCCCCCTGGCGGCTCCCTCGTGCGCTCTCCTGTTCCTGCCTTTCGGTTTACCGGTGTCATTC
CGCTGTTATGGCCGCGTTTGTCTCATTCCACGCCTGACACTCAGTTCCGGGTAGGCAGTTCGCTCCAAGCTGGAC
TGTATGCACGAACCCCCCGTTCAGTCCGACCGCTGCGCCTTATCCGGTAACTATCGTCTTGAGTCCAACCCGGAA
AGACATGCAAAAGCACCACTGGCAGCAGCCACTGGTAATTGATTTAGAGGAGTTAGTCTTGAAGTCATGCGCCGG
TTAAGGCTAAACTGAAAGGACAAGTTTTGGTGACTGCGCTCCTCCAAGCCAGTTACCTCGGTTCAAAGAGTTGGT
AGCTCAGAGAACCTTCGAAAAACCGCCCTGCAAGGCGGTTTTTTCGTTTTCAGAGCAAGAGATTACGCGCAGACC
AAAACGATCTCAAGAAGATCATCTTATTAATCAGATAAAATATTTGCTCATGAGCCCGAAGTGGCGAGCCCGATC
TTCCCCATCGGTGATGTCGGCGATATAGGCGCCAGCAACCGCACCTGTGGCGCCGGTGATGCCGGCCACGATGCG
TCCGGCGTAGAGGATCTGCTCATGTTTGACAGCTTATC (SEQ ID NO:7)
```

FIG. 20A pHMGR plasmid sequence

ATCGATGCATAATGTGCCTGTCAAATGGACGAAGCAGGGATTCTGCAAACCCTATGCTACTCCGTCAAGCCGTCA
ATTGT

├▶                                  araC

CTGATTCGTTACCAATTATGACAACTTGACGGCTACATCATTCACTTTTTCTTCACAACCGGCACGGAACTCGCT
CGGGCTGGCCCCGGTGCATTTTTAAATACCCGCGAGAAATAGAGTTGATCGTCAAAACCAACATTGCGACCGAC
GGTGGCGATAGGCATCCGGGTGGTGCTCAAAAGCAGCTTCGCCTGGCTGATACGTTGGTCCTCGCGCCAGCTTAA
GACGCTAATCCCTAACTGCTGGCGGAAAAGATGTGACAGACGCGACGGCGACAAGCAAACATGCTGTGCGACGCT
GGCGATATCAAAATTGCTGTCTGCCAGGTGATCGCTGATGTACTGACAAGCCTCGCGTACCCGATTATCCATCGG
TGGATGGAGCGACTCGTTAATCGCTTCCATGCGCCGCAGTAACAATTGCTCAAGCAGATTTATCGCCAGCAGCTC
CGAATAGCGCCCTTCCCCTTGCCCGGCGTTAATGATTTGCCCAAACAGGTCGCTGAAATGCGGCTGGTGCGCTTC
ATCCGGGCGAAAGAACCCCGTATTGGCAAATATTGACGGCCAGTTAAGCCATTCATGCCAGTAGGCGCGCGGACG
AAAGTAAACCCACTGGTGATACCATTCGCGAGCCTCCGGATGACGACCGTAGTGATGAATCTCTCCTGGCGGGAA
CAGCAAAATATCACCCGGTCGGCAAACAAATTCTCGTCCCTGATTTTTCACCACCCCCTGACCGCGAATGGTGAG
ATTGAGAATATAACCTTTCATTCCCAGCGGTCGGTCGATAAAAAAATCGAGATAACCGTTGGCCTCAATCGGCGT
TAAACCCGCCACCAGATGGGCATTAAACGAGTATCCCGGCAGCAGGGGATCATTT araC   ◀┤

TGCGCTTCAGCCATACTTTTCATACTCCCGCCATTCAGAGAAGAAACCAATTGTCCATATTGCATCAGACATTGC
CGTCACTGCGTCTTTTACTGGCTCTTCTCGCTAACCAAACCGGTAACCCGCTTATTAAAAGCATTCTGTAACAA
AGCGGGACCAAAGCCATGACAAAAACGCGTAACAAAAGTGTCTATAATCACGGCAGAAAAGTCCACATTGATTAT
TTGCACGGCGTCACA

├▶  $P_{BAD}$ Promoter

CTTTGCTATGCCATAGCATTTTTATCCATAAGATTAGCGGATCCTACCT|GACGCTTTTTATCGCAACTCTCTACT|
|GT|TTC

├▶   HMGR

TCCATACCCGTTTTTTTGGGCTAGCGAATTCGAGCTCGGTACCCGGGAGGAGGATTACACTATGGTTTTAACCAA
TAAAACAGTCATTTCTGGATCGAAAGTCAAAAGTTTATCATCTGCGCAATCGAGCTCATCAGGACCTTCATCATC
TAGTGAGGAAGATGATTCCCGCGATATTGAAAGCTTGGATAAGAAAATACGTCCTTTAGAAGAATTAGAAGCATT
ATTAAGTAGTGGAAATACAAAACAATTGAAGAACAAAGAGGTCGCTGCCTTGGTTATTCACGGTAAGTTACCTTT
GTACGCTTTGGAGAAAAAATTAGGTGATACTACGAGAGCGGTTGCGGTACGTAGGAAGGCTCTTTCAATTTTGGC
AGAAGCTCCTGTATTAGCATCTGATCGTTTACCATATAAAAATTATGACTACGACCGCGTATTTGGCGCTTGTTG
TGAAAATGTTATAGGTTACATGCCTTTGCCCGTTGGTGTTATAGGCCCCTTGGTTATCGATGGTACATCTTATCA
TATACCAATGGCAACTACAGAGGGTTGTTTGGTAGCTTCTGCCATGCGTGGCTGTAAGGCAATCAATGCTGGCGG
TGGTGCAACAACTGTTTTAACTAAGGATGGTATGACAAGAGGCCCAGTAGTCCGTTTCCCAACTTTGAAAAGATC
TGGTGCCTGTAAGATATGGTTAGACTCAGAAGAGGGACAAAACGCAATTAAAAAAGCTTTTAACTCTACATCAAG
ATTTGCACGTCTGCAACATATTCAAACTTGTCTAGCAGGAGATTTACTCTTCATGAGATTTAGAACAACTACTGG
TGACGCAATGGGTATGAATATGATTTCTAAAGGTGTCGAATACTCATTAAAGCAAATGGTAGAAGAGTATGGCTG
GGAAGATATGGAGGTTGTCTCCGTTTCTGGTAACTACTGTACCGACAAAAAACCAGCTGCCATCAACTGGATCGA
AGGTCGTGGTAAGAGTGTCGTCGCAGAAGCTACTATTCCTGGTGATGTTGTCAGAAAAGTGTTAAAAAGTGATGT
TTCCGCATTGGTTGAGTTGAACATTGCTAAGAATTTGGTTGGATCTGCAATGGCTGGGTCTGTTGGTGGATTTAA
CGCACATGCAGCTAATTTAGTGACAGCTGTTTTCTTGGCATTAGGACAAGATCCTGCACAAAATGTTGAAAGTTC
CAACTGTATAACATTGATGAAAGAAGTGGACGGTGATTTGAGAATTTCCGTATCCATGCCATCCATCGAAGTAGG
TACCATCGGTGGTGGTACTGTTCTAGAACCACAAGGTGCCATGTTGGACTTATTAGGTGTAAGAGGCCCGCATGC
TACCGCTCCTGGTACCAACGCACGTCAATTAGCAAGAATAGTTGCCTGTGCCGTCTTGGCAGGTGAATTATCCTT
ATGTGCTGCCCTAGCAGCCGGCCATTTGGTTCAAAGTCATATGACCCACAACAGGAAACCTGCTGAACCAACAAA
ACCTAACAATTTGGACGCCA

HMGR                                          ◀┤     rrnB terminator

CTGATATAAATCGTTTGAAAGATGGGTCCGTCACCTGCATTAAATCCTAAGTCGACCTGCAGGCATGCAAGCTTG
GCTGTTTTGGCGGATGAGAGAAGATTTTCAGCCTGATACAGATTAAATCAGAACGCAGAAGCGGTCTGATAAAAC
AGAA

FIG. 20B

TTTGCCTGGCGGCAGTAGCGCGGTGGTCCCACCTGACCCCATGCCGAACTCAGAAGTGAAACGCCGTAGCGCCGA
TGGTAGTGTGGGGTCTCCCCATGCGAGAGTAGGGAACTGCCAGGCATCAAATAAAACGAAAGGCTCAGTCGAAAG
ACTGGGCCTTTCGTTTTATCTGTTGTTTGTCGGTGAACGCTCTCCTGAGTAGGACAAATCCGCCGGGAGCGGATT
TGAACGTTGCGAAGCAACGGCCCGGAGGGTGGCGGGCAGGACGCCCGCCATAAACTGCCAGGCATCAAATTAAGC
AGAAGGCCATCCTGACGGATGGCCTTTTTGCGTTTCTACAAACTCTTTTGTTTATTTTTCTAAATACATTCAAAT
ATGTATCCGCTCATGAGACAATAACCCTGATAAATGCTTCAATAATATTGAAAAAGGAAGAGTATGAGTATTCAA
CATTTCCGTGTCGCCCTTATTCCCTTTTTTGCGGCATTTTGCCTTCCTGTTTTTGCTCACCCAGAAACGCTGGTG
AAAGTAAAAGATGCTGAAGATCAGTTGGGTGCAGCAAACTATTAACTGGCGAACTACTTACTCTAGCTTCCCGGC
AACAATTAATAGACTGGATGGAGGCGGATAAAGTTGCAGGACCACTTCTGCGCTCGGCCCTTCCGGCTGGCTGGT
TTATTGCTGATAAATCTGGAGCCGGTGAGCGTGGGTCTCGCGGTATCATTGCAGCACTGGGGCCAGATGGTAAGC
CCTCCCGTATCGTAGTTATCTACACGACGGGGAGTCAGGCAACTATGGATGAACGAAATAGACAGATCGCTGAGA
TAGGTGCCTCACTGATTAAGCATTGGTAACTGTCAGACCAAGTTTACTCATATATACTTTAGATTGATTTACGCG
CCCTGTAGCGGCGCATTAAGCGCGGCGGGTGTGGTGGTTACGCGCAGCGTGACCGCTACACTTGCCAGCGCCCTA
GCGCCCGCTCCTTTCGCTTTCTTCCCTTCCTTTCTCGCCACGTTCGCCGGCTTTCCCCGTCAAGCTCTAAATCGG
GGGCTCCCTTTAGGGTTCCGATTTAGTGCTTTACGGCACCTCGACCCCAAAAAACTTGATTTGGGTGATGGTTCA
CGTAGTGGGCCATCGCCCTGATAGACGGTTTTTCGCCCTTTGACGTTGGAGTCCACGTTCTTTAATAGTGGACTC
TTGTTCCAAACTTGAACAACACTCAACCCTATCTCGGGCTATTCTTTTGATTTATAAGGGATTTTGCCGATTTCG
GCCTATTGGTTAAAAAATGAGCTGATTTAACAAAAATTTAACGCGAATTTTAACAAAATATTAACGTTTACAATT
TAAAAGGATCTAGGTGAAGATCCTTTTTGATAATCTCATGACCAAAATCCCTTAACGTGAGTTTTCGTTCCACTG
AGCGTCAGACCCCGTAGAAAAGATCAAAGGATCTTCTTGAGATCCTTTTTTTCTGCGCGTAATCTGCTGCTTGCA
AACAAAAAAACCACCGCTACCAGCGGTGGTTTGTTTGCCGGATCAAGAGCTACCAACTCTTTTTCCGAAGGTAAC
TGGCTTCAGCAGAGCGCAGATACCAAATACTGTCCTTCTAGTGTAGCCGTAGTTAGGCCACCACTTCAAGAACTC
TGTAGCACCGCCTACATACCTCGCTCTGCTAATCCTGTTACCAGTGGGGCATTTGAGAAGCACACGGTCACACTG
CTTCCGGTAGTCAATAAACCGGTAAACCAGCAATAGACATAAGCGGCTATTTAACGACCCTGCCCTGAACCGACG
ACCGGGTCGAATTTGCTTTCGAATTTCTGCCATTCATCCGCTTATTATCACTTATTCAGGC

Chloramphenicol resistance gene
→

GTAGCACCAGGCGTTTAAGGGCACCAATAACTGCCTTAAAAAAATTACGCCCCGCCCTGCCACTCATCGCAGTAC
TGTTGTAATTCATTAAGCATTCTGCCGACATGGAAGCCATCACAGACGGCATGATGAACCTGAATCGCCAGCGGC
ATCAGCACCTTGTCGCCTTGCGTATAATATTTGCCCATGGTGAAAACGGGGGCGAAGAAGTTGTCCATATTGGCC
ACGTTTAAATCAAAACTGGTGAAACTCACCCAGGGATTGGCTGAGACGAAAAACATATTCTCAATAAACCCTTTA
GGGAAATAGGCCAGGTTTTCACCGTAACACGCCACATCTTGCGAATATATGTGTAGAAACTGCCGGAAATCGTCG
TGGTATTCACTCCAGAGCGATGAAAACGTTTCAGTTTGCTCATGGAAAACGGTGTAACAAGGGTGAACACTATCC
CATATCACCAGCTCACCGTCTTTCATTGCCATACGGAATTCCGGATGAGCATTCATCAGGCGGGCAAGAATGTGA
ATAAAGGCCGGATAAAACTTGTGCTTATTTTTCTTTACGGTCTTTAAAAAGGCCGTAATATCCAGCTGAACGGTC
TGGTTATAGGTACATTGAGCAACTGACTGAAATGCCTCAAAATGTTCTTTACGATGCCATTGGGATATATCAACG
GTGGTATATCCAGTGATTTTTTTCTCCAT
←

TTTAGCTTCCTTAGCTCCTGAAAATCTCGATAACTCAAAAAATACGCCCGGTAGTGATCTTATTTCATTATGGTG
AAAGTTGGAACCTCTTACGTGCCGATCAACGTCTCATTTTCGCCAAAAGTTGGCCCAGGGCTTCCCGGTATCAAC
AGGGACACCAGGATTTATTTATTCTGCGAAGTGATCTTCCGTCACAGGTATTTATTCGGCGCAAAGTGCGTCGGG
TGATGCTGCCAACTTACTGATTTAGTGTATGATGGTGTTTTTGAGGTGCTCCAGTGGCTTCTGTTTCTATCAGCT
GTCCCTCCTGTTCAGCTACTGACGGGGTGGTGCGTA pACYC184 origin ACGGCAAAAGCACCGCCGGACATCAGCGCTAGCGGAGTGTATACTGGCTTACTATGTTGGCACTGATGAGGGTGT
CAGTGAAGTGCTTCATGTGGCAGGAGAAAAAAGGCTGCACCGGTGCGTCAGCAGAATATGTGATACAGGATATAT
TCCGCTTCCTCGCTCACTGACTCGCTACGCTCGGTCGTTCGACTGCGGCGAGCGGAAATGGCTTACGAACGGGGC
GGAGATTTCCTGGAAGATGCCAGGAAGATACTTAACAGGGAAGTGAGAGGGCCGCGGCAAAGCCGTTTTTCCATA
GGCTCCGCCCCCCTGACAAGCATCACGAAATCTGACGCTCAAATCAGTGGTGGCGAAACCCGACAGGACTATAAA
GATACCAGGCGTTTCCCCCTGGCGGCTCCCTCGTGCGCTCTCCTGTTCCTGCCTTTCGGTTTACCGGTGTCATTC
CGCTGTTATGGCCGCGTTTGTCTCATTCCACGCCTGACACTCAGTTCCGGGTAGGCAGTTCGCTCCAAGCTGGAC
TGTATGCACGAACCCCCCGTTCAGTCCGACCGCTGCGCCTTATCCGGTAACTATCGTCTTGAGTCCAACCCGGAA
AGACATGCAAAAGCACCACTGGCAGCAGCCACTGGTAATTGATTTAGAGGAGTTAGTCTTGAAGTCATGCGCCGG
TTAAGGCTAAACTGAAAGGACAAGTTTTGGTGACTGCGCTCCTCCAAGCCAGTTACCTCGGTTCAAAGAGTTGGT
AGCTCAGAGAACCTTCGAAAAACCGCCCTGCAAGGCGGTTTTTTCGTTTTCAGAGCAAGAGATTACGCGCAGACC

FIG. 20C

AAAACGATCTCAAGAAGATCATCTTATTAATCAGATAAAATATTTGCTCATGAGCCCGAAGTGGCGAGCCCGATC
TTCCCCATCGGTGATGTCGGCGATATAGGCGCCAGCAACCGCACCTGTGGCGCCGGTGATGCCGGCCACGATGCG
TCCGGCGTAGAGGATCTGCTCATGTTTGACAGCTTATC (SEQ ID NO:8)

FIG. 21A pBAD18HMGR plasmid sequence

ATCGATGCATAATGTGCCTGTCAAATGGACGAAGCAGGGATTCTGCAAACCCTATGCTACTCCGTCAAGCCGTCAAT
TGT araC CTGATTCGTTACCAATTATGACAACTTGACGGCTACATCATTCACTTTTTCTTCACAACCGGCACGGAACTCGCTCG
GGCTGGCCCCGGTGCATTTTTTAAATACCCGCGAGAAATAGAGTTGATCGTCAAAACCAACATTGCGACCGACGGTG
GCGATAGGCATCCGGGTGGTGCTCAAAAGCAGCTTCGCCTGGCTGATACGTTGGTCCTCGCGCCAGCTTAAGACGCT
AATCCCTAACTGCTGGCGGAAAAGATGTGACAGACGCGACGGCGACAAGCAAACATGCTGTGCGACGCTGGCGATAT
CAAAATTGCTGTCTGCCAGGTGATCGCTGATGTACTGACAAGCCTCGCGTACCCGATTATCCATCGGTGGATGGAGC
GACTCGTTAATCGCTTCCATGCGCCGCAGTAACAATTGCTCAAGCAGATTTATCGCCAGCAGCTCCGAATAGCGCCC
TTCCCCTTGCCCGGCGTTAATGATTTGCCCAAACAGGTCGCTGAAATGCGGCTGGTGCGCTTCATCCGGGCGAAAGA
ACCCCGTATTGGCAAATATTGACGGCCAGTTAAGCCATTCATGCCAGTAGGCGCGCGGACGAAAGTAAACCCACTGG
TGATACCATTCGCGAGCCTCCGGATGACGACCGTAGTGATGAATCTCTCCTGGCGGGAACAGCAAAATATCACCCGG
TCGGCAAACAAATTCTCGTCCCTGATTTTTCACCACCCCCTGACCGCGAATGGTGAGATTGAGAATATAACCTTTCA
TTCCCAGCGGTCGGTCGATAAAAAAATCGAGATAACCGTTGGCCTCAATCGGCGTTAAACCCGCCACCAGATGGGCA
TTAAACGAGTATCCCGGCAGCAGGGGATCATTT araC TGCGCTTCAGCCATACTTTTCATACTCCCGCCATTCAGAGAAGAAACCAATTGTCCATATTGCATCAGACATTGCCG
TCACTGCGTCTTTTACTGGCTCTTCTCGCTAACCAAACCGGTAACCCCGCTTATTAAAAGCATTCTGTAACAAAGCG
GGACCAAAGCCATGACAAAAACGCGTAACAAAAGTGTCTATAATCACGGCAGAAAAGTCCACATTGATTATTTGCAC
GGCGTCACA P_BAD Promoter CTTTGCTATGCCATAGCATTTTTATCCATAAGATTAGCGGATCCTACCT GACGCTTTTTATCGCAACTCTCTACTGT
TTC truncated HMGR TCCATACCCGTTTTTTTGGGCTAGCGAATTCGAGCTCGGTACCCGGGAGGAGGATTACACTATGGTTTTAACCAATA
AAACAGTCATTTCTGGATCGAAAGTCAAAAGTTTATCATCTGCGCAATCGAGCTCATCAGGACCTTCATCATCTAGT
GAGGAAGATGATTCCCGCGATATTGAAAGCTTGGATAAGAAAATACGTCCTTTAGAAGAATTAGAAGCATTATTAAG
TAGTGGAAATACAAAACAATTGAAGAACAAAGAGGTCGCTGCCTTGGTTATTCACGGTAAGTTACCTTTGTACGCTT
TGGAGAAAAAATTAGGTGATACTACGAGAGCGGTTGCGGTACGTAGGAAGGCTCTTTCAATTTTGGCAGAAGCTCCT
GTATTAGCATCTGATCGTTTACCATATAAAAATTATGACTACGACCGCGTATTTGGCGCTTGTTGTGAAAATGTTAT
AGGTTACATGCCTTTGCCCGTTGGTGTTATAGGCCCCTTGGTTATCGATGGTACATCTTATCATATACCAATGGCAA
CTACAGAGGGTTGTTTGGTAGCTTCTGCCATGCGTGGCTGTAAGGCAATCAATGCTGGCGGTGGTGCAACAACTGTT
TTAACTAAGGATGGTATGACAAGAGGCCCAGTAGTCCGTTTCCCAACTTTGAAAAGATCTGGTGCCTGTAAGATATG
GTTAGACTCAGAAGAGGGACAAAACGCAATTAAAAAAGCTTTTAACTCTACATCAAGATTTGCACGTCTGCAACATA
TTCAAACTTGTCTAGCAGGAGATTTACTCTTCATGAGATTTAGAACAACTACTGGTGACGCAATGGGTATGAATATG
ATTTCTAAAGGTGTCGAATACTCATTAAAGCAAATGGTAGAAGAGTATGGCTGGGAAGATATGGAGGTTGTCTCCGT
TTCTGGTAACTACTGTACCGACAAAAAACCAGCTGCCATCAACTGGATCGAAGGTCGTGGTAAGAGTGTCGTCGCAG
AAGCTACTATTCCTGGTGATGTTGTCAGAAAAGTGTTAAAAAGTGATGTTTCCGCATTGGTTGAGTTGAACATTGCT
AAGAATTTGGTTGGATCTGCAATGGCTGGGTCTGTTGGTGGATTTAACGCACATGCAGCTAATTTAGTGACAGCTGT
TTTCTTGGCATTAGGACAAGATCCTGCACAAAATGTTGAAAGTTCCAACTGTATAACATTGATGAAAGAAGTGGACG
GTGATTTGAGAATTTCCGTATCCATGCCATCCATCGAAGTAGGTACCATCGGTGGTGGTACTGTTCTAGAACCACAA
GGTGCCATGTTGGACTTATTAGGTGTAAGAGGCCCGCATGCTACCGCTCCTGGTACCAACGCACGTCAATTAGCAAG
AATAGTTGCCTGTGCCGTCTTGGCAGGTGAATTATCCTTATGTGCTGCCCTAGCAGCCGGCCATTTGGTTCAAAGTC
ATATGACCCACAACAGGAAACCTGCTGAACCAACAAAACCTAACAATTTGGACGCCA

FIG. 21B

```
              truncated HMGR                              rrnB terminator
CTGATATAAATCGTTTGAAAGATGGGTCCGTCACCTGCATTAAATCCTAAGTCGACCTGCAGGCATGCAAGCTTGGC
TGTTTTGGCGGATGAGAGAAGATTTTCAGCCTGATACAGATTAAATCAGAACGCAGAAGCGGTCTGATAAAACAGAA
TTTGCCTGGCGGCAGTAGCGCGGTGGTCCCACCTGACCCCATGCCGAACTCAGAAGTGAAACGCCGTAGCGCCGATG
GTAGTGTGGGGTCTCCCCATGCGAGAGTAGGGAACTGCCAGGCATCAAATAAAACGAAAGGCTCAGTCGAAAGACTG
GGCCTTTCGTTTTATCTGTTGTTTGTCGGTGAACGCTCTCCTGAGTAGGACAAATCCGCCGGGAGCGGATTTGAACG
TTGCGAAGCAACGGCCCGGAGGGTGGCGGGCAGGACGCCCGCCATAAACTGCCAGGCATCAAATTAAGCAGAAGGCC
ATCCTGACGGATGGCCTT rrnB
TTTGCGTTTCTACAAACTCTTTTGTTTATTTTTCTAAATACATTCAAATATGTATCCGCTCATGAGACAATAAC
├──► Ampicillin resistance gene
CCTGATAAATGCTTCAATAATATTGAAAAAGGAAGAGTATGAGTATTCAACATTTCCGTGTCGCCCTTATTCCCTTT
TTTGCGGCATTTTGCCTTCCTGTTTTTGCTCACCCAGAAACGCTGGTGAAAGTAAAAGATGCTGAAGATCAGTTGGG
TGCACGAGTGGGTTACATCGAACTGGATCTCAACAGCGGTAAGATCCTTGAGAGTTTTCGCCCCGAAGAACGTTTTC
CAATGATGAGCACTTTTAAAGTTCTGCTATGTGGCGCGGTATTATCCCGTGTTGACGCCGGGCAAGAGCAACTCGGT
CGCCGCATACACTATTCTCAGAATGACTTGGTTGAGTACTCACCAGTCACAGAAAAGCATCTTACGGATGGCATGAC
AGTAAGAGAATTATGCAGTGCTGCCATAACCATGAGTGATAACACTGCGGCCAACTTACTTCTGACAACGATCGGAG
GACCGAAGGAGCTAACCGCTTTTTTGCACAACATGGGGGATCATGTAACTCGCCTTGATCGTTGGGAACCGGAGCTG
AATGAAGCCATACCAAACGACGAGCGTGACACCACGATGCCTGCAGCAATGGCAACAACGTTGCGCAAACTATTAAC
TGGCGAACTACTTACTCTAGCTTCCCGGCAACAATTAATAGACTGGATGGAGGCGGATAAAGTTGCAGGACCACTTC
TGCGCTCGGCCCTTCCGGCTGGCTGGTTTATTGCTGATAAATCTGGAGCCGGTGAGCGTGGGTCTCGCGGTATCATT
GCAGCACTGGGGCCAGATGGTAAGCCCTCCCGTATCGTAGTTATCTACACGACGGGGAGTCAGGCAACTATGGATGA
ACGAAATAGACAGATCGCTGAGATAGGTGCCTCACTGATTAAGCATTGGTAACTG
                                                      ◄─┤

TCAGACCAAGTTTACTCATATATACTTTAGATTGATTTACGCGCCCTGTAGCGGCGCATTAAGCGCGGCGGGTGTGG
TGGTTACGCGCAGCGTGACCGCTACACTTGCCAGCGCCCTAGCGCCCGCTCCTTTCGCTTTCTTCCCTTCCTTTCTC
GCCACGTTCGCCGGCTTTCCCCGTCAAGCTCTAAATCGGGGGCTCCCTTTAGGGTTCCGATTTAGTGCTTTACGGCA
CCTCGACCCCAAAAAACTTGATTTGGGTGATGGTTCACGTAGTGGGCCATCGCCCTGATAGACGGTTTTTCGCCCTT
TGACGTTGGAGTCCACGTTCTTTAATAGTGGACTCTTGTTCCAAACTTGAACAACACTCAACCCTATCTCGGGCTAT
TCTTTTGATTTATAAGGGATTTTGCCGATTTCGGCCTATTGGTTAAAAAATGAGCTGATTTAACAAAAATTTAACGC
GA                                                    modified pBR332 origin
ATTTTAACAAAATATTAACGTTTACAATTTAAAAGGATCTAGGTGAAGATCCTTTTTGATAATCTCATGACCAAAAT
CCCTTAACGTGAGTTTTCGTTCCACTGAGCGTCAGACCCCGTAGAAAAGATCAAAGGATCTTCTTGAGATCCTTTTT
TTCTGCGCGTAATCTGCTGCTTGCAAACAAAAAAACCACCGCTACCAGCGGTGGTTTGTTTGCCGGATCAAGAGCTA
CCAACTCTTTTTCCGAAGGTAACTGGCTTCAGCAGAGCGCAGATACCAAATACTGTCCTTCTAGTGTAGCCGTAGTT
AGGCCACCACTTCAAGAACTCTGTAGCACCGCCTACATACCTCGCTCTGCTAATCCTGTTACCAGTGGCTGCTGCCA
GTGGCGATAAGTCGTGTCTTACCGGGTTGGACTCAAGACGATAGTTACCGGATAAGGCGCAGCGGTCGGGCTGAACG
GGGGGTTCGTGCACACAGCCCAGCTTGGAGCGAACGACCTACACCGAACTGAGATACCTACAGCGTGAGCTATGAGA
AAGCGCCACGCTTCCCGAAGGGAGAAAGGCGGACAGGTATCCGGTAAGCGGCAGGGTCGGAACAGGAGAGCGCACGA
GGGAGCTTCCAGGGGGAAACGCCTGGTATCTTTATAGTCCTGTCGGGTTTCGCCACCTCTGACTTGAGCGTCGATTT
TTGTGATGCTCGTCAGGGGGGCGGAGCCTATGGAAAAACGCCAGCAACGCGGCCTTTTACGGTTCCTGGCCTTTTG
CTGGCCTTTTGCTCACATGTTCTTTCCTGCGTTATCCCTGATTCTGTGGATAACCGTATTACCGCCTTTGAGTGAG
CTGATACCGCTCGCCGCAGCCGAACGACCGAGCGCAGCGAGTCAGTGAGCGAGGAAGCGGAAGAGCGCCTGATGCGG
TATTTTCTCCTTACGCATCTGTGCGGTATTTCACACCGCATATGGTGCACTCTCAGTACAATCTGCTCTGATGCCGC
ATAGTTAAGCCAGTATACACTCCGCTATCGCTACGTGACTGGGTCATGGCTGCGCCCCGACACCCGCCAACACCCGC
TGACGCGCCCTGACGGGCTTGTCTGCTCCCGGCATCCGCTTACAGACAAGCTGTGACCGTCTCCGGGAGCTGCATGT
```

FIG. 21C

```
GTCAGAGGTTTTCACCGTCATCACCGAAACGCGCGAGGCAGCAAGGAGATGGCGCCCAACAGTCCCCCGGCCACGGG
GCCTGCCACCATACCCACGCCGAAACAAGCGCTCATGAGCCCGAAGTGGCGAGCCCGATCTTCCCCATCGGTGATGT
CGGCGATATAGGCGCCAGCAACCGCACCTGTGGCGCCGGTGATGCCGGCCACGATGCGTCCGGCGTAGAGGATCTGC
TCATGTTTGACAGCTTATC (SEQ ID NO:9)
```

FIG. 22A pHMGSR plasmid sequence

```
ATCGATGCATAATGTGCCTGTCAAATGGACGAAGCAGGGATTCTGCAAACCCTATGCTACTCCGTCAAGCCGTCAAT
TGT
```
    |→                                          araC

```
CTGATTCGTTACCAATTATGACAACTTGACGGCTACATCATTCACTTTTTCTTCACAACCGGCACGGAACTCGCTCG
GGCTGGCCCCGGTGCATTTTTTAAATACCCGCGAGAAATAGAGTTGATCGTCAAAACCAACATTGCGACCGACGGTG
GCGATAGGCATCCGGGTGGTGCTCAAAAGCAGCTTCGCCTGGCTGATACGTTGGTCCTCGCGCCAGCTTAAGACGCT
AATCCCTAACTGCTGGCGGAAAAGATGTGACAGACGCGACGGCGACAAGCAAACATGCTGTGCGACGCTGGCGATAT
CAAAATTGCTGTCTGCCAGGTGATCGCTGATGTACTGACAAGCCTCGCGTACCCGATTATCCATCGGTGGATGGAGC
GACTCGTTAATCGCTTCCATGCGCCGCAGTAACAATTGCTCAAGCAGATTTATCGCCAGCAGCTCCGAATAGCGCCC
TTCCCCTTGCCCGGCGTTAATGATTTGCCCAAACAGGTCGCTGAAATGCGGCTGGTGCGCTTCATCCGGGCGAAAGA
ACCCGTATTGGCAAATATTGACGGCCAGTTAAGCCATTCATGCCAGTAGGCGCGCGGACGAAAGTAAACCCACTGG
TGATACCATTCGCGAGCCTCCGGATGACGACCGTAGTGATGAATCTCTCCTGGCGGGAACAGCAAAATATCACCCGG
TCGGCAAACAAATTCTCGTCCCTGATTTTTCACCACCCCCTGACCGCGAATGGTGAGATTGAGAATATAACCTTTCA
TTCCCAGCGGTCGGTCGATAAAAAAATCGAGATAACCGTTGGCCTCAATCGGCGTTAAACCCGCCACCAGATGGGCA
TTAAACGAGTATCCCGGCAGCAGGGGATCATTT
``` araC   ←|

```
TGCGCTTCAGCCATACTTTTCATACTCCCGCCATTCAGAGAAGAAACCAATTGTCCATATTGCATCAGACATTGCCG
TCACTGCGTCTTTTACTGGCTCTTCTCGCTAACCAAACCGGTAACCCGCTTATTAAAAGCATTCTGTAACAAAGCG
GGACCAAAGCCATGACAAAAACGCGTAACAAAAGTGTCTATAATCACGGCAGAAAAGTCCACATTGATTATTTGCAC
GGCGTCACA
```
                                                                |→ $P_{BAD}$ Promoter

```
CTTTGCTATGCCATAGCATTTTTATCCATAAGATTAGCGGATCCTACCT GACGCTTTTTATCGCAACTCTCTACTGT
TTC                                              HMGS
TCCATACCCGTTTTTTTGGGCTAGCGAATTCGAGCTCGGTACCCGGGGATCCTCTAGAGTCGACAGGAGGACAGCTA
A
|→
TGAAACTCTCAACTAAACTTTGTTGGTGTGGTATTAAAGGAAGACTTAGGCCGCAAAAGCAACAACAATTACACAAT
ACAAACTTGCAAATGACTGAACTAAAAAAACAAAAGACCGCTGAACAAAAAACCAGACCTCAAAATGTCGGTATTAA
AGGTATCCAAATTTACATCCCAACTCAATGTGTCAACCAATCTGAGCTAGAGAAATTTGATGGCGTTTCTCAAGGTA
AATACACAATTGGTCTGGGCCAAACCAACATGTCTTTTGTCAATGACAGAGAAGATATCTACTCGATGTCCCTAACT
GTTTTGTCTAAGTTGATCAAGAGTTACAACATCGACACCAACAAAATTGGTAGATTAGAAGTCGGTACTGAAACTCT
GATTGACAAGTCCAAGTCTGTCAAGTCTGTCTTGATGCAATTGTTTGGTGAAAACACTGACGTCGAAGGTATTGACA
CGCTTAATGCCTGTTACGGTGGTACCAACGCGTTGTTCAACTCTTTGAACTGGATTGAATCTAACGCATGGGATGGT
AGAGACGCCATTGTAGTTTGCGGTGATATTGCCATCTACGATAAGGGTGCCGCAAGACCAACCGGTGGTGCCGGTAC
TGTTGCTATGTGGATCGGTCCTGATGCTCCAATTGTATTTGACTCTGTAAGAGCTTCTTACATGGAACACGCCTACG
ATTTTTACAAGCCAGATTTCACCAGCGAATATCCTTACGTCGATGGTCATTTTTCATTAACTTGTTACGTCAAGGCT
CTTGATCAAGTTTACAAGAGTTATTCCAAGAAGGCTATTTCTAAAGGGTTGGTTAGCGATCCCGCTGGTTCGGATGC
TTTGAACGTTTTGAAATATTTCGACTACAACGTTTTCCATGTTCCAACCTGTAAATTGGTCACAAAATCATACGGTA
GATTACTATATAACGATTTCAGAGCCAATCCTCAATTGTTCCCAGAAGTTGACGCCGAATTAGCTACTCGCGATTAT
GACGAATCTTTAACCGATAAGAACATTGAAAAAACTTTTGTTAATGTTGCTAAGCCATTCCACAAAGAGAGTTGC
CCAATCTTTGATTGTTCCAACAAACACAGGTAACATGTACACCGCATCTGTTTATGCCGCCTTTGCATCTCTATTAA
ACTATGTTGGATCTGACGACTTACAAGGCAAGCGTGTTGGTTTATTTTCTTACGGTTCCGGTTTAGCTGCATCTCTA
TATTCTTGCAAAATTGTTGGTGACGTCCAACATATTATCAAGGAATTAGATATTACTAACAAATTAGCCAAGAGAAT
CACCGAAACTCCAAAGGATTACGAAGCTGCCATCGAATTGAGAGAAAATGCCCATTTGAAGAAGAACTTCAAACCTC
AAGGTTCCATTGAGCATTTGCAAAGTGGTGTTTACTACTTGACCAACATCGATGA
```

FIG. 22B

HMGS ◄┤  ├► truncated HMGR

CAAATTTAGAAGATCTTACGATGTTAAAAAATAAGGAGGATTACACTATGGTTTTAACCAATAAAACAGTCATTTCT
GGATCGAAAGTCAAAAGTTTATCATCTGCGCAATCGAGCTCATCAGGACCTTCATCATCTAGTGAGGAAGATGATTC
CCGCGATATTGAAAGCTTGGATAAGAAAATACGTCCTTTAGAAGAATTAGAAGCATTATTAAGTAGTGGAAATACAA
AACAATTGAAGAACAAAGAGGTCGCTGCCTTGGTTATTCACGGTAAGTTACCTTTGTACGCTTTGGAGAAAAAATTA
GGTGATACTACGAGAGCGGTTGCGGTACGTAGGAAGGCTCTTTCAATTTTGGCAGAAGCTCCTGTATTAGCATCTGA
TCGTTTACCATATAAAAATTATGACTACGACCGCGTATTTGGCGCTTGTTGTGAAAATGTTATAGGTTACATGCCTT
TGCCCGTTGGTGTTATAGGCCCCTTGGTTATCGATGGTACATCTTATCATATACCAATGGCAACTACAGAGGGTTGT
TTGGTAGCTTCTGCCATGCGTGGCTGTAAGGCAATCAATGCTGGCGGTGGTGCAACAACTGTTTTAACTAAGGATGG
TATGACAAGAGGCCCAGTAGTCCGTTTCCCAACTTTGAAAAGATCTGGTGCCTGTAAGATATGGTTAGACTCAGAAG
AGGGACAAAACGCAATTAAAAAAGCTTTTAACTCTACATCAAGATTTGCACGTCTGCAACATATTCAAACTTGTCTA
GCAGGAGATTTACTCTTCATGAGATTTAGAACAACTACTGGTGACGCAATGGGTATGAATATGATTTCTAAAGGTGT
CGAATACTCATTAAAGCAAATGGTAGAAGAGTATGGCTGGGAAGATATGGAGGTTGTCTCCGTTTCTGGTAACTACT
GTACCGACAAAAAACCAGCTGCCATCAACTGGATCGAAGGTCGTGGTAAGAGTGTCGTCGCAGAAGCTACTATTCCT
GGTGATGTTGTCAGAAAAGTGTTAAAAAGTGATGTTTCCGCATTGGTTGAGTTGAACATTGCTAAGAATTTGGTTGG
ATCTGCAATGGCTGGGTCTGTTGGTGGATTTAACGCACATGCAGCTAATTTAGTGACAGCTGTTTTCTTGGCATTAG
GACAAGATCCTGCACAAAATGTTGAAAGTTCCAACTGTATAACATTGATGAAAGAAGTGGACGGTGATTTGAGAATT
TCCGTATCCATGCCATCCATCGAAGTAGGTACCATCGGTGGTGGTACTGTTCTAGAACCACAAGGTGCCATGTTGGA
CTTATTAGGTGTAAGAGGCCCGCATGCTACCGCTCCTGGTACCAACGCACGTCAATTAGCAAGAATAGTTGCCTGTG
CCGTCTTGGCAGGTGAATTATCCTTATGTGCTGCCCTAGCAGCCGGCCATTTGGTTCAAAGTCATATGACCCACAAC
AGGAAACCTGCTGAACCAACAAAACCTAACAATTTGGACGCCACTGATATAAATCGT truncated HMGR ◄┤  rrnB terminator TTGAAAGATGGGTCCGTCACCTGCATTAAATCCTAAGTCGACCTGCAGGCATGCAAGCTT<u>GGCTGTTTTGGCGGATG</u>
<u>AGAGAAGATTTTCAGCCTGATACAGATTAAATCAGAACGCAGAAGCGGTCTGATAAAACAGAATTTGCCTGGCGGCA</u>
<u>GTAGCGCGGTGGTCCCACCTGACCCCATGCCGAACTCAGAAGTGAAACGCCGTAGCGCCGATGGTAGTGTGGGGTCT</u>
<u>CCCCATGCGAGAGTAGGGAACTGCCAGGCATCAAATAAAACGAAAGGCTCAGTCGAAAGACTGGGCCTTTCGTTTTA</u>
<u>TCTGTTGTTTGTCGGTGAACGCTCTCCTGAGTAGGACAAATCCGCCGGGAGCGGATTTGAACGTTGCGAAGCAACGG</u>
<u>CCCGGAGGGTGGCGGGCAGGACGCCCGCCATAAACTGCCAGGCATCAAATTAAGCAGAAGGCCATCCTGACGGATGG</u>
<u>CCTTTTTGCGTTTCTACAAACTCT</u>TTTGTTTATTTTTCTAAATACATTCAAATATGTATCCGCTCATGAGACAATAA
CCCTGATAAATGCTTCAATAATATTGAAAAAGGAAGAGTATGAGTATTCAACATTTCCGTGTCGCCCTTATTCCCTT
TTTTGCGGCATTTTGCCTTCCTGTTTTTGCTCACCCAGAAACGCTGGTGAAAGTAAAAGATGCTGAAGATCAGTTGG
GTGCAGCAAACTATTAACTGGCGAACTACTTACTCTAGCTTCCCGGCAACAATTAATAGACTGGATGGAGGCGGATA
AAGTTGCAGGACCACTTCTGCGCTCGGCCCTTCCGGCTGGCTGGTTTATTGCTGATAAATCTGGAGCCGGTGAGCGT
GGGTCTCGCGGTATCATTGCAGCACTGGGGCCAGATGGTAAGCCCTCCCGTATCGTAGTTATCTACACGACGGGGAG
TCAGGCAACTATGGATGAACGAAATAGACAGATCGCTGAGATAGGTGCCTCACTGATTAAGCATTGGTAACTGTCAG
ACCAAGTTTACTCATATATACTTTAGATTGATTTACGCGCCCTGTAGCGGCGCATTAAGCGCGGCGGGTGTGGTGGT
TACGCGCAGCGTGACCGCTACACTTGCCAGCGCCCTAGCGCCCGCTCCTTTCGCTTTCTTCCCTTCCTTTCTCGCCA
CGTTCGCCGGCTTTCCCCGTCAAGCTCTAAATCGGGGGCTCCCTTTAGGGTTCCGATTTAGTGCTTTACGGCACCTC
GACCCCAAAAAACTTGATTTGGGTGATGGTTCACGTAGTGGGCCATCGCCCTGATAGACGGTTTTTCGCCCTTTGAC
GTTGGAGTCCACGTTCTTTAATAGTGGACTCTTGTTCCAAACTTGAACAACACTCAACCCTATCTCGGGCTATTCTT
TTGATTTATAAGGGATTTTGCCGATTTCGGCCTATTGGTTAAAAAATGAGCTGATTTAACAAAAATTTAACGCGAAT
TTTAACAAAATATTAACGTTTACAATTTAAAAGGATCTAGGTGAAGATCCTTTTTGATAATCTCATGACCAAAATCC
CTTAACGTGAGTTTTCGTTCCACTGAGCGTCAGACCCCGTAGAAAAGATCAAAGGATCTTCTTGAGATCCTTTTTTT
CTGCGCGTAATCTGCTGCTTGCAAACAAAAAAACCACCGCTACCAGCGGTGGTTTGTTTGCCGGATCAAGAGCTACC
AACTCTTTTTCCGAAGGTAACTGGCTTCAGCAGAGCGCAGATACCAAATACTGTCCTTCTAGTGTAGCCGTAGTTAG
GCCACCACTTCAAGAACTCTGTAGCACCGCCTACATACCTCGCTCTGCTAATCCTGTTACCAGTGGGGCATTTGAGA
AGCACACGGTCACACTGCTTCCGGTAGTCAATAAACCGGTAAACCAGCAATAGACATAAGCGGCTATTTAACGACCC
TGCCCTGAACCGACGACCGGGTCGAATTTGCTTTCGAATTTCTGCCATTCATCCGCTTATTATCACTTATTCAGG ├► Chloramphenicol resistance gene
CGTAGCACCAGGCGTTTAAGGGCACCAATAACTGCCTTAAAAAAATTACGCCCCGCCCTGCCACTCATCGCAGTACT
GTTGTAATTCATTAAGCATTCTGCCGACATGGAAGCCATCACAGACGGCATGATGAACCTGAATCGCCAGCGGCATC
AGCACCTTGTCGCCTTGCGTATAATATTTGCCCATGGTGAAAACGGGGGCGAAGAAGTTGTCCATATTGGCCACGTT

FIG. 22C

```
TAAATCAAAACTGGTGAAACTCACCCAGGGATTGGCTGAGACGAAAAACATATTCTCAATAAACCCTTTAGGGAAAT
AGGCCAGGTTTTCACCGTAACACGCCACATCTTGCGAATATATGTGTAGAAACTGCCGGAAATCGTCGTGGTATTCA
CTCCAGAGCGATGAAAACGTTTCAGTTTGCTCATGGAAAACGGTGTAACAAGGGTGAACACTATCCCATATCACCAG
CTCACCGTCTTTCATTGCCATACGGAATTCCGGATGAGCATTCATCAGGCGGGCAAGAATGTGAATAAAGGCCGGAT
AAAACTTGTGCTTATTTTTCTTTACGGTCTTTAAAAAGGCCGTAATATCCAGCTGAACGGTCTGGTTATAGGTACAT
TGAGCAACTGACTGAAATGCCTCAAAATGTTCTTTACGATGCCATTGGGATATATCAACGGTGGTATATCCAGTGAT
TTTTTTCTCCAT
```
←⊣

```
TTTAGCTTCCTTAGCTCCTGAAAATCTCGATAACTCAAAAAATACGCCCGGTAGTGATCTTATTTCATTATGGTGAA
AGTTGGAACCTCTTACGTGCCGATCAACGTCTCATTTTCGCCAAAAGTTGGCCCAGGGCTTCCCGGTATCAACAGGG
ACACCAGGATTTATTTATTCTGCGAAGTGATCTTCCGTCACAGGTATTTATTCGGCGCAAAGTGCGTCGGGTGATGC
TGCCAACTTACTGATTTAGTGTATGATGGTGTTTTTGAGGTGCTCCAGTGGCTTCTGTTTCTATCAGCTGTCCCTCC
TGTTCAGCTACTGACGGGGTGGTGCGT
``` pACYC184 origin

```
AACGGCAAAAGCACCGCCGGACATCAGCGCTAGCGGAGTGTATACTGGCTTACTATGTTGGCACTGATGAGGGTGTC
AGTGAAGTGCTTCATGTGGCAGGAGAAAAAAGGCTGCACCGGTGCGTCAGCAGAATATGTGATACAGGATATATTCC
GCTTCCTCGCTCACTGACTCGCTACGCTCGGTCGTTCGACTGCGGCGAGCGGAAATGGCTTACGAACGGGGCGGAGA
TTTCCTGGAAGATGCCAGGAAGATACTTAACAGGGAAGTGAGAGGGCCGCGGCAAAGCCGTTTTTCCATAGGCTCCG
CCCCCCTGACAAGCATCACGAAATCTGACGCTCAAATCAGTGGTGGCGAAACCCGACAGGACTATAAAGATACCAGG
CGTTTCCCCCTGGCGGCTCCCTCGTGCGCTCTCCTGTTCCTGCCTTTCGGTTTACCGGTGTCATTCCGCTGTTATGG
CCGCGTTTGTCTCATTCCACGCCTGACACTCAGTTCCGGGTAGGCAGTTCGCTCCAAGCTGGACTGTATGCACGAAC
CCCCCGTTCAGTCCGACCGCTGCGCCTTATCCGGTAACTATCGTCTTGAGTCCAACCCGGAAAGACATGCAAAAGCA
CCACTGGCAGCAGCCACTGGTAATTGATTTAGAGGAGTTAGTCTTGAAGTCATGCGCCGGTTAAGGCTAAACTGAAA
GGACAAGTTTTGGTGACTGCGCTCCTCCAAGCCAGTTACCTCGGTTCAAAGAGTTGGTAGCTCAGAGAACCTTCGAA
AAACCGCCCTGCAAGGCGGTTTTTTCGTTTTCAGAGCAAGAGATTACGCGCAGACCAAAACGATCTCAAGAAGATCA
TCTTATTAATCAGATAAAATATTTGCTCATGAGCCCGAAGTGGCGAGCCCGATCTTCCCCATCGGTGATGTCGGCGA
TATAGGCGCCAGCAACCGCACCTGTGGCGCCGGTGATGCCGGCCACGATGCGTCCGGCGTAGAGGATCTGCTCATGT
TTGACAGCTTATC (SEQ ID NO:10)
```

FIG. 23A pBAD33MevT(C159A) plasmid sequence

ATCGATGCATAATGTGCCTGTCAAATGGACGAAGCAGGGATTCTGCAAACCCTATGCTACTCCGTCAAGCCGTCAAT
TGT

|→                                              araC
CTGATTCGTTACCAATTATGACAACTTGACGGCTACATCATTCACTTTTTCTTCACAACCGGCACGGAACTCGCTCG
GGCTGGCCCCGGTGCATTTTTTAAATACCCGCGAGAAATAGAGTTGATCGTCAAAACCAACATTGCGACCGACGGTG
GCGATAGGCATCCGGGTGGTGCTCAAAAGCAGCTTCGCCTGGCTGATACGTTGGTCCTCGCGCCAGCTTAAGACGCT
AATCCCTAACTGCTGGCGGAAAAGATGTGACAGACGCGACGGCGACAAGCAAACATGCTGTGCGACGCTGGCGATAT
CAAAATTGCTGTCTGCCAGGTGATCGCTGATGTACTGACAAGCCTCGCGTACCCGATTATCCATCGGTGGATGGAGC
GACTCGTTAATCGCTTCCATGCGCCGCAGTAACAATTGCTCAAGCAGATTTATCGCCAGCAGCTCCGAATAGCGCCC
TTCCCCTTGCCCGGCGTTAATGATTTGCCCAAACAGGTCGCTGAAATGCGGCTGGTGCGCTTCATCCGGGCGAAAGA
ACCCCGTATTGGCAAATATTGACGGCCAGTTAAGCCATTCATGCCAGTAGGCGCGCGGACGAAAGTAAACCCACTGG
TGATACCATTCGCGAGCCTCCGGATGACGACCGTAGTGATGAATCTCTCCTGGCGGGAACAGCAAAATATCACCCGG
TCGGCAAACAAATTCTCGTCCCTGATTTTTCACCACCCCCTGACCGCGAATGGTGAGATTGAGAATATAACCTTTCA
TTCCCAGCGGTCGGTCGATAAAAAAATCGAGATAACCGTTGGCCTCAATCGGCGTTAAACCCGCCACCAGATGGGCA
TTAAACGAGTATCCCGGCAGCAGGGGATCATTT
     araC    ◀|
TGCGCTTCAGCCATACTTTTCATACTCCCGCCATTCAGAGAAGAAACCAATTGTCCATATTGCATCAGACATTGCCG
TCACTGCGTCTTTTACTGGCTCTTCTCGCTAACCAAACCGGTAACCCCGCTTATTAAAAGCATTCTGTAACAAAGCG
GGACCAAAGCCATGACAAAAACGCGTAACAAAAGTGTCTATAATCACGGCAGAAAAGTCCACATTGATTATTTGCAC
GGCGTCACA

|→    P_BAD Promoter
CTTTGCTATGCCATAGCATTTTTATCCATAAGATTAGCGGATCCTACCT[GACGCTTTTTATCGCAACTCTCTACTGT]
TTC
TCCATACCCGTTTTTTTGGGCTAGCGAATTCGAGCTCGGTACCCGGGGATCCTCTAGAGTCGACTAGGAGGAATATA
AA
|→ atoB
ATGAAAAATTGTGTCATCGTCAGTGCGGTACGTACTGCTATCGGTAGTTTTAACGGTTCACTCGCTTCCACCAGCGC
CATCGACCTGGGGGCGACAGTAATTAAAGCCGCCATTGAACGTGCAAAAATCGATTCACAACACGTTGATGAAGTGA
TTATGGGTAACGTGTTACAAGCCGGGCTGGGGCAAAATCCGGCGCGTCAGGCACTGTTAAAAAGCGGGCTGGCAGAA
ACGGTGTGCGGATTCACGGTCAATAAAGTATGTGGTTCGGGTCTTAAAAGTGTGGCGCTTGCCGCCCAGGCCATTCA
GGCAGGTCAGGCGCAGAGCATTGTGGCGGGGGGTATGGAAAATATGAGTTTAGCCCCCTACTTACTCGATGCAAAAG
CACGCTCTGGTTATCGTCTTGGAGACGGACAGGTTTATGACGTAATCCTGCGCGATGGCCTGATGTGCGCCACCCAT
GGTTATCATATGGGGATTACCGCCGAAAACGTGGCTAAAGAGTACGGAATTACCCGTGAAATGCAGGATGAACTGGC
GCTACATTCACAGCGTAAAGCGGCAGCCGCAATTGAGTCCGGTGCTTTTACAGCCGAAATCGTCCCGGTAAATGTTG
TCACTCGAAAGAAAACCTTCGTCTTCAGTCAAGACGAATTCCCGAAAGCGAATTCAACGGCTGAAGCGTTAGGTGCA
TTGCGCCCGGCCTTCGATAAAGCAGGAACAGTCACCGCTGGGAACGCGTCTGGTATTAACGACGGTGCTGCCGCTCT
GGTGATTATGGAAGAATCTGCGGCGCTGGCAGCAGGCCTTACCCCCCTGGCTCGCATTAAAAGTTATGCCAGCGGTG
GCGTGCCCCCGCATTGATGGGTATGGGGCCAGTACCTGCCACGCAAAAAGCGTTACAACTGGCGGGGCTGCAACTG
GCGGATATTGATCTCATTGAGGCTAATGAAGCATTTGCTGCACAGTTCCTTGCCGTTGGGAAAAACCTGGGCTTTGA
TTCTGAGAAAGTGAATGTCAACGGCGGGGCCATCGCGCTCGGGCATCCATCGGTGCCAGTGGTGCTCGTATTCTGG
TCACACTATTACATGCCATGCAGGCACGCGATAAAACGCTGGG
                               atoB                                 ◀|
GCTGGCAACACTGTGCATTGGCGGCGGTCAGGGAATTGCGATGGTGATTGAACGGTTGAATTAAGGAGGACAGCTAA

|→ HMGS
ATGAAACTCTCAACTAAACTTTGTTGGTGTGGTATTAAAGGAAGACTTAGGCCGCAAAAGCAACAACAATTACACAA

FIG. 23B

TACAAACTTGCAAATGACTGAACTAAAAAAACAAAAGACCGCTGAACAAAAAACCAGACCTCAAAATGTCGGTATTA
AAGGTATCCAAATTTACATCCCAACTCAATGTGTCAACCAATCTGAGCTAGAGAAATTTGATGGCGTTTCTCAAGGT
AAATACACAATTGGTCTGGGCCAAACCAACATGTCTTTTGTCAATGACAGAGAAGATATCTACTCGATGTCCCTAAC
TGTTTTGTCTAAGTTGATCAAGAGTTACAACATCGACACCAACAAAATTGGTAGATTAGAAGTCGGTACTGAAACTC
TGATTGACAAGTCCAAGT (C159A)

CTGTCAAGTCTGTCTTGATGCAATTGTTTGGTGAAAACACTGACGTCGAAGGTATTGACACGCTTAATGCC|GCG|TAC
GGTGGTACCAACGCGTTGTTCAACTCTTTGAACTGGATTGAATCTAACGCATGGGATGGTAGAGACGCCATTGTAGT
TTGCGGTGATATTGCCATCTACGATAAGGGTGCCGCAAGACCAACCGGTGGTGCCGGTACTGTTGCTATGTGGATCG
GTCCTGATGCTCCAATTGTATTTGACTCTGTAAGAGCTTCTTACATGGAACACGCCTACGATTTTTACAAGCCAGAT
TTCACCAGCGAATATCCTTACGTCGATGGTCATTTTTCATTAACTTGTTACGTCAAGGCTCTTGATCAAGTTTACAA
GAGTTATTCCAAGAAGGCTATTTCTAAAGGGTTGGTTAGCGATCCCGCTGGTTCGGATGCTTTGAACGTTTTGAAAT
ATTTCGACTACAACGTTTTCCATGTTCCAACCTGTAAATTGGTCACAAAATCATACGGTAGATTACTATATAACGAT
TTCAGAGCCAATCCTCAATTGTTCCCAGAAGTTGACGCCGAATTAGCTACTCGCGATTATGACGAATCTTTAACCGA
TAAGAACATTGAAAAAACTTTTGTTAATGTTGCTAAGCCATTCCACAAAGAGAGAGTTGCCCAATCTTTGATTGTTC
CAACAAACACAGGTAACATGTACACCGCATCTGTTTATGCCGCCTTTGCATCTCTATTAAACTATGTTGGATCTGAC
GACTTACAAGGCAAGCGTGTTGGTTTATTTTCTTACGGTTCCGGTTTAGCTGCATCTCTATATTCTTGCAAAATTGT
TGGTGACGTCCAACATATTATCAAGGAATTAGATATTACTAACAAATTAGCCAAGAGAATCACCGAAACTCCAAAGG
ATTACGAAGCTGCCATCGAATTGAGAGAAAATGCCCATTTGAAGAAGAACTTCAAACCTCAAGGTTCCATTGAGCAT
TTGCAAAGTGGTGTTTACTACTTGACCAACATCGATGAC

HMGS       ◄┤       ├►          truncated HMGR
AAATTTAGAAGATCTTACGATGTTAAAAAATAAGGAGGATTACACTATGGTTTTAACCAATAAAACAGTCATTTCTG
GATCGAAAGTCAAAAGTTTATCATCTGCGCAATCGAGCTCATCAGGACCTTCATCATCTAGTGAGGAAGATGATTCC
CGCGATATTGAAAGCTTGGATAAGAAAATACGTCCTTTAGAAGAATTAGAAGCATTATTAAGTAGTGGAAATACAAA
ACAATTGAAGAACAAAGAGGTCGCTGCCTTGGTTATTCACGGTAAGTTACCTTTGTACGCTTTGGAGAAAAAATTAG
GTGATACTACGAGAGCGGTTGCGGTACGTAGGAAGGCTCTTTCAATTTTGGCAGAAGCTCCTGTATTAGCATCTGAT
CGTTTACCATATAAAAATTATGACTACGACCGCGTATTTGGCGCTTGTTGTGAAAATGTTATAGGTTACATGCCTTT
GCCCGTTGGTGTTATAGGCCCCTTGGTTATCGATGGTACATCTTATCATATACCAATGGCAACTACAGAGGGTTGTT
TGGTAGCTTCTGCCATGCGTGGCTGTAAGGCAATCAATGCTGGCGGTGGTGCAACAACTGTTTTAACTAAGGATGGT
ATGACAAGAGGCCCAGTAGTCCGTTTCCCAACTTTGAAAAGATCTGGTGCCTGTAAGATATGGTTAGACTCAGAAGA
GGGACAAAACGCAATTAAAAAAGCTTTTAACTCTACATCAAGATTTGCACGTCTGCAACATATTCAAACTTGTCTAG
CAGGAGATTTACTCTTCATGAGATTTAGAACAACTACTGGTGACGCAATGGGTATGAATATGATTTCTAAAGGTGTC
GAATACTCATTAAAGCAAATGGTAGAAGAGTATGGCTGGGAAGATATGGAGGTTGTCTCCGTTTCTGGTAACTACTG
TACCGACAAAAAACCAGCTGCCATCAACTGGATCGAAGGTCGTGGTAAGAGTGTCGTCGCAGAAGCTACTATTCCTG
GTGATGTTGTCAGAAAAGTGTTAAAAAGTGATGTTTCCGCATTGGTTGAGTTGAACATTGCTAAGAATTTGGTTGGA
TCTGCAATGGCTGGGTCTGTTGGTGGATTTAACGCACATGCAGCTAATTTAGTGACAGCTGTTTTCTTGGCATTAGG
ACAAGATCCTGCACAAAATGTTGAAAGTTCCAACTGTATAACATTGATGAAAGAAGTGGACGGTGATTTGAGAATTT
CCGTATCCATGCCATCCATCGAAGTAGGTACCATCGGTGGTGGTACTGTTCTAGAACCACAAGGTGCCATGTTGGAC
TTATTAGGTGTAAGAGGCCCGCATGCTACCGCTCCTGGTACCAACGCACGTCAATTAGCAAGAATAGTTGCCTGTGC
CGTCTTGGCAGGTGAATTATCCTTATGTGCTGCCCTAGCAGCCGGCCATTTGGTTCAAAGTCATATGACCCACAACA
GGAAACCTGCTGAACCAACAAAACCTAACAATTTGGACGCCACTGATATAAATCGTT truncated HMGR           ◄┤                                    rrnB terminator
TGAAAGATGGGTCCGTCACCTGCATTAAATCCTAAGTCGACCTGCAGGCATGCAAGCTT<u>GGCTGTTTTGGCGGATGA
GAGAAGATTTTCAGCCTGATACAGATTAAATCAGAACGCAGAAGCGGTCTGATAAAACAGAATTTGCCTGGCGGCAG
TAGCGCGGTGGTCCCACCTGACCCCATGCCGAACTCAGAAGTGAAACGCCGTAGCGCCGATGGTAGTGTGGGGTCTC
CCCATGCGAGAGTAGGGAACTGCCAGGCATCAAATAAAACGAAAGGCTCAGTCGAAAGACTGGGCCTTTCGTTTTAT
CTGTTGTTTGTCGGTGAACGCTCTCCTGAGTAGGACAAATCCGCCGGGAGCGGATTTGAACGTTGCGAAGCAACGGC
CCGGAGGGTGGCGGGCAGGACGCCCGCCATAAACTGCCAGGCATCAAATTAAGCAGAAGGCCATCCTGACGGATGGC
CTTTTTGCGTTTCTACAAACTCTTTTGTTTATTTTTCTAAATACATTCAAATATGTATCCGCTCATGAGACAATAAC</u>
CCTGATAAATGCTTCAATAATATTGAAAAAGGAAGAGTATGAGTATTCAACATTTCCGTGTCGCCCTTATTCCCTTT

FIG. 23C

TTTGCGGCATTTTGCCTTCCTGTTTTTGCTCACCCAGAAACGCTGGTGAAAGTAAAAGATGCTGAAGATCAGTTGGG
TGCAGCAAACTATTAACTGGCGAACTACTTACTCTAGCTTCCCGGCAACAATTAATAGACTGGATGGAGGCGGATAA
AGTTGCAGGACCACTTCTGCGCTCGGCCCTTCCGGCTGGCTGGTTTATTGCTGATAAATCTGGAGCCGGTGAGCGTG
GGTCTCGCGGTATCATTGCAGCACTGGGGCCAGATGGTAAGCCCTCCCGTATCGTAGTTATCTACACGACGGGGAGT
CAGGCAACTATGGATGAACGAAATAGACAGATCGCTGAGATAGGTGCCTCACTGATTAAGCATTGGTAACTGTCAGA
CCAAGTTTACTCATATATACTTTAGATTGATTTACGCGCCCTGTAGCGGCGCATTAAGCGCGGCGGGTGTGGTGGTT
ACGCGCAGCGTGACCGCTACACTTGCCAGCGCCCTAGCGCCCGCTCCTTTCGCTTTCTTCCCTTCCTTTCTCGCCAC
GTTCGCCGGCTTTCCCCGTCAAGCTCTAAATCGGGGGCTCCCTTTAGGGTTCCGATTTAGTGCTTTACGGCACCTCG
ACCCCAAAAAACTTGATTTGGGTGATGGTTCACGTAGTGGGCCATCGCCCTGATAGACGGTTTTTCGCCCTTTGACG
TTGGAGTCCACGTTCTTTAATAGTGGACTCTTGTTCCAAACTTGAACAACACTCAACCCTATCTCGGGCTATTCTTT
TGATTTATAAGGGATTTTGCCGATTTCGGCCTATTGGTTAAAAAATGAGCTGATTTAACAAAAATTTAACGCGAATT
TTAACAAAATATTAACGTTTACAATTTAAAAGGATCTAGGTGAAGATCCTTTTTGATAATCTCATGACCAAAATCCC
TTAACGTGAGTTTTCGTTCCACTGAGCGTCAGACCCCGTAGAAAAGATCAAAGGATCTTCTTGAGATCCTTTTTTTC
TGCGCGTAATCTGCTGCTTGCAAACAAAAAAACCACCGCTACCAGCGGTGGTTTGTTTGCCGGATCAAGAGCTACCA
ACTCTTTTTCCGAAGGTAACTGGCTTCAGCAGAGCGCAGATACCAAATACTGTCCTTCTAGTGTAGCCGTAGTTAGG
CCACCACTTCAAGAACTCTGTAGCACCGCCTACATACCTCGCTCTGCTAATCCTGTTACCAGTGGGGCATTTGAGAA
GCACACGGTCACACTGCTTCCGGTAGTCAATAAACCGGTAAACCAGCAATAGACATAAGCGGCTATTTAACGACCCT
GCCCTGAACCGACGACCGGGTCGAATTTGCTTTCGAATTTCTGCCATTCATCCGCTTATTATCACTTATTCAGGC

Chloramphenicol resistance gene →

GTAGCACCAGGCGTTTAAGGGCACCAATAACTGCCTTAAAAAAATTACGCCCCGCCCTGCCACTCATCGCAGTACTG
TTGTAATTCATTAAGCATTCTGCCGACATGGAAGCCATCACAGACGGCATGATGAACCTGAATCGCCAGCGGCATCA
GCACCTTGTCGCCTTGCGTATAATATTTGCCCATGGTGAAAACGGGGGCGAAGAAGTTGTCCATATTGGCCACGTTT
AAATCAAAACTGGTGAAACTCACCCAGGGATTGGCTGAGACGAAAAACATATTCTCAATAAACCCTTTAGGGAAATA
GGCCAGGTTTTCACCGTAACACGCCACATCTTGCGAATATATGTGTAGAAACTGCCGGAAATCGTCGTGGTATTCAC
TCCAGAGCGATGAAAACGTTTCAGTTTGCTCATGGAAAACGGTGTAACAAGGGTGAACACTATCCCATATCACCAGC
TCACCGTCTTTCATTGCCATACGGAATTCCGGATGAGCATTCATCAGGCGGGCAAGAATGTGAATAAAGGCCGGATA
AAACTTGTGCTTATTTTTCTTTACGGTCTTTAAAAAGGCCGTAATATCCAGCTGAACGGTCTGGTTATAGGTACATT
GAGCAACTGACTGAAATGCCTCAAAATGTTCTTTACGATGCCATTGGGATATATCAACGGTGGTATATCCAGTGATT
TTTTTCTCCAT ←

TTTAGCTTCCTTAGCTCCTGAAAATCTCGATAACTCAAAAAATACGCCCGGTAGTGATCTTATTTCATTATGGTGAA
AGTTGGAACCTCTTACGTGCCGATCAACGTCTCATTTTCGCCAAAAGTTGGCCCAGGGCTTCCCGGTATCAACAGGG
ACACCAGGATTTATTTATTCTGCGAAGTGATCTTCCGTCACAGGTATTTATTCGGCGCAAAGTGCGTCGGGTGATGC
TGCCAACTTACTGATTTAGTGTATGATGGTGTTTTTGAGGTGCTCCAGTGGCTTCTGTTTCTATCAGCTGTCCCTCC
TGTTCAGCTACTGACGGGGTGGTGCGTA pACYC184 origin
ACGGCAAAAGCACCGCCGGACATCAGCGCTAGCGGAGTGTATACTGGCTTACTATGTTGGCACTGATGAGGGTGTCA
GTGAAGTGCTTCATGTGGCAGGAGAAAAAAGGCTGCACCGGTGCGTCAGCAGAATATGTGATACAGGATATATTCCG
CTTCCTCGCTCACTGACTCGCTACGCTCGGTCGTTCGACTGCGGCGAGCGGAAATGGCTTACGAACGGGGCGGAGAT
TTCCTGGAAGATGCCAGGAAGATACTTAACAGGGAAGTGAGAGGGCCGCGGCAAAGCCGTTTTTCCATAGGCTCCGC
CCCCCTGACAAGCATCACGAAATCTGACGCTCAAATCAGTGGTGGCGAAACCCGACAGGACTATAAAGATACCAGGC
GTTTCCCCCTGGCGGCTCCCTCGTGCGCTCTCCTGTTCCTGCCTTTCGGTTTACCGGTGTCATTCCGCTGTTATGGC
CGCGTTTGTCTCATTCCACGCCTGACACTCAGTTCCGGGTAGGCAGTTCGCTCCAAGCTGGACTGTATGCACGAACC
CCCCGTTCAGTCCGACCGCTGCGCCTTATCCGGTAACTATCGTCTTGAGTCCAACCCGGAAAGACATGCAAAGCAC
CACTGGCAGCAGCCACTGGTAATTGATTTAGAGGAGTTAGTCTTGAAGTCATGCGCCGGTTAAGGCTAAACTGAAAG
GACAAGTTTTGGTGACTGCGCTCCTCCAAGCCAGTTACCTCGGTTCAAAGAGTTGGTAGCTCAGAGAACCTTCGAAA
AACCGCCCTGCAAGGCGGTTTTTTCGTTTTCAGAGCAAGAGATTACGCGCAGACCAAAACGATCTCAAGAAGATCAT
CTTATTAATCAGATAAAATATTTGCTCATGAGCCCGAAGTGGCGAGCCCGATCTTCCCCATCGGTGATGTCGGCGAT
ATAGGCGCCAGCAACCGCACCTGTGGCGCCGGTGATGCCGGCCACGATGCGTCCGGCGTAGAGGATCTGCTCATGTT
TGACAGCTTATC (SEQ ID NO:11)

FIG. 24A pHMGS(C159A) plasmid sequence

```
ATCGATGCATAATGTGCCTGTCAAATGGACGAAGCAGGGATTCTGCAAACCCTATGCTACTCCGTCAAGCCGTCAAT
TGT
```

┠▶                              araC

```
CTGATTCGTTACCAATTATGACAACTTGACGGCTACATCATTCACTTTTTCTTCACAACCGGCACGGAACTCGCTCG
GGCTGGCCCCGGTGCATTTTTTAAATACCCGCGAGAAATAGAGTTGATCGTCAAAACCAACATTGCGACCGACGGTG
GCGATAGGCATCCGGGTGGTGCTCAAAAGCAGCTTCGCCTGGCTGATACGTTGGTCCTCGCGCCAGCTTAAGACGCT
AATCCCTAACTGCTGGCGGAAAAGATGTGACAGACGCGACGGCGACAAGCAAACATGCTGTGCGACGCTGGCGATAT
CAAAATTGCTGTCTGCCAGGTGATCGCTGATGTACTGACAAGCCTCGCGTACCCGATTATCCATCGGTGGATGGAGC
GACTCGTTAATCGCTTCCATGCGCCGCAGTAACAATTGCTCAAGCAGATTTATCGCCAGCAGCTCCGAATAGCGCCC
TTCCCCTTGCCCGGCGTTAATGATTTGCCCAAACAGGTCGCTGAAATGCGGCTGGTGCGCTTCATCCGGGCGAAAGA
ACCCCGTATTGGCAAATATTGACGGCCAGTTAAGCCATTCATGCCAGTAGGCGCGCGGACGAAAGTAAACCCACTGG
TGATACCATTCGCGAGCCTCCGGATGACGACCGTAGTGATGAATCTCTCCTGGCGGGAACAGCAAAATATCACCCGG
TCGGCAAACAAATTCTCGTCCCTGATTTTTCACCACCCCTGACCGCGAATGGTGAGATTGAGAATATAACCTTTCA
TTCCCAGCGGTCGGTCGATAAAAAAATCGAGATAACCGTTGGCCTCAATCGGCGTTAAACCCGCCACCAGATGGGCA
TTAAACGAGTATCCCGGCAGCAGGGGATCATTT
``` araC  ◀┨

```
TGCGCTTCAGCCATACTTTTCATACTCCCGCCATTCAGAGAAGAAACCAATTGTCCATATTGCATCAGACATTGCCG
TCACTGCGTCTTTTACTGGCTCTTCTCGCTAACCAAACCGGTAACCCCGCTTATTAAAAGCATTCTGTAACAAAGCG
GGACCAAAGCCATGACAAAAACGCGTAACAAAAGTGTCTATAATCACGGCAGAAAAGTCCACATTGATTATTTGCAC
GGCGTCACA
```

┠▶   P$_{BAD}$ Promoter

```
CTTTGCTATGCCATAGCATTTTTATCCATAAGATTAGCGGATCCTACCTGACGCTTTTTATCGCAACTCTCTACTGT
TTC
```

┠▶   *HMGS*

```
TCCATACCCGTTTTTTTGGGCTAGCGAATTCGAGCTCGGTACCCGGGAGGAGGACAGCTAAATGAAACTCTCAACTA
AACTTTGTTGGTGTGGTATTAAAGGAAGACTTAGGCCGCAAAAGCAACAACAATTACACAATACAAACTTGCAAATG
ACTGAACTAAAAAAACAAAAGACCGCTGAACAAAAAACCAGACCTCAAATGTCGGTATTAAAGGTATCCAAATTTA
CATCCCAACTCAATGTGTCAACCAATCTGAGCTAGAGAAATTTGATGGCGTTTCTCAAGGTAAATACACAATTGGTC
TGGGCCAAACCAACATGTCTTTTGTCAATGACAGAGAAGATATCTACTCGATGTCCCTAACTGTTTTGTCTAAGTTG
ATCAAGAGTTACAACATCGACACCAACAAAATTGGTAGATTAGAAGTCGGTACTGAAACTCTGATTGACAAGTCCAA
GTCTGTCAAGTCTGTCTT
```

C159A

```
GATGCAATTGTTTGGTGAAAACACTGACGTCGAAGGTATTGACACGCTTAATGCCGCGTACGGTGGTACCAACGCGT
TGTTCAACTCTTTGAACTGGATTGAATCTAACGCATGGGATGGTAGAGACGCCATTGTAGTTTGCGGTGATATTGCC
ATCTACGATAAGGGTGCCGCAAGACCAACCGGTGGTGCCGGTACTGTTGCTATGTGGATCGGTCCTGATGCTCCAAT
TGTATTTGACTCTGTAAGAGCTTCTTACATGGAACACGCCTACGATTTTTACAAGCCAGATTTCACCAGCGAATATC
CTTACGTCGATGGTCATTTTTCATTAACTTGTTACGTCAAGGCTCTTGATCAAGTTTACAAGAGTTATTCCAAGAAG
GCTATTTCTAAAGGGTTGGTTAGCGATCCCGCTGGTTCGGATGCTTTGAACGTTTTGAAATATTTCGACTACAACGT
TTTCCATGTTCCAACCTGTAAATTGGTCACAAAATCATACGGTAGATTACTATATAACGATTTCAGAGCCAATCCTC
AATTGTTCCCAGAAGTTGACGCCGAATTAGCTACTCGCGATTATGACGAATCTTTAACCGATAAGAACATTGAAAAA
ACTTTTGTTAATGTTGCTAAGCCATTCCACAAAGAGAGAGTTGCCCAATCTTTGATTGTTCCAACAAACACAGGTAA
CATGTACACCGCATCTGTTTATGCCGCCTTTGCCATCTCTATTAAACTATGTTGGATCTGACGACTTACAAGGCAAGC
GTGTTGGTTTATTTTCTTACGGTTCCGGTTTAGCTGCATCTCTATATTCTTGCAAAATTGTTGGTGACGTCCAACAT
ATTATCAAGGAATTAGATATTACTAACAAATTAGCCAAGAGAATCACCGAAACTCCAAAGGATTACGAAGCTGCCAT
CGAATTGAGAGAAAATGCCCATTTGAAGAAGAACTTCAAACCTCAAGGTTCCATTGAGCATTTGCAAAGTGGTGTTT
ACTACTTGACCAACATCGATGACAAATTTAGAAGATCTT
```

FIG. 24B

```
       HMGS        ◄┤                                              rrnB terminator
ACGATGTTAAAAAATAAGTCGACCTGCAGGCATGCAAGCTTGGCTGTTTTGGCGGATGAGAGAAGATTTTCAGCCTG
ATACAGATTAAATCAGAACGCAGAAGCGGTCTGATAAAACAGAATTTGCCTGGCGGCAGTAGCGCGGTGGTCCCACC
TGACCCCATGCCGAACTCAGAAGTGAAACGCCGTAGCGCCGATGGTAGTGTGGGGTCTCCCCATGCGAGAGTAGGGA
ACTGCCAGGCATCAAATAAAACGAAAGGCTCAGTCGAAAGACTGGGCCTTTCGTTTTATCTGTTGTTTGTCGGTGAA
CGCTCTCCTGAGTAGGACAAATCCGCCGGGAGCGGATTTGAACGTTGCGAAGCAACGGCCCGGAGGGTGGCGGGCAG
GACGCCCGCCATAAACTGCCAGGCATCAAATTAAGCAGAAGGCCATCCTGACGGATGGCCTTTTTGCGTTTCTACAA
ACTCTTTTGTTTATTTTTCTAAATACATTCAAATATGTATCCGCTCATGAGACAATAACCCTGATAAATGCTTCAAT
AATATTGAAAAAGGAAGAGTATGAGTATTCAACATTTCCGTGTCGCCCTTATTCCCTTTTTTGCGGCATTTTGCCTT
CCTGTTTTTGCTCACCCAGAAACGCTGGTGAAAGTAAAAGATGCTGAAGATCAGTTGGGTGCAGCAAACTATTAACT
GGCGAACTACTTACTCTAGCTTCCCGGCAACAATTAATAGACTGGATGGAGGCGGATAAAGTTGCAGGACCACTTCT
GCGCTCGGCCCTTCCGGCTGGCTGGTTTATTGCTGATAAATCTGGAGCCGGTGAGCGTGGGTCTCGCGGTATCATTG
CAGCACTGGGGCCAGATGGTAAGCCCTCCCGTATCGTAGTTATCTACACGACGGGGAGTCAGGCAACTATGGATGAA
CGAAATAGACAGATCGCTGAGATAGGTGCCTCACTGATTAAGCATTGGTAACTGTCAGACCAAGTTTACTCATATAT
ACTTTAGATTGATTTACGCGCCCTGTAGCGGCGCATTAAGCGCGGCGGGTGTGGTGGTTACGCGCAGCGTGACCGCT
ACACTTGCCAGCGCCCTAGCGCCCGCTCCTTTCGCTTTCTTCCCTTCCTTTCTCGCCACGTTCGCCGGCTTTCCCCG
TCAAGCTCTAAATCGGGGGCTCCCTTTAGGGTTCCGATTTAGTGCTTTACGGCACCTCGACCCCAAAAAACTTGATT
TGGGTGATGGTTCACGTAGTGGGCCATCGCCCTGATAGACGGTTTTTCGCCCTTTGACGTTGGAGTCCACGTTCTTT
AATAGTGGACTCTTGTTCCAAACTTGAACAACACTCAACCCTATCTCGGGCTATTCTTTTGATTTATAAGGGATTTT
GCCGATTTCGGCCTATTGGTTAAAAAATGAGCTGATTTAACAAAAATTTAACGCGAATTTTAACAAAATATTAACGT
TTACAATTTAAAAGGATCTAGGTGAAGATCCTTTTTGATAATCTCATGACCAAAATCCCTTAACGTGAGTTTTCGTT
CCACTGAGCGTCAGACCCCGTAGAAAAGATCAAAGGATCTTCTTGAGATCCTTTTTTTCTGCGCGTAATCTGCTGCT
TGCAAACAAAAAAACCACCGCTACCAGCGGTGGTTTGTTTGCCGGATCAAGAGCTACCAACTCTTTTTCCGAAGGTA
ACTGGCTTCAGCAGAGCGCAGATACCAAATACTGTCCTTCTAGTGTAGCCGTAGTTAGGCCACCACTTCAAGAACTC
TGTAGCACCGCCTACATACCTCGCTCTGCTAATCCTGTTACCAGTGGGGCATTTGAGAAGCACACGGTCACACTGCT
TCCGGTAGTCAATAAACCGGTAAACCAGCAATAGACATAAGCGGCTATTTAACGACCCTGCCCTGAACCGACGACCG
GGTCGAATTTGCTTTCGAATTTCTGCCATTCATCCGCTTATTATCACTTATTCAGGC Chloramphenicol resistance gene
                                                        ├─►
GTAGCACCAGGCGTTTAAGGGCACCAATAACTGCCTTAAAAAAATTACGCCCCGCCCTGCCACTCATCGCAGTACTG
TTGTAATTCATTAAGCATTCTGCCGACATGGAAGCCATCACAGACGGCATGATGAACCTGAATCGCCAGCGGCATCA
GCACCTTGTCGCCTTGCGTATAATATTTGCCCATGGTGAAAACGGGGGCGAAGAAGTTGTCCATATTGGCCACGTTT
AAATCAAAACTGGTGAAACTCACCCAGGGATTGGCTGAGACGAAAACATATTCTCAATAAACCCTTTAGGGAAATA
GGCCAGGTTTTCACCGTAACACGCCACATCTTGCGAATATATGTGTAGAAACTGCCGGAAATCGTCGTGGTATTCAC
TCCAGAGCGATGAAAACGTTTCAGTTTGCTCATGGAAAACGGTGTAACAAGGGTGAACACTATCCCATATCACCAGC
TCACCGTCTTTCATTGCCATACGGAATTCCGGATGAGCATTCATCAGGCGGGCAAGAATGTGAATAAAGGCCGGATA
AAACTTGTGCTTATTTTTCTTTACGGTCTTTAAAAAGGCCGTAATATCCAGCTGAACGGTCTGGTTATAGGTACATT
GAGCAACTGACTGAAATGCCTCAAAATGTTCTTTACGATGCCATTGGGATATATCAACGGTGGTATATCCAGTGATT
TTTTTCTCCAT
         ◄┤
TTTAGCTTCCTTAGCTCCTGAAAATCTCGATAACTCAAAAAATACGCCCGGTAGTGATCTTATTTCATTATGGTGAA
AGTTGGAACCTCTTACGTGCCGATCAACGTCTCATTTTCGCCAAAAGTTGGCCCAGGGCTTCCCGGTATCAACAGGG
ACACCAGGATTTATTTATTCTGCGAAGTGATCTTCCGTCACAGGTATTTATTCGGCGCAAAGTGCGTCGGGTGATGC
TGCCAACTTACTGATTTAGTGTATGATGGTGTTTTTGAGGTGCTCCAGTGGCTTCTGTTTCTATCAGCTGTCCCTCC
TGTTCAGCTACTGACGGGGTGGTGCGTA
                         pACYC184 origin
ACGGCAAAAGCACCGCCGGACATCAGCGCTAGCGGAGTGTATACTGGCTTACTATGTTGGCACTGATGAGGGTGTCA
GTGAAGTGCTTCATGTGGCAGGAGAAAAAAGGCTGCACCGGTGCGTCAGCAGAATATGTGATACAGGATATATTCCG
```

FIG. 24C

CTTCCTCGCTCACTGACTCGCTACGCTCGGTCGTTCGACTGCGGCGAGCGGAAATGGCTTACGAACGGGGCGGAGAT
TTCCTGGAAGATGCCAGGAAGATACTTAACAGGGAAGTGAGAGGGCCGCGGCAAAGCCGTTTTTCCATAGGCTCCGC
CCCCCTGACAAGCATCACGAAATCTGACGCTCAAATCAGTGGTGGCGAAACCCGACAGGACTATAAAGATACCAGGC
GTTTCCCCCTGGCGGCTCCCTCGTGCGCTCTCCTGTTCCTGCCTTTCGGTTTACCGGTGTCATTCCGCTGTTATGGC
CGCGTTTGTCTCATTCCACGCCTGACACTCAGTTCCGGGTAGGCAGTTCGCTCCAAGCTGGACTGTATGCACGAACC
CCCCGTTCAGTCCGACCGCTGCGCCTTATCCGGTAACTATCGTCTTGAGTCCAACCCGGAAAGACATGCAAAAGCAC
CACTGGCAGCAGCCACTGGTAATTGATTTAGAGGAGTTAGTCTTGAAGTCATGCGCCGGTTAAGGCTAAACTGAAAG
GACAAGTTTTGGTGACTGCGCTCCTCCAAGCCAGTTACCTCGGTTCAAAGAGTTGGTAGCTCAGAGAACCTTCGAAA
AACCGCCCTGCAAGGCGGTTTTTTCGTTTTCAGAGCAAGAGATTACGCGCAGACCAAAACGATCTCAAGAAGATCAT
CTTATTAATCAGATAAAATATTTGCTCATGAGCCCGAAGTGGCGAGCCCGATCTTCCCCATCGGTGATGTCGGCGAT
ATAGGCGCCAGCAACCGCACCTGTGGCGCCGGTGATGCCGGCCACGATGCGTCCGGCGTAGAGGATCTGCTCATGTT
TGACAGCTTATC (SEQ ID NO:12)

METHOD FOR ENHANCING PRODUCTION OF ISOPRENOID COMPOUNDS

CROSS-REFERENCE

This application claims the benefit of U.S. Provisional Patent Application No. 60/573,492, filed May 21, 2004, which application is incorporated herein by reference in its entirety.

STATEMENT REGARDING FEDERALLY SPONSORED RESEARCH

The U.S. government may have certain rights in this invention, pursuant to grant no. BES-9911463 awarded by the National Science Foundation and grant no. FDN00014-99-0182 awarded by the Office of Naval Research.

FIELD OF THE INVENTION

The present invention is in the field of production of isoprenoid compounds, and in particular host cells that are genetically modified to produce isoprenoid compounds.

BACKGROUND OF THE INVENTION

Isoprenoids constitute an extremely large and diverse group of natural products that have a common biosynthetic origin, i.e., a single metabolic precursor, isopentenyl diphosphate (IPP). At least 20,000 isoprenoids have been described. By definition, isoprenoids are made up of so-called isoprene (C5) units. The number of C-atoms present in the isoprenoids is typically divisible by five (C5, C10, C15, C20, C25, C30 and C40), although irregular isoprenoids and polyterpenes have been reported. Isoprenoid compounds are also referred to as "terpenes" or "terpenoids." Important members of the isoprenoids include the carotenoids, sesquiterpenoids, diterpenoids, and hemiterpenes. Carotenoids include, e.g., lycopene, β-carotene, and the like, many of which function as antioxidants. Sesquiterpenoids include, e.g., artemisinin, a compound having antimalarial activity. Diterpenoids include, e.g., taxol, a cancer chemotherapeutic agent.

Isoprenoids comprise the most numerous and structurally diverse family of natural products. In this family, terpenoids isolated from plants and other natural sources are used as commercial flavor and fragrance compounds as well as antimalarial and anticancer drugs. A majority of the terpenoid compounds in use today are natural products or their derivatives. The source organisms (e.g., trees, marine invertebrates) of many of these natural products are neither amenable to the large-scale cultivation necessary to produce commercially viable quantities nor to genetic manipulation for increased production or derivatization of these compounds. Therefore, the natural products must be produced semi-synthetically from analogs or synthetically using conventional chemical syntheses. Furthermore, many natural products have complex structures, and, as a result, are currently uneconomical or impossible to synthesize. Such natural products must be either extracted from their native sources, such as trees, sponges, corals and marine microbes; or produced synthetically or semi-synthetically from more abundant precursors. Extraction of a natural product from a native source is limited by the availability of the native source; and synthetic or semi-synthetic production of natural products can suffer from low yield and/or high cost. Such production problems and limited availability of the natural source can restrict the commercial and clinical development of such products.

The biosynthesis of isoprenoid natural products in engineered microbes could tap the unrealized commercial and therapeutic potential of these natural resources and yield less expensive and more widely available fine chemicals and pharmaceuticals. A major obstacle to high level terpenoid biosynthesis is the production of terpene precursors. Previous studies have shown that, when expressed in E. coli, the mevalonate pathway provides for production of isopentenyl pyrophosphate (IPP), which can be isomerized and polymerized into isoprenoids and terpenes of commercial value. Optimal redirection of microbial metabolism toward isoprenoid production requires that introduced biosynthetic pathway be properly engineered to both efficiently funnel carbon to IPP and not allow build up of intermediates, which can be toxic. In fact, it has been shown that the expression of mevalonate-producing enzymes can inhibit cell growth and limit the productivity of microbial cultures. It was suggested that the previously reported growth inhibition upon the expression of the mevalonate pathway in the absence of an IPP isomerase, FPP synthase, and terpene synthase led to the accumulation of toxic levels of IPP.

There is a need in the art for improved isoprenoid-producing or isoprenoid precursor-producing host cells that provide for both robust host cell growth and high-level production of isoprenoid compounds, as well as the polyprenyl diphosphate precursors of such compounds. The present invention addresses this need and provides related advantages.

Literature

U.S. Patent Publication No. 2004/005678; U.S. Patent Publication No. 2003/0148479; Martin et al. (2003) Nat. Biotech. 21(7):796–802; Polakowski et al. (1998) Appl. Microbiol. Biotechnol. 49: 67–71; Wilding et al. (2000) J Bacteriol 182(15): 4319–27; U.S. Patent Publication No. 2004/0194162; Donald et al. (1997) Appl. Env. Microbiol. 63:3341–3344; Jackson et al. (2003) Organ. Lett. 5:1629–1632; U.S. Patent Publication No. 2004/0072323; U.S. Patent Publication No. 2004/0029239; U.S. Patent Publication No. 2004/0110259; U.S. Patent Publication No. 2004/0063182; U.S. Pat. No. 5,460,949; U.S. Patent Publication No. 2004/0077039; U.S. Pat. Nos. 6,531,303; 6,689,593; Hamano et al. (2001) Biosci. Biotechnol. Biochem. 65:1627–1635; T. Kuzuyama. (2004) Biosci. Biotechnol. Biochem. 68(4): 931–934; T. Kazuhiko. (2004) Biotechnology Letters. 26: 1487–1491; Brock et al. (2004) Eur J Biochem. 271: 3227–3241; Choi, et al. (1999) Appl. Environ. Microbio. 65 4363–4368; Parke et al., (2004) Appl. Environ. Microbio. 70: 2974–2983; Subrahmanyam et al. (1998) J Bact. 180: 4596–4602; Murli et al. (2003) J Ind. Microbiol. Biotechnol. 30: 560–509.

SUMMARY OF THE INVENTION

The present invention provides methods of producing an isoprenoid or an isoprenoid precursor in a genetically modified host cell. The methods generally involve modulating the level of hydroxymethylglutaryl-CoA (HMG-CoA) in the cell, such that the level of HMG-CoA is not toxic to the cell and/or does not substantially inhibit cell growth, but is maintained at a level that provides for high-level production of mevalonate, IPP, and other downstream products of an isoprenoid or isoprenoid pathway, e.g., polyprenyl diphosphates and isoprenoid compounds. The present invention further provides genetically modified host cells that are suitable for use in a subject method. The present invention further provides recombinant nucleic acid constructs for use in generating a subject genetically modified host cell, including recombinant nucleic acid constructs comprising nucleotide sequences encoding one or more mevalonate pathway enzymes, and recombinant vectors (e.g., recombinant expression vectors) comprising same. The present invention further provides methods for identifying nucleic acids that encode HMG-CoA reductase (HMGR) variants that provide for relief of HMG-CoA accumulation-induced toxicity. The present invention further provides methods for identifying agents that reduce intracellular accumulation of HMG-CoA.

BRIEF DESCRIPTION OF THE DRAWINGS

FIGS. 13A–C depict the nucleotide sequence of the pBAD24MevT plasmid (SEQ ID NO:1).

FIGS. 14A–C depict the nucleotide sequence of the pBAD33MevT plasmid (SEQ ID NO:2).

FIGS. 15A–C depict the nucleotide sequence of the pMevT plasmid (SEQ ID NO:3).

FIGS. 16A–D depict the nucleotide sequence of the pMBIS plasmid (SEQ ID NO:4).

FIGS. 17A–B depict the nucleotide sequence of the pADS plasmid (SEQ ID NO:5).

FIGS. 18A–B depict the nucleotide sequence of the pAtoB plasmid (SEQ ID NO:6).

FIGS. 19A–B depict the nucleotide sequence of the pHMGS plasmid (SEQ ID NO:7).

FIGS. 20A–C depict the nucleotide sequence of the pHMGR plasmid (SEQ ID NO:8).

FIGS. 21 A–C depict the nucleotide sequence of the pBAD 18HMGR plasmid (SEQ ID NO:9).

FIGS. 22A–C depict the nucleotide sequence of the pHMGSR plasmid (SEQ ID NO:10).

FIGS. 23A–C depict the nucleotide sequence of the pBAD33MevT(C159A) plasmid (SEQ ID NO:11).

FIGS. 24A–C depict the nucleotide sequence of the pHMGS(C 159A) plasmid (SEQ ID NO:12).

DEFINITIONS

The terms "isoprenoid," "isoprenoid compound," "terpene," "terpene compound," "terpenoid," and "terpenoid compound" are used interchangeably herein. Isoprenoid compounds are made up various numbers of so-called isoprene (C5) units.

The number of C-atoms present in the isoprenoids is typically evenly divisible by five (e.g., C5, C10, C15, C20, C25, C30 and C40). Irregular isoprenoids and polyterpenes have been reported, and are also included in the definition of "isoprenoid." Isoprenoid compounds include, but are not limited to, monoterpenes, sesquiterpenes, triterpenes, polyterpenes, and diterpenes.

As used herein, the term "prenyl diphosphate" is used interchangeably with "prenyl pyrophosphate," and includes monoprenyl diphosphates having a single prenyl group (e.g., IPP and DMAPP), as well as polyprenyl diphosphates that include 2 or more prenyl groups. Monoprenyl diphosphates include isopentenyl pyrophosphate (IPP) and its isomer dimethylallyl pyrophosphate (DMAPP).

As used herein, the term "terpene synthase" refers to any enzyme that enzymatically modifies IPP, DMAPP, or a polyprenyl pyrophosphate, such that a terpenoid compound is produced. The term "terpene synthase" includes enzymes that catalyze the conversion of a prenyl diphosphate into an isoprenoid.

The word "pyrophosphate" is used interchangeably herein with "diphosphate." Thus, e.g., the terms "prenyl diphosphate" and "prenyl pyrophosphate" are interchangeable; the terms "isopentenyl pyrophosphate" and "isopentenyl diphosphate" are interchangeable; the terms farnesyl diphosphate" and farnesyl pyrophosphate" are interchangeable; etc.

The term "mevalonate pathway" or "MEV pathway" is used herein to refer to the biosynthetic pathway that converts acetyl-CoA to IPP. The mevalonate pathway comprises enzymes that catalyze the following steps: (a) condensing two molecules of acetyl-CoA to acetoacetyl-CoA; (b) condensing acetoacetyl-CoA with acetyl-CoA to form HMG-CoA; (c) converting HMG-CoA to mevalonate; (d) phosphorylating mevalonate to mevalonate 5-phosphate; (e) converting mevalonate 5-phosphate to mevalonate 5-pyrophosphate; and (f) converting mevalonate 5-pyrophosphate to isopentenyl pyrophosphate. The mevalonate pathway is illustrated schematically in FIG. 2. The "top half" of the mevalonate pathway refers to the enzymes responsible for the conversion of acetyl-CoA to mevalonate through a MEV pathway intermediate.

Figure 3:
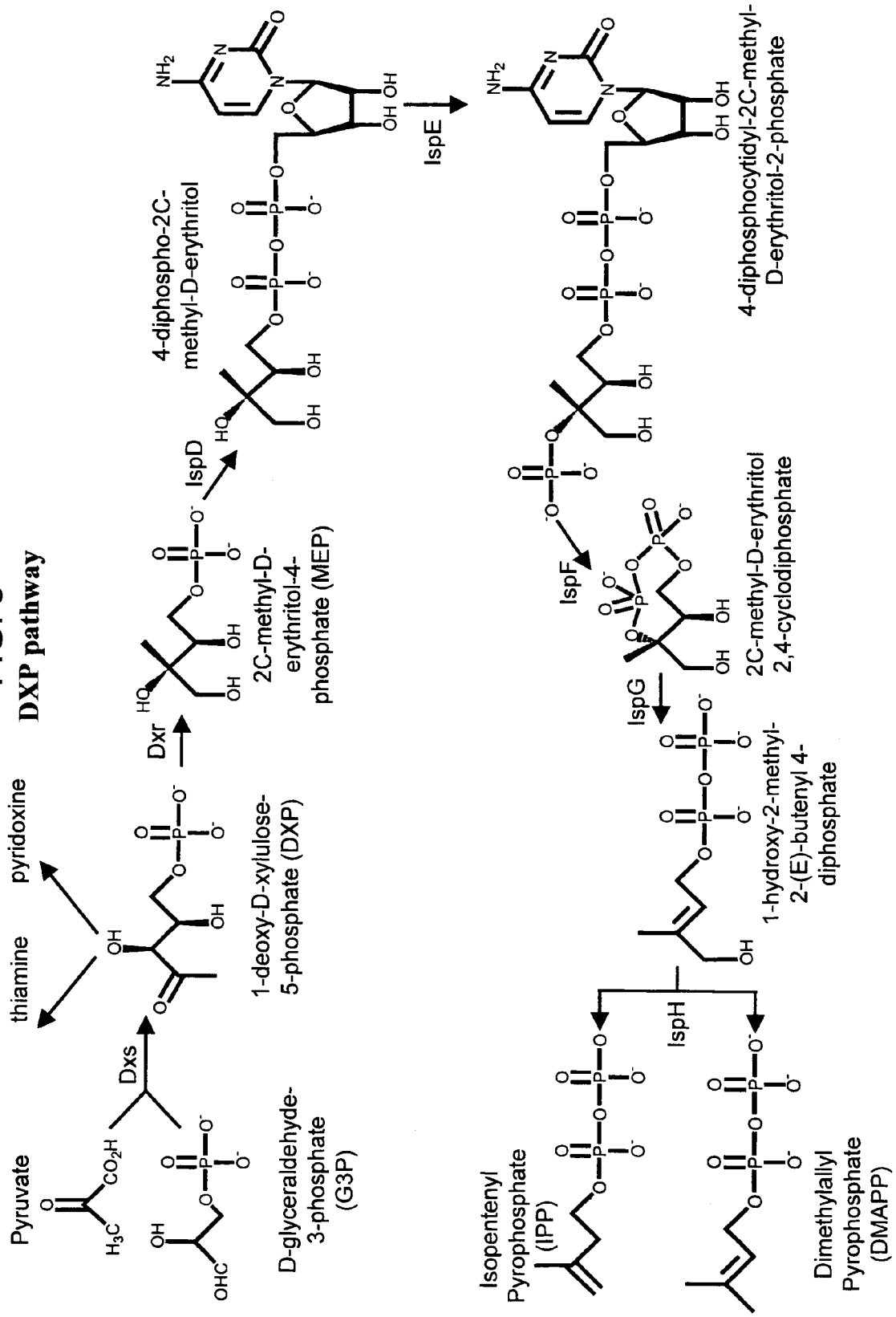
FIG. 3 is a schematic representation of the DXP pathway for the production of IPP and dimethylallyl pyrophosphate (DMAPP).

The term "1-deoxy-D-xylulose 5-diphosphate pathway" or "DXP pathway" is used herein to refer to the pathway that converts glyceraldehyde-3-phosphate and pyruvate to IPP and DMAPP through a DXP pathway intermediate, where DXP pathway comprises enzymes that catalyze the reactions depicted schematically in FIG. 3.

As used herein, the term "prenyl transferase" is used interchangeably with the terms "isoprenyl diphosphate synthase" and "polyprenyl synthase" (e.g., "GPP synthase," "FPP synthase," "OPP synthase," etc.) to refer to an enzyme that catalyzes the consecutive 1'–4 condensation of isopentenyl diphosphate with allylic primer substrates, resulting in the formation of prenyl diphosphates of various chain lengths.

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

As used herein, the terms "operon" and "single transcription unit" are used interchangeably to refer to two or more contiguous coding regions (nucleotide sequences that encode a gene product such as an RNA or a protein) that are coordinately regulated by one or more controlling elements (e.g., a promoter). As used herein, the term "gene product" refers to RNA encoded by DNA (or vice versa) or protein that is encoded by an RNA or DNA, where a gene will typically comprise one or more nucleotide sequences that encode a protein, and may also include introns and other non-coding nucleotide sequences.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

The term "naturally-occurring" as used herein as applied to a nucleic acid, a cell, or an organism, refers to a nucleic acid, cell, or organism that is found in nature. For example, a polypeptide or polynucleotide sequence that is present in an organism (including viruses) that can be isolated from a source in nature and which has not been intentionally modified by a human in the laboratory is naturally occurring.

The term "heterologous nucleic acid," as used herein, refers to a nucleic acid wherein at least one of the following is true: (a) the nucleic acid is foreign ("exogenous") to (i.e., not naturally found in) a given host microorganism or host cell; (b) the nucleic acid comprises a nucleotide sequence that is naturally found in (e.g., is "endogenous to") a given host microorganism or host cell (e.g., the nucleic acid comprises a nucleotide sequence endogenous to the host microorganism or host cell); however, in the context of a heterologous nucleic acid, the same nucleotide sequence as found endogenously is produced in an unnatural (e.g., greater than expected or greater than naturally found) amount in the cell, or a nucleic acid comprising a nucleotide sequence that differs in sequence from the endogenous nucleotide sequence but encodes the same protein (having the same or substantially the same amino acid sequence) as found endogenously is produced in an unnatural (e.g., greater than expected or greater than naturally found) amount in the cell; (c) the nucleic acid comprises two or more nucleotide sequences that are not found in the same relationship to each other in nature, e.g., the nucleic acid is recombinant. An example of a heterologous nucleic acid is a nucleotide sequence encoding HMGR operably linked to a transcriptional control element (e.g., a promoter) to which an endogenous (naturally-occurring) HMGR coding sequence is not normally operably linked. Another example of a heterologous nucleic acid a high copy number plasmid comprising a nucleotide sequence encoding HMGR. Another example of a heterologous nucleic acid is a nucleic acid encoding HMGR, where a host cell that does not normally produce HMGR is genetically modified with the nucleic acid encoding HMGR; because HMGR-encoding nucleic acids are not naturally found in the host cell, the nucleic acid is heterologous to the genetically modified host cell.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below).

Thus, e.g., the term "recombinant" polynucleotide or nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

By "construct" is meant a recombinant nucleic acid, generally recombinant DNA, which has been generated for the purpose of the expression of a specific nucleotide sequence(s), or is to be used in the construction of other recombinant nucleotide sequences.

As used herein, the term "exogenous nucleic acid" refers to a nucleic acid that is not normally or naturally found in and/or produced by a given bacterium, organism, or cell in nature. As used herein, the term "endogenous nucleic acid" refers to a nucleic acid that is normally found in and/or produced by a given bacterium, organism, or cell in nature. An "endogenous nucleic acid" is also referred to as a "native nucleic acid" or a nucleic acid that is "native" to a given bacterium, organism, or cell. For example, the nucleic acids encoding HMGS, mevalonate kinase, and phosphomevalonate kinase in Example 1 represent exogenous nucleic acids to *E. coli*. These mevalonate pathway nucleic acids were cloned from *Sacchromyces cerevisiae*. In *S. cerevisiae*, the gene sequences encoding HMGS, MK, and PMK on the chromosome would be "endogenous" nucleic acids.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The term "transformation" is used interchangeably herein with "genetic modification" and refers to a permanent or transient genetic change induced in a cell following introduction of new nucleic acid (i.e., DNA exogenous to the cell). Genetic change ("modification") can be accomplished either by incorporation of the new DNA into the genome of the host cell, or by transient or stable maintenance of the new DNA as an episomal element. Where the cell is a eukaryotic cell, a permanent genetic change is generally achieved by introduction of the DNA into the genome of the cell. In prokaryotic cells, permanent changes can be introduced into the chromosome or via extrachromosomal elements such as plasmids and expression vectors, which may contain one or more selectable markers to aid in their maintenance in the recombinant host cell.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid (e.g., an expression vector that comprises a nucleotide sequence encoding one or more biosynthetic pathway gene products such as mevalonate pathway gene products), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject prokaryotic host cell is a genetically modified prokaryotic host cell (e.g., a bacterium), by virtue of introduction into a suitable prokaryotic host cell a heterologous nucleic acid, e.g., an exogenous nucleic acid that is foreign to (not normally found in nature in) the prokaryotic host cell, or a recombinant nucleic acid that is not normally found in the prokaryotic host cell; and a subject eukaryotic host cell is a genetically modified eukaryotic host cell, by virtue of introduction into a suitable eukaryotic host cell a heterologous nucleic acid, e.g., an exogenous nucleic acid that is foreign to the eukaryotic host cell, or a recombinant nucleic acid that is not normally found in the eukaryotic host cell.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

Expression cassettes may be prepared comprising a transcription initiation or transcriptional control region(s) (e.g., a promoter), the coding region for the protein of interest, and a transcriptional termination region. Transcriptional control regions include those that provide for over-expression of the protein of interest in the genetically modified host cell; those that provide for inducible expression, such that when an inducing agent is added to the culture medium, transcription of the coding region of the protein of interest is induced or increased to a higher level than prior to induction.

A nucleic acid is "hybridizable" to another nucleic acid, such as a cDNA, genomic DNA, or RNA, when a single stranded form of the nucleic acid can anneal to the other nucleic acid under the appropriate conditions of temperature and solution ionic strength. Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Hybridization conditions and post-hybridization washes are useful to obtain the desired determine stringency conditions of the hybridization. One set of illustrative post-hybridization washes is a series of washes starting with 6×SSC (where SSC is 0.15 M NaCl and 15 mM citrate buffer), 0.5% SDS at room temperature for 15 minutes, then repeated with 2×SSC, 0.5% SDS at 45° C. for 30 minutes, and then repeated twice with 0.2×SSC, 0.5% SDS at 50° C. for 30 minutes. Other stringent conditions are obtained by using higher temperatures in which the washes are identical to those above except for the temperature of the final two 30 minute washes in 0.2×SSC, 0.5% SDS, which is increased to 60° C. Another set of highly stringent conditions uses two final washes in 0.1×SSC, 0.1% SDS at 65° C. Another example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C. Stringent hybridization conditions and post-hybridization wash conditions are hybridization conditions and post-hybridization wash conditions that are at least as stringent as the above representative conditions.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art.

The greater the degree of similarity or homology between two nucleotide sequences, the greater the value of the melting temperature (Tm) for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). Typically, the length for a hybridizable nucleic acid is at least about 10 nucleotides. Illustrative minimum lengths for a hybridizable nucleic acid are: at least about 15 nucleotides; at least about 20 nucleotides; and at least about 30 nucleotides. Furthermore, the skilled artisan will recognize that the temperature and wash solution salt concentration may be adjusted as necessary according to factors such as length of the probe.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acids substitution groups are: valine-leucine-isoleucine, phenylalanine-tyrosine, lysine-arginine, alanine-valine, and asparagine-glutamine.

"Synthetic nucleic acids" can be assembled from oligonucleotide building blocks that are chemically synthesized using procedures known to those skilled in the art. These building blocks are ligated and annealed to form gene segments which are then enzymatically assembled to construct the entire gene. "Chemically synthesized," as related to a sequence of DNA, means that the component nucleotides were assembled in vitro. Manual chemical synthesis of DNA may be accomplished using well-established procedures, or automated chemical synthesis can be performed using one of a number of commercially available machines. The nucleotide sequence of the nucleic acids can be modified for optimal expression based on optimization of nucleotide sequence to reflect the codon bias of the host cell. The skilled artisan appreciates the likelihood of successful expression if codon usage is biased towards those codons favored by the host. Determination of preferred codons can be based on a survey of genes derived from the host cell where sequence information is available.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), J. Mol. Biol. 215:403–10. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See Meth. Mol. Biol. 70: 173–187 (1997). Also, the GAP program using the Needleman and Wunsch alignment method can be utilized to align sequences. See J. Mol. Biol. 48: 443–453 (1970).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a genetically modified host cell" includes a plurality of such host cells and reference to "the HMG-CoA reductase" includes reference to one or more HMG-CoA reductases and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides methods of reducing the inhibitory accumulation of HMG-CoA in genetically modified host cells useful in the production of isoprenoids or isoprenoid precursor and methods for increasing production of an isoprenoid or isoprenoid precursor in these host cells through the elimination of this toxicity. The methods generally involve modulating the level of hydroxymethylglutaryl-CoA (HMG-CoA) in the host cell, such that the level of HMG-CoA is not toxic to the host cell, and/or does not substantially inhibit cell growth of the host cell. The present invention further provides genetically modified host cells that are suitable for use in a subject method. The present invention further provides recombinant nucleic acid constructs for use in generating a subject genetically modified host cell. The present invention further provides methods for identifying variant HMGR polypeptides that provide for relief of HMG-CoA accumulation-induced toxicity. The methods generally involve determining the effect, if any, of a test HMGR variant on HMG-CoA accumulation-induced cell toxicity. The present invention further provides methods for identifying inhibitors of HMGS. The methods generally involve determining the effect, if any, of a test compound on HMG-CoA accumulation-induced cell toxicity.

Figure 2:
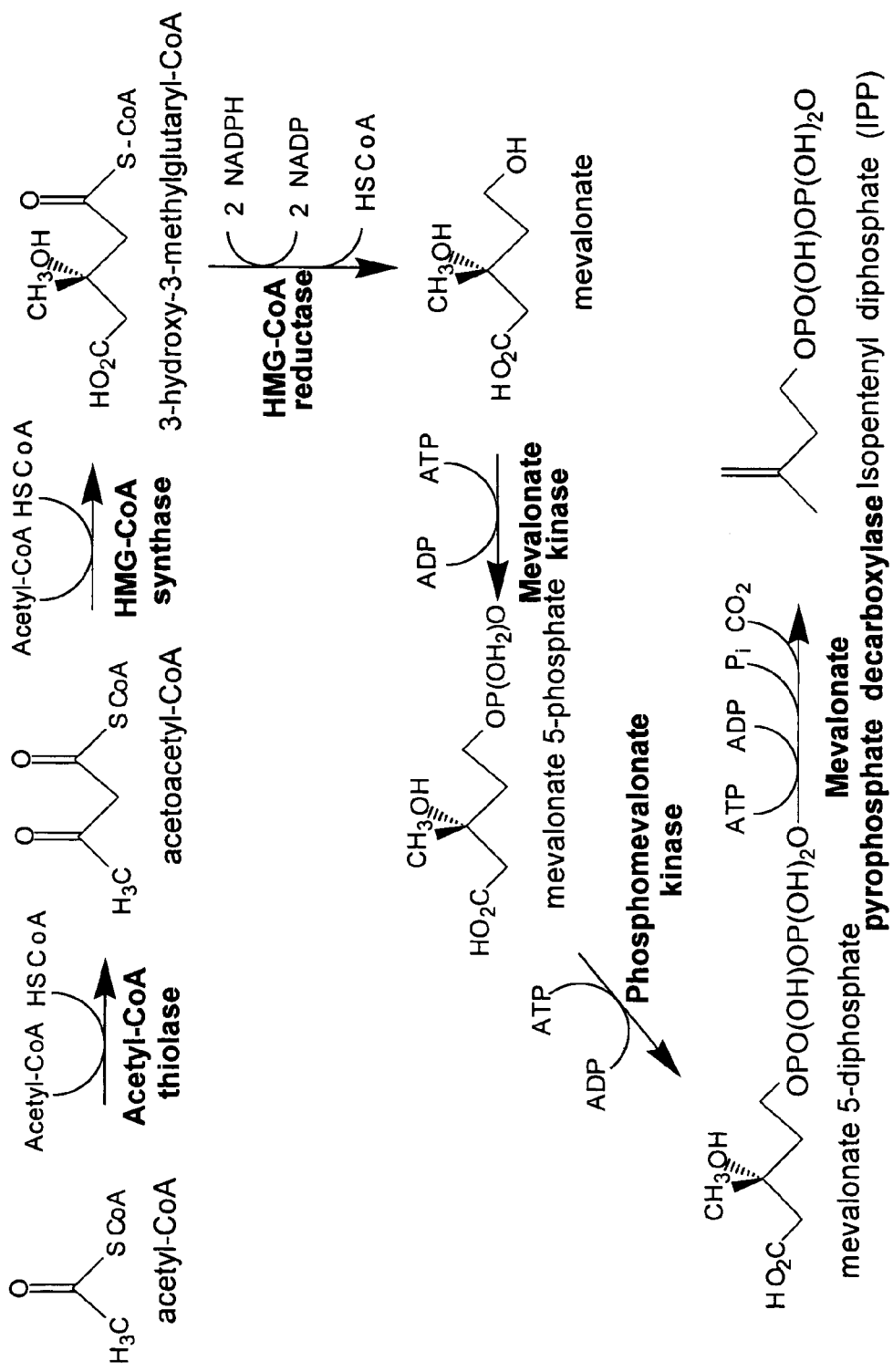
FIG. 2 is a schematic representation of the mevalonate (MEV) pathway for the production of IPP.

The present invention is based in part on the unexpected observation that HMG-CoA, an intermediate in the mevalonate pathway, is toxic when it accumulates in a microbial host genetically modified to produce isoprenyl pyrophosphate (IPP) or an IPP precursor via the mevalonate pathway. This observation was made by studying the increased production of isoprenoid compounds (and/or precursors such as mevalonate, IPP, and polyprenyl diphosphates) in host cells (e.g., a host microorganism) that were transformed ("genetically modified") with one or more heterologous nucleic acids comprising nucleotide sequences encoding one or more mevalonate pathway enzymes. Mevalonate pathway enzymes are depicted in FIG. 2. The mevalonate pathway comprises the following enzymatic reactions: (a) condensing two molecules of acetyl-CoA to acetoacetyl-CoA; (b) condensing acetoacetyl-CoA with acetyl-CoA to form HMG-CoA; (c) converting HMG-CoA to mevalonate; (d) phosphorylating mevalonate to mevalonate 5-phosphate; (e) converting mevalonate 5-phosphate to mevalonate 5-pyrophosphate; and (f) converting mevalonate 5-pyrophosphate to isopentenyl pyrophosphate. The observation that increasing the expression level of the mevalonate pathway resulted in inhibition of cell growth was unexpected.

One can generate isoprenoid compounds (for suitable constructs and methods, see U.S. Patent Publication Nos. 20030148479, and 20040005678; and Martin et al. (2003) *Nature Biotech.* 21(7):796–802) by expressing the mevalonate pathway in a bacterium. The mevalonate pathway enzymes required for production of IPP vary, depending on the culture conditions. For example, in some embodiments, a host cell that produces isoprenoid or isoprenoid precursor compounds is one that has been genetically modified with two or more heterologous nucleic acids comprising nucleotide sequences encoding mevalonate kinase (MK), phosphomevalonate kinase (PMK), and mevalonate pyrophosphate decarboxylase (MPD) (and optionally also isopentenyl pyrophosphate isomerase); and the host cell is cultured in medium that includes mevalonate. In other embodiments, a host cell that produces isoprenoid or isoprenoid precursor compounds is one that has been genetically modified with two or more heterologous nucleic acids comprising nucleotide sequences encoding acetoacetyl-CoA thiolase, hydroxymethylglutaryl-CoA synthase (HMGS), hydroxymethylglutaryl-CoA reductase (HMGR), MK, PMK, and MPD (and optionally also IPP isomerase).

In an effort to increase the levels of isoprenoid production in hosts genetically altered to contain an exogenous mevalonate pathway or in hosts that already contain a native (endogenous) mevalonate pathway, one can increase the level of activity of the individual enzymes in the pathway within the cell. A common tool used to modulate levels of activity of engineered enzymes within a cell is to modulate the rate at which an mRNA encoding the enzyme is transcribed. One can attempt to achieve this goal by changing the promoter (transcription initiation or transcription control sequence) to a stronger promoter.

In host cells expressing the mevalonate pathway, one would generally expect that changing the strength of the promoter controlling expression of the entire mevalonate pathway would change the levels of production of isoprenoids. For example, when changing from a modified lactose-inducible promoter, such as the one found in pBluescript and the pBBR1MCS plasmids, to a stronger promoter, such as a consensus arabinose- or lactose-inducible promoter, one would generally expect the expression of each of the enzymes to increase, thus increasing the levels of isoprenoid production. Because the mevalonate pathway feeds off the abundant cellular precursor acetyl-CoA, production of IPP is not expected to be limited by precursor production. Contrary to what would be expected, it was observed that increasing the expression level of the first half of the mevalonate pathway (i.e., increasing the expression level of acetoacetyl CoA thiolase, HMGS, and HMGR) resulted in inhibition of cell growth, yet the amount of the desired isoprenoid product was not increased.

When introducing a recombinant DNA molecule into an organism for the production of an enzyme, whether that enzyme is to be used catalytically within the cell or purified from the cell, toxic effects can be observed (B. R. Glick. (1995) *Biotech Advances.* 13(12): 247–261). These effects can be due to utilization of the host's cellular resources, to an unexpected activity of the enzyme or to the accumulation of a toxic intermediate. The latter case may be caused by the increased levels of the final product of the pathway, or be a specific to a single enzyme for which the activity is out of balance with that of the other enzymes in the pathway leading to accumulation of an intermediate to levels that are toxic to the cell. Further, it is difficult to predict a priori at what level metabolites of an introduced pathway will be toxic, or the levels at which they will begin to show toxic effects as chemically similar intermediates can have drastically different intracellular effects.

For example, acetyl-CoA levels can be quite high within a cell, without any toxic effects. Propionyl-CoA has been shown to be toxic to *Aspirgillus nidulans* grown on glucose (Brock et al. *Eur J. Biochem.* 271, 3227–3241 (2004)). *E. coli* engineered for PHA accumulation using a propionyl-coA synthetase do not show apparent propinoyl-CoA induced growth inhibition, and can be grown to high cell densities (Choi, et al. *Appl Environ. Microbio.* 65 4363–4368 (1999)). Sensitivity to caffeate, p-coumarate, and ferulate was observed in *Acinetobacter* strains with a knockout of hydroxycinnamoyl-CoA hydratase/lyase potentially due to Hydroxycinnamoyl-CoA accumulation (Parke et al., *Appl. Environ. Microbio.* 70, 2974–2983 (2004)). The same reference demonstrated sensitivity to the same three substrates in *E. coli* upon overexpression of hcaC, potentially due to hydroxycinnamoyl-CoA accumulation. Over-production of a β-ketoacyl carrier protein synthetase II (KAS II) in *E. coli* led to the accumulation of malonyl-CoA to levels that inhibited growth. Expression of malonyl-CoA:ACP transacylase, the enzyme catalyzing the conversion of malonyl-CoA to malonyl-ACP, along with KAS II partially relieved this toxicity (Subrahmanyam et al. *J. Bact.* 180 4596–4602 (1998)). The expression of malonyl/methylmalonyl-CoA ligase in *E. coli* combined with methylmalonate feeding led to accumulations of methylmalonyl-CoA to as much as 90% of the acyl-coA pool. Growth inhibition in this strain was not reported (Murli et al. *J. Ind. Microbiol. Biotechnol.* 30 500–509 (2003)).

Most mevalonate pathway containing organisms, *Homo sapiens* for instance, utilize HMGR as a regulatory point in the production of isoprenoids. To limit isoprenoid production, these organisms reduce HMGR activity, which would naturally promote a build-up of its precursor HMG-CoA. This HMG-CoA build-up would presumably also occur in patients taking cholesterol lowering drugs [(such as the statins Atorvastatin (Lipitor) Fluvastatin (Lescol) Lovastatin (Altocor, Mevacor) Pravastatin (Pravachol) Rosuvastatin (Crestor), and Simvastatin (Zocor)],)), which inhibit the activity of HMGR. The widespread use of statin drugs without systemic toxicity due to HMG-CoA accumulation would indicate that HMG-CoA is a non-toxic metabolite for *Homo sapiens*.

In the case of toxicity due to expression of mevalonate pathway enzymes, metabolite analysis using liquid chromatography—mass spectrometry linked the growth inhibition phenotype with the accumulation of pathway intermediate, 3-hydroxy-3-methylglutaryl-coenzyme A (HMG-CoA). This finding demonstrates that in engineered ("genetically modified") microbial host cells, the intermediate HMG-CoA can accumulate and cause cell death or prevent the cell from further growth and therefore impede the production of IPP by both limiting cell growth and/or indicating a bottleneck in the flow of carbon to the desired isoprenoids.

The accumulation of HMG-CoA implies that there exists an imbalance between the production of HMG-CoA and the subsequence conversion of HMG-CoA to mevalonate in the engineered mevalonate pathway. By increasing the total activity of HMG-CoA Reductase (HMGR), which is the enzyme that converts HMG-CoA into mevalonate, this toxicity is overcome, resulting in an increase in production of mevalonate and isoprenoids synthesized from mevalonate. Another way to decrease the accumulation of HMG-CoA is to limit production of HMG-CoA by decreasing the total activity of HMG-CoA synthase (HMGS), which is the enzyme that converts acetoacetyl-CoA to HMG-CoA. Yet another way to decrease the accumulation of HMG-CoA is to decrease the level and/or activity of an enzyme, such as acetoacetyl-CoA thiolase, that affects the production of acetoacetyl-CoA, which is the direct precursor of HMG-CoA.

In accordance with the methods of the invention, one can tune the HMG-CoA levels to those that eliminate toxicity and allow proper growth of microbial cells, thus allowing significant increases in isoprenoid or isoprenoid precursor production. It is important to note that while tuning the HMG-COA levels may not lead to an increase in isoprenoid produced per cell and may even lead to a decrease, an increase in cell growth may more than offset such losses, resulting in the production of more isoprenoid in a culture. For example and illustration, if HMGS activities are modified such that levels of HMG-CoA are decreased within the cell and the level of isoprenoid per cell is decrease by 10% but cell growth is doubled the total productivity of the culture (the activity per cell multiplied by the number of cells in the culture) will, in fact, increase. Thus, the production of IPP or an isoprenoid compound can be increased by reducing the level of HMG-CoA Synthase activity and/or by increasing the level of HMG-CoA Reductase activity in the cell.

Modulating (increasing or decreasing) the level of active HMGS and/or HMGR activity in a cell is achievable by: 1) modulating (increasing or decreasing) transcription of a nucleic acid encoding the enzyme; 2) modulating (increasing or decreasing) translation of an mRNA encoding the enzyme; 3) modulating (increasing or decreasing) stability of the mRNA encoding the enzyme; 4) modulating (increasing or decreasing) stability of the enzyme itself; and 5) modulating (increasing or decreasing) enzymatic activity of the enzyme. To reduce or eliminate the toxic effect of HMG-CoA and increase isoprenoid and/or isoprenoid precursor production, the present invention also provides cells, and nucleic acids and expression vectors useful in preparing such cells, in which the mevalonate pathway has been re-designed such that HMG-CoA levels do not become toxic.

Efforts to achieve higher IPP production have focused on the over-expression of putatively rate limiting enzymes including HMGR in cells containing an endogenous mevalonate pathway. See, e.g., Polakowski et al. (1998) *Appl. Microbiol. Biotechnol.* 49: 67–71 (producing the isoprenoid squalene); Donald et al. (1997) *Appl. Env. Microbiol.* 63:3341–3344 (producing the isoprenoid squalene); and Jackson et al. (2003) *Org. Letters* 5:1629–1632 (producing the isoprenoid epi-cedrol). These reports do not discuss relief of HMG-CoA-induced toxicity via expression of HMGR but instead are driven by the observation that in many organisms HMGR is the evolved regulation point for production of isoprenoids in organism that naturally utilize the mevalonate pathway to produce isoprenoids. In these cases, the production of the respective isoprenoid increased three to ten-fold upon overexpression of the HMGR.

The following studies have looked at mevalonate pathway enzymes in *E coli*. Hamano et al ((2001) *Biosci. Biotechnol. Biochem.* 65: 1627–1635) reported that attempts to transform *E. coli* strain DYM1 with a high-copy construct pGEM-MEV, containing a mevalonate pathway cluster from *Streptomyces*, were unsuccessful. Attempts to transform the same strain with pMW-MEV, a low copy construct containing the same mevalonate pathway cluster, were successful. The authors suggested that high expression of the *Streptomyces* mevalonate pathway genes in *E. coli* might be lethal. Wilding et al. (2000) *J Bacteriol* 182(15): 4319–27) reported that in the presence of mevalonate the gram-positive bacterium *S. pneumoniae*, mutants lacking both HMG-CoA synthase and HMG-CoA reductase were viable while mutants lacking just HMG-CoA synthase were non-viable.

Additionally, the present invention provides screening methods for identifying a gene product having HMG-CoA detoxification activity. The methods generally involve a) producing a test cell by introducing into a genetically modified host cell an exogenous nucleic acid comprising a nucleotide sequence encoding a candidate gene product, wherein the genetically modified host cell produces, in the absence of such exogenous nucleic acid, HMG-CoA at levels effective to inhibit growth of the genetically modified host cell; and b) determining the effect, if any, of expression of the candidate gene product on the growth of the test cell. A reduction in growth inhibition indicates that the exogenous nucleic acid encodes a gene product having sufficient activity to relieve HMG-CoA toxicity.

Additionally, the present invention provides screening methods for identifying compounds that inhibit the accumulation of HMG-CoA. The methods generally involve a) contacting a test cell that produces HMG-CoA at levels effective to inhibit its growth with the test compound; and b) determining the effect on cell growth, if any, of contacting the test compound with the cell. A reduction in growth inhibition indicates that the exogenous compound has sufficient activity to relieve HMG-CoA toxicity.

As mentioned above, most mevalonate pathway containing organisms, Homo sapiens for instance, utilize HMGR as a regulatory point in the production of isoprenoids. To limit isoprenoid production, these organisms reduce HMGR activity, which would cause a build-up of its precursor HMG-CoA. This HMG-CoA build-up would also occur in patients taking cholesterol lowering drugs which inhibit the activity of HMGR.

Figure 1:
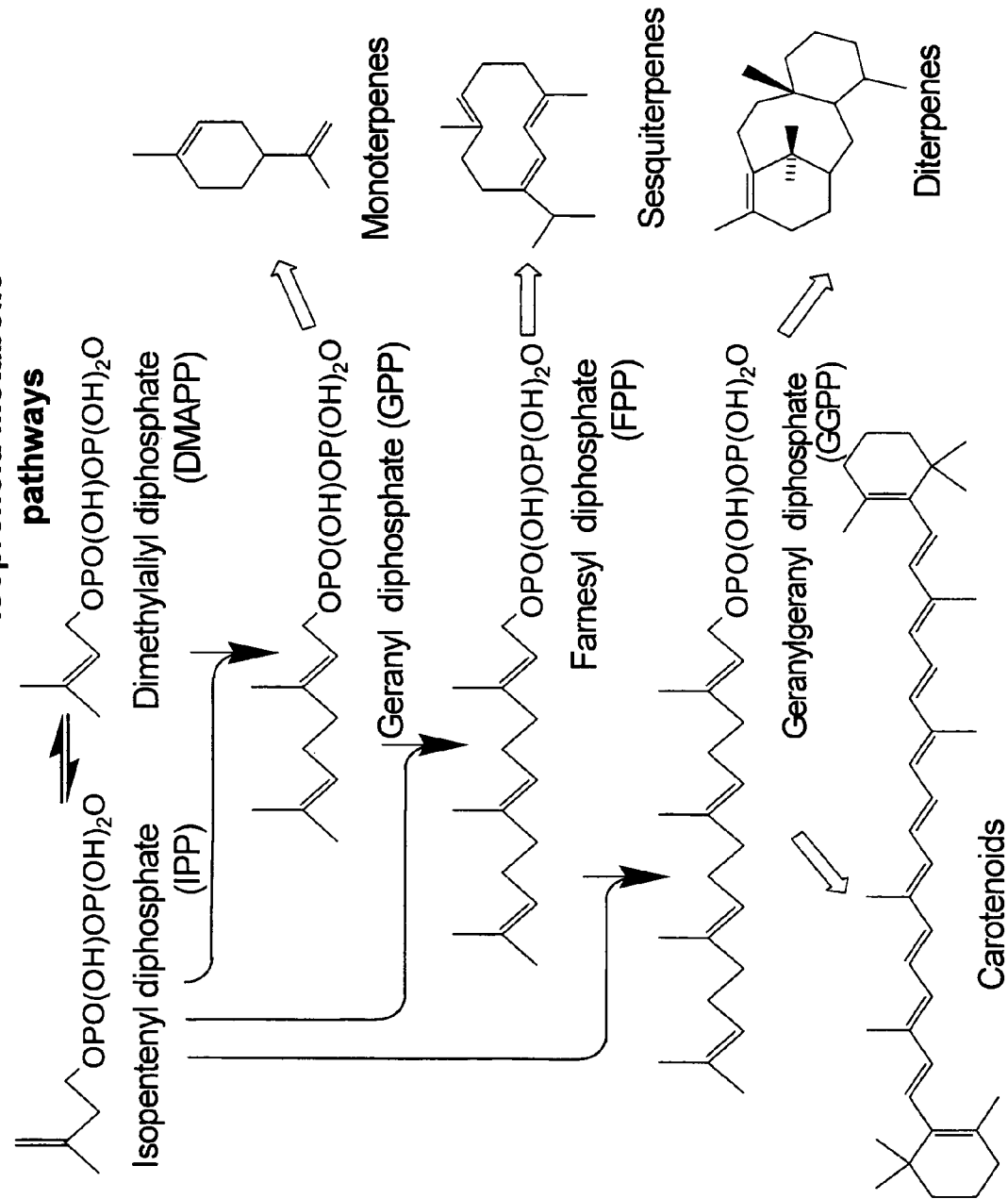
FIG. 1 is a schematic representation of isoprenoid metabolic pathways that result in the production of the isoprenoid biosynthetic pathway intermediates polyprenyl diphosphates geranyl diphosphate (GPP), farnesyl diphosphate (FPP), and geranylgeranyl diphosphate (GGPPP), from isopentenyl diphosphate (IPP) and dimethylallyl diphosphate (DMAPP).

To aid in an understanding of the present invention, FIGS. 1–3 are provided, which figures illustrate schematically biosynthetic pathways leading to isoprenoid or isoprenoid precursor production.

FIG. 1 depicts isoprenoid pathways involving modification of isopentenyl diphosphate (IPP) and/or its isomer dimethylallyl diphosphate (DMAPP) by prenyl transferases to generate the polyprenyl diphosphates geranyl diphosphate (GPP), farnesyl diphosphate (FPP), and geranylgeranyl diphosphate (GGPP). GPP and FPP are further modified by terpene synthases to generate monoterpenes and sesquiterpenes, respectively; and GGPP is further modified by terpene synthases to generate diterpenes and carotenoids. IPP and DMAPP are generated by one of two pathways: the mevalonate (MEV) pathway and the 1-deoxy-D-xylulose-5-phosphate (DXP) pathway.

FIG. 2 depicts schematically the MEV pathway, where acetyl CoA is converted via a series of reactions to IPP.

FIG. 3 depicts schematically the DXP pathway, in which pyruvate and D-glyceraldehyde-3-phosphate are converted via a series of reactions to IPP and DMAPP. Eukaryotic cells other than plant cells use the MEV isoprenoid pathway exclusively to convert acetyl-coenzyme A (acetyl-CoA) to IPP, which is subsequently isomerized to DMAPP. Plants use both the MEV and the mevalonate-independent, or DXP pathways for isoprenoid synthesis. Prokaryotes, with some exceptions, use the DXP pathway to produce IPP and DMAPP separately through a branch point.

Methods of Relieving HMG-CoA Toxicity and Enhancing Production Isoprenoids and Isoprenoid Precursors The present invention provides methods of producing an isoprenoid or isoprenoid precursor in a host cell that comprises, or is genetically modified to comprise, nucleic acids comprising nucleotide sequences encoding one or more enzymes in the mevalonate pathway. The methods generally involve modulating the level of HMG-CoA in the cell, such that the level of HMG-CoA is not toxic to the cell and/or does not substantially inhibit cell growth, yet that the level of HMG-CoA provides for enhanced production of isoprenoid or isoprenoid precursors by the cell. The methods generally involve culturing a genetically modified host cell in a suitable medium, where the genetically modified host cell is one that is genetically modified with one or more nucleic acids heterologous to the host cell, where the one or more nucleic acids comprise nucleotide sequences encoding one or more polypeptides that provide for relief or reduction of HMG-CoA accumulation-induced cell growth inhibition or toxicity. Polypeptides that provide for relief or reduction of HMG-CoA accumulation-induced cell growth inhibition or toxicity include, but are not limited to, HMG-CoA reductase (HMGR), HMG-CoA synthase (HMGS), and an enzyme affecting the level of acetoactyl-CoA (the precursor of HMG-CoA) or mevalonate. The level of an isoprenoid compound (and/or an isoprenoid precursor downstream of HMG-CoA, such as mevalonate, isoprenyl pyrophosphate (IPP), or a polyprenyl diphosphate) produced in the genetically modified host cell is higher than the level of the isoprenoid compound (and/or an isoprenoid precursor downstream of HMG-CoA, such as mevalonate, IPP, or a polyprenyl diphosphate) produced in a control ("parent") host cell that is not genetically modified with the one or more nucleic acids encoding HMGS and/or HMGR. The present invention further provides genetically modified host cells that are suitable for use in a subject method. The present invention further provides recombinant nucleic acid constructs for use in generating a subject genetically modified host cell.

In some embodiments, the present invention provides a method for reducing HMG-CoA toxicity and enhancing production of an isoprenoid or isoprenoid precursor via a mevalonate pathway in a host cell, where the host cell produces the isoprenoid or isoprenoid precursor via a mevalonate pathway. The method generally involves: (a) genetically modifying the host cell to contain one or more heterologous nucleic acids encoding one or more enzymes that, when produced in the cell, reduce HMG-CoA accumulation-induced growth inhibition, as compared to a control parent host cell that is not genetically modified with said heterologous nucleic acids; and (b) culturing the genetically modified host cell under conditions such that the level of isoprenoid or isoprenoid precursor produced in the genetically modified host cell is higher than the level of isoprenoid or isoprenoid precursor produced in the control parent host cell.

The level of HMG-CoA in a parent host cell is modulated by decreasing the level of HMGS activity and/or by increasing the level of HMGR activity in the cell and/or by balancing the level of HMGS activity and HMGR activity such that HMG-CoA accumulation-induced cell toxicity is relieved. The level of HMG-CoA in a parent host cell is also modulated by genetic modifications that promote balanced flux of metabolites through the mevalonate pathway, as described in more detail below.

The present invention is applicable to host cells that produce IPP and/or mevalonate via the mevalonate pathway. Such host cells are referred to herein as "parent" host cells and comprise, or are genetically modified to comprise, nucleic acids comprising nucleotide sequences encoding one or more enzymes in the mevalonate pathway (and therefore produce IPP and/or mevalonate via the mevalonate pathway). Parent host cells exhibit HMG-CoA accumulation-induced toxicity, where the level of intracellular HMG-CoA inhibits cell growth, in the absence of an additional genetic modification, as described herein; thus, e.g., a parent host cell is one that, but for a genetic modification as described herein, would accumulate HMG-CoA intracellularly and exhibit HMG-CoA accumulation-induced toxicity. Parent host cells are genetically modified to include one or more nucleic acids heterologous to the host cell, where the one or more nucleic acids comprise nucleotide sequences encoding HMGR and/or HMGS and that provide for an increased level of HMGR activity and/or a decreased level of HMGS activity in the cell. HMG-CoA accumulation-induced growth inhibition in the host cell genetically modified with the one or more heterologous nucleic acids comprising nucleotide sequences encoding HMGR and/or HMGS is reduced, compared a parent host cell not genetically modified with the one or more heterologous nucleic acids comprising nucleotide sequences encoding HMGR and/or HMGS. Genetically modifying a host cell with one or more heterologous nucleic acids comprising nucleotide sequences encoding HMGR and/or HMGS results in: a) a decreased level of HMGS activity in the cell; b) an increased level of HMGR activity in the cell; c) a decreased level of HMGS activity and an increased level of HMGR activity in the cell; or d) a balance between the level of HMGS activity and the HMGR activity, such that HMG-CoA accumulation-induced toxicity in the cell is relieved.

Thus, e.g., a "parent" (or "parental") host cell is genetically modified to include one or more nucleic acids heterologous to the host cell, where the one or more nucleic acids comprise nucleotide sequences encoding HMGR and/or HMGS. The parent host cell is one that produces IPP via a mevalonate pathway and/or that produces mevalonate via a mevalonate pathway. The parent cell comprises, or is genetically modified to comprise, nucleic acids comprising nucleotide sequences encoding one or more enzymes in the mevalonate pathway (and produces IPP via the mevalonate pathway and/or produces mevalonate via a mevalonate pathway). The parent cell exhibits HMG-CoA accumulation-induced growth inhibition.

A parent cell that has been genetically modified to include one or more nucleic acids heterologous to the host cell, where the one or more nucleic acids comprise nucleotide sequences encoding HMGR and/or HMGS, is referred to as a "genetically modified host cell." HMG-CoA accumulation-induced growth inhibition in the genetically modified parent host cell is reduced, compared a parent host cell not genetically modified with the one or more heterologous nucleic acids comprising nucleotide sequences encoding HMGR and/or HMGS. In addition, production of an isoprenoid or an isoprenoid precursor is increased in the genetically modified host cell, compared to the parent host cell. Thus, e.g., production of an isoprenoid or isoprenoid precursor is increased by at least about 10%, at least about 20%, at least about 50%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, or at least about 500-fold, or more, in the genetically modified host cell, compared to the parent host cell.

Decreasing the Level of HMGS Activity and/or Increasing the Level of HMGR Activity In some embodiments, a subject method of decreasing HMG-CoA accumulation-induced cell toxicity in a host cell comprises decreasing the level of HMGS activity in the cell and/or increasing the level of HMGR activity in the cell. Decreasing the level of HMGS activity in a cell includes decreasing the total amount of HMGS polypeptide within the cell; and decreasing the specific activity of HMGS polypeptide within the cell. Thus, in some embodiments, the level of HMGS activity in a cell is decreased by decreasing the total amount of HMGS in the cell. In other embodiments, the level of HMGS activity in a cell is decreased by decreasing the specific activity of HMGS in the cell. Similarly, increasing the level of HMGR activity in a cell includes increasing the total amount of HMGR polypeptide within the cell; and increasing the specific activity of HMGR polypeptide within the cell. Thus, in some embodiments, the level of HMGR activity in a cell is increase by increasing the total amount of HMGR in the cell. In other embodiments, the level of HMGR activity in a cell is increased by increasing the specific activity of HMGR in the cell.

Decreasing the level of HMGS activity in a cell is achieved in a number of ways, including, but not limited to: 1) decreasing transcription of a nucleic acid encoding HMGS; 2) decreasing translation of an mRNA encoding HMGS; 3) decreasing stability of the mRNA encoding HMGS; 4) decreasing stability of the HMGS polypeptide; and 5) decreasing enzymatic activity of the HMGS enzyme. Increasing the level of HMGR activity in a cell is achieved in a number of ways, including, but not limited to: 1) increasing transcription of a nucleic acid encoding HMGR; 2) increasing translation of an mRNA encoding HMGR; 3) increasing stability of the mRNA encoding HMGR; 4) increasing stability of the HMGR enzyme; and 5) increasing enzymatic activity of the HMGR enzyme.

Thus, in some embodiments of the invention, the desired non-toxic level of HMG-CoA is achieved with through modulation of both HMG-CoA synthase and HMG-CoA reductase activity in the cell. In one embodiment, the parent host cell is a naturally occurring yeast cell, or an *E. coli* host cell, that is genetically modified with a vector or vectors that contain HMGS and HMGR coding sequences. The encoded HMGS and HMGR enzymes are produced in the cell so that toxic levels of HMG-CoA are not reached and optimum flux through the pathway is achieved, providing high yields of the desired products (isoprenoid or isoprenoid precursor compound). In one embodiment, the HMGS and HMGR coding regions are controlled by different promoters. In another embodiment, the HMGS and HMGR coding sequences are on different vectors, with the HMGS coding sequence optionally located on a lower copy number vector. In one embodiment, the HMGS and HMGR coding sequences are on the same operon, but the HMGR coding sequence is located upstream of the HMGS coding sequence, and this arrangement is different from a naturally occurring operon containing both HMGS and HMGR coding sequences.

In some embodiments, decreasing the level of HMGS activity and/or increasing the level of HMGR activity in a cell reduces the level of HMG-CoA in the cell such that the toxicity and/or growth inhibition of the HMG-CoA level is reduced. Thus, in some embodiments, decreasing the level of HMGS activity and/or increasing the level of HMGR activity in a cell reduces the level of HMG-CoA by at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, compared to a control parent cell that exhibits HMG-CoA accumulation-induced growth inhibition. The level of HMG-CoA in a cell is readily determined using liquid chromatography-mass spectrometry, and the like.

In some embodiments, decreasing the level of HMGS activity and/or increasing the level of HMGR activity in a cell reduces growth inhibition by HMG-CoA accumulation in the cell. Thus, in some embodiments, decreasing the level of HMGS activity and/or increasing the level of HMGR activity in a cell reduces HMG-CoA accumulation-mediated growth inhibition by at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, compared to a control cell that exhibits HMG-CoA accumulation-induced growth inhibition. Growth of genetically modified host cells is readily determined using well-known methods, e.g., optical density (OD) measurement at about 600 nm ($OD_{600}$) of liquid cultures of bacteria; colony size; growth rate; and the like.

In one exemplary embodiment, a control parent cell is a prokaryotic host cell that has been genetically modified with one or more nucleic acids comprising nucleotide sequences encoding acetoacetyl-CoA thiolase, HMGS, and HMGR, where HMG-CoA is produced and accumulates intracellularly at levels that are growth inhibiting or toxic to the cell. As one non-limiting example, a control parent cell is an E. coli host cell that has been genetically modified with an expression construct comprising a nucleotide sequence encoding acetoacetyl-CoA thiolase, HMGS, and HMGR in a single polycistronic operon in the recited order on a plasmid or in the chromosome; and the genetically modified host cell is an E. coli genetically modified with expression construct(s) comprising the nucleotide sequences encoding acetoacetyl-CoA thiolase, HMGR, and HMGS in a single polycistronic operon in the adjusted recited order on a plasmid or in the chromosome. As an additional non-limiting example, a control parent cell is an E. coli host cell that has been genetically modified with an expression construct comprising a nucleotide sequence encoding acetoacetyl-CoA thiolase, HMGS, and HMGR in a single polycistronic operon in the recited order on a medium copy plasmid; and the genetically modified host cell is an E. coli genetically modified with expression construct(s) comprising a nucleotide sequence encoding acetoacetyl-CoA thiolase and HMGS in the recited order on a low copy plasmid, and a nucleotide sequence HMGR on a separate high copy plasmid. As an additional non-limiting example, a control parent cell is an E. coli host cell that has been genetically modified with an expression construct comprising a nucleotide sequence encoding acetoacetyl-CoA thiolase, HMGS, and HMGR in a single polycistronic operon in the recited order on a medium copy plasmid; and the genetically modified host cell is an E. coli genetically modified with expression construct(s) comprising a nucleotide sequence encoding acetoacetyl-CoA thiolase and HMGS in the recited order on a medium copy plasmid in which the ribosome binding site has been altered to reduce translation, and a nucleotide sequence HMGR on a separate medium copy plasmid for which the promoter has been changed to a stronger version. As an additional non-limiting example, a control parent cell is an E. coli host cell that has been genetically modified with an expression construct comprising a nucleotide sequence encoding acetoacetyl-CoA thiolase, HMGS, and HMGR in a single polycistronic operon in the recited order on a medium copy plasmid; and the genetically modified host cell is an E. coli genetically modified with expression construct(s) comprising a nucleotide sequence encoding acetoacetyl-CoA thiolase, HMGS with a engineered protease site, and HMGR to which a highly soluble protein such as glutathione transferase has been fused in the recited order on a medium copy plasmid.

Genetic alteration resulting in changes to the amino acid sequence of proteins, such as those recited above, will result in changes in the relative catalytic activity (as measured by Vmax or Vmax/Km) of HMGS and HMGR. Thus, in some embodiments, decreasing the level of HMGS activity and/or increasing the level of HMGR activity results in an increase of the ratio of HMGR catalytic activity to HMGS catalytic activity on a per cell basis of HMGR at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, or at least about 500-fold, or more, than HMGS in the genetically modified host cell, compared to the parent host cell. Growth of genetically modified host cells is readily determined using well-known methods, e.g., optical density (OD) measurement at about 600 nm ($OD_{600}$) of liquid cultures of bacteria; colony size; growth rate; and the like.

In another embodiment, the control parent cell is a eukaryotic cell, e.g., a yeast cell such as *Saccharomyces cerevisiae*. In some of these embodiments, the control parent eukaryotic cell comprises one or more mutations in the endogenous pyruvate decarboxylase gene, such that the pyruvate decarboxylase gene is functionally disabled, and such that HMG-CoA accumulates intracellularly at a level that is growth inhibiting or toxic to the cell. In practicing the invention, the control parent cell is further modified with modifications to the nucleic acid encoding HMGR or its control elements which increase transcription, translation, or specific activity levels, creating the genetically modified host cell. In one embodiment, the control parent cell is further modified through the introduction of HMGR on a plasmid under the control of an inducible promoter.

Modifications that Reduce HMG-CoA Accumulation by Decreasing the Level of Activity of HMG-CoA Synthase Those of skill in the art will appreciate, upon contemplation of this disclosure, that the level of HMG-CoA depends, at least in part, on the level of HMGS activity in the cell. The aforementioned decreases in HMG-CoA accumulation-induced cell growth inhibition and/or decreases in intracellular HMG-CoA levels are in some embodiments achieved through modulation of HMGS activity levels in the cell. Thus, in some embodiments, relief of HMG-CoA accumulation-induced toxicity and/or a non-toxic level of HMG-CoA is achieved via modulation of the level of HMG-CoA synthase activity in the cell. In these embodiments, a parent host cell that comprises, or is genetically modified to comprise, nucleic acids comprising nucleotide sequences encoding one or more enzymes in the mevalonate pathway (and produces IPP and/or mevalonate via the mevalonate pathway) is genetically modified to include a nucleic acid heterologous to the host cell, where the nucleic acid comprises a nucleotide sequence encoding HMGS, where HMG-CoA accumulation-induced growth inhibition in the host cell genetically modified with the heterologous nucleic acid comprising nucleotide sequences encoding HMGS is reduced, compared to a parent host cell not genetically modified with the heterologous nucleic acid comprising nucleotide sequences encoding HMGS.

In one embodiment, the heterologous HMGS-encoding nucleic acid is used to replace all or a part of an endogenous HMGS gene. In another embodiment, the parent host cell is one that has been genetically modified to contain an exogenous HMGS gene; and the exogenous HMGS gene of the parent host cell is replaced by a modified HMGS gene that provides for a lower level of HMGS activity, e.g., the amount of HMGS and/or the activity of the HMGS is lower than in the parent host cell. In another embodiment, the heterologous nucleic acid that reduces the HMGS activity level encodes an HMGS inhibitor or an anti-sense RNA that reduces translation of the HMGS transcript. In both cases, while the modified host cell's specific isoprenoid or isoprenoid precursor production rate may decrease when compared to the parent strain, the resulting relief in HMG-CoA associated growth inhibition would lead to greater cell densities, resulting in an overall increase in production.

In some embodiments, a heterologous nucleic acid is introduced into a parent host cell, and the heterologous nucleic acid recombines with an endogenous nucleic acid encoding HMGS, thereby genetically modifying the parent host cell. In some embodiments, the heterologous nucleic acid comprises a promoter that has reduced promoter strength compared to the endogenous promoter that controls transcription of the endogenous HMGS, and the recombination event results in substitution of the endogenous promoter with the heterologous promoter. In other embodiments, the heterologous nucleic acid comprises a nucleotide sequence encoding an HMGS that exhibits reduced enzymatic activity compared to the endogenous HMGS, and the recombination event results in substitution of the endogenous HMGS coding sequence with the heterologous HMGS coding sequence.

A genetically modified host cell suitable for use in a subject method is genetically modified with one or more heterologous nucleic acids, including a nucleic acid comprising a nucleotide sequence encoding HMGS, such that the level of HMGS activity in the cell is decreased. The level of HMGS activity is decreased in the cell by at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, compared to a parent host cell not genetically modified with the one or more nucleic acids comprising a nucleotide sequence encoding HMGS. The parent host cell exhibits HMG-CoA accumulation-induced growth inhibition.

In one exemplary embodiment, a control parent cell is a prokaryotic host cell that has been genetically modified with one or more nucleic acids comprising nucleotide sequences encoding acetoacetyl-CoA thiolase, HMGS, and HMGR, where HMG-CoA is produced and accumulates intracellularly at levels that are growth inhibiting or toxic to the cell. As one non-limiting example, a control parent cell is an *E. coli* host cell that has been genetically modified with an expression construct comprising the nucleotide sequence set forth in SEQ ID NO:1; and the genetically modified host cell is an *E. coli* genetically modified with expression construct(s) comprising a modified version of the nucleotide sequences set forth in SEQ ID NO:1 in which the ribosome binding site upstream of HMGS has been altered such that translation is reduced. As one non-limiting example, a control parent cell is an *E. coli* host cell that has been genetically modified with an expression construct comprising the nucleotide sequence set forth in SEQ ID NO:1; and the genetically modified host cell is an *E. coli* genetically modified with expression construct(s) comprising a modified version of the nucleotide sequences set forth in SEQ ID NO:1 in which a RNase site has been introduced into the coding region of HMGS. As one non-limiting example, a control parent cell is an *E. coli* host cell that has been genetically modified with an expression construct comprising the nucleotide sequence set forth in SEQ ID NO:1; and the genetically modified host cell is an *E. coli* genetically modified with expression construct(s) comprising the nucleotide sequences set forth in SEQ ID NO:2. See, e.g., FIG. 5 and Example 2. As one non-limiting example, a control parent cell is an *E. coli* host cell that has been genetically modified with an expression construct comprising the nucleotide sequence set forth in SEQ ID NO:1; and the genetically modified host cell is an *E. coli* genetically modified with expression construct(s) comprising the nucleotide sequences set forth in SEQ ID NO:1 and SEQ ID NO:8.

In another embodiment, the control parent cell is a eukaryotic cell, e.g., a yeast cell such as *Saccharomyces cerevisiae*. In some of these embodiments, the control parent eukaryotic cell comprises one or more mutations in the endogenous pyruvate decarboxylase gene, such that the pyruvate decarboxylase gene is functionally disabled, and such that HMG-CoA accumulates intracellularly at a level that is growth inhibiting or toxic to the cell.

The level of HMGS activity in the genetically modified host cell can be decreased in a number of ways, including, but not limited to, 1) decreasing the promoter strength of the promoter to which the HMGS coding region is operably linked; 2) decreasing the copy number of the plasmid comprising a nucleotide sequence encoding HMGS; 3) decreasing the stability of an HMGS mRNA (where an "HMGS mRNA" is an mRNA comprising a nucleotide sequence encoding HMGS); 4) modifying the sequence of the ribosome binding site of an HMGS mRNA such that the level of translation of the HMGS mRNA is decreased; 5) modifying the distance and/or sequence between the ribosome binding site of the HMGS mRNA and start codon of the HMGS coding sequence, such that the level of translation of the HMGS mRNA is decreased; 6) modifying the entire intercistronic region 5' of the start codon of the HMGS coding sequence such that the level of translation of the HMGS mRNA is decreased; 7) modifying the codon usage of HMGS such that the level of translation of the HMGS mRNA is decreased; 8) decreasing the enzyme stability of HMGS; 9) decreasing the specific activity (units activity per unit protein) of HMGS; and 10) where HMGS is encoded on an operon, changing the order of the coding regions on the polycistronic mRNA. Two or more of the aforementioned modifications can be made, in order to decrease the level of HMGS activity in the genetically modified host cell.

In some embodiments, the level of HMGS activity is decreased relative to the HMGS activity in a control parent cell by using a low-copy number plasmid, which plasmid comprises a nucleotide sequence encoding HMGS. Decreasing the plasmid copy number of a vector comprises a nucleotide sequence encoding HMGS is achieved by selecting a plasmid backbone that is known to be a low copy number plasmid. Low copy number plasmids generally provide for fewer than about 20 plasmid copies per cell, e.g., from about 5 plasmid copies per cell to about 20 plasmid copies per cell. Suitable low copy number plasmids include, but are not limited to, pACYC184, pBR332, pBAD33, pBBR1MCS, and pSC101. For example, pSC101 is generally present in a cell at about 5 copies per cell. In one embodiment of the invention, the HMGS and HMGR levels are modulated by placing the two genes on two different expression vectors, such that the HMGS coding sequence is on a low copy vector and the HMGR coding sequence is on a high copy vector. In another embodiment of the invention, the genes are on the same vector but under the control of different promoters, with the HMGS coding sequence being under the control of the weaker of the two promoters.

Modifications that Reduce Intracellular HMG-CoA Accumulation by Increasing the Level of HMG-CoA Reductase Activity Those of skill in the art will appreciate, upon contemplation of this disclosure, that the level of HMG-CoA depends, at least in part, on the level of HMGR activity in the cell. The aforementioned decreases in HMG-CoA accumulation-induced cell growth inhibition and/or decreases in intracellular HMG-CoA levels can be achieved in accordance with the methods of the invention by modulating HMGR activity levels in the cell. Thus, in one embodiment of the invention, a non-toxic level of HMG-CoA and/or relief of HMG-CoA accumulation-induced toxicity is achieved with through modulation of the level of HMG-CoA reductase activity in the cell. In these embodiments, a parent host cell that comprises, or is genetically modified to comprise, nucleic acids comprising nucleotide sequences encoding one or more enzymes in the mevalonate pathway, and produces IPP and/or mevalonate via the mevalonate pathway, is genetically modified to include a nucleic acid heterologous to the host cell, where the nucleic acid comprises a nucleotide sequence encoding HMGR, where HMG-CoA accumulation-induced growth inhibition in the host cell genetically modified with the heterologous nucleic acid comprising nucleotide sequences encoding HMGR is reduced, compared to a control parent host cell not genetically modified with the heterologous nucleic acid comprising nucleotide sequences encoding HMGR.

A genetically modified host cell suitable for use in a subject method is genetically modified with one or more nucleic acids, including a nucleic acid comprising a nucleotide sequence encoding HMGR, such that the level of HMGR activity in the cell is increased. The level of HMGR activity is increased in the cell by at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, compared to a control parent cell not genetically modified with the one or more nucleic acids comprising a nucleotide sequence encoding HMGR.

In one exemplary embodiment, a control parent cell is a prokaryotic host cell that has been genetically modified with one or more nucleic acids comprising nucleotide sequences encoding acetoacetyl-CoA thiolase, HMGS, and HMGR, where HMG-CoA is produced and accumulates intracellularly at levels that are growth inhibiting or toxic to the cell. In one embodiment, a control parent cell is a prokaryotic host cell that does not naturally contain a mevalonate pathway and that has been genetically modified to produce mevalonate; and the genetically modified host cell is further engineered to alter HMGR activity such that intracellular levels of HMG-CoA are not inhibitory or toxic to the cell. In one exemplary embodiment, a control parent cell is an *E. coli* host cell that has been genetically modified to produce mevalonate; and the genetically modified host cell is an *E. coli* genetically modified version of the control parent cell augmented with constructs other than those listed in the following references: Kato-Emori et al. *Mol Genet Genomics* (2001) 265:135–42, Learned R M, et al. *PNAS.* (1989) 86:2779–83, T. Dairi, et al. *Mol Gen Genet* (2000) 262: 957–964, Allen, et al. *Appl Environ. Microbio.* (1997). 63:3341–3344, Hedl, et al. *J. Bacteriol.*, (2002), 184:2116–2122, Jackson, et al. *Org. Lett.* (2003) 5:1629–1632, Randolph Y. Hampton, et al. (1994) *Cell,* 125:299–312, Markus Veen, et al. *FEMS Yeast Res* (2003) 4:87–95, Beach M J, et al. *J Bacteriol* (1989) 171:2994–3001, Bischoff K M, et al. *Protein Sci* (1997) 6:156–161, Friesen J A, et al. *Biochemistry.* (1997) 36:2173–7, Frimpong, et al. *J Biol Chem.* (1994) 269: 11478–83, Panda, et al. *Appl Microbiol Biotechnol* (2004) 66: 143–152.

As one non-limiting example, a control parent cell is an *E. coli* host cell that has been genetically modified with an expression construct comprising the nucleotide sequence set forth in SEQ ID NO:1; and the genetically modified host cell is an *E. coli* genetically modified with the expression construct comprising the nucleotide sequences set forth in SEQ ID NO:1 and SEQ ID NO:8. See, e.g., FIGS. 6 and 7 and Examples 3 and 4. As one non-limiting example, a control parent cell is an *E. coli* host cell that has been genetically modified with an expression construct comprising the nucleotide sequence set forth in SEQ ID NO:2; and the genetically modified host cell is an *E. coli* genetically modified with the expression construct comprising the nucleotide sequences set forth in SEQ ID NO:2 and SEQ ID NO:9. See, e.g., FIG. 10 and Example 6.

In another embodiment, the control parent cell is a eukaryotic cell, e.g., a yeast cell such as *Saccharomyces cerevisiae*. In some of these embodiments, the control parent eukaryotic cell comprises one or more mutations in the endogenous pyruvate decarboxylase gene, such that the pyruvate decarboxylase gene is functionally disabled, and such that HMG-CoA accumulates intracellularly at a level that is growth inhibiting or toxic to the cell.

The level of HMGR activity in the genetically modified host cell can be increased in a number of ways, including, but not limited to, 1) increasing the promoter strength of the promoter to which the HMGR coding region is operably linked; 2) increasing the copy number of the plasmid comprising a nucleotide sequence encoding HMGR; 3) increasing the stability of an HMGR mRNA (where an "HMGR mRNA" is an mRNA comprising a nucleotide sequence encoding HMGR); 4) modifying the sequence of the ribosome binding site of an HMGR mRNA such that the level of translation of the HMGR mRNA is increased; 5) modifying the sequence between the ribosome binding site of an HMGR mRNA and the start codon of the HMGR coding sequence such that the level of translation of the HMGR mRNA is increased; 6) modifying the entire intercistronic region 5' of the start codon of the HMGR coding region such that translation of the HMGR mRNA is increased; 7) modifying the codon usage of HMGR such that the level of translation of the HMGR mRNA is increased, 8) expressing rare codon tRNAs used in HMGR such that the level of translation of the HMGR MRNA is increased; 9) increasing the enzyme stability of HMGR; or 10) increasing the specific activity (units activity per unit protein) of HMGR. Two or more of the foregoing modifications may be made to provide for an increased level of HMGR activity.

In the nucleotide sequence set forth in SEQ ID NO:2, the HMGR coding region is under transcriptional control of the $P_{BAD}$ promoter. In some embodiments, the promoter to which the HMGR coding region is operably linked is a stronger promoter than the $P_{BAD}$ promoter, e.g., the level of mRNA transcribed is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 5-fold, at least about 10-fold, or more, higher than the level of mRNA transcribed using the $P_{BAD}$ promoter. Suitable promoters include, but are not limited to, a consensus lac promoter, a trp promoter, a tac promoter, a trc promoter, a lambda promoter, and a T7 promoter.

Increasing the plasmid copy number is achieved by selecting a plasmid backbone that is known to be a medium or high copy number plasmid. Low copy number plasmids generally provide for fewer than about 20 plasmid copies per cell. Medium copy number plasmids generally provide for from about 20 plasmid copies per cell to about 50 plasmid copies per cell, or from about 20 plasmid copies per cell to about 80 plasmid copies per cell. High copy number plasmids generally provide for from about 80 plasmid copies per cell to about 200 plasmid copies per cell, or more. In many embodiments, a nucleic acid comprising a nucleotide sequence encoding HMGR is a high copy number plasmid vector comprising a nucleic acid comprising a nucleotide sequence encoding HMGR. Suitable high copy number plasmids include, but are not limited to, pUC vectors (e.g., pUC8, pUC18, pUC19, and the like), pBluescript vectors, pGEM vectors, and pTZ vectors.

Those of skill in the art will appreciate, upon contemplation of this disclosure, that the level of HMG-CoA in a cell can be modified by modulating relative levels of HMGS and HMGR activities in the cell. Thus, in one embodiment of the invention, the desired non-toxic level of HMG-CoA is achieved with through modulation of both HMG-CoA synthase and HMG-CoA reductase activity in the cell. In one embodiment, the parent host cell is a naturally occurring yeast or *E. coli* host cell that is genetically modified with a vector or vectors that contain HMGS and HMGR coding sequences. The encoded HMGS and HMGR enzymes are produced in the cell so that toxic levels of HMG-CoA are not reached and optimum flux through the pathway is achieved, providing high yields of the desired products (isoprenoid or isoprenoid precursor compound). In one embodiment, the HMGS and HMGR coding regions are controlled by different promoters. In another embodiment, the HMGS and HMGR coding sequences are on different vectors, with the HMGS coding sequence optionally located on a lower copy number vector. In one embodiment, the HMGS and HMGR coding sequences are on the same operon, but the HMGR coding sequence is located upstream of the HMGS coding sequence, and this arrangement is different from a naturally occurring operon containing both HMGS and HMGR coding sequences.

Modifications that Reduce HMG-CoA Accumulation by Balancing the Flux through the Mevalonate Pathway In some embodiments, HMG-CoA accumulation-induced growth inhibition or toxicity is reduced by balancing the metabolite flow through the pathway. Metabolite flux can be balanced in a number of ways, including, but not limited to 1) mutations in enzymes upstream (ie, AtoB, AtoC, AtoA, AtoD) of HMGS that limit the substrate (AcetoAcetyl-CoA) available to the enzyme; 2) changes in expression of enzymes upstream (for example, AtoC, AtoA, AtoD, and enzymes involved in fatty acid biosynthesis) of HMGS that limit the substrate (acetoacetyl-CoA) available to the enzyme; 3) changes in expression of enzymes downstream (ie, MK, PMK, MVD) of HMGR that deplete the supply of mevalonate and thus promote conversion of HMG-CoA to mevalonate; 4) mutations that change the catalytic characteristics enzymes downstream (ie, MK, PMK, MVD) of HMGR that deplete the supply of mevalonate and thus promote conversion of HMG-CoA to mevalonate; 5) protein fusions of HMGR with an upstream enzyme (i.e. acetoacetyl-CoA thiolase, HMGS, ) to match expression of an HMG-CoA production enzyme to HMGR; 6) protein fusions of HMGS with an downstream enzyme (i.e. MK) to match expression of an HMG-CoA production enzyme to an enzyme responsible for metabolite movement away from HMG-CoA.

Increasing Isoprenoid or Isoprenoid Precursor Production

The above-described methods result in relief from HMG-CoA accumulation-induced toxicity and/or cell growth inhibition in a cell; and provide for increased production of an isoprenoid compound and/or an isoprenoid precursor compound in the cell. Thus, the present invention provides methods for increasing production of an isoprenoid compound or an isoprenoid precursor compound in a cell, where the methods generally involve modulating the levels of HMG-CoA in the cell such that the levels of HMG-CoA remain below a toxic or growth inhibitory level, and yet are at a level that is high enough to provide for increased production of an isoprenoid compound or an isoprenoid precursor compound.

The present invention provides methods for increasing production of an isoprenoid compound, or an isoprenoid compound precursor (e.g., mevalonate, IPP, a polyprenyl disphosphate, etc.) by a cell or cultures of a cell. The methods generally involve increasing the level of HMGR activity, and/or decreasing the level of HMGS activity, in a cell that exhibits HMG-CoA accumulation-induced cell growth inhibition. A cell that exhibits HMG-CoA accumulation-induced cell growth inhibition is in some embodiments a parent host cell that does not normally synthesize IPP or mevalonate via a mevalonate pathway, and that has been genetically modified with one or more nucleic acids comprising nucleotide sequences encoding mevalonate pathway enzyme(s), which enzymes are produced at levels that result in accumulation of toxic or growth inhibiting levels of HMG-CoA in the cell. A cell that exhibits HMG-CoA accumulation-induced cell growth inhibition is in some embodiments a parent host cell that does normally synthesize IPP or mevalonate via a mevalonate pathway, but that is genetically modified such that intracellular HMG-CoA accumulates at growth inhibiting or toxic levels. In one embodiment, the compound is the isoprenoid precursor compound IPP. In one embodiment, the host cell is an *E. coli* cell. In another embodiment, the host cell is a yeast cell.

In some embodiments, decreasing the level of HMGS activity and/or increasing the level of HMGR activity in a cell increases mevalonate production by the genetically modified host cell, or by a culture of the genetically modified host cell. Thus, in some embodiments, decreasing the level of HMGS activity and/or increasing the level of HMGR activity in a cell increases mevalonate production by at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, or at least about 500-fold, or more, in the genetically modified host cell, compared to the parent host cell. Mevalonate production is readily determined using well-known methods, e.g., gas chromatography-mass spectrometry, liquid chromatography-mass spectrometry, ion chromatography-mass spectrometry, thin layer chromatography, pulsed amperometric detection, uv-vis spectrometry, and the like.

In some embodiments, decreasing the level of HMGS activity and/or increasing the level of HMGR activity in a cell increases IPP production by the genetically modified host cell, or by a culture of the genetically modified host cell. Thus, in some embodiments, decreasing the level of HMGS activity and/or increasing the level of HMGR activity in a cell increases IPP production by at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, or at least about 500-fold, or more, in the genetically modified host cell, compared to the parent host cell. IPP production is readily determined using well-known methods, e.g., liquid chromatography-mass spectrometry, thin layer chromatography, ion chromatography-mass spectrometry, pulsed amperometric detection, uv-vis spectrometry, and the like.

In some embodiments, decreasing the level of HMGS activity and/or increasing the level of HMGR activity in a cell increases isoprenoid production by the genetically modified host cell. Thus, in some embodiments, decreasing the level of HMGS activity and/or increasing the level of HMGR activity in a cell increases mevalonate production by at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, or at least about 500-fold, or more, in the genetically modified host cell, compared to the parent host cell. Isoprenoid production is readily determined using well-known methods, e.g., gas chromatography-mass spectrometry, liquid chromatography-mass spectrometry, ion chromatography-mass spectrometry, pulsed amperometric detection, uv-vis spectrometry, and the like.

In some embodiments, a subject method provides for enhanced production of isoprenoid or isoprenoid precursor per cell, e.g., the amount of isoprenoid or isoprenoid precursor compound produced using a subject method is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, or at least about 500-fold, or more, higher than the amount of the isoprenoid or isoprenoid precursor compound produced by a control parent cell, on a per cell basis. Amount of cells measured by measuring dry cell weight or measuring optical density of the cell culture.

In other embodiments, a subject method provides for enhanced production of isoprenoid or isoprenoid precursor per unit volume of cell culture, e.g., the amount of isoprenoid or isoprenoid precursor compound produced using a subject method is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, or at least about 500-fold, or more, higher than the amount of the isoprenoid or isoprenoid precursor compound produced by a control parent cell, on a per unit volume of cell culture basis.

In some embodiments, a subject method for increasing production of an isoprenoid compound or an isoprenoid precursor compound comprises modulating the composition of the medium in which a host cell is cultured, such that the level of a mevalonate pathway intermediate (e.g., acetyl-CoA) is increased. In some embodiments, the culture medium comprises acetate, which increases the level of acetyl-CoA, and which in turn increases the level of HMG-CoA in the cell.

Isoprenoids that can be produced using the method of the invention include, but are not limited to, monoterpenes, including but not limited to, limonene, citranellol, geraniol, menthol, perillyl alcohol, linalool, thujone; sesquiterpenes, including but not limited to, periplanone B, gingkolide B, amorphadiene, artemisinin, artemisinic acid, valencene, nootkatone, epi-cedrol, epi-aristolochene, farnesol, gossypol, sanonin, periplanone, and forskolin; diterpenes, including but not limited to, casbene, eleutherobin, paclitaxel, prostratin, and pseudopterosin; triterpenes, including but not limited to, arbrusideE, bruceantin, testosterone, progesterone, cortisone, digitoxin. Isoprenoids also include, but are not limited to, carotenoids such as lycopene, $\alpha$- and $\beta$-carotene, $\alpha$- and $\beta$-cryptoxanthin, bixin, zeaxanthin, astaxanthin, and lutein. Isoprenoids also include, but are not limited to triterpenes, steroid compounds, and compounds that are composed of isoprenoids modified by other chemical groups, such as mixed terpene-alkaloids, and coenzyme Q-10.

Genetically Modified Host Cells

The present invention provides genetically modified host cells; and compositions comprising the genetically modified host cells. The genetically modified host cells are useful for producing an isoprenoid compound or an isoprenoid precursor compound, as discussed above.

As discussed above, a subject method for producing an isoprenoid or isoprenoid precursor generally involves culturing a genetically modified host cell in a suitable medium. The genetically modified host cell is one that has been genetically modified with one or more heterologous nucleic acids comprising nucleotide sequences encoding one or more enzymes that, when produced in the cell, relieve HMG-CoA accumulation-induced growth inhibition (toxicity) in the cell. The parent cell (e.g., the cell not genetically modified with one or more heterologous nucleic acids comprising nucleotide sequences encoding one or more enzymes that, when produced in the cell, relieve HMG-CoA accumulation-induced growth inhibition and/or toxicity in the cell) is a cell that produces, or is genetically modified to produce, IPP via a mevalonate pathway.

Thus, e.g., a "parent" (or "parental") host cell is genetically modified to include one or more nucleic acids heterologous to the host cell, where the one or more nucleic acids comprise nucleotide sequences encoding HMGR and/or HMGS. The parent host cell produces IPP via a mevalonate pathway and/or produces mevalonate via a mevalonate pathway. The parent cell comprises, or is genetically modified to comprise, nucleic acids comprising nucleotide sequences encoding one or more enzymes in the mevalonate pathway (and produces IPP via the mevalonate pathway and/or produces mevalonate via a mevalonate pathway). A parent cell that has been genetically modified to include one or more nucleic acids heterologous to the host cell, where the one or more nucleic acids comprise nucleotide sequences encoding HMGR and/or HMGS, is referred to as a "genetically modified host cell." HMG-CoA accumulation-induced growth inhibition in the genetically modified parent host cell is reduced, compared a parent host cell not genetically modified with the one or more heterologous nucleic acids comprising nucleotide sequences encoding HMGR and/or HMGS. Further the genetically modified host cell exhibits increased levels of mevalonate or isoprenoid products derived from a combination of increased per cell production of mevalonate and/or increased cell viability. It is understood that this invention can be iteratively applied to incrementally increase production of isoprenoid compounds so that in one context a particular cell line may be a genetically modified host cell and then in a later context it may be a parent host cell utilized as a starting point for further improvement. Alternately, this invention teaches of the toxicity of HMG-CoA accumulation and allows the de novo construction of genetic systems and associated host cells that avoid HMG-CoA toxicity otherwise associated with high-level isoprenoid prodution. Thus, if a genetically modified host cell can be further genetically modified to produce a cell that exhibits decreased cell viability due to HMG-CoA accumulation the further genetically modified cell will in fact be a parent host cell with respect to the initial genetically modified host cell.

In some embodiments, the parent cell is a cell that does not normally produce IPP or mevalonate via the mevalonate pathway; e.g., the parent cell is one that has been genetically modified with one or more heterologous nucleic acids comprising nucleotide sequences encoding one or more enzymes in the mevalonate pathway. As an example, a parent cell is a prokaryotic cell that does not normally produce IPP or mevalonate via the mevalonate pathway, and that has been genetically modified with one or more nucleic acids comprising nucleotide sequences encoding acetoacetyl-CoA thiolase, HMGS, and HMGR, where the levels of acetoacetyl-CoA thiolase and HMGS activity are such that HMG-CoA accumulates intracellularly at a level that is growth inhibiting or toxic. An example is an E. coli cell that has been genetically modified with a construct comprising a nucleotide sequence as set forth in SEQ ID NO:1. A second example of a parent host cell is an E. coli cell that has been genetically modified with a construct comprising a nucleotide sequence as set forth in SEQ ID NO:2.

In other embodiments, the parent cell is a cell that normally produces IPP and/or mevalonate via the mevalonate pathway, e.g., the parent cell is a cell that comprises endogenous nucleic acids encoding one or more enzymes in the mevalonate pathway. In these embodiments, the parent cell is genetically modified such that the level of HMG-CoA that accumulates intracellularly is toxic or growth inhibiting to the cell. As an example, one or more mutations are introduced in a pyruvate decarboxylase gene of the host cell that normally produces IPP and/or mevalonate via the mevalonate pathway, such that the pyruvate decarboxylase gene is functionally disabled, and such that HMG-CoA accumulates intracellularly at a level that is toxic to the cell. The parent cell in this case is a host cell that normally produces IPP and/or mevalonate via the mevalonate pathway, and that has been genetically modified to introduce one or more mutations in the endogenous pyruvate decarboxylase gene such that the pyruvate decarboxylase gene is functionally disabled.

To generate a subject genetically modified host cell, one or more nucleic acids comprising nucleotide sequences encoding an enzyme(s) that relieve HMG-CoA accumulation-induced growth inhibition is introduced stably or transiently into a parent host cell, using established techniques, including, but not limited to, electroporation, calcium phosphate precipitation, DEAE-dextran mediated transfection, liposome-mediated transfection, and the like. For stable transformation, a nucleic acid will generally further include a selectable marker, e.g., any of several well-known selectable markers such as neomycin resistance, ampicillin resistance, tetracycline resistance, chloramphenicol resistance, kanamycin resistance, and the like.

Mevalonate Pathway Enzymes

As noted above, a parent cell is a host cell that produces, or is genetically modified to produce, IPP via a mevalonate pathway and/or mevalonate via a mevalonate pathway, and that exhibits HMG-CoA accumulation-induced toxicity or growth inhibition. The mevalonate pathway comprises: (a) condensing two molecules of acetyl-CoA to acetoacetyl-CoA; (b) condensing acetoacetyl-CoA with acetyl-CoA to form HMG-CoA; (c) converting HMG-CoA to mevalonate; (d) phosphorylating mevalonate to mevalonate 5-phosphate; (e) converting mevalonate 5-phosphate to mevalonate 5-pyrophosphate; and (f) converting mevalonate 5-pyrophosphate to isopentenyl pyrophosphate. The mevalonate pathway enzymes required for production of IPP vary, depending on the culture conditions.

In some embodiments, a parent host cell is one that has been genetically modified with one or more heterologous nucleic acids comprising nucleotide sequences encoding acetoacetyl-CoA thiolase, HMGS, and HMGR, and the parent host cell is one that produces mevalonate. An non-limiting example of a parent host cell is an E. coli cell that has been genetically modified with a construct comprising a nucleotide sequence as set forth in SEQ ID NO:1 or a nucleotide sequence encoding enzymes functionally analogous to those enzymes encoded in SEQ ID NO:1 A further non-limiting example of a parent host cell is an E. coli cell that has been genetically modified with a construct comprising a nucleotide sequence as set forth in SEQ ID NO:2 or a nucleotide sequence encoding enzymes functionally analogous to those enzymes encoded in SEQ ID NO:2 A further non-limiting example of a parent host cell is an yeast cell that has been genetically modified with a construct comprising a nucleotide sequence as set forth in SEQ ID NO:7 or a nucleotide sequence encoding enzymes functionally analogous to those enzymes encoded in SEQ ID NO:7. A further non-limiting example of a parent host cell is an E. coli cell that has been genetically modified with one or more constructs comprising nucleotide sequences as set forth in SEQ ID NO:1 and SEQ ID NO:6 or nucleotide sequences that encode enzymes functionally analogous to those enzymes encoded in SEQ ID NO:1 and SEQ ID NO:6. A further non-limiting example of a parent host cell is an E. coli cell that has been genetically modified with one or more constructs comprising the nucleotide sequences as set forth in SEQ ID NO:1 and SEQ ID NO:7 or nucleotide sequences that encode enzymes functionally analogous to those enzymes encoded in SEQ ID NO:1 and SEQ ID NO:7. A further non-limiting example of a parent host cell is an E. coli cell that has been genetically modified with one or more constructs comprising nucleotide sequences as set forth in SEQ ID NO:1 and SEQ ID NO:11 or nucleotide sequences that encode enzymes functionally analogous to those enzymes encoded in SEQ ID NO:1 and SEQ ID NO:11. A further non-limiting example of a parent host cell is a yeast cell that has been genetically modified with a construct comprising a nucleotide sequence comprising the mevalonate pathway genes encoded in SEQ ID NO:6 and SEQ ID NO:7 or a nucleotide sequence encoding enzymes functionally analogous to those mevalonate pathway enzymes encoded in SEQ ID NO:6 and SEQ ID NO:7. A further non-limiting example of a parent host cell is an yeast cell that has been genetically modified with a construct comprising a nucleotide sequence comprising mevalonate pathway enzymes seconded in SEQ ID NO:11 or a nucleotide sequence encoding enzymes functionally analogous to those enzymes encoded in SEQ ID NO:11.

In other embodiments, a parent host cell is one that has been genetically modified with one or more heterologous nucleic acids comprising nucleotide sequences encoding acetyoacetyl-CoA thiolase, HMGS, HMGR, mevalonate kinase (MK), phosphomevalonate kinase (PMK), and mevalonate pyrophosphate decarboxylase (MPD) (and optionally also IPP isomerase). An example of a parent host cell is an *E. coli* cell that has been genetically modified with a construct comprising a nucleotide sequence as set forth in SEQ ID NO:2 and SEQ ID NO:4. A further example of a parent host cell is an *E. coli* cell that has been genetically modified with a construct comprising a nucleotide sequence as set forth in SEQ ID NO:3 and SEQ ID NO:4.

In some embodiments, a parent host cell is one that has been genetically modified with one or more heterologous nucleic acids comprising nucleotide sequences encoding mevalonate kinase (MK), phosphomevalonate kinase (PMK), and mevalonate pyrophosphate decarboxylase (MPD) (and optionally also isopentenyl pyrophosphate isomerase); and the parent host cell is cultured in medium that includes mevalonate.

In other embodiments, a parent host cell is one that has been genetically modified with one or more heterologous nucleic acids comprising nucleotide sequences encoding acetoacetyl-CoA thiolase, hydroxymethylglutaryl-CoA synthase (HMGS), hydroxymethylglutaryl-CoA reductase (HMGR), MK, PMK, and MPD (and optionally also IPP isomerase).

In other embodiments, a parent host cell is one that has been genetically modified with one or more heterologous nucleic acids comprising nucleotide sequences encoding MK, PMK, MPD, IPP isomerase, and a prenyl transferase. In other embodiments, a parent host cell is one that is genetically modified with one or more heterologous nucleic acids comprising nucleotide sequences encoding acetoacetyl-CoA thiolase, HMGS, HMGR, MK, PMK, MPD, IPP isomerase, and a prenyl transferase. An example of a parent host cell is an *E. coli* cell that has been genetically modified with a construct comprising a nucleotide sequence as set forth in SEQ ID NO:2, SEQ ID NO: 4 and SEQ ID NO: 5. A further example is an *E. coli* cell that has been genetically modified with a construct comprising a nucleotide sequence as set forth in SEQ ID NO:1 and SEQ ID NO: 4 and SEQ ID NO: 5.

In other embodiments, a parent host cell is one that has a native (endogenous) mevalonate pathway and has been genetically modified such that the level of HMG-CoA is increased relative to an unmodified host cell, and such that HMG-CoA accumulation causes growth inhibition. In an exemplary embodiment, the parent strain is *Saccharomyces cerevisiae* that has been genetically modified for increased acetyl-CoA production, by introducing one or more genetic modifications such that one or more of a phosphotransacetylase, lactate dehydrogenase, and pyruvate decarboxylase is functionally disabled (e.g., via knockout).

Host cells (including parent host cells and genetically modified host cells) are in many embodiments unicellular organisms, or are grown in culture as single cells. In some embodiments, the host cell is a eukaryotic cell. Suitable eukaryotic host cells include, but are not limited to, yeast cells, insect cells, plant cells, fungal cells, and algal cells. Suitable eukaryotic host cells include, but are not limited to, *Pichia pastoris, Pichiafinlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii*, and the like. In some embodiments, the host cell is a eukaryotic cell other than a plant cell.

In other embodiments, the host cell is a prokaryotic cell. Suitable prokaryotic cells include, but are not limited to, any of a variety of laboratory strains of *Escherichia coli, Lactobacillus* sp., *Salmonella* sp., *Shigella* sp., and the like. See, e.g., Carrier et al. (1992) *J. Immunol.* 148:1176–1181; U.S. Pat. No. 6,447,784; and Sizemore et al. (1995) *Science* 270:299–302. Examples of *Salmonella* strains which can be employed in the present invention include, but are not limited to, *Salmonella typhi* and *S. typhimurium*. Suitable *Shigella* strains include, but are not limited to, *Shigella flexneri, Shigella sonnei*, and *Shigella disenteriae*. Typically, the laboratory strain is one that is non-pathogenic. Non-limiting examples of other suitable bacteria include, but are not limited to, *Bacillus subtilis, Pseudomonaspudita, Pseudomonas aeruginosa, Pseudomonas mevalonii, Rhodobacter sphaeroides, Rhodobacter capsulatus, Rhodospirillum rubrum, Rhodococcus* sp., and the like. In some embodiments, the host cell is *Escherichia coli*.

As noted above, in some embodiments, a parent host cell is one that has been genetically modified with one or more heterologous nucleic acids comprising nucleotide sequences encoding mevalonate pathway enzyme(s). To genetically modify a parent host cell such that it produces IPP via a mevalonate pathway and/or that produces mevalonate via a mevalonate pathyway, one or more nucleic acids comprising nucleotide sequences encoding one or more mevalonate pathway enzymes is introduced stably or transiently into a host cell, using established techniques, including, but not limited to, electroporation, calcium phosphate precipitation, DEAE-dextran mediated transfection, liposome-mediated transfection, and the like. For stable transformation, a nucleic acid will generally further include a selectable marker, e.g., any of several well-known selectable markers such as neomycin resistance, ampicillin resistance, tetracycline resistance, chloramphenicol resistance, kanamycin resistance, and the like.

In many embodiments, the nucleic acid with which the host cell is genetically modified such that it produces IPP and/or mevalonate via a mevalonate pathway is an expression vector that includes a nucleic acid comprising a nucleotide sequence that encodes a mevalonate pathway enzyme(s). Similarly, in many embodiments, the nucleic acid with which a parent host cell is genetically modified, such that HMG-CoA accumulation-induced toxicity and/or cell growth inhibition is reduced, is an expression vector that includes a nucleic acid comprising a nucleotide sequence that encodes one or more enzymes that provide for relief of HMG-CoA accumulation-induced toxicity and/or cell growth inhibition. Suitable expression vectors include, but are not limited to, baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, herpes simplex virus, and the like), P1-based artificial chromosomes, yeast plasmids, yeast artificial chromosomes, and any other vectors specific for specific hosts of interest (such as E. coli and yeast). Thus, for example, a nucleic acid encoding a mevalonate pathway gene product(s) is included in any one of a variety of expression vectors for expressing the mevalonate pathway gene product(s). Such vectors include chromosomal, nonchromosomal and synthetic DNA sequences.

Numerous suitable expression vectors are known to those of skill in the art, and many are commercially available. The following vectors are provided by way of example; for bacterial host cells: pQE vectors (Qiagen), pBluescript plasmids, pNH vectors, lambda-ZAP vectors (Stratagene); pTrc99a, pKK223-3, pDR540, and pRIT2T (Pharmacia); for eukaryotic host cells: pXTI, pSG5 (Stratagene), pSVK3, pBPV, pMSG, and pSVLSV40 (Pharmacia). However, any other plasmid or other vector may be used so long as it is compatible with the host cell.

For generating a parent host cell comprising one or more heterologous nucleic acids encoding nucleotide sequences encoding mevalonate pathway enzymes, a mevalonate pathway enzyme-encoding nucleotide sequence is inserted into an expression vector. The mevalonate pathway enzyme-encoding nucleotide sequence in the expression vector is operably linked to an appropriate expression control sequence(s) (e.g., apromoter) to direct synthesis of the encoded gene product. Similarly, for generating a genetically modified host cell from a parent host cell, an expression vector comprising nucleotide sequences encoding, e.g., HMGS and/or HMGR, will be used. The HMGS and/or HMGR coding sequences are operably linked to appropriate expression control sequence(s) to direct synthesis of the encoded gene product. Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) Methods in Enzymology, 153:516–544).

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, J. Bacteriol., 1991: 173(1): 86–93; Alpuche-Aranda et al., PNAS, 1992; 89(21): 10079–83), a nirB promoter (Harborne et al. (1992) Mol. Micro. 6:2805–2813), and the like (see, e.g., Dunstan et al. (1999) Infect. Immun. 67:5133–5141; McKelvie et al. (2004) Vaccine 22:3243–3255; and Chatfield et al. (1992) Biotechnol. 10:888–892); a sigma70 promoter, e.g., a consensus sigma70 promoter (see, e.g., GenBank Accession Nos. AX798980, AX798961, and AX798183); a stationary phase promoter, e.g., a dps promoter, an spv promoter, and the like; a promoter derived from the pathogenicity island SPI-2 (see, e.g., WO96/17951); an actA promoter (see, e.g., Shetron-Rama et al. (2002) Infect. Immun. 70:1087–1096); an rpsM promoter (see, e.g., Valdivia and Falkow (1996). Mol. Microbiol. 22:367–378); a tet promoter (see, e.g., Hillen, W. and Wissmann, A. (1989) In Saenger, W. and Heinemann, U. (eds), Topics in Molecular and Structural Biology, Protein-Nucleic Acid Interaction. Macmillan, London, UK, Vol. 10, pp. 143–162); an SP6 promoter (see, e.g., Melton et al. (1984) Nucl. Acids Res. 12:7035–7056); and the like.

Non-limiting examples of suitable eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression.

In addition, the expression vectors will in many embodiments contain one or more selectable marker genes to provide a phenotypic trait for selection of transformed host cells such as dihydrofolate reductase or neomycin resistance for eukaryotic cell culture, or such as tetracycline or ampicillin resistance in prokaryotic host cells such as E. coli.

Generally, recombinant expression vectors will include origins of replication and selectable markers permitting transformation of the host cell, e.g., the ampicillin resistance gene of E. coli, the S. cerevisiae TRP1 gene, etc.; and a promoter derived from a highly-expressed gene to direct transcription of the coding sequence. Such promoters can be derived from operons encoding glycolytic enzymes such as 3-phosphoglycerate kinase (PGK), α-factor, acid phosphatase, or heat shock proteins, among others.

In many embodiments, a parent host cell comprises a mevalonate pathway enzyme-encoding nucleotide sequence operably linked to an inducible promoter. Similarly, in many embodiments, a genetically modified host cell will comprise an HMGR and/or an HMGS encoding nucleotide sequence operably linked to an inducible promoter. Inducible promoters are well known in the art. Suitable inducible promoters include, but are not limited to, the pL of bacteriophage λ; Plac; Ptrp; Ptac (Ptrp-lac hybrid promoter); an isopropyl-beta-D-thiogalactopyranoside (IPTG)-inducible promoter, e.g., a lacZ promoter; a tetracycline-inducible promoter; an arabinose inducible promoter, e.g., $P_{BAD}$ (see, e.g., Guzman et al. (1995) J. Bacteriol. 177:4121–4130); a xylose-inducible promoter, e.g., Pxyl (see, e.g., Kim et al. (1996) Gene 181:71–76); a GAL1 promoter; a tryptophan promoter; a lac promoter; an alcohol-inducible promoter, e.g., a methanol-inducible promoter, an ethanol-inducible promoter; a raffinose-inducible promoter; a heat-inducible promoter, e.g., heat inducible lambda $P_L$ promoter, a promoter controlled by a heat-sensitive repressor (e.g., C1857-repressed lambda-based expression vectors; see, e.g., Hoffmann et al. (1999) FEMS Microbiol Lett. 177(2):327–34); and the like.

In many embodiments, a parent host cell is generated by genetically modifying a host cell with a nucleic acid that includes a nucleotide sequence encoding a mevalonate pathway gene product, where the nucleotide sequence encoding a mevalonate pathway gene product is operably linked to a constitutive promoter. Similarly, in some embodiments, an HMGS and/or an HMGR coding sequence is operably linked to a constitutive promoter. Suitable constitutive promoters for use in prokaryotic cells are known in the art and include, but are not limited to, a sigma70 promoter, e.g., a consensus sigma70 promoter.

In yeast, a number of vectors containing constitutive or inducible promoters may be used. For a review see, Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu & Grossman, 31987, Acad. Press, N.Y., Vol. 153, pp. 516–544; Glover, 1986, DNA Cloning, Vol. 11, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673–684; and The Molecular Biology of the Yeast Saccharomyces, 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. D M Glover, 1986, IRL Press, Wash., D.C.). Alternatively, vectors may be used which promote integration of foreign DNA sequences into the yeast chromosome.

Where a parent host cell has been genetically modified to produce two or more mevalonate pathway enzymes, nucleotide sequences encoding the two or more enzymes will in some embodiments each be contained on separate expression vectors. Where the host cell is genetically modified to express one or more mevalonate pathway enzymes, nucleotide sequences encoding the one or more mevalonate pathway enzymes will in some embodiments be contained in a single expression vector. Where nucleotide sequences encoding the one or more mevalonate pathway enzymes are contained in a single expression vector, in some embodiments, the nucleotide sequences will be operably linked to a common control element (e.g., a promoter), e.g., the common control element controls expression of all of the mevalonate pathway enzyme-encoding nucleotide sequences on the single expression vector.

Where nucleotide sequences encoding the mevalonate pathway enzyme(s) are contained in a single expression vector, in some embodiments, the nucleotide sequences will be operably linked to different control elements (e.g., a promoters), e.g., the different control elements control expression of each of the mevalonate pathway enzyme-encoding nucleotide sequences separately on a single expression vector.

Where a parent host cell is genetically modified with one or more nucleic acids comprising nucleotide sequences encoding enzyme(s) that provide for relief of HMG-CoA accumulation-induced toxicity, in some embodiments the enzymes will be encoded on two different (separate) expression constructs. For example, in some embodiments, HMGR will be expressed from a high-copy plasmid plasmid, while HMGS will be expressed from a low-copy plasmid, under the control of an identical promoter. In other embodiments, HMGR and HMGS will be expressed from similar copy-number plasmids, with HMGR being expressed by a stronger promoter than HMGS. Where a parent host cell is genetically modified with one or more nucleic acids comprising nucleotide sequences encoding enzyme(s) that provide for relief of HMG-CoA accumulation-induced toxicity, in some embodiments the enzymes will be encoded on a single expression construct. For example, in some embodiments, HMGR and HMGS will be expressed from a single plasmid under the control of a single promoter such that the engineered transcript stability of HMGR will be greater than that of HMGS.

Where nucleotide sequences encoding the enzyme(s) that provide for relief of HMG-CoA accumulation-induced toxicity are contained in a single expression construct, in some embodiments, the nucleotide sequences will be operably linked to different control elements (e.g., promoters), e.g. the different control elements control expression of each of the enzyme(s) that provide for relief of HMG-CoA accumulation-induced toxicity separately on a single expression construct. For example, in some embodiments, HMGR and HMGS will be expressed from a single plasmid, with HMGR being expressed by a stronger promoter than HMGS.

Nucleotide Sequences Encoding Mevalonate Pathway Enzymes

Nucleotide sequences encoding MEV pathway gene products are known in the art, and any known MEV pathway gene product-encoding nucleotide sequence can used to generate a subject genetically modified host cell. For example, nucleotide sequences encoding acetoacetyl-CoA thiolase, HMGS, HMGR, MK, PMK, MPD, and IDI are known in the art. The following are non-limiting examples of known nucleotide sequences encoding MEV pathway gene products, with GenBank Accession numbers and organism following each MEV pathway enzyme, in parentheses: acetoacetyl-CoA thiolase: (NC_000913 REGION: 2324131 . . . 2325315; *E. coli*), (D49362; *Paracoccus denitrificans*), and (L20428; *Saccharomyces cerevisiae*); HMGS: (NC_001145 complement 19061 . . . 20536; *Saccharomyces cerevisiae*), (X96617; *Saccharomyces cerevisiae*), (X83882; *Arabidopsis thaliana*), (AB037907; *Kitasatospora griseola*), and (BT007302; *Homo sapiens*); HMGR: (NM_206548; *Drosophila melanogaster*), (NM_204485; *Gallus gallus*), (AB015627; *Streptomyces* sp. KO-3988), (AF542543; *Nicotiana attenuata*), (ABO37907; *Kitasatospora griseola*), (AX128213, providing the sequence encoding a truncated HMGR; *Saccharomyces cerevisiae*), and (NC_001145: complement (115734 . . . 118898; *Saccharomyces cerevisiae*)); MK: (L77688; *Arabidopsis thaliana*), and (X55875; *Saccharomyces cerevisiae*); PMK: (AF429385; *Hevea brasiliensis*), (NM_006556; *Homo sapiens*), (NC_001145 complement 712315 . . . 713670; *Saccharomyces cerevisiae*); MPD: (X97557; *Saccharomyces cerevisiae*), (AF290095; *Enterococcus faecium*), and (U49260; *Homo sapiens*); and IDI: (NC_000913, 3031087 . . . 3031635; *E. coli*), and (AF082326; *Haematococcus pluvialis*).

In some embodiments, the HMGR coding region is set forth in SEQ ID NO: 13, which encodes a truncated form of HMGR ("tHMGR") that lacks the transmembrane domain of wild-type HMGR. The transmembrane domain of HMGR contains the regulatory portions of the enzyme and has no catalytic activity.

The coding sequence of any known MEV pathway enzyme may be altered in various ways known in the art to generate targeted changes in the amino acid sequence of the encoded enzyme. The amino acid of a variant MEV pathway enzyme will usually be substantially similar to the amino acid sequence of any known MEV pathway enzyme, i.e. will differ by at least one amino acid, and may differ by at least two, at least 5, at least 10, or at least 20 amino acids, but typically not more than about fifty amino acids. The sequence changes may be substitutions, insertions or deletions. For example, as described below, the nucleotide sequence can be altered for the codon bias of a particular host cell. In addition, one or more nucleotide sequence differences can be introduced that result in conservative amino acid changes in the encoded protein. In one embodiment, the desired relative levels of HMGS and HMGR and the non-toxic levels of HMG-CoA are achieved by expressing an altered HMGS or HMGR protein, or both.

Prenyl Transferases

In some embodiments, a subject genetically modified host cell is genetically modified to include one or more nucleic acids comprising a nucleotide sequence(s) encoding one or more mevalonate pathway enzymes, as described above; and a nucleic acid comprising a nucleotide sequence that encodes a prenyl transferase.

Prenyltransferases constitute a broad group of enzymes catalyzing the consecutive condensation of IPP resulting in the formation of prenyl diphosphates of various chain lengths. Suitable prenyltransferases include enzymes that catalyze the condensation of IPP with allylic primer substrates to form isoprenoid compounds with from about 2 isoprene units to about 6000 isoprene units or more, e.g., 2 isoprene units (Geranyl Pyrophosphate synthase), 3 isoprene units (Farnesyl pyrophosphate synthase), 4 isoprene units (geranylgeranyl pyrophosphate synthase), 5 isoprene units, 6 isoprene units (hexadecylpyrophosphate synthase), 7 isoprene units, 8 isoprene units (phytoene synthase, octaprenyl pyrophosphate synthase), 9 isoprene units (nonaprenyl pyrophosphate synthase, 10 isoprene units (decaprenyl pyrophosphate synthase), from about 10 isoprene units to about 15 isoprene units, from about 15 isoprene units to about 20 isoprene units, from about 20 isoprene units to about 25 isoprene units, from about 25 isoprene units to about 30 isoprene units, from about 30 isoprene units to about 40 isoprene units, from about 40 isoprene units to about 50 isoprene units, from about 50 isoprene units to about 100 isoprene units, from about 100 isoprene units to about 250 isoprene units, from about 250 isoprene units to about 500 isoprene units, from about 500 isoprene units to about 1000 isoprene units, from about 1000 isoprene units to about 2000 isoprene units, from about 2000 isoprene units to about 3000 isoprene units, from about 3000 isoprene units to about 4000 isoprene units, from about 4000 isoprene units to about 5000 isoprene units, or from about 5000 isoprene units to about 6000 isoprene units or more.

Suitable prenyltransferases include, but are not limited to, an E-isoprenyl diphosphate synthase, including, but not limited to, geranyl diphosphate (GPP) synthase, farnesyl diphosphate (FPP) synthase, geranylgeranyl diphosphate (GGPP) synthase, hexaprenyl diphosphate (HexPP) synthase, heptaprenyl diphosphate (HepPP) synthase, octaprenyl (OPP) diphosphate synthase, solanesyl diphosphate (SPP) synthase, decaprenyl diphosphate (DPP) synthase, chicle synthase, and gutta-percha synthase; and a Z-isoprenyl diphosphate synthase, including, but not limited to, nonaprenyl diphosphate (NPP) synthase, undecaprenyl diphosphate (UPP) synthase, dehydrodolichyl diphosphate synthase, eicosaprenyl diphosphate synthase, natural rubber synthase, and other Z-isoprenyl diphosphate synthases.

The nucleotide sequences of a numerous prenyl transferases from a variety of species are known, and can be used or modified for use in generating a subject genetically modified host cell. Nucleotide sequences encoding prenyl transferases are known in the art. See, e.g., Human farnesyl pyrophosphate synthetase mRNA (GenBank Accession No. J05262; *Homo sapiens*); farnesyl diphosphate synthetase (FPP) gene (GenBank Accession No. J05091; *Saccharomyces cerevisiae*); isopentenyl diphosphate:dimethylallyl diphosphate isomerase gene (J05090; *Saccharomyces cerevisiae*); Wang and Ohnuma (2000) *Biochim. Biophys. Acta* 1529:33–48; U.S. Pat. No. 6,645,747; *Arabidopsis thaliana* farnesyl pyrophosphate synthetase 2 (FPS2)/FPP synthetase 2/farnesyl diphosphate synthase 2 (At4gl 7190) mRNA (GenBank Accession No. NM_202836); *Ginkgo biloba* geranylgeranyl diphosphate synthase (ggps) mRNA (GenBank Accession No. AY3 71321); *Arabidopsis thaliana* geranylgeranyl pyrophosphate synthase (GGPS 1)/GGPP synthetase/farnesyltranstransferase (At4g36810) mRNA (GenBank Accession No. NM_119845); *Synechococcus elongatus* gene for farnesyl, geranylgeranyl, geranylfamesyl, hexaprenyl, heptaprenyl diphosphate synthase (SelFHepPS) (GenBank Accession No. ABO 16095); etc.

Codon Usage

In some embodiments, the nucleotide sequence encoding a mevalonate pathway enzyme is modified such that the nucleotide sequence reflects the codon preference for the particular host cell. For example, the nucleotide sequence will in some embodiments be modified for yeast codon preference. See, e.g., Bennetzen and Hall (1982) *J. Biol. Chem.* 257(6): 3026–3031. As another non-limiting example, the nucleotide sequence will in other embodiments be modified for *E. coli* codon preference. See, e.g., Gouy and Gautier (1982) *Nucleic Acids Res.* 10(22):7055–7074; Eyre-Walker (1996) *Mol. Biol. Evol.* 13(6):864–872. See also Nakamura et al. (2000) *Nucleic Acids Res.* 28(1):292.

As noted above, in some embodiments, the codon usage of an HMGS coding sequence is modified such that the level of translation of the HMGS mRNA is decreased. Reducing the level of translation of HMGS mRNA by modifying codon usage is achieved by modifying the sequence to include codons that are rare or not commonly used by the host cell. Codon usage tables for many organisms are available that summarize the percentage of time a specific organism uses a specific codon to encode for an amino acid. Certain codons are used more often than other, "rare" codons. The use of "rare" codons in a sequence generally decreases its rate of translation. Thus, e.g., the coding sequence is modified by introducing one or more rare codons, which affect the rate of translation, but not the amino acid sequence of the enzyme translated. For example, there are 6 codons that encode for arginine: CGT, CGC, CGA, CGG, AGA, and AGG. In *E. coli* the codons CGT and CGC are used far more often (encoding approximately 40% of the arginines in *E. coli* each) than the codon AGG (encoding approximately 2% of the arginines in *E. coli*). Modifying a CGT codon within the sequence of a gene to an AGG codon would not change the sequence of the enzyme, but would likely decrease the gene's rate of translation.

Additional Genetic Modifications

In some embodiments, a subject genetically modified host cell is one that is genetically modified to include one or more nucleic acids comprising a nucleotide sequence(s) that encode enzymes that relieve HMG-CoA accumulation-induced toxicity; and that is further genetically modified to achieve enhanced production of a terpene biosynthetic pathway intermediate, and/or that is further genetically modified to enhance production of an isoprenoid or isoprenoid precursor, and/or that is further genetically modified such that an endogenous terpene biosynthetic pathway gene is functionally disabled. The term "functionally disabled," as used herein, refers to a genetic modification of a nucleic acid, which modification results in production of a gene product encoded by the nucleic acid that is produced at below normal levels, and/or is non-functional. Such genetic modification(s) may decrease the specific IPP or mevalonate productivity of a strain (production per cell) as compared to a parent strain, but the relief in HMG-CoA induced toxicity would increase the cell density such that the total productivity of the culture (specific productivity multiplied by the cell density of the culture) would increase.

Genetic modifications that enhance production of an endogenous terpene biosynthetic pathway intermediate include, but are not limited to, genetic modifications that result in a reduced level and/or activity of a phosphotransacetylase in the host cell. The intracellular concentration of an isoprenoid biosynthetic pathway intermediate is enhanced by increasing the intracellular concentration of acetyl-CoA. *E. Coli* secretes a significant fraction of intracellular acetyl-CoA in the form of acetate into the medium. Deleting the gene encoding phosphotransacetylase, pta, the first enzyme responsible for transforming acetyl-CoA into acetate, reduces acetate secretion. Genetic modifications that reduce the level and/or activity of phosphotransacetylase in a prokaryotic host cell are particularly useful where the parent host cell is one that is genetically modified with a nucleic acid comprising nucleotide sequences encoding one or more MEV pathway gene products.

Since acetyl-CoA is a reactant used by both acetoacetyl-CoA thiolase and HMGS in the synthesis of HMG-CoA, and in some host cells, increases in the intracellular pool of acetyl-CoA could lead to increases in the intracellular pool of HMG-CoA, which in turn could lead to a toxicity effect. Therefore, genetic modifications that reduce the total activity of phosphotransacetylase could lead to a reduction in growth rate or final cell density due to the accumulation of HMG-CoA, generating a parent strain that could be modified using the method of the invention. Alternatively, genetic modifications that increase the total activity of phosphotransacetylase could be used to overcome a toxicity effect caused by the accumulation of HMG-CoA.

In some embodiments, a genetic modification that results in a reduced level of phosphotransacetylase in a prokaryotic host cell is a genetic mutation that functionally disables the prokaryotic host cell's endogenous pta gene encoding the phosphotransacetylase. The pta gene can be functionally disabled in any of a variety of ways, including insertion of a mobile genetic element (e.g., a transposon, etc.); deletion of all or part of the gene, such that the gene product is not made, or is truncated and is non-functional in converting acetyl-CoA to acetate; mutation of the gene such that the gene product is not made, or is truncated and is non-functional in converting acetyl-CoA to acetate; deletion or mutation of one or more control elements that control expression of the pta gene such that the gene product is not made; and the like.

In some embodiments, the endogenous pta gene of a genetically modified host cell is deleted. Any method for deleting a gene can be used. One non-limiting example of a method for deleting a pta gene is by use of the λRed recombination system. Datsenko and Wanner (2000) *Proc Natl Acad Sci USA* 97(12): p. 6640–5. The pta gene will in some embodiments be deleted from a host cell (e.g., *E. coli*) that is genetically modified with a nucleic acid comprising nucleotide sequences encoding MK, PMK, MPD, and IDI. The pta gene will in some embodiments be deleted from a host cell (e.g., *E. coli*) that is genetically modified with a nucleic acid comprising nucleotide sequences encoding MK, PMK, MPD, and IPP. The pta gene will in some embodiments be deleted from a host cell (e.g., *E. coli*) that is genetically modified with a nucleic acid comprising nucleotide sequences encoding MK, PMK, MPD, IPP, and a prenyl transferase.

Other modifications that would increase the levels of intracellular acetyl-CoA include, but are not limited to, modifications that would decrease the total activity of lactate dehydrogenase within the cell, modifications that would decrease the total activity of acetate kinase within the cell, modifications that would decrease the total activity of alcohol dehydrogenase within the cell, modifications that would interrupt the tricarboxylic acid cycle, such as those that would decrease the total activity of 2-ketoglutarate dehydrogenase, or modifications that would interrupt oxidative phosphorylation, such as those that would decrease the total activity of the (F1F0)H+-ATP synthase, or combinations thereof.

Other modifications that would decrease the levels of intracellular acetyl-CoA include, but are not limited to, modifications that would increase the total activity of lactate dehydrogenase within the cell, modifications that would increase the total activity of acetate kinase within the cell, and modifications that would increase the total activity of alcohol dehydrogenase within the cell, or combinations thereof.

In some embodiments, a parent host cell is one that is genetically modified, as described above to increase levels of HMG-CoA; and is further genetically modified such that an endogenous DXP biosynthetic pathway gene is functionally disabled. Such a genetically modified host cell is useful in screening for enzymes that convert HMG-CoA to mevalonate, as described in more detail below, as the HMG-CoA toxicity would be exacerbated by the reliance of the cell on the mevalonate pathway for the production of required isoprenoids.

In other embodiments, a subject genetically modified host cell is one that is genetically modified to include one or more nucleic acids comprising a nucleotide sequence(s) that encode DXP biosynthetic pathway gene product(s); and that is further genetically modified such that an endogenous MEV biosynthetic pathway gene is functionally disabled. Such a host cell would be useful in the instance where for technical reasons screening of enzymes associated with the HMG-CoA toxicity was most facilely carried out in an organism that naturally utilized the mevalonate pathway for production of isoprenoids.

In some embodiments, where subject genetically modified host cell is a prokaryotic host cell that has been genetically modified with nucleic acid(s) comprising nucleotide sequences encoding one or more MEV pathway gene products, the host cell will be further genetically modified such that one or more endogenous DXP pathway genes is functionally disabled. DXP pathway genes that can be functionally disabled include one or more of the genes encoding any of the following DXP gene products: 1-deoxy-D-xylulose-5-phosphate synthase, 1-deoxy-D-xylulose-5-phosphate reductoisomerase, 4-diphosphocytidyl-2-C-methyl-D-erythritol synthase, 4-diphosphocytidyl-2-C-methyl-D)-erythritol kinase, 2C-methyl-D-erythritol 2,4-cyclodiphosphate synthase, and 1-hydroxy-2-methyl-2-(E)-butenyl 4-diphosphate synthase.

An endogenous DXP pathway gene can be functionally disabled in any of a variety of ways, including insertion of a mobile genetic element (e.g., a transposon, etc.); deletion of all or part of the gene, such that the gene product is not made, or is truncated and is enzymatically inactive; mutation of the gene such that the gene product is not made, or is truncated and is enzymatically non-functional; deletion or mutation of one or more control elements that control expression of the gene such that the gene product is not made; and the like.

Compositions Comprising a Subject Genetically Modified Host Cell

The present invention further provides compositions comprising a subject genetically modified host cell. A subject composition comprises a subject genetically modified host cell; and will in some embodiments comprise one or more further components, which components are selected based in part on the intended use of the genetically modified host cell. Suitable components include, but are not limited to, salts;

buffers; stabilizers; protease-inhibiting agents; cell membrane- and/or cell wall-preserving compounds, e.g., glycerol, dimethylsulfoxide, etc.; nutritional media appropriate to the cell; and the like.

Nucleic Acids

The present invention provides nucleic acid(s) comprising nucleotide sequences encoding HMGS and/or HMGR, wherein the nucleic acid(s), when introduced into a parent host cell that includes or is genetically modified to include, relieve HMG-CoA accumulation-induced toxicity or growth inhibition. Thus, a subject nucleic acid, when introduced into a host cell that exhibits HMG-CoA accumulation-induced toxicity, relieves the HMG-CoA accumulation-induced toxicity or growth inhibition. In some embodiments, a subject nucleic acid comprises a nucleotide sequence encoding HMGR operably linked to a strong promoter.

In some embodiments, a subject nucleic acid is an expression construct that comprises a nucleotide sequence encoding HMGR. In some embodiments, the expression construct is one that provides for synthesis of the encoded HMGR in a prokaryotic cell. In some embodiments, the expression construct is one that provides for synthesis of the encoded HMGR in a eukaryotic cell. In some embodiments, a subject nucleic acid comprises a nucleotide sequence encoding HMGR, where the nucleic acid is a medium copy number plasmid. In some embodiments, a subject nucleic acid comprises a nucleotide sequence encoding HMGR, where the nucleic acid is a high copy number plasmid. In some embodiments, a subject nucleic acid comprises a nucleotide sequence encoding HMGR operably linked to a strong promoter, where the nucleic acid is a high copy number plasmid. In some embodiments, a subject nucleic acid comprises a nucleotide sequence encoding HMGR operably linked to a strong promoter, where the nucleic acid is a medium copy number plasmid. In some embodiments, a subject nucleic acid comprises a nucleotide sequence encoding HMGR operably linked to a weak promoter on a medium copy plasmid.

In some embodiments, a subject nucleic acid comprises a nucleotide sequence encoding a fusion protein comprising acetoacetyl-CoA thiolase operably linked to HMGR. In some embodiments, a nucleic acid encoding the acetoacetyl-CoA/HMGR fusion protein is generated by linking the coding sequences of acetoacetyl-CoA thiolase and HMGR. In some embodiments, the fusion protein is one that is found in nature. In other embodiments, the fusion protein is one that is found in nature, and is other than the fusion protein discussed in Hedl et al. ((2002) *J. Bacteriol.* 184:2116–2122). In some embodiments, a subject nucleic acid comprises a nucleotide sequence encoding a fusion protein comprising acetoacetyl-CoA thiolase and HMGS. In some embodiments, a subject nucleic acid comprises a nucleotide sequence encoding a fusion protein comprising acetoacetyl-CoA thiolase, HMGS, and HMGR. In some embodiments, a subject nucleic acid comprises a nucleotide sequence encoding a fusion protein comprising HMGS and HMGR.

In some embodiments, a subject nucleic acid is an expression construct that comprises a nucleotide sequence encoding HMGR, where the expression construct is other than an expression construct disclosed in any of the following references: Kato-Emori et al. *Mol Genet Genomics* (2001) 265:135–42, Learned R M, et al. *PNAS.* (1989) 86:2779–83, T. Dairi, et al. *Mol Gen Genet* (2000) 262: 957–964, Allen, et al. *Appl Environ. Microbio.* (1 997). 63:3341–3344, Hedl, et al. *J. Bacteriol.,* (2002), 184:2116–2122, Jackson, et al. *Org. Lett.* (2003) 5:1629–1632, Randolph Y. Hampton, et al. (1994) *Cell,* 125:299–312, Markus Veen, et al. *FEMS Yeast Res* (2003) 4:87–95, Beach M J, et al. *J. Bacteriol* (1989) 171:2994–3001, Bischoff K M, et al. *Protein Sci* (1997) 6:156–161, Friesen J A, et al. *Biochemistry.* (1997) 36:2173–7, Frimpong, et al. *J Biol Chem.* (1994) 269: 11478–83, Panda, et al. *Appl Microbiol Biotechnol* (2004) 66: 143–152.

Screening Methods

The present invention provides screening methods for identifying a gene product having HMG-CoA detoxification activity; and methods for identifying an agent that inhibits accumulation of HMG-CoA. In one embodiment the gene produce identified is one that encodes an HMGR, e.g., a variant HMGR. In one embodiment the gene product identified is one that encodes a variant HMGR, where the variant HMGR provides for an increase in the total HMGR activity in the cell. In another embodiment, the gene product identified produces a product that decreases HMGS activity. In another embodiment, the gene product identified produces a product that utilizes mevalonate as a substrate. In another embodiment, the gene identified produces a product that encodes a MK. In another example, the gene product identified provides for transport of mevalonate from the cell. In another embodiment, the gene product identified is an HMG-CoA lyase or encodes an HMG-CoA lyase. In another embodiment the gene product identified encodes a succinate-hydroxymethylglutarate CoA-transferase, or is a succinate-hydroxymethylglutarate CoA-transferase.

For identifying a gene product that reduces HMG-CoA accumulation-induced toxicity, the methods generally involve producing a test cell by introducing into a host cell an exogenous nucleic acid comprising a nucleotide sequence encoding a candidate gene product, where the host cell produces HMG-CoA at levels effective to inhibit growth of the host cell; and b) determining the effect, if any, of expression of the candidate gene product on the growth of the test cell. For identifying an agent that reduces accumulation of intracellular HMG-CoA, and/or that reduces the level of HMGS activity in a cell, the methods generally involve a) contacting a test cell with a test agent, where the test cell synthesizes mevalonate via a mevalonate pathway, and where the test cell exhibits HMG-CoA accumulation-induced growth inhibition; and b) determining the effect, if any, of the test agent on HMG-CoA accumulation-induced growth inhibition. As used herein, the term "determining" refers to both quantitative and qualitative determinations and as such, the term "determining" is used interchangeably herein with "assaying," "measuring," and the like.

The subject screening methods are in vitro cell-based assays. Any of a variety of cells can be used. The cells used in the assay are in some embodiments eukaryotic cells, as described above. In other embodiments, the cells used in the assay are prokaryotic cells, as described above.

Methods of Identifying a Gene Product having HMG-CoA Detoxification Activity

The present invention provides in vitro screening methods for identifying a gene product having HMG-CoA detoxification activity. The gene products so identified are useful for relieving HMG-CoA accumulation-induced toxicity, and are therefore useful in methods of producing isoprenoid compounds or isoprenoid precursors. The methods generally involve a) producing a test cell by introducing into a host cell an exogenous nucleic acid comprising a nucleotide sequence encoding a candidate gene product, where the host cell produces HMG-CoA at levels effective to inhibit growth of the host cell; and b) determining the effect, if any, of expression of the candidate gene product on the growth of the test cell, compared to the host cell. The ability of the candidate gene product to reduce HMG-CoA accumulation and relieve HMG-CoA accumulation-induced toxicity is determined by the ability of the candidate gene product to reduce HMG-CoA accumulation-induced growth inhibition. A reduction in growth inhibition in the test cell, compared to the host cell, indicates that the exogenous nucleic acid encodes a gene product having sufficient activity to relieve HMG-CoA accumulation-induced toxicity. The host cell is one that produces one or more enzymes in the mevalonate pathway, such that HMG-CoA is produced. In some embodiments, the host cell is one that does not normally produce mevalonate via a mevalonate pathway, and has been genetically modified with one or more nucleic acids comprising nucleotide sequences encoding one or more mevalonate pathway enzymes, such that HMG-CoA is produced and accumulated intracellularly at growth-inhibiting levels. In other embodiments, the host cell is one that naturally produces HMG-CoA at growth-inhibiting levels or that has been genetically modified, other than via introduction of one or more exogenous MEV pathway genes, to do so.

HMG-CoA is produced in the host cell in an amount that inhibits growth of the host cell, e.g., the intracellular concentration of HMG-CoA inhibits the growth of the host cell. Typically, HMG-CoA accumulates in the host cell in an amount that inhibits growth of the host cell by at least about 10%, at least about 20%, at least about 30%, at least about 40%, at least about 50%, at least about 60%, at least about 70%, at least about 80%, or at least about 90%, or more, compared to the growth rate of a control host cell that does not produce HMG-CoA, or compared to the growth rate of the host cell that is cultured under conditions that are not conducive to synthesis of growth-inhibiting amounts of HMG-CoA. In some embodiments, HMG-CoA accumulates intracellularly in the host cell in an amount that is lethal to the host cell, e.g., induces death of the host cell.

In some embodiments, a host cell that exhibits HMG-CoA accumulation-induced cell growth inhibition is a cell that does not normally synthesize mevalonate or IPP via a mevalonate pathway, and has been genetically modified with one or more nucleic acids comprising nucleotide sequences encoding mevalonate pathway enzyme(s). For example, in some embodiments, a host cell that exhibits HMG-CoA accumulation-induced cell growth inhibition is a prokaryotic cell that has been genetically modified with one or more nucleic acids comprising nucleotide sequences encoding acetoacetyl-CoA thiolase, HMGS, and HMGR, where the acetoacetyl-CoA thiolase, HMGS, and HMGR are produced in the cell in amounts that result in HMG-CoA accumulation-induced cell growth inhibition.

In other embodiments, a host cell that exhibits HMG-CoA accumulation-induced cell growth inhibition is a cell that normally produces mevalonate or IPP via a mevalonate pathway, and that has been genetically modified such that the levels intracellular HMG-CoA are increased, resulting in HMG-CoA accumulation-induced cell growth inhibition.

The test cell is cultured in vitro under conditions such that HMG-CoA accumulates intracellularly in an amount that is growth inhibiting and/or death inducing. In some embodiments, the test cell is cultured in the presence of an inducer that induces expression of a nucleotide sequence encoding HMGS or HMGR, where the nucleotide sequence is under control of an inducible promoter. Whether the HMG-CoA is present in the test cell in an amount that inhibits growth of the test cell can be determined using any standard method for detecting growth inhibition of a cell. For example, growth is frequently measured as an increase in optical density when cells are grown in liquid culture; and growth inhibition can be detected by comparing the optical density (e.g., at 600 nm) of a liquid culture of host cells that produce a growth-inhibiting amount of HMG-CoA, with the optical density of a liquid culture of the same host cells that do produce a growth-inhibiting amount of the intermediate. Growth inhibition can also be detected by visually inspecting the colony size of cells plated on agar containing suitable growth media.

A subject screening method involves introducing an exogenous nucleic acid into a host cell, producing a test cell, where the host cell is one that exhibits growth inhibition when HMG-CoA is produced in a growth-inhibiting amount. When an exogenous nucleic acid comprising a nucleotide sequence that encodes HMGR is introduced into the host cell, growth inhibition of the test cell is relieved. Thus, a reduction in growth inhibition indicates that the exogenous nucleic acid encodes HMGR, where the encoded HMGR is produced at a level and/or has an activity that relieves the HMG-CoA accumulation-induced growth inhibition. A reduction in growth inhibition includes an at least about 20%, at least about 30%, at least about 40%, at least about 50%, at least about 60%, at least about 70%, at least about 80%, at least about 90%, or more, reduction in growth inhibition. In some embodiments, the HMGR encoded by the exogenous nucleic acid reduces the growth inhibition such that the rate of cell growth is restored to the rate of cell growth of the host cell when grown under conditions such that HMG-CoA is not produced in growth inhibiting amounts.

In some embodiments, e.g., where the exogenous nucleic acid is a plurality of exogenous nucleic acids (e.g., a cDNA library, a genomic library, a population of nucleic acids, each encoding an HMGR with a different amino acid sequence, etc.), the exogenous nucleic acid are introduced into a plurality of host cells, forming a plurality of test cells. The test cells are in some embodiments grown in liquid culture under conditions such that HMG-CoA is accumulated intracellularly in a growth inhibiting and/or death-inducing amount; those test cells comprising an exogenous nucleic acid that comprises nucleotide sequences encoding HMGR will grow faster than test cells that do not comprise an exogenous nucleic acid that comprises nucleotide sequences encoding HMGR, or those test cells comprising an exogenous nucleic acid that comprises nucleotide sequences encoding HMGR will live, while test cells that do not comprise an exogenous nucleic acid that comprises nucleotide sequences encoding HMGR will die.

In some embodiments, the method further involves isolating an exogenous nucleic acid from a test cell, where the exogenous nucleic acid is one that that relieves growth inhibition in a subject screening method. Methods of isolating the exogenous nucleic acid from a test cell are well known in the art. Suitable methods include, but are not limited to, any of a number of alkaline lysis methods that are standard in the art.

In some embodiments, a subject screening method will further comprise further characterizing a candidate gene product. In these embodiments, the exogenous nucleic acid comprising nucleotide sequence(s) encoding HMGR are isolated from a test cell; the gene product(s) are expressed in a cell and/or in an in vitro cell-free transcription/translation system. In some embodiments, the exogenous nucleic acid is subjected to nucleotide sequence analysis, and the amino acid sequence of the gene product deduced from the nucleotide sequence. In some embodiments, the amino acid sequence of the gene product is compared with other amino acid sequences in a public database of amino acid sequences, to determine whether any significant amino acid sequence identity to an amino acid sequence of a known protein exists. In addition, the gene product(s) are expressed in a cell and/or in an in vitro cell-free transcription/translation system; and the effect of the gene product(s) on a metabolic pathway intermediate or other metabolite is analyzed.

Exogenous nucleic acids that are suitable for introducing into a host cell, to produce a test cell, include, but are not limited to, naturally-occurring nucleic acids isolated from a cell; naturally-occurring nucleic acids that have been modified (e.g., by mutation) before or subsequent to isolation from a cell; synthetic nucleic acids, e.g., nucleic acids synthesized in a laboratory using standard methods of chemical synthesis of nucleic acids, or generated by recombinant methods; synthetic or naturally-occurring nucleic acids that have been amplified in vitro, either within a cell or in a cell-free system; and the like.

Exogenous nucleic acids that are suitable for introducing into a host cell include, but are not limited to, genomic DNA; RNA; a complementary DNA (cDNA) copy of mRNA isolated from a cell; recombinant DNA; and DNA synthesized in vitro, e.g., using standard cell-free in vitro methods for DNA synthesis. In some embodiments, exogenous nucleic acids are a cDNA library made from cells, either prokaryotic cells or eukaryotic cells. In some embodiments, exogenous nucleic acids are a genomic DNA library made from cells, either prokaryotic cells or eukaryotic cells.

Nucleic acids will in some embodiments be mutated before being introduced into a host cell. Methods of mutating a nucleic acid are well know in the art and include well-established chemical mutation methods, radiation-induced mutagenesis, and methods of mutating a nucleic acid during synthesis. Chemical methods of mutating DNA include exposure of DNA to a chemical mutagen, e.g., ethyl methanesulfonate (EMS), methyl methanesulfonate (MMS), N-nitrosourea (ENU), N-methyl-N-nitro-N'-nitrosoguanidine, 4-nitroquinoline N-oxide, diethylsulfate, benzopyrene, cyclophosphamide, bleomycin, triethylmelamine, acrylamide monomer, nitrogen mustard, vincristine, diepoxyalkanes (e.g., diepoxybutane), ICR-170, formaldehyde, procarbazine hydrochloride, ethylene oxide, dimethylnitrosamine, 7,12 dimethylbenz(a)anthracene, chlorambucil, hexamethylphosphoramide, bisulfan, and the like. Radiation mutation-inducing agents include ultraviolet radiation, γ-irradiation, X-rays, and fast neutron bombardment. Mutations can also be introduced into a nucleic acid using, e.g., trimethylpsoralen with ultraviolet light. Random or targeted insertion of a mobile DNA element, e.g., a transposable element, is another suitable methods for generating mutations. Mutations can be introduced into a nucleic acid during amplification in a cell-free in vitro system, e.g., using a polymerase chain reaction (PCR) technique such as error-prone PCR. Mutations can be introduced into a nucleic acid in vitro using DNA shuffling techniques (e.g., exon shuffling, domain swapping, and the like). Mutations can also be introduced into a nucleic acid as a result of a deficiency in a DNA repair enzyme in a cell, e.g., the presence in a cell of a mutant gene encoding a mutant DNA repair enzyme is expected to generate a high frequency of mutations (i.e., about 1 mutation/100 genes-1 mutation/10,000 genes) in the genome of the cell. Examples of genes encoding DNA repair enzymes include but are not limited to Mut H, Mut S, Mut L, and Mut U, and the homologs thereof in other species (e.g., MSH 1–6, PMS 1–2, MLH 1, GTBP, ERCC-1, and the like). Methods of mutating nucleic acids are well known in the art, and any known method is suitable for use. See, e.g., Stemple (2004) *Nature* 5:1–6; Chiang et al. (1993) *PCR Methods Appl* 2(3): 210–217; Stemmer (1994) *Proc. Nail. Acad. Sci. USA* 91:10747–51; and U.S. Pat. Nos. 6,033,861, and 6,773,900.

In many embodiments, the exogenous nucleic acid is inserted into an expression vector. Expression vectors that are suitable for use in prokaryotic and eukaryotic host cells are known in the art, and any suitable expression vector can be used. Suitable expression vectors are as described above.

As noted above, an exogenous nucleic acid will in some embodiments be isolated from a cell or an organism in its natural environment. In some embodiments, the nucleic acid of the cell or organism will be mutated before nucleic acid is isolated from the cell or organism. In other embodiments, the exogenous nucleic acid is synthesized in a cell-free system in vitro.

Exogenous nucleic acids that are suitable for introducing into a host cell include nucleic acids isolated from cells or organism of a different species from the host cell. Suitable sources of exogenous nucleic acids include, but are not limited to, a cell or organism of any of the six kingdoms, e.g., Bacteria (e.g., Eubacteria); Archaebacteria; Protista; Fungi; Plantae; and Animalia. Suitable sources of exogenous nucleic acids include plant-like members of the kingdom Protista, including, but not limited to, algae (e.g., green algae, red algae, glaucophytes, cyanobacteria); fungus-like members of Protista, e.g., slime molds, water molds, etc.; animal-like members of Protista, e.g., flagellates (e.g., Euglena), amoeboids (e.g., amoeba), sporozoans (e.g, Apicomplexa, Myxozoa, Microsporidia), and ciliates (e.g., Paramecium). Suitable sources of exogenous nucleic acids include members of the kingdom Fungi, including, but not limited to, members of any of the phyla: Basidiomycota (club fungi; e.g., members of Agaricus, Amanita, Boletus, Cantherellus, etc.); Ascomycota (sac fungi, including, e.g., Saccharomyces); Mycophycophyta (lichens); Zygomycota (conjugation fungi); and Deuteromycota. Suitable sources of exogenous nucleic acids include members of the kingdom Plantae, including, but not limited to, members of any of the following divisions: Bryophyta (e.g., mosses), Anthocerotophyta (e.g., hornworts), Hepaticophyta (e.g., liverworts), Lycophyta (e.g., club mosses), Sphenophyta (e.g., horsetails), psilophyta (e.g., whisk ferns), Ophioglossophyta, Pterophyta (e.g., ferns), Cycadophyta, Gingkophyta, Pinophyta, Gnetophyta, and Magnoliophyta (e.g., flowering plants). Suitable sources of exogenous nucleic acids include members of the kingdom Animalia, including, but not limited to, members of any of the following phyla: Porifera (sponges); Placozoa; Orthonectida (parasites of marine invertebrates); Rhombozoa; Cnidaria (corals, anemones, jellyfish, sea pens, sea pansies, sea wasps); Ctenophora (comb jellies); Platyhelminthes (flatworms); Nemertina (ribbon worms); Ngathostomulida (jawed worms)p Gastrotricha; Rotifera; Priapulida; Kinorhyncha; Loricifera; Acanthocephala; Entoprocta; Nemotoda; Nematomorpha; Cycliophora; Mollusca (mollusks); Sipuncula (peanut worms); Annelida (segmented worms); Tardigrada (water bears); Onychophora (velvet worms); Arthropoda (including the subphyla: Chelicerata, Myriapoda, Hexapoda, and Crustacea, where the Chelicerata include, e.g., arachnids, Merostomata, and Pycnogonida, where the Myriapoda include, e.g., Chilopoda (centipedes), Diplopoda (millipedes), Paropoda, and Symphyla, where the Hexapoda include insects, and where the Crustacea include shrimp, krill, barnacles, etc.; Phoronida; Ectoprocta (moss animals); Brachiopoda; Echinodermata (e.g. starfish, sea daisies, feather stars, sea urchins, sea cucumbers, brittle stars, brittle baskets, etc.); Chaetognatha (arrow worms); Hemichordata (acorn worms); and Chordata. Suitable members of Chordata include any member of the following subphyla: Urochordata (sea squirts; including Ascidiacea, Thaliacea, and Larvacea); Cephalochordata (lancelets); Myxini (hagfish); and Vertebrata, where members of Vertebrata include, e.g., members of Petromyzontida (lampreys), Chondrichthyces (cartilaginous fish), Actinopterygii (ray-finned fish), Actinista (coelacanths), Dipnoi (lungfish), Reptilia (reptiles, e.g., snakes, alligators, crocodiles, lizards, etc.), Aves (birds); and Mammalian (mammals). Suitable plants include any monocotyledon and any dicotyledon.

Thus, e.g., suitable cells include cells from organisms that include, but are not limited to, a protozoan, a plant, a fungus, an algal cell, a yeast, a reptile, an amphibian, a mammal, a marine microorganism, a marine invertebrate, an arthropod, an isopod, an insect, an arachnid, an archaebacterium, and a eubacterium.

In some embodiments, the exogenous nucleic acid will be isolated from a tissue taken from an organism; from a particular cell or group of cells isolated from an organism; etc. For example, where the organism is a plant, the exogenous nucleic acid will in some embodiments be isolated from the xylem, the phloem, the cambium layer, leaves, roots, etc. Where the organism is an animal, the exogenous nucleic acid will in some embodiments be isolated from a particular tissue (e.g., lung, liver, heart, kidney, brain, spleen, skin, fetal tissue, etc.), or a particular cell type (e.g., neuronal cells, epithelial cells, endothelial cells, astrocytes, macrophages, glial cells, islet cells, T lymphocytes, B lymphocytes, etc.).

In some embodiments, the exogenous nucleic acid is a synthetic nucleic acid. In some embodiments, a synthetic nucleic acid comprises a nucleotide sequence encoding a variant HMGR, e.g., a HMGR that differs in amino acid sequence by one or more amino acids from a naturally-occurring HMGR or other parent HMGR. In some embodiments, a variant HMGR differs in amino acid sequence by one amino acid, two amino acids, three amino acids, four amino acids, five amino acids, six amino acids, seven amino acids, eight amino acids, nine amino acids, or amino acids, or more, compared to the amino acid sequence of a naturally-occurring parent HMGR. In some embodiments, a variant HMGR differs in amino acid sequence by from about 10 amino acids to about 15 amino acids, from about 15 amino acids to about 20 amino acids, from about 20 amino acids to about 25 amino acids, from about 25 amino acids to about 30 amino acids, from about 30 amino acids to about 35 amino acids, from about 35 amino acids to about 40 amino acids, from about 40 amino acids to about 50 amino acids, or from about 50 amino acids to about 60 amino acids, or more, compared to the amino acid sequence of a naturally-occurring parent HMGR.

In some embodiments, a variant HMGR is encoded by a nucleic acid that hybridizes under stringent hybridization conditions to a nucleic acid encoding a known HMGR. In other embodiments, a variant HMGR is encoded by a nucleic acid that hybridizes under moderate hybridization conditions to a nucleic acid encoding a known HMGR. In other embodiments, a variant HMGR is encoded by a nucleic acid that hybridizes under low stringency hybridization conditions to a nucleic acid encoding a known HMGR.

In some embodiments, a nucleic acid comprising a nucleotide sequence encoding a naturally-occurring HMGR is mutated, using any of a variety of well-established methods, giving rise to a nucleic acid comprising a nucleotide sequence encoding a variant HMGR. Suitable mutagenesis methods include, but are not limited to, chemical mutation methods, radiation-induced mutagenesis, and methods of mutating a nucleic acid during synthesis, as described supra. Thus, e.g., a nucleic acid comprising a nucleotide sequence encoding a naturally-occurring HMGR is exposed to a chemical mutagen, as described above, or subjected to radiation mutation, or subjected to an error-prone PCR, and the mutagenized nucleic acid introduced into a genetically modified host cell(s) as described above. Methods for random mutagenesis using a "mutator" strain of bacteria are also well known in the art and can be used to generate a variant HMGR. See, e.g., Greener et al., "An Efficient Random Mutagenesis Technique Using an *E. coli* Mutator Strain", *Methods in Molecular Biology*, 57:375–385 (1995). Saturation mutagenesis techniques employing a polymerase chain reaction (PCR) are also well known and can be used. See, e.g., U.S. Pat. No. 6,171,820. Nucleic acids comprising a nucleotide sequence encoding a variant HMGR are identified by the ability to relieve growth inhibition caused by HMG-CoA accumulation.

Nucleotide sequences encoding HMGR are known in the art, and any known HMGR-encoding nucleotide sequence can be altered to generate a synthetic nucleic acid for use in a subject method.

Of particular interest in some embodiments is identification of variant HMGR that exhibit increased enzymatic activity, that that therefore reduce HMG-CoA accumulation-induced cell growth inhibition. A variant HMGR that exhibits increased enzymatic activity exhibits at least about 10%, at least about 20%, at least about 30%, at least about 40%, at least about 50%, at least about 60%, at least about 70%, at least about 80%, at least about 90%, at least about 2-fold, at least about 2.5-fold, at least about 5-fold, at least about 10-fold, or at least about 25-fold, or more, greater enzymatic activity compared to a parent HMGR.

Methods of Identifying an Agent that Reduces Accumulation of HMG-CoA

The present invention further provides in vitro screening methods for identifying an agent that inhibits or reduces accumulation of HMG-CoA; methods of identifying agents that reduce the level of HMGS activity in a cell; methods of identifying an agent that inhibits production of HMG-CoA; and methods of identifying an agent that converts or accelerates the conversion of HMG-CoA to another compound. The methods generally involve a) contacting a test cell with a test agent, where the test cell synthesizes mevalonate via a mevalonate pathway, and where the test cell exhibits HMG-CoA accumulation-induced growth inhibition; and b) determining the effect, if any, of the test agent on HMG-CoA accumulation-induced growth inhibition. A reduction in growth inhibition indicates that the agent reduces intracellular accumulation of growth-inhibiting levels of HMG-CoA.

Agents that inhibit or reduce accumulation of HMG-CoA in a cell and promote cell growth are useful for increasing production of an isoprenoid compound, as described herein. Agents that inhibit or reduce accumulation of HMG-CoA in a cell, and that reduce the level of HMGS activity in the cell, are also useful in reducing cholesterol biosynthesis, and thus are useful for treating a variety of disorders associated with high blood cholesterol levels.

The terms "candidate agent," "test agent", "agent", "substance" and "compound" are used interchangeably herein.

Candidate agents encompass numerous chemical classes, typically synthetic, semi-synthetic, or naturally occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.) and can also be used. Alternatively, libraries of natural compounds in the form of bacterial, fungal, plant and animal extracts are available from Pan Labs (Bothell, Wash.) or are readily producible.

Candidate agents may be small organic or inorganic compounds having a molecular weight of more than 50 and less than about 2,500 daltons. Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Assays of the invention include controls, where suitable controls include a cell that exhibits HMG-CoA accumulation-induced growth inhibition in the absence of the test agent. Generally a plurality of assay mixtures is run in parallel with different agent concentrations to obtain a differential response to the various concentrations. Typically, one of these concentrations serves as a negative control, i.e. at zero concentration or below the level of detection.

A suitable period of time for contacting the agent with the cell can be determined empirically, and is generally a time sufficient to allow entry of the agent into the cell and to allow the agent to have a measurable effect on HMG-CoA accumulation-induced cell growth inhibition. Generally, a suitable time is between 10 minutes and 24 hours, or from about 1 hour to about 8 hours.

The screening methods may be designed a number of different ways, where a variety of assay configurations and protocols may be employed, as are known in the art. For example, test cells (cells that exhibit HMG-CoA accumulation-induced growth inhibition) can be plated in wells of a multi-well plate (e.g., a 96-well plate, a 384-well plate, etc.) and various test agents added individually to the wells of the plate. The screening method can be automated.

A candidate agent is assessed for any cytotoxic activity it may exhibit toward the cell used in the assay, using well-known assays, such as trypan blue dye exclusion, an MTT (3-(4,5-dimethylthiazol-2-yl)-2,5-diphenyl-2H-tetrazolium bromide) assay, and the like. Agents that do not exhibit cytotoxic activity are considered candidate agents.

A test agent of interest is one that reduces HMG-CoA accumulation-induced cell growth inhibition by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, or more, when compared to a control in the absence of the test agent. Whether the test agent has an effect on cell growth inhibition is readily determined using standard methods, as described above.

In some embodiments, the test agent is one that reduces the level of HMGS activity in the cell. A test agent of interest is one that reduces the level of HMGS activity by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, or more, when compared to a control in the absence of the test agent.

Whether a test agent reduces the level of HMGS activity in the cell is readily determined using a variety of assay methods. As one non-limiting example, HMGS enzymatic activity is measured in a cell lysate from cell samples in which a test agent reduces HMG-CoA accumulation-induced cell growth inhibition. HMGS can be assayed by adding an excess of acetyl-CoA and acetoacetyl-CoA to a buffered solution (for example, 100 mM Tris-HCl) containing cell extract or purified enzyme. After five minutes, the reaction can be stopped (e.g. by freezing the sample) and the HMG-CoA created can be measured by LC-MS.

As another example, HMGS mRNA levels in a cell are measured. A number of methods are available for analyzing nucleic acids for the presence and/or level of a specific mRNA in a cell. The mRNA may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al (1985), *Science* 239:487; a review of techniques may be found in Sambrook, et al. *Molecular Cloning: A Laboratory Manual*, CSH Press 1989, pp. 14.2–14.33; and various PCR protocols are described amply in a number of textbooks, including, e.g., *PCR Protocols* J. Bartlett and D. Stirling, eds. (2003) Humana Press.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2', 7'-dimethoxy-4',5'-dichloro-6-carboxyfluorescein (JOE), 6-carboxy-X-rhodamine (ROX), 6-carboxy-2', 4', 7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}$P, $^{35}$S, $^{3}$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

A variety of different methods for determining the nucleic acid abundance in a sample are known to those of skill in the art, where particular methods of interest include those described in: Pietu et al., Genome Res. (June 1996) 6: 492–503; Zhao et al., Gene (Apr. 24, 1995) 156: 207–213; Soares, Curr. Opin. Biotechnol. (October 1997) 8: 542–546; Raval, J. Pharmacol Toxicol Methods (November 1994) 32: 125–127; Chalifour et al., Anal. Biochem (Feb. 1, 1994) 216: 299–304; Stolz & Tuan, Mol. Biotechnol. (December 1996) 6: 225–230; Hong et al., Bioscience Reports (1982) 2: 907; and McGraw, Anal. Biochem. (1984) 143: 298. Also of interest are the methods disclosed in WO 97/27317, the disclosure of which is herein incorporated by reference.

A number of methods are available for determining the expression level of a protein in a particular sample. For example, detection may utilize staining of cells or histological sections with labeled antibodies specific for the protein, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. Alternatively, the secondary antibody conjugated to a fluorescent compound, e.g. fluorescein, rhodamine, Texas red, etc. The absence or presence of antibody binding may be determined by various methods, including flow cytometry of dissociated cells, microscopy, radiography, scintillation counting, etc.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

In vivo Production of Mevalonate Limits the Production of Amorphadiene

The following strains, vectors, growth conditions and analytical methods were used in the following examples.

Strains, Plasmid Construction, and Growth Media

Strains

E. coli strains TOP10 and DH10B, both from Invitrogen, were used for cloning and plasmid construction. E. coli DH10B was used for isoprenoid production, growth and metabolite assays.

Growth Media

For cloning and propagation of E. coli strains harboring the various recombinant vectors described herein, Luria broth with Miller's modification (Sigma-Aldrich) was used with appropriate antibiotics for plasmid selection. For production, growth and metabolite assays, engineered ("genetically modified" or "recombinant") E. coli strains were grown in Luria broth with Miller's modification (LB), 1% (wt/vol) glycerol and appropriate antibiotics. DL-mevalonate used for media supplementation was prepared by mixing 1 volume of 2 M DL-mevalonic acid lactone (Sigma-Aldrich) with 1.02 volumes of 2 M KOH and incubating at 37° C. for 30 minutes (Campos et al. (2001) *Biochem. J.* 353:59–67). To maintain plasmids, required antibiotics, as appropriate, were added to the growth media. Isopropyl-Beta-D-thiogalactoside (IPTG), from Roche, and L-Arabinose, from Sigma-Aldrich, were used for the induction of promoter systems.

Plasmids/Operons Construction

The heterologous mevalonate pathway multi-gene operons were assembled as described in U.S. Patent Application publication Nos. 20030148479 and 20040005678, and Martin et al. (2003) *Nat. Biotech.* 21(7):796–802. The MevT operon encodes the genes atoB from *E. coli*, HMGS from *S. cerevisiae*, and a truncated form of HMGR1 from *S. cerevisiae* named "tHMGR." The MevT operon encodes the enzymes responsible for the conversion of acetyl-CoA to mevalonate (FIG. 2). The assembled operon was cloned into pCR4 TOPO vector using the Invitrogen TOPO TA cloning system (Carlsbad, Calif.) for sequencing purposes. Ligation into pCR4 TOPO vector and transformation of *Escherichia coli* TOP10 cells were carried out according to the manufacturer's instructions.

As expression of biochemical pathways is often optimal at a specific expression level, the MevT operon was cloned in a variety of expression vectors to determine the effect of plasmid copy number and promoter strength on expression of the cloned pathway. The MevT operon was cloned into the SalI site of pBAD24 (Guzman et al. (1995) *J. Bacteriology* 177:4121–4130), M. Ehrmann et al., (1997) *Proc. Natl. Acad. Sci. USA* 94: 13111–13115), medium copy number, arabinose inducible plasmid, by digesting both the empty vector and the MevT operon in pCR4 TOPO with SalI restriction enzyme and ligating with T4 DNA ligase. The resulting plasmid was named pBAD24MevT (SEQ ID NO:1) (U.S. Patent Application publication Nos. 20030148479, 20040005678).

The MevT operon was also cloned into the XmaI-PstI sites of pBAD33 (Guzman et al. (1995) *J. Bacteriology* 177:4121–4130); Hiszczynska-Sawicka. (1997) *PLASMID* 38: 174–179), low copy, arabinose inducible plasmid, by digesting both the empty vector and the MevT operon in pCR4 TOPO with XmaI and PstI restriction enzymes and ligating with T4 DNA ligase. The resulting plasmid, was named pBAD33MevT (SEQ ID NO:2), see Martin et al. (2003) supra.

To place the MevT operon under the control of a modified $P_{LAC}$ promoter (weaker promoter), the araC-$P_{BAD}$ NsiI-XmaI fragment of pBAD33MevT was replaced with the NsiI-XmaI fragment of pBBR1lMCS (Kovach et al. (1995) *Gene* 166:175–176) containing the modified $P_{LAC}$ promoter. Digestion of both pBAD33MevT and pBBR1MCS was conducted using NsiI and XmaI restriction enzymes and ligated using T4 DNA ligase. The resulting plasmid was named pMevT (SEQ ID NO:3), see U.S. Patent Application publication No. 20040005678 and Martin et al. (2003) supra.

To generate the empty plasmid control for pMevT, the MevT operon was excised from pMevT using SalI restriction enzyme. The resulting plasmid containing only the $P_{LAC}$ promoter was called pLac33 (Martin et al. (2003) supra).

To produce FPP, IPP, and DMAPP from mevalonate, the operon called MBIS was constructed as described in U.S. Patent Application publication Nos. 20030148479, 20040005678, and Martin et al. (2003) supra. MBIS contains the genes MK, PMK and MPD from *S. cerevisiea* and idi, and ispA from *E. coli* (FIG. 2). As described, the MBIS operon was assembled in the plasmid pBBR1MCS-3 (Kovach et al. (1995) supra) under the control of a modified $P_{LAC}$ promoter. The IPTG inducible plasmid was named pMBIS (SEQ ID NO 4).

To produce amorpha-4,11-diene from FPP, a synthetic amorphadine synthase gene was created as described in U.S. Patent Application publication No. 20040005678 and Martin et al. (2003) supra. The synthetic gene was cloned into the vector pTrc99A (Amann et al. (1988) Gene 69:301–315), as described, and the IPTG inducible plasmid was named pADS (SEQ ID NO 5).

In order to determine the source of toxicity caused by the increased expression of the MevT operon, the individual genes of the MevT operon and combinations thereof were amplified and cloned into expression vectors.

AtoB was amplified from pBAD24MevT using standard PCR protocols and primers complementary to the 5' and 3' ends of the gene. AtoB was cloned into the XmaI-SalI sites of pBAD33, low copy, arabinose inducible plasmid, by digesting both the empty vector and PCR product with XmaI and SalI restriction enzymes and ligating with T4 DNA ligase. The resulting plasmid was named pAtoB (SEQ ID NO 6).

HMGS was amplified from pBAD24MevT using standard PCR protocols and primers complementary to the 5' and 3' ends of the gene. HMGS was cloned into the XmaI-SalI sites of pBAD33, low copy, arabinose inducible plasmid, by digesting both the empty vector and PCR product with XmaI and SalI restriction enzymes and ligating with T4 DNA ligase. The resulting plasmid was named pHMGS (SEQ ID NO 7).

The truncated HMGR was amplified from pBAD24MevT using standard polymerase chain reaction (PCR) protocols and primers complementary to the 5' and 3' ends of the gene. The truncated HMGR (tHMGR) was cloned into the XmaI-SalI sites of pBAD33, low copy, arabinose inducible plasmid, and pBAD18 (Guzman et al. (1995) J. Bacteriology 177:4121–4130), medium copy, arabinose inducible plasmid, by digesting both the empty vectors and PCR product with XmaI and SalI restriction enzymes and ligating with T4 DNA ligase. The resulting low copy number plasmid was named pHMGR (SEQ ID NO 8) and the resulting medium copy number plasmid was named pBAD18HMGR (SEQ ID NO 9).

An operon containing only HMGS and the truncated HMGR was created by amplifying the two gene segment from pBAD24MevT using standard PCR protocols and primers complementary to the 5' end of HMGS and the 3' end of HMGR. The HMGS and HMGR fragment was cloned into the SalI site of pBAD33, low copy, arabinose inducible plasmid, by digesting both the empty vector and PCR product with SalI restriction enzyme and ligating with T4 DNA ligase. The resulting plasmid was named pHMGSR (SEQ ID NO 10).

The nucleotide sequences of plasmid constructs discussed in the Examples are depicted in FIGS. 13A–C to FIGS. 24A–C; and various features are highlighted. Coding sequences, terminators, and origins are depicted by bold text, or bold and underlined text. Promoter sequences are in boxes. The "modified pBR322 origin" depicted in FIGS. 13A–C and FIGS. 21A–C includes a truncated rop gene, and thus provides for a higher copy number plasmid than the (unmodified) pBR322 origin; the plasmid copy number of plasmids containing the modified pBR322 origin is estimated to be from about 30 copies per cell to about 50 copies per cell. See, e.g., Guzman et al. ((1995) J. Bacteriol. 177:4121–4130; and Ehrmann et al. ((1997) Proc. Natl. Acad. Sci. USA 94:13111–13115).

Measuring Cell Growth

The cell growth of E. coli cultures were measured by assaying the optical density of the cultures at 600 nm ($OD_{600}$). The $OD_{600}$ of samples taken from cultures in baffled flasks were measured using a UV-Spectrophotometer (Beckman), while the $OD_{600}$ of cultures in microtiter 96-well plates was measured using a microtiter plate reader (SpectraMax, Molecular Devices).

Amorpha-4,11-diene Measurement

Amorpha-4,11-diene concentration was determined by extracting 0.7 mL samples with 0.7 ml of ethyl acetate (Sigma-Aldrich) in glass gas chromatography (GC) vials. The samples were then shaken at maximum speed on a Fisher Vortex Genie 2 mixer (Fischer Scientific) for three minutes. The samples were allowed to settle in order to separate the ethyl acetate-water emulsions.

Ethyl acetate culture extracts were analyzed on a Hewlett-Packard 6890 gas chromatograph/mass spectrometer (GC/MS). The LEAP technologies auto-injector was programmed to extend the sampling needle into the ethyl acetate layer of the two phase mixture. A 1μL sample was separated on the GC using a DB-5 column (available from, for example, Agilent Technologies, Inc., Palo Alto, Calif.) and helium carrier gas. The oven cycle for each sample was 80° C. for two minutes, increasing temperature at 30° C./minute to a temperature of 160° C., increasing temperature at 3° C./min to 170° C., increasing temperature at 50° C./minute to 300° C., and a hold at 300° C. for two minutes. The resolved samples were analyzed by a Hewlett-Packard model 5973 mass selective detector that monitored ions 189 and 204 m/z. Previous mass spectra demonstrated that the amorpha-4,11-diene synthase product was amorphadiene and that amorphadiene had a retention time of 7.9 minutes using this GC protocol. Because pure standards of amorpha-4,11-diene are not available, the concentrations must be quantified in terms of caryophyllene equivalence. A standard curve for caryophyllene has been determined previously, based on a pure standard from Sigma (St. Louis, Mo.). The amorpha-4,11-diene concentration is based on the relative abundance of 189 and 204 m/z ions to the abundance of the total ions in the mass spectra of the two compounds.

3-hydroxy-3-methylglutaryl-coenzyme A (HMG-CoA) Measurement

Intracellular 3-hydroxy-3-methylglutaryl-coenzyme A (HMG-CoA) levels were determined by separating E. coli cells from growth media, halting cellular metabolism and extracting HMG-CoA from cells with Trichloroacetic Acid (TCA), and measuring HMG-CoA concentrations by Liquid Chromatograph/Mass Spectrometer (LC/MS). In order to quickly halt cellular metabolism and separate cells from the culture medium, layered TCA extraction was employed. Prior to sampling the cell culture, a layered TCA and silicone oil sample tube was prepared. In a 15 ml Falcon tube (Fischer Scientific), 500 μl of 10% trichloroacetic acid in deuterium oxide (both Sigma-Adrich) was added to the bottom of the tube followed by a layer of 2 ml of Silicone oil (AR200 by Fluka). Prepared sample tubes were set in ice/water bath to allow the silicone oil layer to become more viscous in order to avoid layer inversion when sampling.

10 ml of cell culture were carefully added to the 15 ml sample tube above the silicone oil layer. The sample tubes were quickly centrifuged at 4° C. at top speed using an Alegra centrifuge for 3 minutes. During this time the centrifugal force moves the cells through the silicone oil layer and into the TCA layer, thereby separating the cells from the culture medium and simultaneously lysing the cells and stopping metabolism.

After spinning down cells, the layer of culture medium was removed by aspiration. Next, the TCA layer was transferred to a 2 ml centrifuge tube and neutralized with 1 ml of 0.5 M Tri-n-octyl-amine in 1,1,2-Trichloro-1,2,2-trifluoroethane (both Aldrich). The aqueous layer was removed, filtered and assayed by LC/MS.

The aqueous TCA extract was analyzed on a Hewlett-Packard 1100 LC/MS. A 50 µL sample was separated on a C-18 reversed phase HPLC column (Varian) using a two component gradient solvent system. Solvent A was 100 mM Ammonium Acetate buffer at pH 6 and Solvent B was 70% 100 mM Ammonium Acetate buffer and 30% Acetonitrile. The HPLC column was equilibrated each run with 8% Solvent B (92% Solvent A) for 10 minutes. The gradient profile was 8% Solvent B at time 0 minutes to 100% Solvent B at time 15 minutes and isocratic at 100% Solvent B until 28 minutes.

The resolved HMG-CoA samples were analyzed by mass selective detector that monitored ion 912 m/z. Retention time and mass spectrum of extracted HMG-CoA was confirmed using commercial HMG-CoA (Sigma).

Mevalonate (mevalonic acid) Measurement

Mevalonate (mevalonic acid) concentration in cultures of engineered *E. coli* was determined by GC/MS analysis. 560 µL of *E. coli* culture were mixed with 140 µL of 300 mM HCl in a glass GC vial to convert mevalonate from acid to lactone form, from mevalonic acid to mevalonic acid lactone. 700 µL of ethyl acetate was added to each vial and then the samples were shaken at maximum speed on a Fisher Vortex Genie 2 mixer (Fischer Scientific) for three minutes.

Ethyl acetate extracts of acidified culture were analyzed on a Hewlett-Packard 6890 gas chromatograph/mass spectrometer (GC/MS). The LEAP technologies auto-injector was programmed to extend the sampling needle into ethyl acetate layer of the two phase mixture. A 1 µL sample was separated on the GC using a DB-5 column (available from, for example, Agilent Technologies, Inc., Palo Alto, Calif.) and helium carrier gas. The oven cycle of each sample was modified version of the method of B. H. Woollen et al. (B. H. Woollen et al. *J. Chromatogr. B*. 760 (2001) 179–184). The oven cycle for each sample was 75° C. for two minutes, increasing temperature at 20° C./minute to a temperature of 150° C., increasing temperature at 15° C./min to 250° C., increasing temperature at 50° C./minute to 300° C., and a hold at 300° C. for two minutes. The resolved samples were analyzed by a Hewlett-Packard model 5973 mass selective detector that monitored ion 71 m/z. Retention time and mass spectrum of extracted mevalonic acid lactone was confirmed using commercial DL-mevalonic acid lactone (Sigma).

Results

Isoprenoid production in *E. coli* engineered to contain an exogenous mevalonate pathway is often limited by the production of mevalonate. Increases in mevalonate production can lead to increases in the isoprenoid that the host cell is engineered to produce. Relief of HMG-CoA toxicity leading to the increased production of mevalonate therefore leads to increased production of isoprenoid.

To improve isoprenoid production from the mevalonate pathway in *E. coli*, the limiting steps of the heterologous pathway had to be determined. To do so, plasmids pMevT, pMBIS, and pADS, as described above, were transformed into a single strain of *E. coli* DH10B by standard methods. Transformants were selected on LB agar plates containing 50 µg/ml carbenicillin, 5 µg/ml tetracycline, and 25 µg/ml chloramphenicol. A single colony of the strain was transferred from the LB agar plate to 5 ml of LB liquid medium containing the same antibiotics. This seed culture was incubated by shaking at 37° C. until growth reached a stationary phase.

Inducing the expression of both operons and ADS with IPTG allows the production of amorphadiene from *E. coli*'s supply of acetyl-CoA. To determine which operon was limiting the production of amorphadiene, *E. coli* containing all three plasmids was incubated in multiple shake flasks of liquid media consisting of LB media and 1% (wt/vol) glycerol and appropriate antibiotics. Shake flasks were inoculated from the 5 ml seed culture. Cultures were incubated at 37° C. with continuous shaking. Two hours after inoculation, 0.5 mM IPTG was added to each culture to induce expression of the operons. In addition, 10 mM and 20 mM mevalonate was added to different cultures two hours after inoculation. The cultures were incubated at 37° C. with continuous shaking. At multiple time points, the cell growth of the strain and amorphadiene production were assayed.

Figure 4:
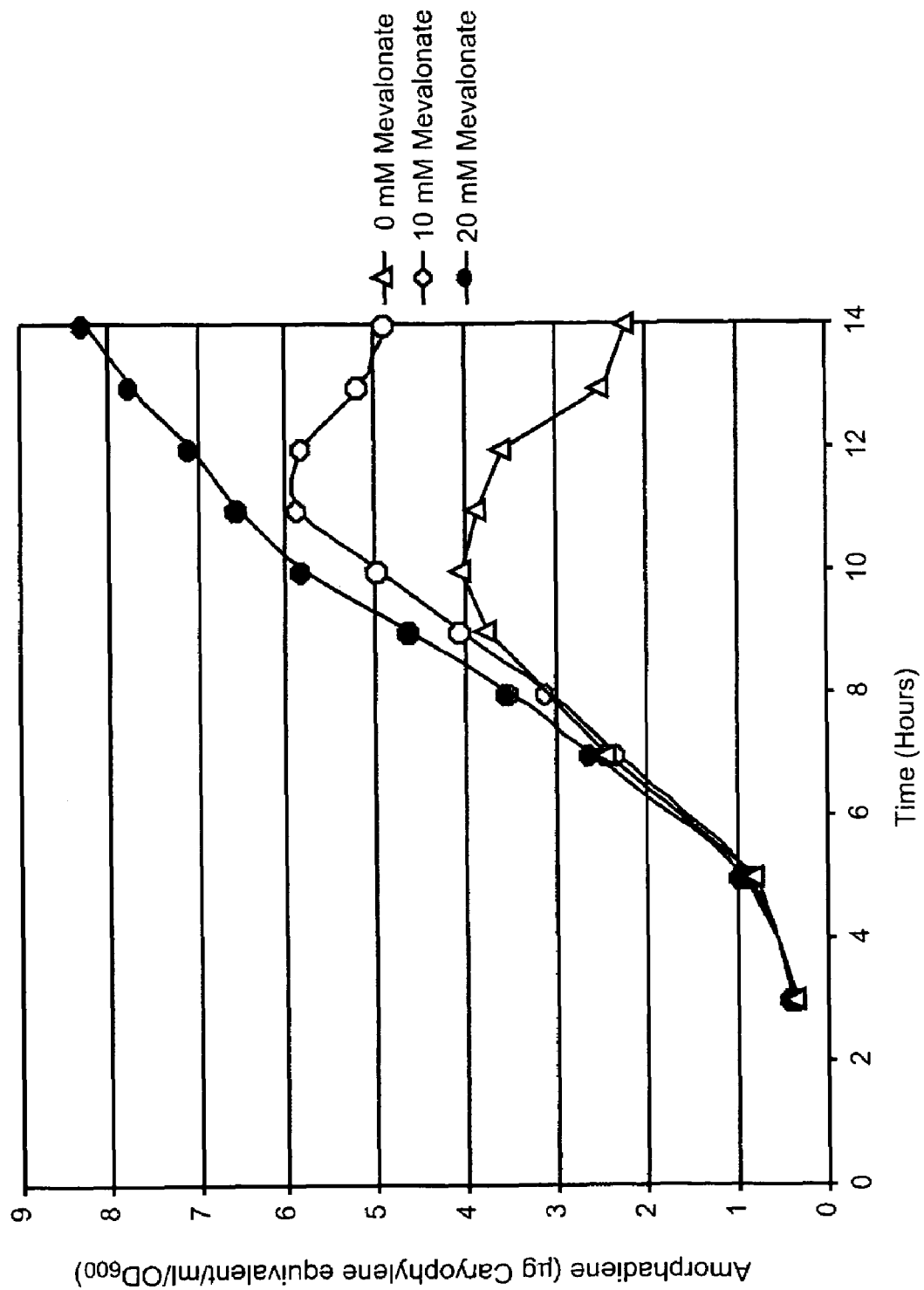
FIG. 4 depicts amorphadiene production in an *E. coli* strain genetically modified to produce IPP via the mevalonate pathway, cultured in medium supplemented with no mevalonate, 10 mM mevalonate, or 20 mM mevalonate.

As shown in FIG. 4, increasing the amount of mevalonate added to the cultures increased the production of amorphadiene from the *E. coli* strains expressing all three operons. This result demonstrates that the in vivo production of mevalonate by the MevT operon limits the production of the sesquiterpene amorphadiene in these test systems.

FIG. 4. Comparison of amorphadiene production in *E. coli* strain using the engineered mevlonate pathway [pMevT, pMBIS, pADS] from cultures with varying concentrations of exogenous mevalonate. LB media with 1% Glycerol was supplemented with no mevalonate (0 mM), 10 mM mevalonate or 20 mM mevalonate.

Example 2

Increased Expression of the MevT Operon from Stronger Promoter Systems and Higher Copy Number Plasmid Vectors Results in Growth Inhibition The following example demonstrates that the increased over-expression of the "top half" (acetoacetyl thiolase, HMGS, and HMGR) of the mevalonate pathway can lead to growth inhibition of the modified host cell.

To increase the in vivo production of mevalonate in *E. coli*, the MevT operon was transferred to expression systems that would give increased expression of the MevT genes. *E. coli* DH10B was transformed with the following MevT plasmids, listed in order of increasing expression: pMevT and pTrc99A (where both pMevT and pTrc99A were transformed into the same host cell), pBAD33MevT, and pBAD24MevT. In addition, the corresponding empty control plasmids were transformed into *E. coli* DH10B: pLac33 and pTrc99A (two plasmids in the same host), pBAD33, and pBAD24. pMevT and pLac33 were co-transformed with pTrc99A to control pMevT and pLac33's modified $P_{LAC}$ promoter with the copy of LacI$^Q$ on pTrc99A.

Transformants of strains containing pMevT & pTrc99A, or pLac33 & pTrc99A were selected on LB agar plates containing 50 µg/ml carbenicillin and 50 µg/ml chloramphenicol. Transformants of the remaining strains were selected on LB agar plates containing 50 µg/ml chloramphenicol. A single colony of each strain was transferred from the LB agar plate to 5 ml of LB liquid medium containing the same antibiotics. This seed culture was incubated by shaking at 37° C. until growth reached a stationary phase.

The six seed cultures were used to inoculate 96-well titer plates containing LB media plus 1% (wt/vol) glycerol with antibiotics. After 2 hours of continuous shaking at 37° C. in a microtiter plate reader, the strains were induced with either 0.5 mM IPTG (for the induction of pMevT and pLac33) or 2 mM arabinose (for the induction of pBAD33MevT, pBAD24MevT, pBAD33, and pBAD24). After induction, the cultures continued to incubate with continuous shaking at 37° C. Cell growth of each 0.2 mL culture was measured every ten minutes by the micro titer plate reader.

Figure 5:
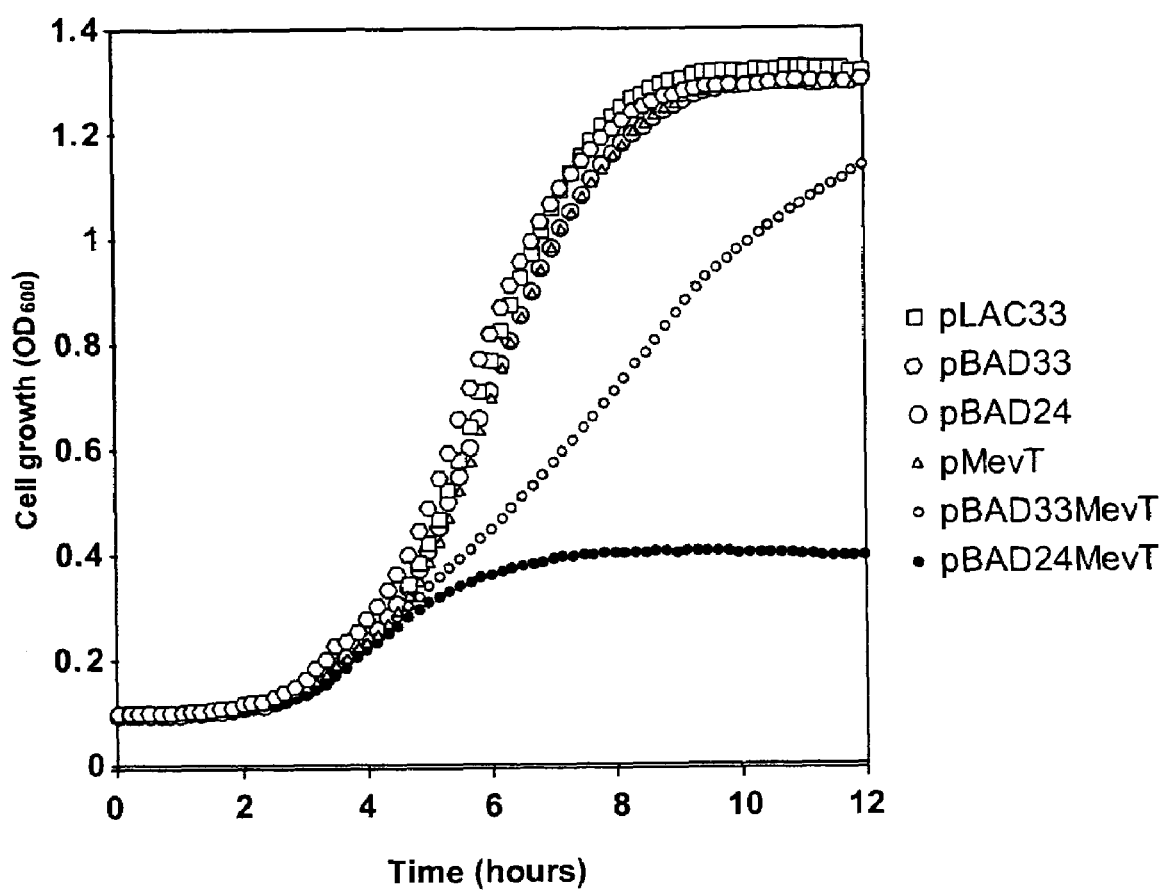
FIG. 5 depicts the inhibitory effect of increased expression of the MevT operon on cell growth of *E. coli* genetically modified with the MevT operon.

As shown in FIG. 5, induction of MevT from the weak, modified $P_{LAC}$ promoter, contained in pMevT, caused no substantial change in cell growth in comparison to the empty plasmid controls (pLac33/pTrc99A, pBAD33, and pBAD24). However, the increased expression of the MevT operon from araC-$P_{BAD}$ promoter system of pBAD33MevT causes growth inhibition. Retaining the araC-$P_{BAD}$ promoter system but increasing the plasmid copy number, thereby further increasing the total expression of MevT, as occurs in pBAD24MevT, only exacerbates the problem of growth inhibition. As these data demonstrate, increasing the expression of the MevT operon from a medium copy plasmid with a modified $P_{LAC}$ promoter system to a medium copy plasmid with an araC-$P_{BAD}$ promoter system and finally to a high copy plasmid with an araC-$P_{BAD}$ promoter system causes increasing toxicity to the engineered strains.

FIG. 5. Effect of increasing expression of the MevT operon on cell growth of E. coli. Comparison of E. coli harboring empty plasmids pLac33 +pTrc99A, pBad33, and pBAD24 with E. coli harboring MevT operons pMevT+ pTrc99A, pBAD33MevT, and pBAD24MevT (listed in order of increasing expression).

Example 3

Increased Expression of HMGS Causes Growth Inhibition, but Increased Expression of HMGS and HMGR Together does not The following example shows that the growth inhibition caused by increased expression of the top half of the mevalonate pathway, as discussed in Example 2, is due to the expression of HMGS, which catalyzes the production of HMG-CoA. Expression of HMGR, which catalyzes a reaction in which HMG-CoA is a reactant, along with HMGS, as provided by the methods of the present invention avoids this toxicity.

In order to determine the source of toxicity caused by the increased expression of the MevT operon, the individual genes of the MevT operon and combinations thereof were amplified and cloned into expression vectors. AtoB was amplified from pBAD24MevT using standard PCR protocols and primers complementary to the 5' and 3' ends of the gene. AtoB was cloned into the XmaI-SalI sites of pBAD33, low copy, arabinose inducible plasmid, by digesting both the empty vector and PCR product with XmaI and SalI restriction enzymes and ligating with T4 DNA ligase. The resulting plasmid was named pAtoB (SEQ ID NO 6). HMGS was amplified from pBAD24MevT using standard PCR protocols and primers complementory to the 5' and 3' ends of the gene. HMGS was cloned into the XmaI-SalI sites of pBAD33, low copy, arabinose inducible plasmid, by digesting both the empty vector and PCR product with XmaI and SalI restriction enzymes and ligating with T4 DNA ligase. The resulting plasmid was named pHMGS (SEQ ID NO 7). The truncated HMGR was amplified from pBAD24MevT using standard polymerase chain reaction (PCR) protocols and primers complementary to the 5' and 3' ends of the gene. The truncated HMGR (tHMGR) was cloned into the XmaI-SalI sites of pBAD33, low copy, arabinose inducible plasmid, and pBAD18 (Guzman et al. (1995) J. Bacteriology 177:4121–4130), medium copy, arabinose inducible plasmid, by digesting both the empty vectors and PCR product with XmaI and SalI restriction enzymes and ligating with T4 DNA ligase. The resulting low copy number plasmid was named pHMGR (SEQ ID NO 8), and the resulting medium copy number plasmid was named pBAD18HMGR (SEQ ID NO 9).

An operon containing only HMGS and the truncated HMGR was created by amplifying the two gene segment from pBAD24MevT using standard PCR protocols and primers complementary to the 5' end of HMGS and the 3' end of HMGR. The HMGS and HMGR fragment was cloned into the SalI site of pBAD33, low copy, arabinose inducible plasmid, by digesting both the empty vector and PCR product with SalI restriction enzyme and ligating with T4 DNA ligase. The resulting plasmid was named pHMGSR (SEQ ID NO 10).

To determine the cause of growth inhibition associated with increased expression of the MevT operon, the operon was broken down into individual components. The plasmids pAtoB, pHMGS, and pHMGR, expressing each of the individual genes, and pHMGSR, expressing the combination of HMGS and HMGR were constructed as described above. These four plasmids, along with pBAD33 (empty plasmid control) and pBAD33MevT were transformed into E. coli DH10B using standard procedures. Transformants were selected on LB agar plates containing 50 μg/ml chloramphenicol. A single colony of each strain was transferred from the LB agar plate to 5 ml of LB liquid medium containing the same antibiotic. This seed culture was incubated by shaking at 37° C. until growth reached a stationary phase.

The six seed cultures were used to inoculate 96-well microtiter plates containing 0.2 ml volumes of LB media, 1% (wt/vol) Glycerol, and antibiotics. The 96-well plate cultures were shaken continuously at 37° C. in a micro-titer plate reader and induced with 2 mM arabinose at 2 hours post inoculation. The cell growth of each culture is displayed in FIG. 6.

Figure 6:
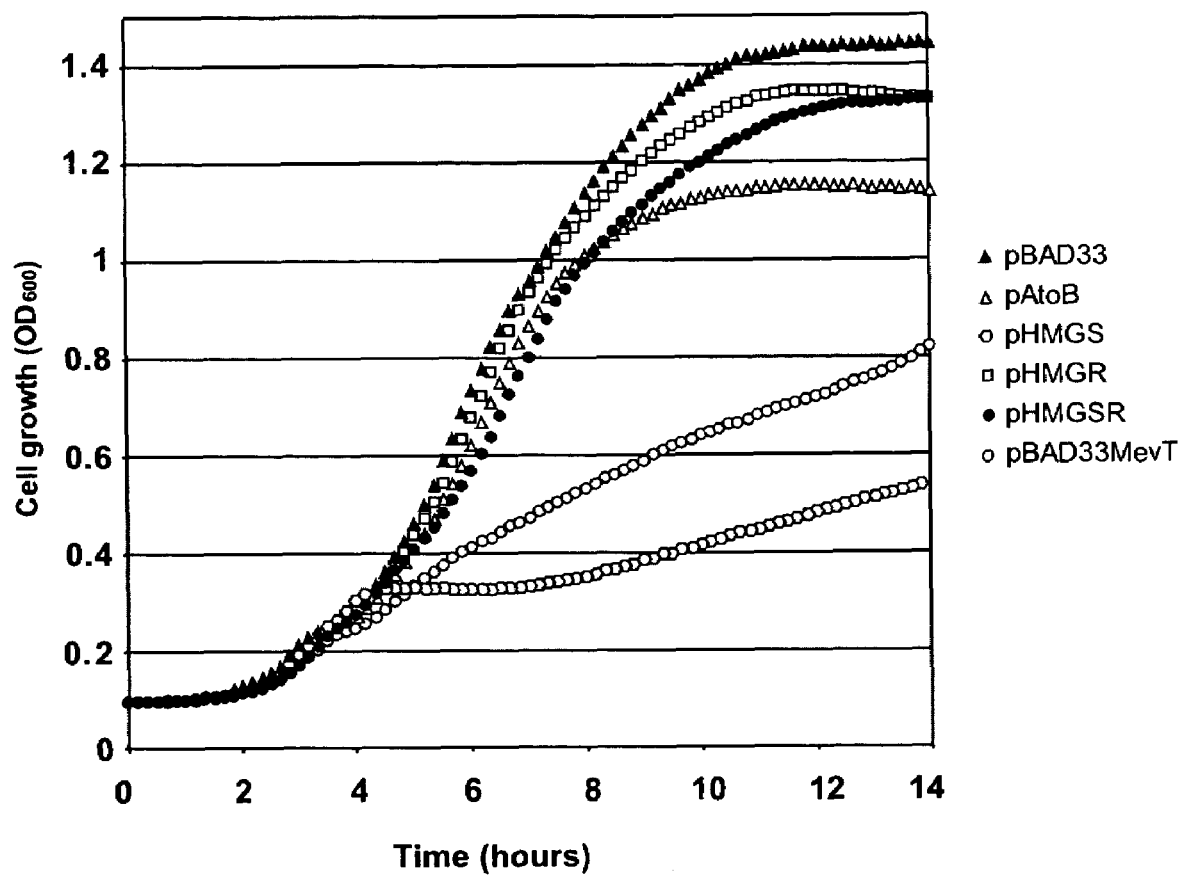
FIG. 6 depicts the effect of increased expression of each of the individual genes contained in the MevT operon and combinations thereof on cell growth.

As shown in FIG. 6, in comparison to the empty plasmid control, the increased expression of atoB and HMGR in E. coli (in strains harboring plasmids pAtoB and pHMGR, respectively), have no significant effect on cell growth. However, the increased expression of HMGS (in strain harboring pHMGS) causes substantial growth inhibition. Interestingly, with the increased co-expression of both HMGS and HMGR (as in strain harboring pHMGSR), cell growth is restored to that of the empty plasmid control. This relief of toxicity is hypothesized to be due to the ability of HMGR to convert the HMG-CoA that is produced by HMGS (and not degraded by any known enzymes in E. coli) into mevalonate. Mevalonate then passed through the cell membrane into the media, as described in (Campos et al. (2001) Biochem. J. 353:59–67; and Martin et al. (2003) Nature Biotech. 21(7):796–802). However, the increased expression of all three genes in the MevT operon (as in the strain harboring pBAD33MevT), again inhibits cell growth. Because the data show that the increased expression of atoB alone does not cause growth inhibition, toxicity caused by the increased co-expression of atoB with HMGS and HMGR is likely due to the increased production of acetoacetyl-CoA by atoB. Increased production of acetoacetyl-CoA by the increased expression of the E. coli keto thiolase (atoB)

provides HMGS with additional substrate and dramatically increases the production of mevalonate (T. Kuzuyama. (2004) *Biosci. Biotechnol. Biochem.* 68(4): 931–934). However, if the total activity of HMGS is greater than that of HMGR, HMG-CoA will accumulate and likely cause growth inhibition. To verify these hypotheses, the Acyl-CoA pathway intermediates were measured in the engineered strains.

FIG. 6. Comparison of cell growth of *E. coli* expressing individual MevT genes and combinations thereof at high levels. Cell growth of *E. coli* harboring plasmids pBad33 (empty plasmid control), pAtoB, pHMGR, pHMGS, pHMGSR, and pBAD33MevT.

Example 4

Toxicity Caused by Increased Expression of HMGS is Due to the Increased Enzymatic Activity of the Protein and not Simply Increased Production of the Protein Itself The following example demonstrates that the toxicity observed in the expression of HMGS is not due to the expression of the enzyme, but is due to its activity—the production of HMG-CoA from acetoacetyl-CoA and acetyl-CoA. That is, the growth inhibition observed is not due to the metabolic burden incurred through the production of additional enzyme, but rather through the action of the enzyme in the cell.

Creating a Full Length but Catalytically Inactive HMGS

The toxicity caused by the high expression of *S. cerevisiae* HMGS alone in *E. coli* might have been be due to the toxicity caused by the high level production of a heterologous protein (B. R. Glick. (1995) *Biotech Advances.* 13(12): 247–261) as opposed to the metabolic activity of HMGS. To differentiate between the two possibilities, a full length but catalytically inactive HMGS was created. The active site of the wild-type *S. cerevisiae* HMGS protein was determined by comparing the protein sequence of the yeast HMGS to the active site sequences of several mammalian HMGS proteins listed in L. L. Rokosz et al. ((1994) *Arch. Biochem. Biophysics.* 312(1), 1–13). The active site residues of *S. cerevisiae* HMGS were identical to the active site amino acid residues of the mammalian HMG-CoA synthases.

Rokosz et al. ((1994) supra) demonstrated that changing the catalytic cysteine amino acid of Human HMG-CoA synthase to an alanine created a full length HMG-CoA synthase protein that was catalytically inactive. Accordingly, the catalytic cysteine amino acid of the *S. cervisiae* HMGS active site in pBAD33MevT was replaced with an alanine amino acid using site-directed mutagenesis (QuickChange Site-directed mutagenesis kit, Stratagene). The cysteine at amino acid position 159 to alanine mutant of the yeast HMGS, named HMGS(C159A), was verified by DNA sequence of the entire operon. The plasmid pBad33MevT containing the HMGS(C159A) mutant was named pBAD33MevT(C159A) (SEQ ID NO 11). High expression of pBAD33MevT(C159A) in *E. coli* DH10B produced no detectable mevalonate as measured by LC tandem MS (liquid chromatography tandem mass spectrometry), or MHG-CoA, as measured by liquid chromatography-mass spectrometry. This result shows that the HMGS(C159A) mutant is also catalytically inactive.

To construct a plasmid that expressed mutant HMG-CoA synthase alone, HMGS(C159A) was amplified from pBAD33MevT(C159A) using standard PCR protocols and primers complementary to the 5' and 3' ends of the gene. HMGS(C159A) gene was cloned into the XmaI-SalI sites of pBAD33, low copy number, arabinose inducible plasmid, by digesting both the empty vector and PCR product with XmaI and SalI restriction enzymes and ligating with T4 DNA ligase. The resulting plasmid was named pHMGS(C159A) (SEQ ID NO 12).

Determination of the Cause of the Growth Inhibition

To determine why the high expression of HMGS in *E. coli* causes growth inhibition, the effect of high expression of the wild-type HMGS was compared to the effect of high expression of the full length, catalytically inactive HMGS, HMGS (C159A). Plasmids pBAD33 (the empty plasmid control), pHMGS, pHMGS(C159A), pBAD33MevT and pBAD33MevT(C159A) were transformed into *E. coli* DH10B using standard procedures. Transformants were selected on LB agar plates containing 50 µg/ml chloramphenicol. A single colony of each strain was transferred from the LB agar plate to 5 ml of LB liquid medium containing the same antibiotic. This seed culture was incubated with shaking at 37° C. until growth reached a stationary phase.

The five different seed cultures were used to inoculate 96-well microtiter plates containing 0.2 ml volumes of LB media, 1% (wt/vol) Glycerol, and antibiotics. The 96-well plate cultures were shaken continuously at 37° C. in a micro-titer plate reader and induced with 2 mM arabinose at 2 hours post inoculation. The cell growth of each culture is displayed in FIG. 7.

Figure 7:
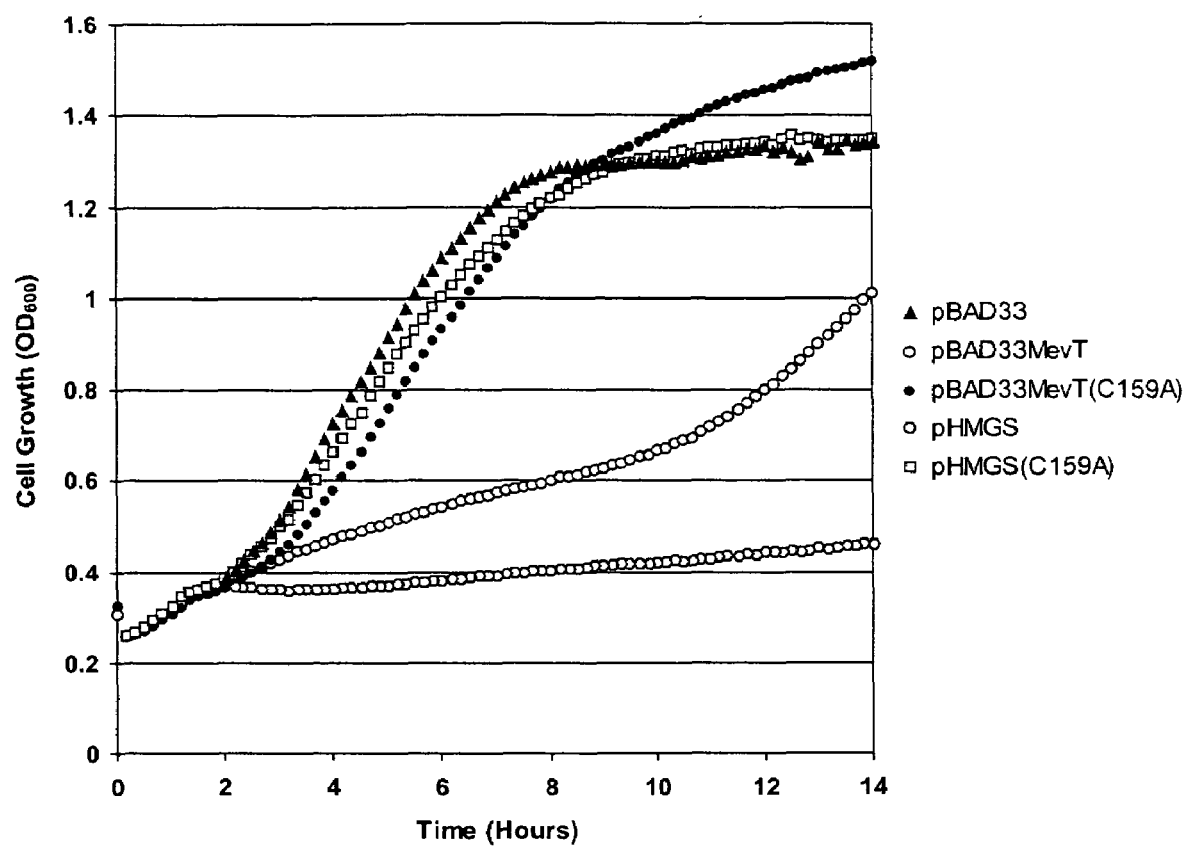
FIG. 7 depicts the effect of catalytically inactive HMGS on cell growth of *E. coli.*

As shown in FIG. 7, in comparison to the control (strain harboring pBAD33), high expression of HMGS in *E. coli* (in strain harboring pHMGS) causes growth inhibition while high expression of the HMGS(C159A) mutant in *E. coli* (in strains harboring pHMGS(C159A)) does not. Because the only difference between pHMGS and pHMGS(C159A) is the conversion of the catalytic cysteine to an alanine, this result demonstrates that the toxicity caused by high expression of wild-type HMGS is due to the enzymatic activity of the protein and not merely the growth inhibition that can be caused by high expression of heterologous proteins (B. R. Glick. (1995) *Biotech Advances.* 13(12): 247–261). Furthermore, *E. coli* expressing the inactive MevT operon at high levels (in strain harboring pBAD33MevT(C159A)) portrays the same growth profile as the control, while high expression of the functional MevT operon (in strain harboring pBAD33MevT) inhibits cell growth. This result demonstrates that growth inhibition caused by high expression of all the genes in the MevT operon is not due to growth inhibition caused by high expression of heterologous proteins.

In addition, FIG. 7 demonstrates that the toxicity from high expression of the MevT operon, caused by the intercellular accumulation of HMG-CoA (see Examples 5 and 6, above), can be alleviated by reducing the activity of HMGS. Although the activity of HMGS is reduced to zero in this example, there are a reduced levels of HMGS activity that will alleviate the growth inhibition while still allowing the production of mevalonate. High expression of a pathway balanced in enzyme activity results in the increased production of mevalonate per volume of cell culture.

FIG. 7. Effect of high expression of catalytically inactive HMGS on *E. coli* cell growth. Comparison of cell growth of *E. coli* harboring plasmids pBad33 (empty plasmid control), pBAD33MevT, pBAD33MevT(C159A) (contains inactive HMGS), pHMGS, and pHMGS(C159A) (contains inactive HMGS).

Example 5

Growth Inhibition of *E. coli* Over Expressing the MevT Operon is Due to the Intracellular Accumulation of HMG-CoA The following examples demonstrate that the growth inhibition seen upon expressing the MevT operon is due to the accumulation of HMG-CoA.

*E. coli* DH10B strains harboring plasmids pBAD33 (the empty plasmid control), pHMGS, pHMGSR, and pBAD33MevT were grown overnight at 37° C. in 5 ml of LB media and antibiotics under non-inducing conditions. The overnight cultures were used to inoculate baffled shake flasks containing 100 ml of LB media, 1% (wt/vol) Glycerol, and antibiotics. The cultures were shaken continuously at 37° C. and induced with 2 mM arabinose at 2 hours post inoculation. The intracellular levels of HMG-CoA in each strain and the cell growth of each culture were measured and the results are displayed in FIG. 8 and FIG. 9, respectively.

Figure 8:
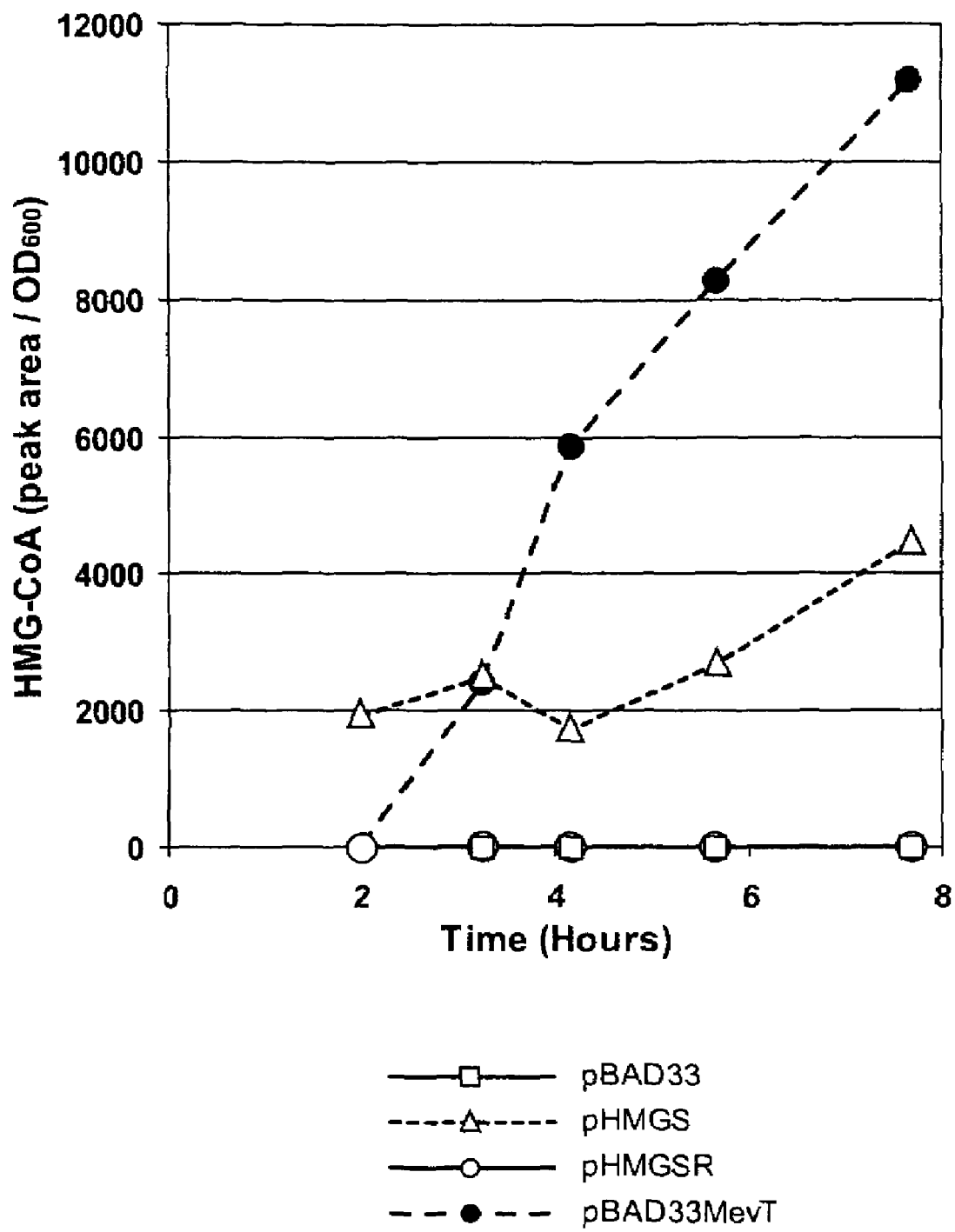
FIG. 8 depicts intracellular accumulation of HMG-CoA in *E. coli* strains expressing toxic mevalonate pathway constructs.
Figure 9:
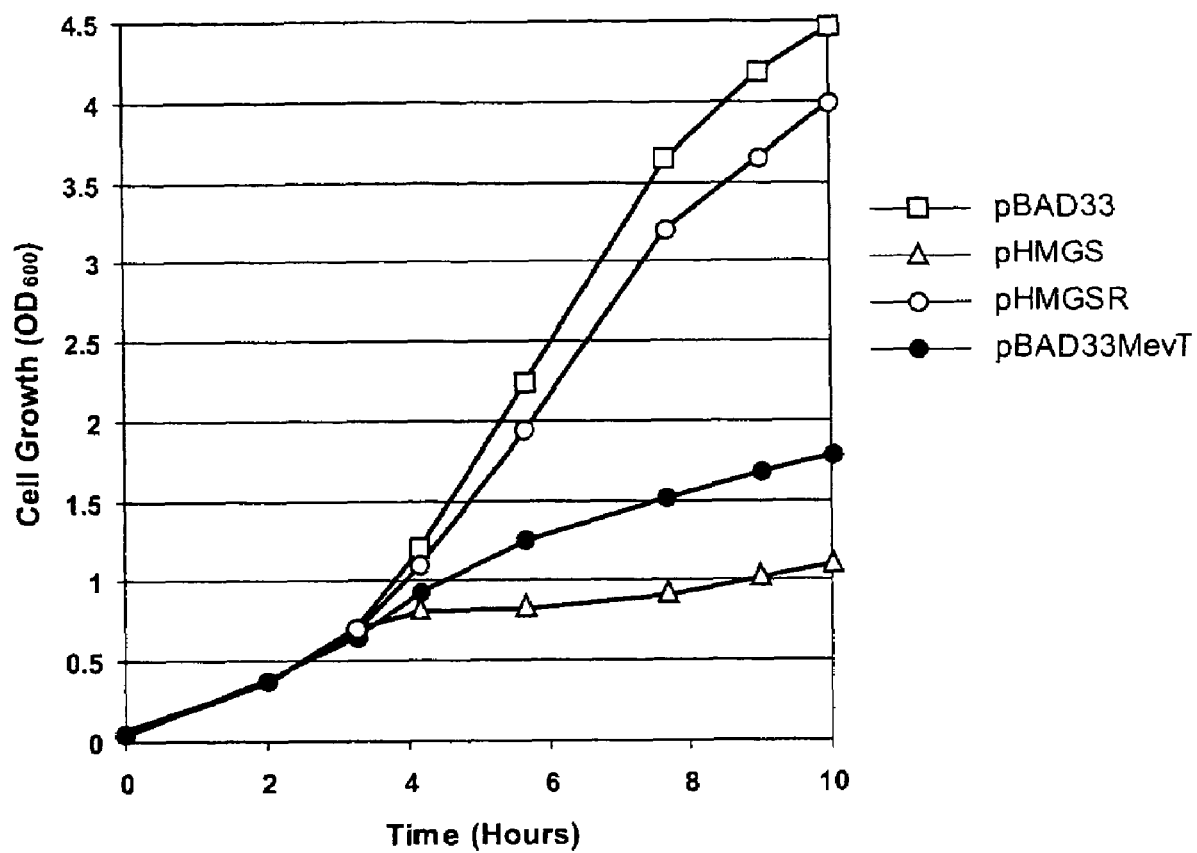
FIG. 9 depicts the effect of HMG-CoA accumulation on cell growth.

As shown in FIGS. 8 and 9, in comparison to the empty vector control (the strain harboring pBAD33), high expression of HMGS (in the strain harboring pHMGS) causes the accumulation of HMG-CoA and growth inhibition. Interestingly, high level expression of both HMGS and HMGR in conjunction (in the strain harboring pHMGSR) causes no growth inhibition and accumulates no detectable level of HMG-CoA, and is generally similar to the control in these respects. However, the high expression of atoB, HMGS and HMGR together in the MevT operon in *E. coli* (in the strain harboring pBAD33MevT) causes growth inhibition and the accumulation of HMG-CoA at later times.

*E. coli* naturally produces aceoacetyl-CoA at a low level from the native expression of atoB and the degradation of short chain fatty acids. The results shown in FIGS. 8 and 9 demonstrate that high expression of HMGS alone in *E. coli* produces HMG-CoA from the native supply of acetoacetyl f-CoA. Because HMG-CoA is not native to *E. coli*, it is not known to be acted upon by any enzyme in *E. coli* and will not cross the cell membrane; therefore, HMG-CoA accumulates in the cell. At a certain level, HMG-CoA inhibits cellular processes. However, high expression of HMGS and HMGR together allows the HMG-CoA that is produced from the native supply of acetoacetyl-CoA by HMGS to be converted to mevalonate. Mevalonate will pass across the cellular membrane and accumulate in the media. Additionally, high extra-cellular concentrations of mevalonate appear to have no significant effect on the growth of *E. coli* (Martin et al. (2003) supra.

FIG. 8. Intracellular HMG-CoA levels of *E. coli* strains expressing mevalonate pathway constructs. HMG-CoA accumulation in *E. coli* harboring pBad33 (empty plasmid control), pHMGS, pHMGSR, and pBAD33MevT.

FIG. 9. Cell growth of *E. coli* strains expressing mevalonate pathway constructs. Comparison of cell growth of *E. coli* harboring plasmids pBad33 (empty plasmid control), pHMGS, pHMGSR, and pBAD33MevT.

High expression of atoB, together with HMGS and HMGR, provides increased substrate for HMGS and substantially increases the production of mevalonate (T. Kuzuyarna. (2004) *Biosci. Biotechnol. Biochem.* 68(4): 931–934); however, if the total activity of HMGS is greater than that of HMGR, the intermediate HMG-CoA will again accumulate and cause growth inhibition. Thus, in one embodiment, the present invention provides a method for relieving the growth inhibition toxicity of HMG CoA accumulation in a cell, which method comprises modifying the cell to increase expression of HMGR, relative to HMGS. In one embodiment, the HMGR activity is increased to a level about equal to the HMGS activity. In other embodiments, the HMGR activity is increased to levels 1.5, 2, 5, and 10 times the HMGS activity.

Example 6

Increased Expression of HMGR Alleviates the Growth Inhibition Caused by High Expression of MevT, Decreases the Accumulation of HMG-CoA, and Increases the Production of Mevalonate The following example shows how one can increase mevalonate production and overcome the toxicity problem caused by the accumulation of HMG-CoA due to overexpression of HMGR.

To demonstrate that the intracellular accumulation of HMG-CoA was toxic to *E. Coli* and to begin optimizing the pathway to correct this problem, the activity of HMGR was increased in strains expressing the MevT operon at high levels. *E. coli* DH10B was transformed with the following combinations of two plasmids to create three dual plasmid systems: pBAD33 & pBAD18 (empty plasmid control strain), pBAD33MevT & pBAD18, and pBAD33MevT & pBAD18HMGR. Transformants were selected on LB agar plates containing 50 µg/ml carbenicillin and 50 µg/ml chloramphenicol. A single colony of each strain was transferred from the LB agar plate to 5 ml of LB liquid medium containing the same antibiotic. This seed culture was incubated by shaking at 37° C. until growth reached a stationary phase.

The three different seed cultures were used to inoculate baffled shake flasks containing 100 ml of LB media, 1% (wt/vol) Glycerol, and antibiotics. The cultures were shaken continuously at 37° C. and induced with 2 mM arabinose at 2 hours post inoculation. The cell growth of each culture, the intracellular levels of HMG-CoA in each strain and mevalonate produced in each culture were measured by the methods described in Example 1. The results for the three dual plasmid systems are displayed in FIGS. 10, 11 and 12, respectively.

Figure 10:
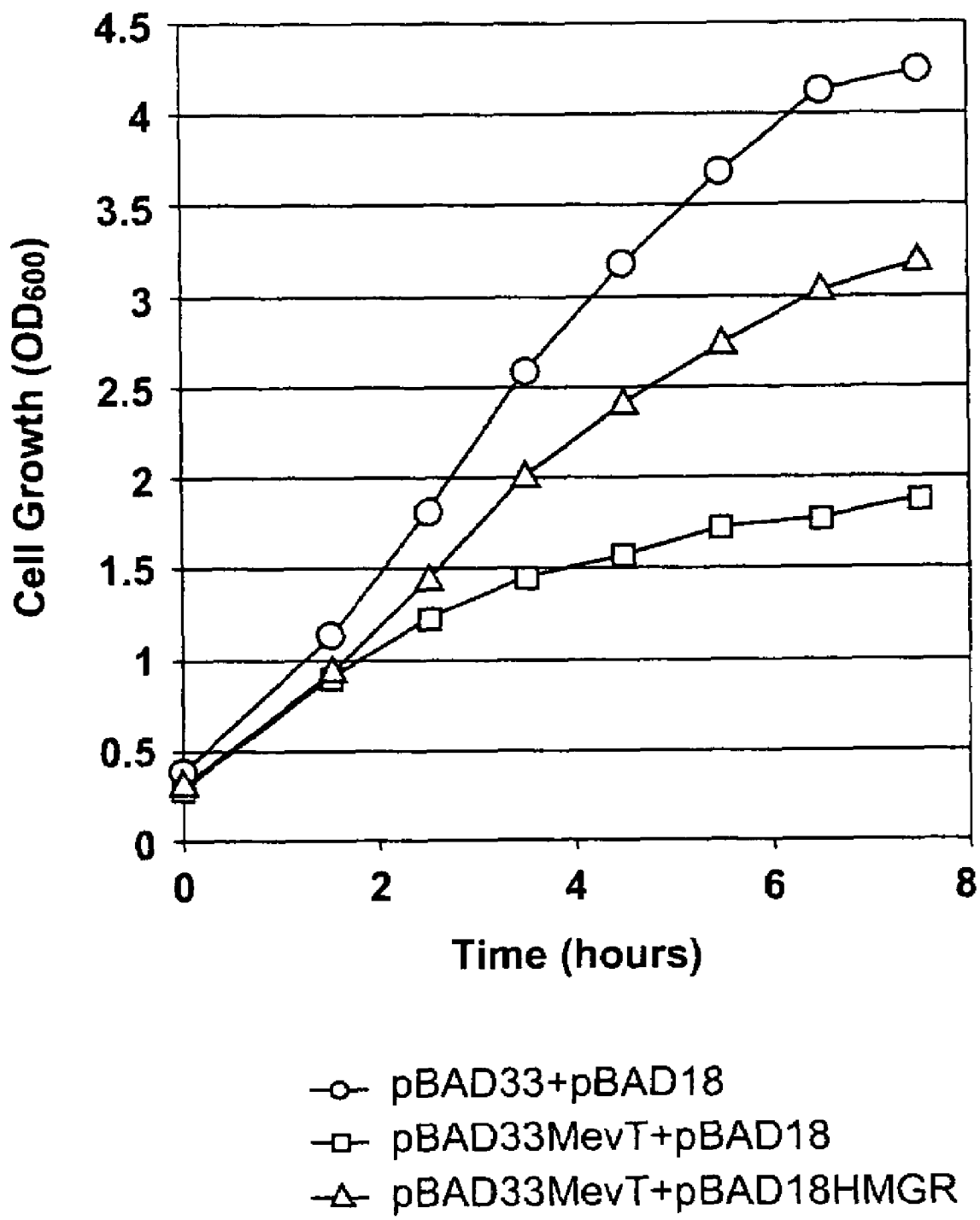
FIG. 10 depicts the effect of increased expression of tHMGR on cell growth.
Figure 11:
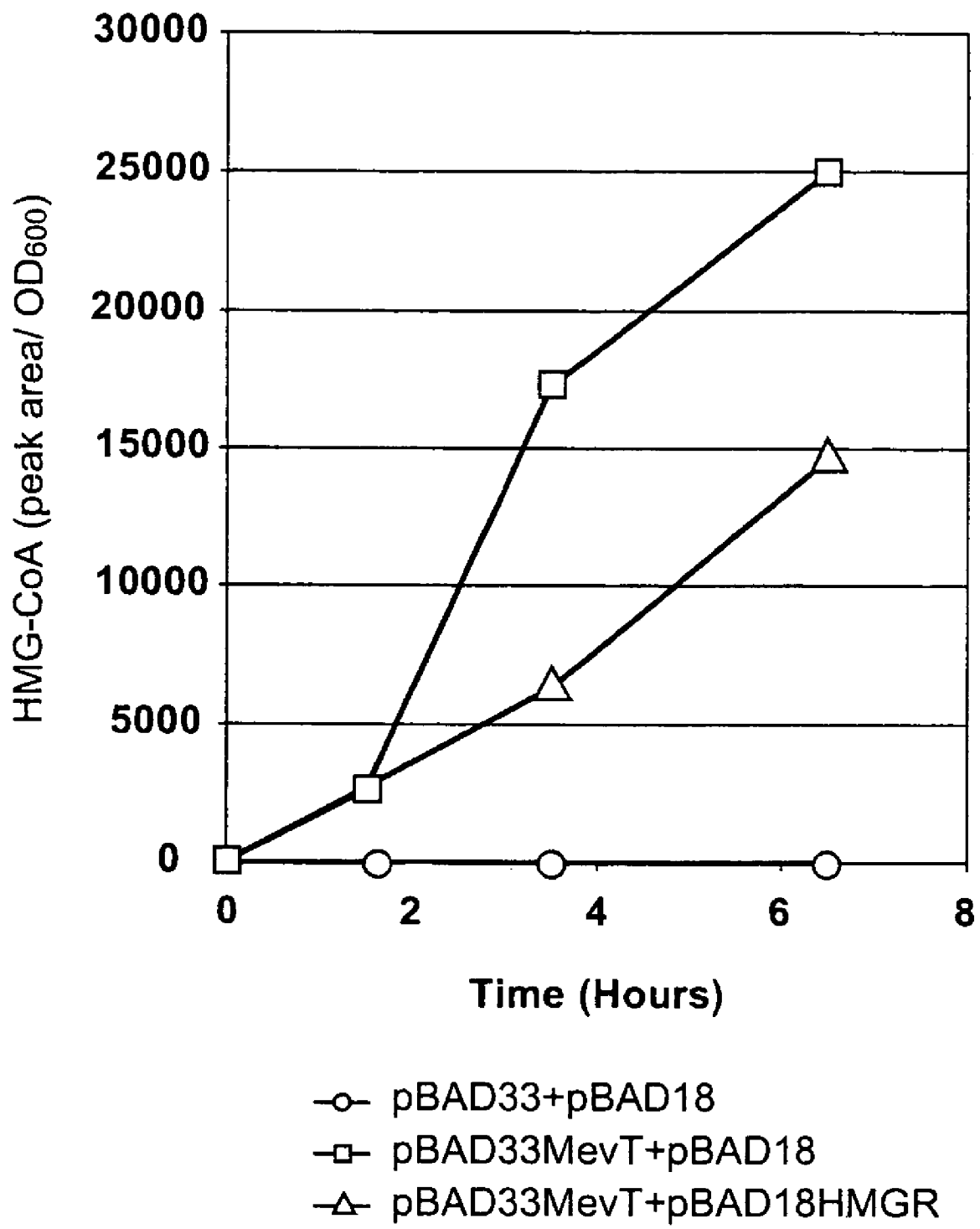
FIG. 11 depicts the effect of increased expression of tHMGR on HMG-CoA accumulation.
Figure 12:
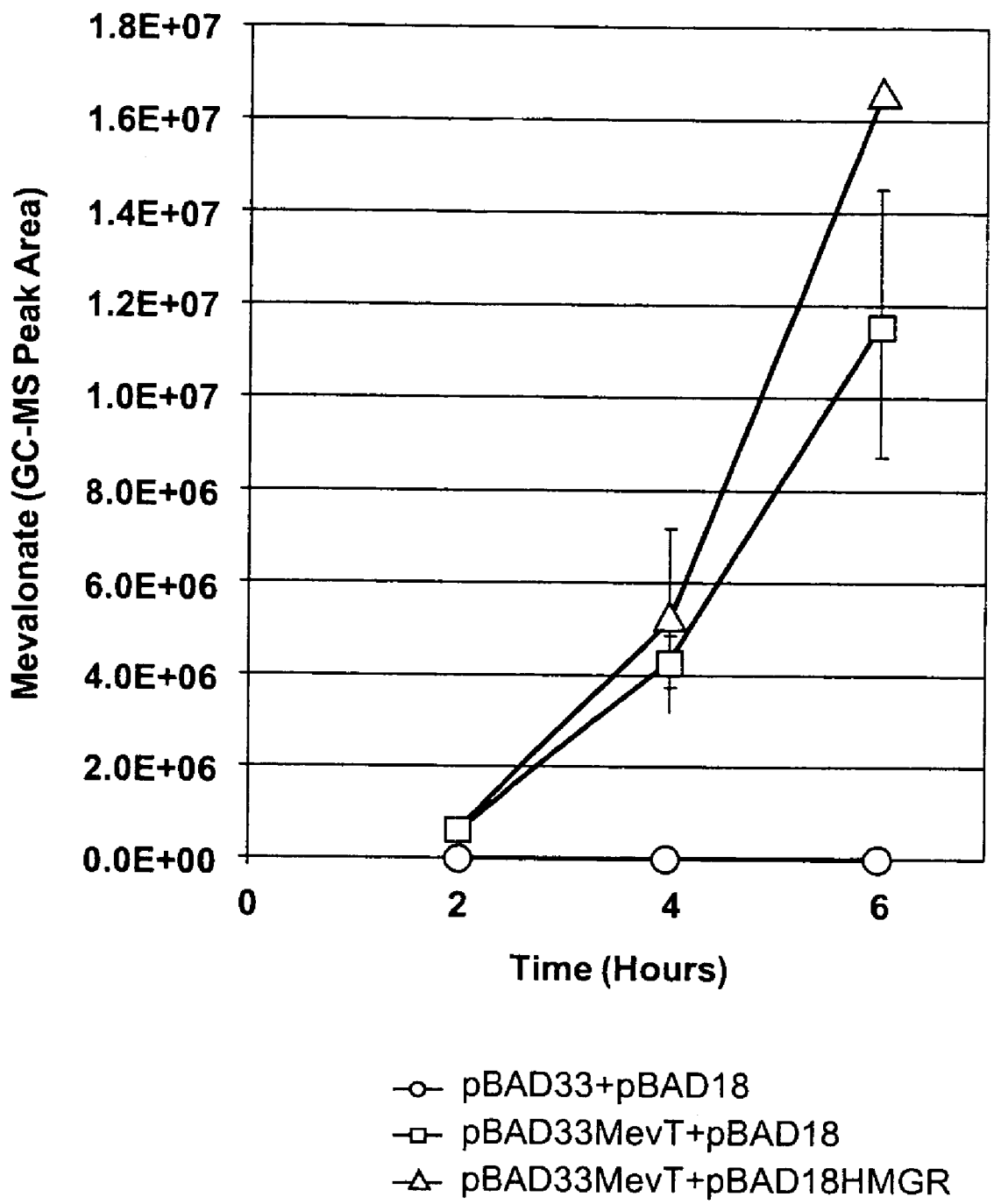
FIG. 12 depicts the effect of increased expression of tHMGR on mevalonate production.

As shown in FIGS. 10 and 11, in comparison to the control strain (the strain harboring pBAD33 and pBAD 18), the high expression of MevT in the strain harboring pBAD33MevT and pBAD18 again causes growth inhibition and the accumulation of HMG-CoA. However, increased expression of HMGR in a strain expressing MevT at a high level (the strain harboring pBAD33MevT and pBAD18HMGR), alleviates the growth inhibition in part and reduces the accumulation of HMG-CoA. Additionally, as shown in FIG. 12, the increased expression of HMGR leads to increased production of mevalonate. Increasing the expression of HMGR is only one illustrative method of the invention to increase the activity of HMGR in *E. Coli* cells. Other methods of the invention for increasing the activity of HMGR would lead to similar results.

Expression of MBIS and ADS in the strain with increased activity of HMGR and high expression of MevT, can result in increased production of amorphadiene. In addition, increasing the activity of HMGR and alleviating the toxicity caused by the high expression of MevT can increase the production of any isoprenoid given that an enzymatic pathway from mevalonate to the isoprenoid of interest is co-expressed.

FIG. 10. Effect of increased expression of HMGR on cell growth of *E. coli* expressing the MevT operon. Cell growth of *E. coli* harboring plasmids pBad33+pBad18 (empty vector control), pBad33MevT+pBad18, and pBad33MevT+ pBad18HMGR.

FIG. 11. Effect of increased expression of HMGR on HMG-CoA levels of *E. coli* expressing the MevT operon. Intracellular HMG-CoA levels of *E. coli* harboring plasmids pBad33+pBad18 (empty vector control), pBad33MevT+ pBad18, and pBad33MevT+pBad18HMGR.

FIG. 12. Effect of increased expression of HMGR on mevalonate production of *E. coli* expressing the MevT operon. Mevalonate levels in cultures of *E. coli* harboring plasmids pBad33+pBad18 (empty vector control), pBad33MevT+pBad18, and pBad3 3MevT+pBad18HMGR.

Example 7

Application of a Subject Method to a Mevalonate Producing Host Cell

The present example illustrates how the methods of the invention can be applied to any mevalonate producing host strain in which HMG-CoA levels accumulate to toxic levels. In general, a host cell is modified in some way in an attempt to achieve higher levels of isoprenoid or isoprenoid precursor (e.g., mevalonate, IPP, a polyprenyl diphosphate, and the like), to generate a "parent" cell. Suitable modifications include, e.g., modifications that increase the intracellular pool of acetyl-CoA, modifications that increase the level of acetoacetyl-CoA thiolase activity, and modifications that increase the level of HMGS activity. These modifications could be effectuated by genetic or chemical alterations or treatments intended to modify transcript levels, enzyme levels, or specific activity of enzymes.

The growth characteristics of the parent host cell are observed, and compared to the growth characteristics of the unmodified host cell. If the parent host cells grows significantly slower than the unmodified host cell, then the observed growth inhibition may be due to HMG-CoA toxicity, and the resulting levels of mevalonate or isoprenoid production would be suboptimal.

The levels of HMG-CoA in the host cell and the parent cell are determined through established extraction and LC-MS techniques (see Example 1) to verify the predicted reason for the growth inhibition. If the level of HMG-CoA per unit biomass (biomass measured as dry cell weight or by measuring the optical density at, for example 600 nm) is higher in the modified host cell, then those measurements support the conclusion that the toxicity is due to HMG-CoA accumulation, and, if so, decreasing levels within the cell will serve to alleviate this toxicity and increase total mevalonate, IPP, or isoprenoid production. While measurement of HMG-CoA levels in an HMG-CoA producing cell that is growth inhibited is not a required step in a subject method of relieving toxicity induced by HMG-CoA accumulation, such measurements may be conducted from time to time in certain embodiments HMG-CoA toxicity and improved isoprenoid or isoprenoid precursor production can be relieved by practice of the present invention. For example, the parent host cell can be genetically modified in a number of ways, resulting in a genetically modified host cell that produces an increased level of HMGR compared to the parent host cell. For example, the copy number of a vector comprising a nucleotide sequence that encodes HMGR is increased within the parent host cell, e.g., by genetically modifying the parent host cell with a high copy number plasmid that expresses HMGR under the control of a promoter. As another example, the level of HMGR mRNA in the parent cell is increased, e.g., by genetically modifying the parent cell with a construct that comprises an HMGR-encoding nucleotide sequence that is under control of a stronger promoter.

As another example, the ribosome binding site upstream of hmgR in the parent host cell is modified to generate a genetically modified host cell that produces an increased level of HMGR. By observing the growth characteristics of the genetically modified host cell and comparing them to the growth characteristics of the parent host cell, one can determine that the method has been successful when the genetically modified host cell shows less or none of the growth inhibition of the parent. Relief of HMG-CoA toxicity will be observed as an increase in growth rate and/or increase in final cell density of the culture.

As another example, a parent host cell is generated by increasing the level of HMG-CoA in a cell that has an endogenous mevalonate pathway. For example, the level of intracellular acetyl-CoA within a yeast cell, such as *Saccharomyces cerevisiae*, is increased by introducing mutations into (genetically modifying) the yeast cell, creating a "parent" host cell. For example, the intracellular acetyl-CoA level is increased by introducing a mutation within the pyruvate decarboxylase gene on the chromosome. This is accomplished using one-step gene disruption (Rothstein, R. J. (1983) Methods Enzymol. 101 202–211 One-step gene disruption in yeast) to disrupt pyruvate decarboxylase. Similarly, inactive or partially active alleles of pyruvate decarboxylase are generated by integrative DNA transformation in yeast (Rothstein, R. (1991) Methods Enzymol. 194 281–301). PCR-based disruption of pyruvate decarboxylase is accomplished using a prior knockout in a different *Saccharomyces cerevisiae* strain, such as strain S288C (Reid et al. Yeast. 2002 Mar 15; 19(4):319–28., Mehdi, K. Yeast 2002 June 30; 19(9):803). Such alterations decrease the flux of pyruvate to ethanol via acetaldehyde and indirectly increases acetyl-coA levels.

The increase in the intracellular acetyl-CoA level can, in turn, result in an increase in acetylacetyl-CoA levels, which can, in turn, lead to an increase in intracellular HMG-CoA levels. To achieve increased HMG-CoA levels, a host cell can be further genetically modified to increase the level of acetoacetyl CoA thiolase activity and/or the level of HMGS activity within the cell to increase the conversion of acetyl-CoA into HMG-CoA, generating a parent yeast host cell that exhibits high intracellular levels of HMG-CoA. Any vector designed for replication and selection in yeast and incorporating a promoter active in yeast, typically also including a yeast terminator downstream of the promoter, will be used to express genes in yeast. Examples of yeast replicons include the 2μ or CEN replicons such as CEN6/ARSH4; examples of selectable markers include the HIS3, TRP1, LEU2 or URA3 markers; examples of yeast promoters include the CYC1, ADH, TEF or GPD promoters; an example of a yeast terminator is the yeast CYC1 terminator. Examples of expression vectors are given in Mumberg D, Muller R, Funk M., Gene. 1995 Apr. 14; 156(1):119–22. A variety of yeast vectors are available for the controlled expression of heterologous proteins in different genetic backgrounds. Another example of a yeast expression vector is pYES2 (Invitrogen Corporation).

The growth characteristics of the parent host yeast cell to the unmodified host yeast cell are compared by growing each cell separately under standard conditions in standard growth media with selection for the plasmid expressing the gene of interest. Examples of yeast media include Yeast extract peptone dextrose (YPD), Synthetic dextrose minimal medium (SD), supplemented minimal medium (SMM) and synthetic complete (SC or CM) medium (Sambrook and Russell (2001) Molecular Cloning: A laboratory manual. ISBN 0–87969–577–3).

If the growth rate of the parent host cell is significantly slower than the growth rate of the unmodified host yeast cell, HMG-CoA accumulation may be the cause of this toxicity/growth inhibition. To overcome the HMG-CoA accumulation-induced cell growth inhibition, the parent yeast cell is genetically modified, in accordance with the methods of the invention. For example, a parent yeast host cell is genetically modified by replacing the endogenous HMGR gene on the chromosome of S. cerevisiae with a nucleic acid encoding HMGR that lacks the N-terminal regulatory region of the enzyme (Donald et al. Appl Environ Microbiol. 1997 September; 63(9):3341–4. Polakowski et al. Appl Microbiol Biotechnol. 1998 January; 49(1):66–71), thus increasing the level of HMG-CoA activity within the cell. If a comparison of the growth characteristics of the genetically modified host yeast cell with those of the parent host yeast cell shows a significant increase in growth rate, the increase in growth rate can be attributed to a decrease in toxic intracellular HMG-CoA levels.

As a result, the total levels of isoprenoid or isoprenoid precuror produced by the genetically modified host strain will increase, compared to the levels produced by the parent host strain.

For example, the parent and genetically modified S. cerevisiae are engineered to express amorphadiene synthase. For example, the gene for amorphadiene synthase (either the native Artemisia annua gene, the E. coli codon-optimized gene (Martin et al, 2003) or a yeast codon-optimized gene) is cloned into the multiple cloning site of pYES2 such that the amorphadiene synthase gene is transcribed under the control of the GAL1 promoter. A host yeast cell is transformed with the recombinant plasmid, selecting for uracil auxotrophy. Following growth in a medium lacking uracil and glucose, expression of amorphadiene synthase is induced by the addition of galactose. The level of intracellular HMG-CoA is increased in the amorphadiene synthase-producing yeast cell by introducing one or more mutations, as described above, generating a parent host yeast cell. The parent host yeast cell is genetically modified, as described above, e.g., to increase the level of HMGR in the cell. The production of the amorphadiene in cultures of parent host yeast cell and the genetically modified host yeast cell are compared; the level of amorphadiene produced by the genetically modified host cell is greater than the level of amorphadiene produced by the parent host cell. Amorphadiene levels are readily measured using GC-MS analysis.

As another example, HMG-CoA toxicity is observed in parent E. Coli cell engineered to express the mevalonate pathway. The HMG-CoA toxicity is relieved by genetically modifying the parent cell, e.g., to increase the level of HMGR in the cell. This example is outlined in examples 1–6, above. One skilled in the art will appreciate that the method can be performed with any host cell or any construct now in light of the present disclosure.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for producing an isoprenoid or isoprenoid precursor via a mevalonate pathway in *Escherichia coli*, the method comprising:
   (i) culturing in a suitable medium an *E. coli* cell genetically modified to produce heterologous hydroxymethylglutaryl-CoA (HMG-CoA) synthase (HMGS) and heterologous HMG-CoA reductase (HMGR), wherein the relative activity level of the HMGR produced in the genetically modified *E. coli* cell is higher than the relative activity level of the HMGS produced in the genetically modified *E. coli* cell, and wherein the genetically modified *E. coli* cell is further genetically modified to produce one or more additional heterologous mevalonate pathway enzymes selected from:
   (a) an acetoacetyl-CoA thiolase;
   (b) a mevalonate kinase;
   (c) a phosphomevalonate kinase; and
   (d) a mevalonate pyrophosphate decarboxylase;
   wherein the genetically modified *E. coli* cell produces the isoprenoid or isoprenoid precursor at a level at least as high as the level produced in a control *E. coli* strain expressing pBAD33MevT sequence shown in SEQ ID NO:2, and wherein the genetically modified *E. coli* cell exhibits less HMG-CoA induced growth inhibition compared to the control *E. coli* strain; and
   (ii) recovering the produced isoprenoid or isoprenoid precursor.

2. The method of claim 1, wherein the acetoacetyl-CoA thiolase is heterologous to the genetically modified *E. coli* cell.

3. The method of claim 1, wherein the genetically modified *E. coli* cell comprises two or more copies of a heterologous nucleic acid comprising a nucleotide sequence encoding the HMGR.

4. The method of claim 1, wherein the level of isoprenoid or isoprenoid precursor produced in the genetically modified *E. coli* cell is at least about 50% higher than the level of isoprenoid or isoprenoid precursor produced in the control *E. coli* strain.

5. The method of claim 1, wherein the level of isoprenoid or isoprenoid precursor produced in the genetically modified *E. coli* cell is at least about 2-fold higher than the level of isoprenoid or isoprenoid precursor produced in the control *E. coli* strain.

6. The method of claim 1, wherein the level of isoprenoid or isoprenoid precursor produced in the genetically modified *E. coli* cell is at least about 5-fold higher than the level of isoprenoid or isoprenoid precursor produced in the control *E. coli* strain.

7. The method of claim 1, wherein the level of isoprenoid or isoprenoid precursor produced in the genetically modified *E. coli* cell is at least about 10-fold higher than the level of isoprenoid or isoprenoid precursor produced in the control *E. coli* strain.

8. The method of claim 1, wherein the level of isoprenoid or isoprenoid precursor produced in the genetically modified *E. coli* cell is at least about 50-fold higher than the level of isoprenoid or isoprenoid precursor produced in the control *E. coli* strain.

9. A method for producing an isoprenoid or isoprenoid precursor via a mevalonate pathway in *Escherichia coli*, the method comprising: (i) culturing in a suitable medium an *E. coli* cell genetically modified to produce heterologous hydroxymethylglutaryl-CoA (HMG-CoA) synthase (HMGS) and heterologous HMG-CoA reductase (HMGR), wherein the relative activity level of the HMGR produced in the genetically modified *E. coli* cell is higher than the relative activity level of the HMGS produced in the genetically modified *E. coli* cell, and wherein the genetically modified *E. coli* cell is further genetically modified to produce one or more additional heterologous mevalonate pathway enzymes selected from:
   (a) an acetoacetyl-CoA thiolase;
   (b) a mevalonate kinase;
   (c) a phosphomevalonate kinase; and
   (d) a mevalonate pyrophosphate decarboxylase;
   wherein the genetically modified *E. coli* cell produces the isoprenoid or isoprenoid precursor at a level at least as high as the level produced in a control *E. coli* strain expressing pBAD24MevT sequence shown in SEQ ID NO:1, and wherein the genetically modified *E. coli* cell exhibits less HMG-CoA induced growth inhibition compared to the control *E. coli* strain; and
   (ii) recovering the produced isoprenoid or isoprenoid precursor.

10. The method of claim 9, wherein the acetoacetyl-CoA thiolase is heterologous to the genetically modified *E. coli* cell.

11. The method of claim 9, wherein the genetically modified *E. coli* cell comprises two or more copies of a heterologous nucleic acid comprising a nucleotide sequence encoding the HMGR.

12. The method of claim 9, wherein the level of isoprenoid or isoprenoid precursor produced in the genetically modified *E. coli* cell is at least about 50% higher than the level of isoprenoid or isoprenoid precursor produced in the control *E. coli* strain.

13. The method of claim 9, wherein the level of isoprenoid or isoprenoid precursor produced in the genetically modified *E. coli* cell is at least about 2-fold higher than the level of isoprenoid or isoprenoid precursor produced in the control *E. coli* strain.

14. The method of claim 9, wherein the level of isoprenoid or isoprenoid precursor produced in the genetically modified *E. coli* cell is at least about 5-fold higher than the level of isoprenoid or isoprenoid precursor produced in the control *E. coli* strain.

15. The method of claim 9, wherein the level of isoprenoid or isoprenoid precursor produced in the genetically modified *E. coli* cell is at least about 10-fold higher than the level of isoprenoid or isoprenoid precursor produced in the control *E. coli* strain.

16. The method of claim 9, wherein the level of isoprenoid or isoprenoid precursor produced in the genetically modified *E. coli* cell is at least about 50-fold higher than the level of isoprenoid or isoprenoid precursor produced in the control *E. coli* strain.

* * * * *

SEQUENCE LISTING

<160> NUMBER OF SEQ ID NOS: 13

<210> SEQ ID NO 1
<211> LENGTH: 8759
<212> TYPE: DNA
<213> ORGANISM: Artificial Sequence
<220> FEATURE:
<223> OTHER INFORMATION: pBAD24MevT plasmid

<400> SEQUENCE: 1

```
atcgatgcat aatgtgcctg tcaaatggac gaagcaggga ttctgcaaac cctatgctac      60
tccgtcaagc cgtcaattgt ctgattcgtt accaattatg acaacttgac ggctacatca     120 ttcactttt cttcacaacc ggcacggaac tcgctcgggc tggccccggt gcattttta      180 aatacccgcg agaaatagag ttgatcgtca aaaccaacat tgcgaccgac ggtggcgata     240
ggcatccggg tggtgctcaa aagcagcttc gcctggctga tacgttggtc ctcgcgccag     300
cttaagacgc taatccctaa ctgctggcgg aaaagatgtg acagacgcga cggcgacaag     360
caaacatgct gtgcgacgct ggcgatatca aaattgctgt ctgccaggtg atcgctgatg     420
tactgacaag cctcgcgtac ccgattatcc atcggtggat ggagcgactc gttaatcgct     480
tccatgcgcc gcagtaacaa ttgctcaagc agatttatcg ccagcagctc cgaatagcgc     540
ccttcccctt gcccggcgtt aatgatttgc ccaaacaggt cgctgaaatg cggctggtgc     600
gcttcatccg ggcgaaagaa ccccgtattg gcaaatattg acggccagtt aagccattca     660
```

-continued

```
tgccagtagg cgcgcggacg aaagtaaacc cactggtgat accattcgcg agcctccgga    720
tgacgaccgt agtgatgaat ctctcctggc gggaacagca aaatatcacc cggtcggcaa    780
acaaattctc gtccctgatt tttcaccacc ccctgaccgc gaatggtgag attgagaata    840
taacctttca ttcccagcgg tcggtcgata aaaaaatcga gataaccgtt ggcctcaatc    900
ggcgttaaac ccgccaccag atgggcatta acgagtatc ccggcagcag gggatcattt     960
tgcgcttcag ccatactttt catactcccg ccattcagag aagaaaccaa ttgtccatat   1020
tgcatcagac attgccgtca ctgcgtcttt tactggctct ctcgctaac caaaccggta    1080 accccgctta ttaaaagcat tctgtaacaa agcgggacca aagccatgac aaaaacgcgt   1140
aacaaaagtg tctataatca cggcagaaaa gtccacattg attatttgca cggcgtcaca   1200
ctttgctatg ccatagcatt tttatccata agattagcgg atcctacctg acgctttta    1260 tcgcaactct ctactgtttc tccatacccg tttttttggg ctagcaggag gaattcacca   1320
tggtacccgg ggatcctcta gagtcgacta ggaggaatat aaaatgaaaa attgtgtcat   1380
cgtcagtgcg gtacgtactg ctatcggtag ttttaacggt tcactcgctt ccaccagcgc   1440
catcgacctg ggggcgacag taattaaagc cgccattgaa cgtgcaaaaa tcgattcaca   1500
acacgttgat gaagtgatta tgggtaacgt gttacaagcc gggctggggc aaaatccggc   1560
gcgtcaggca ctgttaaaaa gcgggctggc agaaacggtg tgcggattca cggtcaataa   1620
agtatgtggt tcgggtctta aaagtgtggc gcttgccgcc caggccattc aggcaggtca   1680
ggcgcagagc attgtggcgg ggggtatgga aaatatgagt ttagcccct acttactcga    1740 tgcaaaagca cgctctggtt atcgtcttgg agacggacag gtttatgacg taatcctgcg   1800
cgatggcctg atgtgcgcca cccatggtta tcatatgggg attaccgccg aaaacgtggc   1860
taaagagtac ggaattaccc gtgaaatgca ggatgaactg gcgctacatt cacagcgtaa   1920
agcggcagcc gcaattgagt ccggtgcttt tacagccgaa atcgtcccgg taaatgttgt   1980
cactcgaaag aaaaccttcg tcttcagtca agacgaattc ccgaaagcga attcaacggc   2040
tgaagcgtta ggtgcattgc gcccggcctt cgataaagca ggaacagtca ccgctgggaa   2100
cgcgtctggt attaacgacg gtgctgccgc tctggtgatt atggaagaat ctgcggcgct   2160
ggcagcaggc cttaccccc tggctcgcat taaaagttat gccagcggtg gcgtgccccc    2220
cgcattgatg ggtatggggc cagtacctgc cacgcaaaaa gcgttacaac tggcggggct   2280
gcaactggcg gatattgatc tcattgaggc taatgaagca tttgctgcac agttccttgc   2340
cgttgggaaa aacctgggct tgattctga gaaagtgaat gtcaacggcg gggccatcgc    2400
gctcgggcat cctatcggtg ccagtggtgc tcgtattctg gtcacactat acatgccat    2460 gcaggcacgc gataaaacgc tggggctggc aacactgtgc attggcggcg gtcagggaat   2520
tgcgatggtg attgaacggt tgaattaagg aggacagcta atgaaactc tcaactaaac    2580 tttgttggtg tggtattaaa ggaagactta ggccgcaaaa gcaacaacaa ttacacaata   2640
caaacttgca aatgactgaa ctaaaaaaac aaaagaccgc tgaacaaaaa accagacctc   2700
aaaatgtcgg tattaaaggt atccaaattt acatcccaac tcaatgtgtc aaccaatctg   2760
agctagagaa atttgatggc gtttctcaag gtaaatacac aattggtctg gccaaacca    2820 acatgtcttt tgtcaatgac agagaagata tctactcgat gtccctaact gttttgtcta   2880
agttgatcaa gagttacaac atcgacacca acaaaattgg tagattagaa gtcggtactg   2940
aaactctgat tgacaagtcc aagtctgtca agtctgtctt gatgcaattg tttggtgaaa   3000
```

-continued

```
acactgacgt cgaaggtatt gacacgctta atgcctgtta cggtggtacc aacgcgttgt    3060
tcaactcttt gaactggatt gaatctaacg catgggatgg tagagacgcc attgtagttt    3120
gcggtgatat tgccatctac gataagggtg ccgcaagacc aaccggtggt gccggtactg    3180
ttgctatgtg gatcggtcct gatgctccaa ttgtatttga ctctgtaaga gcttcttaca    3240
tggaacacgc ctacgatttt tacaagccaa atttcaccag cgaatatcct tacgtcgatg    3300
gtcatttttc attaacttgt tacgtcaagg ctcttgatca agtttacaag agttattcca    3360
agaaggctat ttctaaaggg ttggttagcg atcccgctgg ttcggatgct ttgaacgttt    3420
tgaaatattt cgactacaac gttttccatg ttccaacctg taaattggtc acaaaatcat    3480
acggtagatt actatataac gatttcagag ccaatcctca attgttccca gaagttgacg    3540
ccgaattagc tactcgcgat tatgacgaat ctttaaccga taagaacatt gaaaaaactt    3600
ttgttaatgt tgctaagcca ttccacaaag agagagttgc ccaatctttg attgttccaa    3660
caaacacagg taacatgtac accgcatctg tttatgccgc ctttgcatct ctattaaact    3720
atgttggatc tgacgactta caaggcaagc gtgttggttt attttcttac ggttccggtt    3780
tagctgcatc tctatattct tgcaaaattg ttggtgacgt ccaacatatt atcaaggaat    3840
tagatattac taacaaatta gccaagagaa tcaccgaaac tccaaaggat tacgaagctg    3900
ccatcgaatt gagagaaaat gcccatttga agaagaactt caaacctcaa ggttccattg    3960
agcatttgca aagtggtgtt tactacttga ccaacatcga tgacaaattt agaagatctt    4020
acgatgttaa aaataagga ggattacact atggttttaa ccataaaaac agtcatttct    4080
ggatcgaaag tcaaaagttt atcatctgcg caatcgagct catcaggacc ttcatcatct    4140
agtgaggaag atgattcccg cgatattgaa agcttggata agaaaatacg tcctttagaa    4200
gaattagaag cattattaag tagtggaaat acaaaacaat gaagaacaa agaggtcgct    4260 gccttggtta ttcacggtaa gttacctttg tacgctttgg agaaaaaatt aggtgatact    4320
acgagagcgg ttgcggtacg taggaaggct ctttcaattt tggcagaagc tcctgtatta    4380
gcatctgatc gtttaccata taaaaattat gactacgacc gcgtatttgg cgcttgttgt    4440
gaaaatgtta taggttacat gcctttgccc gttggtgtta taggcccctt ggttatcgat    4500
ggtacatctt atcatatacc aatggcaact acagagggtt gtttggtagc ttctgccatg    4560
cgtggctgta aggcaatcaa tgctggcggt ggtgcaacaa ctgttttaac taaggatggt    4620
atgacaagag gcccagtagt ccgtttccca actttgaaaa gatctggtgc ctgtaagata    4680
tggttagact cagaagaggg acaaaacgca attaaaaag cttttaactc tacatcaaga    4740
tttgcacgtc tgcaacatat tcaaacttgt ctagcaggag atttactctt catgagattt    4800
agaacaacta ctggtgacgc aatgggtatg aatatgattt ctaaaggtgt cgaatactca    4860
ttaaagcaaa tggtagaaga gtatggctgg aagatatgg aggttgtctc cgtttctggt    4920
aactactgta ccgacaaaaa accagctgcc atcaactgga tcgaaggtcg tggtaagagt    4980
gtcgtcgcag aagctactat tcctggtgat gttgtcagaa aagtgttaaa aagtgatgtt    5040
tccgcattgg ttgagttgaa cattgctaag aatttggttg atctgcaat ggctgggtct    5100 gttggtggat ttaacgcaca tgcagctaat ttagtgacag ctgttttctt ggcattagga    5160
caagatcctg cacaaaatgt tgaaagttcc aactgtataa cattgatgaa agaagtggac    5220
ggtgatttga gaattccgt atccatgcca tccatcgaag taggtaccat cggtggtggt    5280
actgttctag aaccacaagg tgccatgttg acttattag gtgtaagagg cccgcatgct    5340
accgctcctg gtaccaacgc acgtcaatta gcaagaatag ttgcctgtgc cgtcttggca    5400
```

```
ggtgaattat ccttatgtgc tgccctagca gccggccatt tggttcaaag tcatatgacc    5460
cacaacagga aacctgctga accaacaaaa cctaacaatt tggacgccac tgatataaat    5520
cgtttgaaag atgggtccgt cacctgcatt aaatcctaag tcgacctgca ggcatgcaag    5580
cttggctgtt ttggcggatg agagaagatt ttcagcctga tacagattaa atcagaacgc    5640
agaagcggtc tgataaaaca gaatttgcct ggcggcagta gcgcggtggt cccacctgac    5700
cccatgccga actcagaagt gaaacgccgt agcgccgatg gtagtgtggg gtctccccat    5760
gcgagagtag ggaactgcca ggcatcaaat aaaacgaaag gctcagtcga agactgggc    5820 cttttcgtttt atctgttgtt tgtcggtgaa cgctctcctg agtaggacaa atccgccggg    5880
agcggatttg aacgttgcga agcaacggcc cggagggtgg cgggcaggac gcccgccata    5940
aactgccagg catcaaatta agcagaaggc catcctgacg gatggccttt ttgcgtttct    6000
acaaactctt ttgtttattt ttctaaatac attcaaatat gtatccgctc atgagacaat    6060
aaccctgata aatgcttcaa taatattgaa aaaggaagag tatgagtatt caacatttcc    6120
gtgtcgccct tattcccttt tttgcggcat tttgccttcc tgttttttgct cacccagaaa    6180 cgctggtgaa agtaaaagat gctgaagatc agttgggtgc acgagtgggt tacatcgaac    6240
tggatctcaa cagcggtaag atccttgaga gttttcgccc cgaagaacgt tttccaatga    6300
tgagcacttt taaagttctg ctatgtggcg cggtattatc ccgtgttgac gccgggcaag    6360
agcaactcgg tcgccgcata cactattctc agaatgactt ggttgagtac tcaccagtca    6420
cagaaaagca tcttacggat ggcatgacag taagagaatt atgcagtgct gccataacca    6480
tgagtgataa cactgcggcc aacttacttc tgacaacgat cggaggaccg aaggagctaa    6540 ccgcttttt gcacaacatg ggggatcatg taactcgcct tgatcgttgg gaaccggagc    6600
tgaatgaagc cataccaaac gacgagcgtg acaccacgat gcctgtagca atggcaacaa    6660
cgttgcgcaa actattaact ggcgaactac ttactctagc ttcccggcaa caattaatag    6720
actggatgga ggcggataaa gttgcaggac cacttctgcg ctcggccctt ccggctggct    6780
ggtttattgc tgataaatct ggagccggtg agcgtgggtc tcgcggtatc attgcagcac    6840
tggggccaga tggtaagccc tcccgtatcg tagttatcta cacgacgggg agtcaggcaa    6900
ctatggatga acgaaataga cagatcgctg agataggtgc ctcactgatt aagcattggt    6960
aactgtcaga ccaagtttac tcatatatac tttagattga tttacgcgcc ctgtagcggc    7020
gcattaagcg cggcgggtgt ggtggttacg cgcagcgtga ccgctacact tgccagcgcc    7080
ctagcgcccg ctcctttcgc tttcttccct tcctttctcg ccacgttcgc cggctttccc    7140
cgtcaagctc taaatcgggg gctccctta gggttccgat ttagtgcttt acggcacctc    7200
gaccccaaaa aacttgattt gggtgatggt tcacgtagtg ggccatcgcc ctgatagacg    7260
gtttttcgcc ctttgacgtt ggagtccacg ttctttaata gtggactctt gttccaaact    7320
tgaacaacac tcaaccctat ctcgggctat tcttttgatt tataagggat tttgccgatt    7380
tcggcctatt ggttaaaaaa tgagctgatt taacaaaaat ttaacgcgaa ttttaacaaa    7440
atattaacgt ttacaatttta aaaggatcta ggtgaagatc ctttttgata atctcatgac    7500
caaaatccct taacgtgagt tttcgttcca ctgagcgtca gaccccgtag aaaagatcaa    7560
aggatcttct tgagatcctt ttttttctgcg cgtaatctgc tgcttgcaaa caaaaaaacc    7620
accgctacca gcggtggttt gtttgccgga tcaagagcta ccaactcttt ttccgaaggt    7680
aactggcttc agcagagcgc agataccaaa tactgtcctt ctagtgtagc cgtagttagg    7740
```

-continued

```
ccaccacttc aagaactctg tagcaccgcc tacatacctc gctctgctaa tcctgttacc      7800
agtggctgct gccagtggcg ataagtcgtg tcttaccggg ttggactcaa gacgatagtt      7860
accggataag gcgcagcggt cgggctgaac gggggggttcg tgcacacagc ccagcttgga      7920
gcgaacgacc tacaccgaac tgagatacct acagcgtgag ctatgagaaa gcgccacgct      7980
tcccgaaggg agaaaggcgg acaggtatcc ggtaagcggc aggtcggaa caggagagcg       8040
cacgagggag cttccagggg gaaacgcctg gtatctttat agtcctgtcg ggtttcgcca      8100
cctctgactt gagcgtcgat ttttgtgatg ctcgtcaggg gggcggagcc tatgaaaaaa      8160
cgccagcaac gcggcctttt tacggttcct ggccttttgc tggccttttg ctcacatgtt      8220
ctttcctgcg ttatcccctg attctgtgga taaccgtatt accgcctttg agtgagctga      8280
taccgctcgc cgcagccgaa cgaccgagcg cagcgagtca gtgagcgagg aagcggaaga      8340
gcgcctgatg cggtattttc tccttacgca tctgtgcggt atttcacacc gcatagggtc      8400
atggctgcgc cccgacaccc gccaacaccc gctgacgcgc cctgacgggc ttgtctgctc      8460
ccggcatccg cttacagaca agctgtgacc gtctccggga gctgcatgtg tcagaggttt      8520
tcaccgtcat caccgaaacg cgcgaggcag caaggagatg gcgcccaaca gtccccccggc     8580
cacggggcct gccaccatac ccacgccgaa acaagcgctc atgagcccga agtggcgagc      8640
ccgatcttcc ccatcggtga tgtcggcgat ataggcgcca gcaaccgcac ctgtggcgcc      8700
ggtgatgccg gccacgatgc gtccggcgta gaggatctgc tcatgtttga cagcttatc      8759
```

<210> SEQ ID NO 2
<211> LENGTH: 9573
<212> TYPE: DNA
<213> ORGANISM: Artificial Sequence
<220> FEATURE:
<223> OTHER INFORMATION: pBAD33MevT plasmid

<400> SEQUENCE: 2

```
atcgatgcat aatgtgcctg tcaaatggac gaagcaggga ttctgcaaac cctatgctac       60
tccgtcaagc cgtcaattgt ctgattcgtt accaattatg acaacttgac ggctacatca      120
ttcactttt cttcacaacc ggcacggaac tcgctcgggc tggccccggt gcatttttta       180
aatacccgcg agaaatagag ttgatcgtca aaccaacat tgcgaccgac ggtggcgata       240
ggcatccggg tggtgctcaa aagcagcttc gcctggctga tacgttggtc ctcgcgccag      300
cttaagacgc taatccctaa ctgctggcgg aaaagatgtg acagacgcga cggcgacaag      360
caaacatgct gtgcgacgct ggcgatatca aaattgctgt ctgccaggtg atcgctgatg      420
tactgacaag cctcgcgtac ccgattatcc atcggtggat ggagcgactc gttaatcgct      480
tccatgcgcc gcagtaacaa ttgctcaagc agatttatcg ccagcagctc cgaatagcgc      540
ccttcccctt gcccggcgtt aatgatttgc ccaaacaggt cgctgaaatg cggctggtgc      600
gcttcatccg ggcgaaagaa ccccgtattg gcaaatattg acggcagtt aagccattca       660
tgccagtagg cgcgcggacg aaagtaaacc cactggtgat accattcgcg agcctccgga      720
tgacgaccgt agtgatgaat ctctcctggc gggaacagca aaatatcacc cggtcggcaa      780
acaaattctc gtccctgatt tttcaccacc ccctgaccgc gaatggtgag attgagaata      840
taaccttca ttcccagcgg tcggtcgata aaaaaatcga gataaccgtt ggcctcaatc       900
ggcgttaaac ccgccaccag atgggcatta acgagtatc ccggcagcag gggatcattt       960
tgcgcttcag ccatactttt catactcccg ccattcagag aagaaaccaa ttgtccatat     1020
tgcatcagac attgccgtca ctgcgtcttt tactggctct tctcgctaac caaaccggta     1080
```

-continued

```
acccgctta ttaaaagcat tctgtaacaa agcgggacca agccatgac aaaaacgcgt    1140 aacaaaagtg tctataatca cggcagaaaa gtccacattg attatttgca cggcgtcaca    1200
ctttgctatg ccatagcatt tttatccata agattagcgg atcctacctg acgctttta    1260 tcgcaactct ctactgtttc tccatacccg ttttttggg ctagcgaatt cgagctcggt    1320
acccggggat cctctagagt cgactaggag gaatataaaa tgaaaaattg tgtcatcgtc    1380
agtgcggtac gtactgctat cggtagtttt aacggttcac tcgcttccac cagcgccatc    1440
gacctggggg cgacagtaat taaagccgcc attgaacgtg caaaaatcga ttcacaacac    1500
gttgatgaag tgattatggg taacgtgtta caagccgggc tggggcaaaa tccggcgcgt    1560
caggcactgt taaaaagcgg gctggcagaa acggtgtgcg gattcacggt caataaagta    1620
tgtggttcgg gtcttaaaag tgtggcgctt gccgcccagg ccattcaggc aggtcaggcg    1680
cagagcattg tggcggggggg tatggaaaat atgagtttag ccccctactt actcgatgca    1740
aaagcacgct ctggttatcg tcttggagac ggacaggttt atgacgtaat cctgcgcgat    1800
ggcctgatgt gcgccaccca tggttatcat atggggatta ccgccgaaaa cgtggctaaa    1860
gagtacggaa ttacccgtga aatgcaggat gaactggcgc tacattcaca gcgtaaagcg    1920
gcagccgcaa ttgagtccgg tgcttttaca gccgaaatcg tcccggtaaa tgttgtcact    1980
cgaaagaaaa ccttcgtctt cagtcaagac gaattcccga aagcgaattc aacggctgaa    2040
gcgttaggtg cattgcgccc ggccttcgat aaagcaggaa cagtcaccgc tgggaacgcg    2100
tctggtatta acgacggtgc tgccgctctg gtgattatgg aagaatctgc ggcgctggca    2160
gcaggcctta ccccctggc tcgcattaaa agttatgcca gcggtggcgt gcccccccgca    2220 ttgatgggta tggggccagt acctgccacg caaaaagcgt tacaactggc ggggctgcaa    2280
ctggcggata ttgatctcat tgaggctaat gaagcatttg ctgcacagtt ccttgccgtt    2340
gggaaaaacc tgggctttga ttctgagaaa gtgaatgtca acggcggggc catcgcgctc    2400
gggcatccta tcggtgccag tggtgctcgt attctggtca cactattaca tgccatgcag    2460
gcacgcgata aaacgctggg gctggcaaca ctgtgcattg gcggcggtca gggaattgcg    2520
atggtgattg aacggttgaa ttaaggagga cagctaaatg aaactctcaa ctaaactttg    2580
ttggtgtggt attaaaggaa gacttaggcc gcaaaagcaa caacaattac acaatacaaa    2640
cttgcaaatg actgaactaa aaaaacaaaa gaccgctgaa caaaaaacca gacctcaaaa    2700
tgtcggtatt aaaggtatcc aaatttacat cccaactcaa tgtgtcaacc aatctgagct    2760
agagaaattt gatggcgttt ctcaaggtaa atacacaatt ggtctgggcc aaaccaacat    2820
gtcttttgtc aatgacagag aagatatcta ctcgatgtcc ctaactgttt tgtctaagtt    2880
gatcaagagt tacaacatcg acaccaacaa aattggtaga ttagaagtcg gtactgaaac    2940
tctgattgac aagtccaagt ctgtcaagtc tgtcttgatg caattgtttg gtgaaaacac    3000
tgacgtcgaa ggtattgaca cgcttaatgc ctgttacggt ggtaccaacg cgttgttcaa    3060
ctctttgaac tggattgaat ctaacgcatg ggatggtaga gacgccattg tagtttgcgg    3120
tgatattgcc atctacgata agggtgccgc aagaccaacc ggtggtgccg gtactgttgc    3180
tatgtggatc ggtcctgatg ctccaattgt atttgactct gtaagagctt cttcatggaa    3240
acacgcctac gattttttaca agccagattt caccagcgaa tatccttacg tcgatggtca    3300
tttttcatta acttgttacg tcaaggctct tgatcaagtt tacaagagtt attccaagaa    3360
ggctatttct aaagggttgg ttagcgatcc cgctggttcg gatgctttga acgttttgaa    3420
```

```
atatttcgac tacaacgttt tccatgttcc aacctgtaaa ttggtcacaa aatcatacgg    3480
tagattacta tataacgatt tcagagccaa tcctcaattg ttcccagaag ttgacgccga    3540
attagctact cgcgattatg acgaatcttt aaccgataag aacattgaaa aaacttttgt    3600
taatgttgct aagccattcc acaaagagag agttgcccaa tctttgattg ttccaacaaa    3660
cacaggtaac atgtacaccg catctgttta tgccgccttt gcatctctat taaactatgt    3720
tggatctgac gacttacaag gcaagcgtgt tggtttattt tcttacggtt ccggtttagc    3780
tgcatctcta tattcttgca aaattgttgg tgacgtccaa catattatca aggaattaga    3840
tattactaac aaattagcca agagaatcac cgaaactcca aaggattacg aagctgccat    3900
cgaattgaga gaaaatgccc atttgaagaa gaacttcaaa cctcaaggtt ccattgagca    3960
tttgcaaagt ggtgtttact acttgaccaa catcgatgac aaatttagaa gatcttacga    4020
tgttaaaaaa taaggaggat tacactatgg ttttaaccaa taaaacagtc atttctggat    4080
cgaaagtcaa aagtttatca tctgcgcaat cgagctcatc aggaccttca tcatctagtg    4140
aggaagatga ttcccgcgat attgaaagct tggataagaa aatacgtcct ttagaagaat    4200
tagaagcatt attaagtagt ggaaatacaa aacaattgaa gaacaaagag gtcgctgcct    4260
tggttattca cggtaagtta ccttttgtacg ctttggagaa aaaattaggt gatactacga    4320
gagcggttgc ggtacgtagg aaggctcttt caattttggc agaagctcct gtattagcat    4380
ctgatcgttt accatataaa aattatgact acgaccgcgt atttggcgct tgttgtgaaa    4440
atgttatagg ttacatgcct ttgcccgttg gtgttatagg ccccttggtt atcgatggta    4500
catcttatca tataccaatg gcaactacag agggttgttt ggtagcttct gccatgcgtg    4560
gctgtaaggc aatcaatgct ggcggtggtg caacaactgt tttaactaag gatggtatga    4620
caagaggccc agtagtccgt ttcccaactt tgaaaagatc tggtgcctgt aagatatggt    4680
tagactcaga agagggacaa aacgcaatta aaaaagcttt taactctaca tcaagatttg    4740
cacgtctgca acatattcaa acttgtctag caggagattt actcttcatg agatttagaa    4800
caactactgg tgacgcaatg ggtatgaata tgatttctaa aggtgtcgaa tactcattaa    4860
agcaaatggt agaagagtat ggctgggaag atatggaggt tgtctccgtt tctggtaact    4920
actgtaccga caaaaaacca gctgccatca actggatcga aggtcgtggt aagagtgtcg    4980
tcgcagaagc tactattcct ggtgatgttg tcagaaaagt gttaaaaagt gatgtttccg    5040
cattggttga gttgaacatt gctaagaatt tggttggatc tgcaatggct gggtctgttg    5100
gtggatttaa cgcacatgca gctaatttag tgacagctgt tttcttggca ttaggacaag    5160
atcctgcaca aaatgttgaa agttccaact gtataacatt gatgaaagaa gtggacggtg    5220
atttgagaat ttccgtatcc atgccatcca tcgaagtagg taccatcggt ggtggtactg    5280
ttctagaacc acaaggtgcc atgttggact tattaggtgt aagaggcccg catgctaccg    5340
ctcctggtac caacgcacgt caattagcaa gaatagttgc ctgtgccgtc ttggcaggtg    5400
aattatcctt atgtgctgcc ctagcagccg gccatttggt tcaaagtcat atgacccaca    5460
acaggaaacc tgctgaacca acaaaaccta acaatttgga cgccactgat ataaatcgtt    5520
tgaaagatgg gtccgtcacc tgcattaaat cctaagtcga cctgcaggca tgcaagcttg    5580
gctgttttgg cggatgagag aagattttca gcctgataca gattaaatca gaacgcagaa    5640
gcggtctgat aaaacagaat ttgcctggcg gcagtagcgc ggtggtccca cctgacccca    5700
tgccgaactc agaagtgaaa cgccgtagcg ccgatggtag tgtggggtct ccccatgcga    5760
gagtagggaa ctgccaggca tcaaataaaa cgaaaggctc agtcgaaaga ctgggccttt    5820
```

```
cgttttatct gttgtttgtc ggtgaacgct ctcctgagta ggacaaatcc gccgggagcg    5880
gatttgaacg ttgcgaagca acggcccgga gggtggcggg caggacgccc gccataaact    5940
gccaggcatc aaattaagca gaaggccatc ctgacggatg gcctttttgc gtttctacaa    6000
actcttttgt ttatttttct aaatacattc aaatatgtat ccgctcatga gacaataacc    6060
ctgataaatg cttcaataat attgaaaaag gaagagtatg agtattcaac atttccgtgt    6120
cgcccttatt ccctttttg cggcattttg ccttcctgtt tttgctcacc cagaaacgct    6180
ggtgaaagta aaagatgctg aagatcagtt gggtgcagca actattaac tggcgaacta    6240 cttactctag cttcccggca acaattaata gactggatgg aggcggataa agttgcagga    6300
ccacttctgc gctcggccct tccggctggc tggtttattg ctgataaatc tggagccggt    6360
gagcgtgggt ctcgcggtat cattgcagca ctggggccag atggtaagcc ctcccgtatc    6420
gtagttatct acacgacggg gagtcaggca actatggatg aacgaaatag acagatcgct    6480
gagataggtg cctcactgat taagcattgg taactgtcag accaagttta ctcatatata    6540
ctttagattg atttacgcgc cctgtagcgg cgcattaagc gcggcgggtg tggtggttac    6600
gcgcagcgtg accgctacac ttgccagcgc cctagcgccc gctcctttcg ctttcttccc    6660
ttcctttctc gccacgttcg ccggctttcc ccgtcaagct ctaaatcggg gctcccttt    6720 agggttccga tttagtgctt tacggcacct cgaccccaaa aaacttgatt tgggtgatgg    6780
ttcacgtagt gggccatcgc cctgatagac ggtttttcgc cctttgacgt tggagtccac    6840
gttctttaat agtggactct tgttccaaac ttgaacaaca ctcaaccta tctcgggcta    6900 ttcttttgat ttataaggga ttttgccgat ttcggcctat tggttaaaaa atgagctgat    6960
ttaacaaaaa tttaacgcga attttaacaa aatattaacg tttacaattt aaaaggatct    7020
aggtgaagat cctttttgat aatctcatga ccaaaatccc ttaacgtgag ttttcgttcc    7080
actgagcgtc agaccccgta gaaaagatca aaggatcttc ttgagatcct ttttttctgc    7140
gcgtaatctg ctgcttgcaa acaaaaaaac caccgctacc agcggtggtt tgtttgccgg    7200
atcaagagct accaactctt tttccgaagg taactggctt cagcagagcg cagataccaa    7260
atactgtcct tctagtgtag ccgtagttag gccaccactt caagaactct gtagcaccgc    7320
ctacatacct cgctctgcta atcctgttac cagtggggca tttgagaagc acacggtcac    7380
actgcttccg gtagtcaata aaccggtaaa ccagcaatag acataagcgg ctatttaacg    7440 accctgcct gaaccgacga ccgggtcgaa tttgctttcg aatttctgcc attcatccgc    7500
ttattatcac ttattcaggc gtagcaccag gcgtttaagg gcaccaataa ctgccttaaa    7560
aaaattacgc cccgccctgc cactcatcgc agtactgttg taattcatta agcattctgc    7620
cgacatggaa gccatcacag acggcatgat gaacctgaat cgccagcggc atcagcacct    7680
tgtcgccttg cgtataatat ttgcccatgt gaaaacggg ggcgaagaag ttgtccatat    7740
tggccacgtt taaatcaaaa ctggtgaaac tcacccaggg attggctgag acgaaaaaca    7800
tattctcaat aaaccctta gggaaatagg ccaggttttc accgtaacac gccacatctt    7860
gcgaatatat gtgtagaaac tgccggaaat cgtcgtggta ttcactccag agcgatgaaa    7920
acgtttcagt ttgctcatgg aaaacggtgt aacaagggtg aacactatcc catatccacca    7980 gctcaccgtc tttcattgcc atacggaatt ccggatgagc attcatcagg cgggcaagaa    8040
tgtgaataaa ggccggataa aacttgtgct tatttttctt tacggtcttt aaaaaggccg    8100
taatatccag ctgaacggtc tggttatagg tacattgagc aactgactga aatgcctcaa    8160
```

-continued

```
aatgttcttt acgatgccat tgggatatat caacggtggt atatccagtg attttttct    8220
ccatttagc ttccttagct cctgaaaatc tcgataactc aaaaaatacg cccggtagtg    8280
atcttatttc attatggtga agttggaac ctcttacgtg ccgatcaacg tctcattttc    8340
gccaaaagtt ggcccagggc ttcccggtat caacagggac accaggattt atttattctg   8400
cgaagtgatc ttccgtcaca ggtatttatt cggcgcaaag tgcgtcggt gatgctgcca    8460
acttactgat ttagtgtatg atggtgtttt tgaggtgctc cagtggcttc tgtttctatc   8520
agctgtccct cctgttcagc tactgacggg gtggtgcgta acggcaaaag caccgccgga   8580
catcagcgct agcggagtgt atactggctt actatgttgg cactgatgag ggtgtcagtg   8640
aagtgcttca tgtggcagga gaaaaaggc tgcaccggtg cgtcagcaga atatgtgata    8700
caggatatat tccgcttcct cgctcactga ctcgctacgc tcggtcgttc gactgcggcg   8760
agcggaaatg gcttacgaac ggggcggaga tttcctggaa gatgccagga agatacttaa   8820
caggaagtg agagggccgc ggcaaagccg tttttccata ggctccgccc cctgacaag    8880
catcacgaaa tctgacgctc aaatcagtgg tggcgaaacc cgacaggact ataaagatac   8940
caggcgtttc cccctggcgg ctccctcgtg cgctctcctg ttcctgcctt tcggtttacc   9000
ggtgtcattc cgctgttatg gccgcgtttg tctcattcca cgcctgacac tcagttccgg   9060
gtaggcagtt cgctccaagc tggactgtat gcacgaaccc cccgttcagt ccgaccgctg   9120
cgccttatcc ggtaactatc gtcttgagtc caacccggaa agacatgcaa aagcaccact   9180
ggcagcagcc actggtaatt gatttagagg agttagtctt gaagtcatgc gccggttaag   9240
gctaaactga aggacaagt tttggtgact gcgctcctcc aagccagtta cctcggttca    9300
aagagttggt agctcagaga accttcgaaa accgccctg caaggcggtt ttttcgtttt    9360
cagagcaaga gattacgcgc agaccaaaac gatctcaaga agatcatctt attaatcaga   9420
taaaatattt gctcatgagc ccgaagtggc gagcccgatc ttccccatcg gtgatgtcgg   9480
cgataaggc gccagcaacc gcacctgtgg cgccggtgat gccggccacg atgcgtccgg    9540
cgtagaggat ctgctcatgt ttgacagctt atc                                9573
```

<210> SEQ ID NO 3
<211> LENGTH: 8593
<212> TYPE: DNA
<213> ORGANISM: Artificial Sequence
<220> FEATURE:
<223> OTHER INFORMATION: pMevT plasmid

<400> SEQUENCE: 3

```
atcgatgcat gcgcccaata cgcaaaccgc ctctccccgc gcgttggccg attcattaat    60
gcagctggca cgacaggttt cccgactgga aagcgggcag tgagcgcaac gcaattaatg   120
tgagttagct cactcattag gcaccccagg ctttacactt tatgcttccg gctcgtatgt   180
tgtgtggaat tgtgagcgga taacaatttc acacaggaaa cagctatgac catgattacg   240
ccaagcgcgc aattaaccct cactaaaggg aacaaaagct gggtaccggg ccccccctcg   300
aggtcgacgg tatcgataag cttgatatcg aattcctgca gcccgggat cctctagagt    360
cgactaggag gaatataaaa tgaaaaattg tgtcatcgtc agtgcggtac gtactgctat   420
cggtagtttt aacggttcac tcgcttccac cagcgccatc gacctggggg cgacagtaat   480
taaagccgcc attgaacgtg caaaaatcga ttcacaacac gttgatgaag tgattatggg   540
taacgtgtta caagccgggc tggggcaaaa tccggcgcgt caggcactgt aaaaagcgg    600
gctggcagaa acggtgtgcg gattcacggt caataaagta tgtggttcgg gtcttaaaag   660
```

-continued

```
tgtggcgctt gccgcccagg ccattcaggc aggtcaggcg cagagcattg tggcgggggg      720
tatggaaaat atgagtttag cccctactt actcgatgca aaagcacgct ctggttatcg      780
tcttggagac ggacaggttt atgacgtaat cctgcgcgat ggcctgatgt gcgccaccca      840
tggttatcat atggggatta ccgccgaaaa cgtggctaaa gagtacggaa ttacccgtga      900
aatgcaggat gaactggcgc tacattcaca gcgtaaagcg gcagccgcaa ttgagtccgg      960
tgcttttaca gccgaaatcg tcccggtaaa tgttgtcact cgaaagaaaa ccttcgtctt     1020
cagtcaagac gaattcccga aagcgaattc aacggctgaa gcgttaggtg cattgcgccc     1080
ggccttcgat aaagcaggaa cagtcaccgc tgggaacgcg tctggtatta cgacggtgc      1140 tgccgctctg gtgattatgg aagaatctgc ggcgctggca gcaggcctta ccccctggc      1200 tcgcattaaa agttatgcca gcggtggcgt gcccccgca ttgatgggta tggggccagt      1260
acctgccacg caaaaagcgt tacaactggc ggggctgcaa ctggcggata ttgatctcat      1320
tgaggctaat gaagcatttg ctgcacagtt ccttgccgtt gggaaaaacc tgggctttga     1380
ttctgagaaa gtgaatgtca acggcggggc catcgcgctc gggcatccta tcggtgccag     1440
tggtgctcgt attctggtca cactattaca tgccatgcag gcacgcgata aaacgctggg     1500
gctggcaaca ctgtgcattg gcggcggtca gggaattgcg atggtgattg aacggttgaa     1560
ttaaggagga cagctaaatg aaactctcaa ctaaactttg ttggtgtggt attaaaggaa     1620
gacttaggcc gcaaaagcaa caacaattac acaatacaaa cttgcaaatg actgaactaa     1680
aaaaacaaaa gaccgctgaa caaaaaacca gacctcaaaa tgtcggtatt aaaggtatcc     1740
aaatttacat cccaactcaa tgtgtcaacc aatctgagct agagaaattt gatggcgttt     1800
ctcaaggtaa atacacaatt ggtctgggcc aaaccaacat gtcttttgtc aatgacagag     1860
aagatatcta ctcgatgtcc ctaactgttt tgtctaagtt gatcaagagt tacaacatcg     1920
acaccaacaa aattggtaga ttagaagtcg gtactgaaac tctgattgac aagtccaagt     1980
ctgtcaagtc tgtcttgatg caattgtttg gtgaaaacac tgacgtcgaa ggtattgaca     2040
cgcttaatgc ctgttacggt ggtaccaacg cgttgttcaa ctctttgaac tggattgaat     2100
ctaacgcatg ggatggtaga gacgccattg tagtttgcgg tgatattgcc atctacgata     2160
agggtgccgc aagaccaacc ggtggtgccg gtactgttgc tatgtggatc ggtcctgatg     2220
ctccaattgt atttgactct gtaagagctt cttacatgga acacgcctac gatttttaca     2280
agccagattt caccagcgaa tatccttacg tcgatggtca tttttcatta acttgttacg     2340
tcaaggctct tgatcaagtt tacaagagtt attccaagaa ggctatttct aaagggttgg     2400
ttagcgatcc cgctggttcg gatgctttga acgttttgaa atatttcgac tacaacgttt     2460
tccatgttcc aacctgtaaa ttggtcacaa atcatacgg tagattacta taaacgatt      2520 tcagagccaa tcctcaattg ttcccagaag ttgacgccga attagctact cgcgattatg     2580
acgaatcttt aaccgataag aacattgaaa aactttttgt taatgttgct aagccattcc     2640
acaaagagag agttgcccaa tctttgattg ttccaacaaa cacaggtaac atgtacaccg     2700
catctgttta tgccgccttt gcatctctat aaaactatgt tggatctgac gacttacaag     2760
gcaagcgtgt tggttatttt tcttacggtt ccggtttagc tgcatctcta tattcttgca     2820
aaattgttgg tgacgtccaa catattatca aggaattaga tattactaac aaattagcca     2880
agagaatcac cgaaactcca aaggattacg aagctgccat cgaattgaga gaaaatgccc     2940
atttgaagaa gaacttcaaa cctcaaggtt ccattgagca tttgcaaagt ggtgtttact     3000
```

```
acttgaccaa catcgatgac aaatttagaa gatcttacga tgttaaaaaa taaggaggat  3060
tacactatgg ttttaaccaa taaaacagtc atttctggat cgaaagtcaa aagtttatca  3120
tctgcgcaat cgagctcatc aggaccttca tcatctagtg aggaagatga ttcccgcgat  3180
attgaaagct tggataagaa aatacgtcct ttagaagaat tagaagcatt attaagtagt  3240
ggaaatacaa aacaattgaa gaacaaagag gtcgctgcct tggttattca cggtaagtta  3300
cctttgtacg ctttggagaa aaaattaggt gatactacga gagcggttgc ggtacgtagg  3360
aaggctcttt caattttggc agaagctcct gtattagcat ctgatcgttt accatataaa  3420
aattatgact acgaccgcgt atttggcgct tgttgtgaaa atgttatagg ttacatgcct  3480
ttgcccgttg gtgttatagg ccccttggtt atcgatggta catcttatca tataccaatg  3540
gcaactacag agggttgttt ggtagcttct gccatgcgtg gctgtaaggc aatcaatgct  3600
ggcggtggtg caacaactgt tttaactaag gatggtatga caagaggccc agtagtccgt  3660
ttcccaactt tgaaaagatc tggtgcctgt aagatatggt tagactcaga agagggacaa  3720
aacgcaatta aaaaagcttt taactctaca tcaagatttg cacgtctgca acatattcaa  3780
acttgtctag caggagattt actcttcatg agatttagaa caactactgg tgacgcaatg  3840
ggtatgaata tgatttctaa aggtgtcgaa tactcattaa agcaaatggt agaagagtat  3900
ggctgggaag atatggaggt tgtctccgtt tctggtaact actgtaccga caaaaaacca  3960
gctgccatca actggatcga aggtcgtggt aagagtgtcg tcgcagaagc tactattcct  4020
ggtgatgttg tcagaaaagt gttaaaaagt gatgtttccg cattggttga gttgaacatt  4080
gctaagaatt tggttggatc tgcaatggct gggtctgttg gtggatttaa cgcacatgca  4140
gctaatttag tgacagctgt tttcttggca ttaggacaag atcctgcaca aatgttgaa  4200 agttccaact gtataacatt gatgaaagaa gtggacggtg atttgagaat tccgtatcc  4260 atgccatcca tcgaagtagg taccatcggt ggtggtactg ttctagaacc acaaggtgcc  4320
atgttggact tattaggtgt aagaggcccg catgctaccg ctcctggtac caacgcacgt  4380
caattagcaa gaatagttgc ctgtgccgtc ttggcaggtg aattatcctt atgtgctgcc  4440
ctagcagccg gccatttggt tcaaagtcat atgacccaca acaggaaacc tgctgaacca  4500
acaaaaccta acaatttgga cgccactgat ataaatcgtt tgaaagatgg gtccgtcacc  4560
tgcattaaat cctaagtcga cctgcaggca tgcaagcttg gctgttttgg cggatgagag  4620
aagattttca gcctgataca gattaaatca gaacgcagaa gcggtctgat aaaacagaat  4680
ttgcctggcg gcagtagcgc ggtggtccca cctgacccca tgccgaactc agaagtgaaa  4740
cgccgtagcg ccgatggtag tgtgggtct cccatgcga gagtaggaa ctgccaggca  4800 tcaaataaaa cgaaaggctc agtcgaaaga ctgggccttt cgttttatct gttgtttgtc  4860
ggtgaacgct ctcctgagta ggacaaatcc gccgggagcg gatttgaacg ttgcgaagca  4920
acggcccgga gggtggcggg caggacgccc gccataaact gccaggcatc aaattaagca  4980
gaaggccatc ctgacggatg cctttttgc gtttctacaa actctttgt ttatttttct  5040 aaatacattc aaatatgtat ccgctcatga acaataacc ctgataaatg cttcaataat  5100
attgaaaaag gaagagtatg agtattcaac atttccgtgt cgcccttatt ccctttttg  5160 cggcattttg ccttcctgtt tttgctcacc cagaaacgct ggtgaaagta aaagatgctg  5220
aagatcagtt gggtgcagca actattaac tggcgaacta cttactctag cttcccggca  5280
acaattaata gactgatgg aggcggataa agttgcagga ccacttctgc gctcggccct  5340
tccggctggc tggtttattg ctgataaatc tggagccggt gagcgtgggt ctcgcggtat  5400
```

```
cattgcagca ctggggccag atggtaagcc ctcccgtatc gtagttatct acacgacggg    5460
gagtcaggca actatggatg aacgaaatag acagatcgct gagataggtg cctcactgat    5520
taagcattgg taactgtcag accaagttta ctcatatata ctttagattg atttacgcgc    5580
cctgtagcgg cgcattaagc gcggcgggtg tggtggttac gcgcagcgtg accgctacac    5640
ttgccagcgc cctagcgccc gctcctttcg ctttcttccc ttcctttctc gccacgttcg    5700
ccggctttcc ccgtcaagct ctaaatcggg gctcccttt agggttccga tttagtgctt     5760
tacggcacct cgaccccaaa aaacttgatt gggtgatgg ttcacgtagt gggccatcgc     5820
cctgatagac ggtttttcgc cctttgacgt tggagtccac gttctttaat agtggactct    5880
tgttccaaac ttgaacaaca ctcaacccta tctcgggcta ttcttttgat ttataaggga    5940
ttttgccgat ttcggcctat tggttaaaaa atgagctgat ttaacaaaaa tttaacgcga    6000
attttaacaa aatattaacg tttacaattt aaaaggatct aggtgaagat cctttttgat    6060
aatctcatga ccaaaatccc ttaacgtgag ttttcgttcc actgagcgtc agaccccgta    6120
gaaaagatca aaggatcttc ttgagatcct ttttttctgc gcgtaatctg ctgcttgcaa    6180
acaaaaaaac caccgctacc agcggtggtt tgtttgccgg atcaagagct accaactctt    6240
tttccgaagg taactggctt cagcagagcg cagataccaa atactgtcct tctagtgtag    6300
ccgtagttag gccaccactt caagaactct gtagcaccgc ctacatacct cgctctgcta    6360
atcctgttac cagtgggca tttgagaagc acacggtcac actgcttccg gtagtcaata    6420
aaccggtaaa ccagcaatag acataagcgg ctatttaacg accctgccct gaaccgacga    6480
ccgggtcgaa tttgctttcg aatttctgcc attcatccgc ttattatcac ttattcaggc    6540
gtagcaccag gcgtttaagg gcaccaataa ctgccttaaa aaaattacgc cccgccctgc    6600
cactcatcgc agtactgttg taattcatta agcattctgc cgacatggaa gccatcacag    6660
acggcatgat gaacctgaat cgccagcggc atcagcacct tgtcgccttg cgtataatat    6720
ttgcccatgg tgaaaacggg ggcgaagaag ttgtccatat tggccacgtt taaatcaaaa    6780
ctggtgaaac tcacccaggg attggctgag acgaaaaaca tattctcaat aaacccttta    6840
gggaaatagg ccaggttttc accgtaacac gccacatctt gcgaatatat gtgtagaaac    6900
tgccggaaat cgtcgtggta ttcactccag agcgatgaaa acgtttcagt ttgctcatgg    6960
aaaacggtgt aacaagggtg aacactatcc catatcacca gctcaccgtc tttcattgcc    7020
atacggaatt ccgatgagc attcatcagg cgggcaagaa tgtgaataaa ggccggataa    7080
aacttgtgct tatttttctt tacggtcttt aaaaaggccg taatatccag ctgaacggtc    7140
tggttatagg tacattgagc aactgactga atgcctcaa aatgttcttt acgatgccat    7200
tgggatatat caacggtggt atatccagtg attttttttct ccattttagc ttccttagct    7260
cctgaaaatc tcgataactc aaaaaatacg cccggtagtg atcttatttc attatggtga    7320
aagttggaac ctcttacgtg ccgatcaacg tctcatttc gccaaaagtt ggcccagggc    7380
ttcccggtat caacagggac accaggattt atttattctg cgaagtgatc ttccgtcaca    7440
ggtatttatt cggcgcaaag tgcgtcgggt gatgctgcca acttactgat ttagtgtatg    7500
atggtgtttt tgaggtgctc cagtggcttc tgtttctatc agctgtccct cctgttcagc    7560
tactgacggg gtggtgcgta acggcaaaag caccgccgga catcagcgct agcggagtgt    7620
atactggctt actatgttgg cactgatgag ggtgtcagtg aagtgcttca tgtggcagga    7680
gaaaaaaggc tgcaccggtg cgtcagcaga atatgtgata caggatatat tccgcttcct    7740
```

```
cgctcactga ctcgctacgc tcggtcgttc gactgcggcg agcggaaatg gcttacgaac      7800
ggggcggaga tttcctggaa gatgccagga agatacttaa cagggaagtg agagggccgc      7860
ggcaaagccg ttttccata ggctccgccc ccctgacaag catcacgaaa tctgacgctc       7920
aaatcagtgg tggcgaaacc cgacaggact ataaagatac caggcgtttc ccctggcgg       7980 ctccctcgtg cgctctcctg ttcctgcctt tcggtttacc ggtgtcattc cgctgttatg      8040
gccgcgtttg tctcattcca cgcctgacac tcagttccgg gtaggcagtt cgctccaagc      8100
tggactgtat gcacgaaccc cccgttcagt ccgaccgctg cgccttatcc ggtaactatc      8160
gtcttgagtc caacccggaa agacatgcaa aagcaccact ggcagcagcc actggtaatt      8220
gatttagagg agttagtctt gaagtcatgc gccggttaag gctaaactga aaggacaagt      8280
tttggtgact gcgctcctcc aagccagtta cctcggttca aagagttggt agctcagaga      8340
accttcgaaa aaccgccctg caaggcggtt ttttcgtttt cagagcaaga gattacgcgc      8400
agaccaaaac gatctcaaga agatcatctt attaatcaga taaaatattt gctcatgagc      8460
ccgaagtggc gagcccgatc ttccccatcg gtgatgtcgg cgatataggc gccagcaacc      8520
gcacctgtgg cgccggtgat gccggccacg atgcgtccgg cgtagaggat ctgctcatgt      8580
ttgacagctt atc                                                         8593

<210> SEQ ID NO 4
<211> LENGTH: 10633
<212> TYPE: DNA
<213> ORGANISM: Artificial Sequence
<220> FEATURE:
<223> OTHER INFORMATION: pMBIS plasmid

<400> SEQUENCE: 4
accttcggga gcgcctgaag cccgttctgg acgccctggg gccgttgaat cgggatatgc       60
aggccaaggc cgccgcgatc atcaaggccg tgggcgaaaa gctgctgacg gaacagcggg      120
aagtccagcg ccagaaacag gcccagcgcc agcaggaacg cgggcgcgca catttccccg      180
aaaagtgcca cctgacgtct aagaaaccat tattatcatg acattaacct ataaaaatag      240
gcgtatcacg aggccctttc gtcttcaaga attctcatgt ttgacagctt atcatcgata      300
agctttaatg cggtagttta tcacagttaa attgctaacg cagtcaggca ccgtgtatga      360
aatctaacaa tgcgctcatc gtcatcctcg gcaccgtcac cctggatgct gtaggcatag      420
gcttggttat gccggtactg ccgggcctct tgcgggatat cgtccattcc gacagcatcg      480
ccagtcacta tggcgtgctg ctagcgctat atgcgttgat gcaatttcta tgcgcacccg      540
ttctcggagc actgtccgac cgctttggcc gccgcccagt cctgctcgct tcgctacttg      600
gagccactat cgactacgcg atcatggcga ccacacccgt cctgtggatc ctctacgccg      660
gacgcatcgt ggccggcatc accggcgcca caggtgcggt tgctggcgcc tatatcgccg      720
acatcaccga tggggaagat cgggctcgcc acttcgggct catgagcgct tgtttcggcg      780
tgggtatggt ggcaggcccc gtggccgggg gactgttggg cgccatctcc ttgcatgcac      840
cattccttgc ggcggcggtg ctcaacggcc tcaacctact actgggctgc ttcctaatgc      900
aggagtcgca taagggagag cgtcgaccga tgcccttgag agccttcaac ccagtcagct      960
ccttccggtg ggcgcgggc atgactatcg tcgccgcact tatgactgtc ttctttatca     1020
tgcaactcgt aggacaggtg ccggcagcgc tctgggtcat tttcggcgag gaccgctttc     1080
gctggagcgc gacgatgatc ggcctgtcgc ttgcggtatt cggaatcttg cacgccctcg     1140
ctcaagcctt cgtcactggt cccgccacca aacgtttcgg cgagaagcag gccattatcg     1200
```

-continued

```
ccggcatggc ggccgacgcg ctgggctacg tcttgctggc gttcgcgacg cgaggctgga      1260
tggccttccc cattatgatt cttctcgctt ccggcggcat cgggatgccc gcgttgcagg      1320
ccatgctgtc caggcaggta gatgacgacc atcagggaca gcttcaagga tcgctcgcgg      1380
ctcttaccag cctaacttcg atcactggac cgctgatcgt cacggcgatt tatgccgcct      1440
cggcgagcac atgaacggg ttggcatgga ttgtaggcgc cgccctatac cttgtctgcc       1500
tccccgcgtt gcgtcgcggt gcatggagcc gggccacctc gacctgaatg aagccggcg       1560 gcacctcgct aacggattca ccactccaag aattggagcc aatcaattct gcggagaac       1620 tgtgaatgcg caaatgcgcc caatacgcaa accgcctctc ccgcgcgtt ggccgattca       1680 ttaatgcagc tggcacgaca ggtttcccga ctggaaagcg ggcagtgagc gcaacgcaat      1740
taatgtgagt tagctcactc attaggcacc ccaggcttta cactttatgc ttccggctcg      1800
tatgttgtgt ggaattgtga gcggataaca atttcacaca ggaaacagct atgaccatga      1860
ttacgccaag cgcgcaatta accctcacta agggaacaa aagctgggta ccgggccccc       1920
cctcgaggtc gacggtatcg ataagcttga tatcgaattc ctgcagtagg aggaattaac      1980
catgtcatta ccgttcttaa cttctgcacc gggaaaggtt attattttg gtgaacactc       2040 tgctgtgtac aacaagcctg ccgtcgctgc tagtgtgtct gcgttgagaa cctacctgct     2100
aataagcgag tcatctgcac cagatactat tgaattggac ttcccggaca ttagctttaa     2160
tcataagtgg tccatcaatg atttcaatgc catcaccgag gatcaagtaa actcccaaaa      2220
attggccaag gctcaacaag ccaccgatgg cttgtctcag gaactcgtta gtcttttgga     2280
tccgttgtta gctcaactat ccgaatcctt ccactaccat gcagcgtttt gtttcctgta    2340
tatgtttgtt tgcctatgcc cccatgccaa gaatattaag ttttctttaa agtctacttt     2400
acccatcggt gctgggttgg gctcaagcgc ctctatttct gtatcactgg ccttagctat     2460
ggcctacttg gggggttaa taggatctaa tgacttggaa aagctgtcag aaaacgataa      2520
gcatatagtg aatcaatggg ccttcatagg tgaaagtgt attcacggta cccctttcagg     2580 aatagataac gctgtggcca cttatggtaa tgccctgcta tttgaaaaag actcacataa     2640
tggaacaata aacacaaaca attttaagtt cttagatgat ttcccagcca ttccaatgat      2700
cctaacctat actagaattc caaggtctac aaaagatctt gttgctcgcg ttcgtgtgtt     2760
ggtcaccgag aaatttcctg aagttatgaa gccaattcta gatgccatgg gtgaatgtgc    2820
cctacaaggc ttagagatca tgactaagtt aagtaaatgt aaaggcaccg atgacgaggc    2880
tgtagaaact aataatgaac tgtatgaaca actattggaa ttgataagaa taaatcatgg     2940
actgcttgtc tcaatcggtg tttctcatcc tggattagaa cttattaaaa atctgagcga      3000
tgatttgaga attggctcca caaaacttac cggtgctggt ggcggcggtt gctctttgac     3060
tttgttacga agagacatta ctcaagagca aattgacagc ttcaaaaaga aattgcaaga    3120 tgatttttagt tacgagacat ttgaaacaga cttgggtggg actggctgct gtttgttaag    3180
cgcaaaaaat ttgaataaag atcttaaaat caaatcccta gtattccaat tatttgaaaa    3240
taaaactacc acaaagcaac aaattgacga tctattattg ccaggaaaca cgaatttacc      3300
atggacttca taggaggcag atcaaatgtc agagttgaga gccttcagtg ccccagggaa     3360
agcgttacta gctggtggat atttagtttt agatacaaaa tatgaagcat ttgtagtcgg    3420
attatcggca agaatgcatg ctgtagccca tccttacggt tcattgcaag ggtctgataa     3480
gtttgaagtg cgtgtgaaaa gtaaacaatt taaagatggg gagtggctgt accatataag     3540
```

```
tcctaaaagt ggcttcattc ctgtttcgat aggcggatct aagaacccct tcattgaaaa      3600
agttatcgct aacgtatttta gctactttaa acctaacatg gacgactact gcaatagaaa      3660
cttgttcgtt attgatattt tctctgatga tgcctaccat tctcaggagg atagcgttac      3720
cgaacatcgt ggcaacagaa gattgagttt tcattcgcac agaattgaag aagttcccaa      3780
aacagggctg ggctcctcgg caggtttagt cacagtttta actacagctt tggcctcctt      3840
ttttgtatcg gacctggaaa ataatgtaga caaatataga gaagttattc ataatttagc      3900
acaagttgct cattgtcaag ctcagggtaa aattggaagc gggtttgatg tagcggcggc      3960
agcatatgga tctatcagat atagaagatt cccacccgca ttaatctcta atttgccaga      4020
tattggaagt gctacttacg gcagtaaact ggcgcatttg gttgatgaag aagactggaa      4080
tattacgatt aaaagtaacc atttaccttc gggattaact ttatggatgg gcgatattaa      4140
gaatggttca gaaacagtaa aactggtcca gaaggtaaaa aattggtatg attcgcatat      4200
gccagaaagc ttgaaaatat atacagaact cgatcatgca aattctagat ttatggatgg      4260
actatctaaa ctagatcgct tacacgagac tcatgacgat tacagcgatc agatatttga      4320
gtctcttgag aggaatgact gtacctgtca aaagtatcct gaaatcacag aagttagaga      4380
tgcagttgcc acaattagac gttccttttag aaaaataact aaagaatctg gtgccgatat      4440
cgaacctccc gtacaaacta gcttattgga tgattgccag accttaaaag gagttcttac      4500
ttgcttaata cctggtgctg gtggttatga cgccattgca gtgattacta agcaagatgt      4560
tgatcttagg gctcaaaccg ctaatgacaa aagattttct aaggttcaat ggctggatgt      4620
aactcaggct gactggggtg ttaggaaaga aaagatccg gaaacttatc ttgataaata      4680
ggaggtaata ctcatgaccg tttacacagc atccgttacc gcacccgtca acatcgcaac      4740
ccttaagtat tgggggaaaa gggacacgaa gttgaatctg cccaccaatt cgtccatatc      4800
agtgacttta tcgcaagatg acctcagaac gttgacctct gcggctactg cacctgagtt      4860
tgaacgcgac actttgtggt taaatggaga accacacagc atcgacaatg aaagaactca      4920
aaattgtctg cgcgacctac gccaattaag aaaggaaatg gaatcgaagg acgcctcatt      4980
gcccacatta tctcaatgga aactccacat tgtctccgaa ataactttc ctacagcagc      5040 tggtttagct cctccgctg ctggctttgc tgcattggtc tctgcaattg ctaagttata      5100
ccaattacca cagtcaactt cagaaatatc tagaatagca agaaagggt ctggttcagc      5160 ttgtagatcg ttgtttggcg gatacgtggc ctgggaaatg ggaaaagctg aagatggtca      5220
tgattccatg gcagtacaaa tcgcagacag ctctgactgg cctcagatga agcttgtgt      5280 cctagttgtc agcgatatta aaaggatgt gagttccact cagggtatgc aattgaccgt      5340
ggcaacctcc gaactattta agaaagaat tgaacatgtc gtaccaaaga gatttgaagt      5400
catgcgtaaa gccattgttg aaaaagattt cgccacctt gcaaaggaaa caatgatgga      5460
ttccaactct ttccatgcca catgtttgga ctctttccct ccaatattct acatgaatga      5520
cacttccaag cgtatcatca gttggtgcca caccattaat cagttttacg gagaaacaat      5580
cgttgcatac acgtttgatg caggtccaaa tgctgtgttg tactacttag ctgaaaatga      5640
gtcgaaactc tttgcattta tctataaatt gtttggctct gttcctggat gggacaagaa      5700
atttactact gagcagcttg aggctttcaa ccatcaattt gaatcatcta actttactgc      5760
acgtgaattg gatcttgagt tgcaaaagga tgttgccaga gtgattttaa ctcaagtcgg      5820
ttcaggccca caagaaacaa acgaatcttt gattgacgca aagactggtc taccaaagga      5880
ataactgcag cccgggagga ggattactat atgcaaacgg aacacgtcat tttattgaat      5940
```

```
gcacagggag ttcccacggg tacgctggaa aagtatgccg cacacacggc agacacccgc    6000
ttacatctcg cgttctccag ttggctgttt aatgccaaag gacaattatt agttacccgc    6060
cgcgcactga gcaaaaaagc atggcctggc gtgtggacta actcggtttg tgggcaccca    6120
caactgggag aaagcaacga agacgcagtg atccgccgtt gccgttatga gcttggcgtg    6180
gaaattacgc ctcctgaatc tatctatcct gactttcgct accgcgccac cgatccgagt    6240
ggcattgtgg aaaatgaagt gtgtccggta tttgccgcac gcaccactag tgcgttacag    6300
atcaatgatg atgaagtgat ggattatcaa tggtgtgatt tagcagatgt attacacggt    6360
attgatgcca cgccgtgggc gttcagtccg tggatggtga tgcaggcgac aaatcgcgaa    6420
gccagaaaac gattatctgc atttacccag cttaaataac ccgggggatc cactagttct    6480
agagcggccg ccaccgcgga ggaggaatga gtaatggact ttccgcagca actcgaagcc    6540
tgcgttaagc aggccaacca ggcgctgagc cgttttatcg ccccactgcc ctttcagaac    6600
actcccgtgg tcgaaaccat gcagtatggc gcattattag gtggtaagcg cctgcgacct    6660
ttcctggttt atgccaccgg tcatatgttc ggcgttagca caaacacgct ggacgcaccc    6720
gctgccgccg ttgagtgtat ccacgcttac tcattaattc atgatgattt accggcaatg    6780
gatgatgacg atctgcgtcg cggttttgcca acctgccatg tgaagtttgg cgaagcaaac    6840
gcgattctcg ctggcgacgc tttacaaacg ctggcgttct cgattttaag cgatgccgat    6900
atgccggaag tgtcggaccg cgacagaatt tcgatgattt ctgaactggc gagcgccagt    6960
ggtattgccg gaatgtgcgg tggtcaggca ttagatttag acgcggaagg caaacacgta    7020
cctctggacg cgcttgagcg tattcatcgt cataaaaccg gcgcattgat tcgcgccgcc    7080
gttcgccttg gtgcattaag cgccggagat aaaggacgtc gtgctctgcc ggtactcgac    7140
aagtatgcag agagcatcgg ccttgccttc caggttcagg atgacatcct ggatgtggtg    7200
ggagatactg caacgttggg aaaacgccag ggtgccgacc agcaacttgg taaaagtacc    7260
taccctgcac ttctgggtct tgagcaagcc cggaagaaag cccgggatct gatcgacgat    7320
gcccgtcagt cgctgaaaca actggctgaa cagtcactcg ataccctcggc actggaagcg    7380
ctagcggact acatcatcca gcgtaataaa taagagctcc aattcgccct atagtgagtc    7440
gtattacgcg cgctcactgg ccgtcgtttt acaacgtcgt gactgggaaa accctggcgt    7500
tacccaactt aatcgccttg cagcacatcc ccctttcgcc agctggcgta atagcgaaga    7560
ggcccgcacc gatcgccctt cccaacagtt gcgcagcctg aatggcgaat ggaaattgta    7620
agcgttaata ttttgttaaa attcgcgtta aatttttgtt aaatcagctc attttttaac    7680
caataggccg actgcgatga gtggcagggc ggggcgtaat ttttttaagg cagttattgg    7740
tgcccttaaa cgcctggtgc tacgcctgaa taagtgataa taagcggatg aatggcagaa    7800
attcgaaagc aaattcgacc cggtcgtcgg ttcagggcag ggtcgttaaa tagccgctta    7860
tgtctattgc tggtttaccg gtttattgac taccggaagc agtgtgaccg tgtgcttctc    7920
aaatgcctga ggccagtttg ctcaggctct cccgtggag gtaataattg acgatatgat    7980
catttattct gcctcccaga gcctgataaa aacggtgaat ccgttagcga ggtgccgccg    8040
gcttccattc aggtcgaggt ggcccggtc catgcaccgc gacgcaacgc ggggaggcag    8100
acaaggtata gggcggcgag gcggctacag ccgatagtct ggaacagcgc acttacgggt    8160
tgctgcgcaa cccaagtgct accgcgcgcg cagcgtgacc cgtgtcggcg gctccaacgg    8220
ctcgccatcg tccagaaaac acggctcatc gggcatcggc aggcgctgct gcccgcgccg    8280
```

```
ttcccattcc tccgtttcgg tcaaggctgg caggtctggt tccatgcccg gaatgccggg    8340
ctggctgggc ggctcctcgc cggggccggt cggtagttgc tgctcgcccg gatacagggt    8400
cgggatgcgg cgcaggtcgc catgccccaa cagcgattcg tcctggtcgt cgtgatcaac    8460
caccacggcg gcactgaaca ccgacaggcg caactggtcg cggggctggc cccacgccac    8520
gcggtcattg accacgtagg ccgacacggt gccggggccg ttgagcttca cgacggagat    8580
ccagcgctcg gccaccaagt ccttgactgc gtattggacc gtccgcaaag aacgtccgat    8640
gagcttggaa agtgtcttct ggctgaccac cacggcgttc tggtggccca tctgcgccac    8700
gaggtgatgc agcagcattg ccgccgtggg tttcctcgca ataagcccgg cccacgcctc    8760
atgcgctttg cgttccgttt gcacccagtg accgggcttg ttcttggctt gaatgccgat    8820
ttctctggac tgcgtggcca tgcttatctc catgcgtag  ggtgccgcac ggttgcggca    8880
ccatgcgcaa tcagctgcaa ctttccggca gcgcgacaac aattatgcgt tgcgtaaaag    8940
tggcagtcaa ttacagattt tctttaacct acgcaatgag ctattgcggg gggtgccgca    9000
atgagctgtt gcgtaccccc ctttttttaag ttgttgattt ttaagtcttt cgcatttcgc    9060
cctatatcta gttctttggt gcccaaagaa gggcacccct gcggggttcc cccacgcctt    9120
cggcgcggct cccccctccgg caaaaagtgg cccctccggg gcttgttgat cgactgcgcg    9180
gccttcggcc ttgcccaagg tggcgctgcc cccttggaac ccccgcactc gccgccgtga    9240
ggctcggggg gcaggcgggc gggcttcgcc ttcgactgcc cccactcgca taggcttggg    9300
tcgttccagg cgcgtcaagg ccaagccgct gcgcggtcgc tgcgcgagcc ttgacccgcc    9360
ttccacttgg tgtccaaccg gcaagcgaag cgcgcaggcc gcaggccgga ggcttttccc    9420
cagagaaaat taaaaaaatt gatggggcaa ggccgcaggc cgcgcagttg gagccggtgg    9480
gtatgtggtc gaaggctggg tagccggtgg gcaatccctg tggtcaagct cgtgggcagg    9540
cgcagcctgt ccatcagctt gtccagcagg gttgtccacg ggccgagcga agcgagccag    9600
ccggtggccg ctcgcggcca tcgtccacat atccacgggc tggcaaggga gcgcagcgac    9660
cgcgcagggc gaagcccgga gagcaagccc gtagggcgcc gcagccgccg taggcggtca    9720
cgactttgcg aagcaaagtc tagtgagtat actcaagcat tgagtggccc gccggaggca    9780
ccgccttgcg ctgcccccgt cgagccggtt ggacaccaaa agggaggggc aggcatggcg    9840
gcatacgcga tcatgcgatg caagaagctg gcgaaaatgg gcaacgtggc ggccagtctc    9900
aagcacgcct accgcgagcg cgagacgccc aacgctgacg ccagcaggac gccagagaac    9960
gagcactggg cggccagcag caccgatgaa gcgatgggcc gactgcgcga gttgctgcca   10020
gagaagcggc gcaaggacgc tgtgttggcg gtcgagtacg tcatgacggc cagcccggaa   10080
tggtggaagt cggccagcca agaacagcag gcggcgttct tcgagaaggc gcacaagtgg   10140
ctggcggaca agtacggggc ggatcgcatc gtgacggcca gcatccaccg tgacgaaacc   10200
agcccgcaca tgaccgcgtt cgtggtgccg ctgacgcagg acggcaggct gtcggccaag   10260
gagttcatcg gcaacaaagc gcagatgacc cgcgaccaga ccacgtttgc ggccgctgtg   10320
gccgatctag gctgcaacg  gggcatcgag ggcagcaagg cacgtcacac gcgcattcag   10380
gcgttctacg aggccctgga gcggccacca gtgggccacg tcaccatcag cccgcaagcg   10440
gtcgagccac gcgccatgc  accgcaggga ttggccgaaa agctgggaat ctcaaagcgc   10500
gttgagacgc cggaagccgt ggccgaccgg ctgacaaaag cggttcggca ggggtatgag   10560
cctgccctac aggccgccgc aggagcgcgt gagatgcgca agaaggccga tcaagcccaa   10620
gagacggccc gag                                                      10633
```

<210> SEQ ID NO 5
<211> LENGTH: 5799
<212> TYPE: DNA
<213> ORGANISM: Artificial Sequence
<220> FEATURE:
<223> OTHER INFORMATION: pADS plasmid

<400> SEQUENCE: 5

```
caattcgcgc gcgaaggcga agcggcatgc atttacgttg acaccatcga atggtgcaaa      60
acctttcgcg gtatggcatg atagcgcccg gaagagagtc aattcagggt ggtgaatgtg     120
aaaccagtaa cgttatacga tgtcgcagag tatgccggtg tctcttatca gaccgtttcc     180
cgcgtggtga accaggccag ccacgtttct gcgaaaacgc gggaaaaagt ggaagcggcg     240
atggcggagc tgaattacat tcccaaccgc gtggcacaac aactggcggg caaacagtcg     300
ttgctgattg gcgttgccac ctccagtctg gccctgcacg cgccgtcgca aattgtcgcg     360
gcgattaaat ctcgcgccga tcaactgggt gccagcgtgg tggtgtcgat ggtagaacga     420
agcggcgtcg aagcctgtaa agcggcggtg cacaatcttc tcgcgcaacg cgtcagtggg     480
ctgatcatta actatccgct ggatgaccag gatgccattg ctgtggaagc tgcctgcact     540
aatgttccgg cgttatttct tgatgtctct gaccagacac ccatcaacag tattattttc     600
tcccatgaag acggtacgcg actgggcgtg gagcatctgg tcgcattggg tcaccagcaa     660
atcgcgctgt tagcgggccc attaagttct gtctcggcgc gtctgcgtct ggctggctgg     720
cataaatatc tcactcgcaa tcaaattcag ccgatagcgg aacgggaagg cgactggagt     780
gccatgtccg gttttcaaca aaccatgcaa atgctgaatg agggcatcgt tcccactgcg     840
atgctggttg ccaacgatca gatggcgctg ggcgcaatgc gcgccattac cgagtccggg     900
ctgcgcgttg gtgcggatat ctcggtagtg ggatacgacg ataccgaaga cagctcatgt     960
tatatcccgc cgtcaaccac catcaaacag gattttcgcc tgctggggca aaccagcgtg    1020
gaccgcttgc tgcaactctc tcagggccag gcggtgaagg gcaatcagct gttgcccgtc    1080
tcactggtga aaagaaaaac cacccggcg cccaatacgc aaaccgcctc tccccgcgcg    1140
ttggccgatt cattaatgca gctggcacga caggtttccc gactggaaag cgggcagtga    1200
gcgcaacgca attaatgtga gttagcgcga attgatctgg tttgacagct tatcatcgac    1260
tgcacggtgc accaatgctt ctggcgtcag cagccatcg gaagctgtgg tatggctgtg    1320
caggtcgtaa atcactgcat aattcgtgtc gctcaaggcg cactcccgtt ctggataatg    1380
ttttttgcgc cgacatcata acggttctgg caaatattct gaaatgagct gttgacaatt    1440
aatcatccgg ctcgtataat gtgtggaatt gtgagcggat aacaatttca cacaggaaac    1500
agaccatggc cctgaccgaa gagaaaccga tccgcccgat cgctaacttc cgccgtctca    1560
tctgggtga ccagttcctg atctacgaaa agcaggttga gcaggtgttg aacagatcg     1620
taaacgacct gaagaaagaa gttcgtcagc tgctgaaaga agctctggac atcccgatga    1680
aacacgctaa cctgctgaaa ctgatcgacg agatccagcg tctgggtatc ccgtaccact    1740
tcgaacgcga atcgaccac gcactgcagt gcatctacga aacctacggc gacaactgga    1800
acggcgaccg ttcttctctg tggtttcgtc tgatgcgtaa acagggctac tacgttacct    1860
gtgacgtttt taacaactac aaggacaaga cggtgctttt caaacagtct ctggctaacg    1920
acgttgaagg cctgctggaa ctgtacgaag cgacctccat gcgtgtaccg ggtgaaatca    1980
tcctggagga cgcgctgggt ttcacccgtt ctcgtctgtc cattatgact aaagacgctt    2040
```

```
tctctactaa cccggctctg ttcaccgaaa tccagcgtgc tctgaaacag ccgctgtgga   2100
aacgtctgcc gcgtatcgaa gcagcacagt acattccgtt ttaccagcag caggactctc   2160
acaacaagac cctgctgaaa ctggctaagc tggaattcaa cctgctgcag tctctgcaca   2220 agaagaact gtctcacgtt tgtaagtggt ggaaggcatt tgacatcaag aaaaacgcgc   2280
cgtgcctgcg tgaccgtatc gttgaatgtt acttctgggg tctgggttct ggttatgaac   2340
cacagtactc ccgtgcacgt gtgttcttca ctaaagctgt agctgttatc accctgatcg   2400
atgacactta cgatgcttac ggcacctacg aagaactgaa gatctttact gaagctgtag   2460
aacgctggtc tatcacttgc ctggacactc tgccggagta catgaaaccg atctacaaac   2520
tgttcatgga tacctacacc gaaatggagg aattcctggc aaagaaggc cgtaccgacc   2580 tgttcaactg cggtaaagag tttgttaaag aattcgtacg taacctgatg gttgaagcta   2640
aatgggctaa cgaaggccat atcccgacta ccgaagaaca tgaccgggtt gttatcatca   2700
ccggcggtgc aaacctgctg accaccactt gctatctggg tatgtccgac atctttacca   2760
aggaatctgt tgaatgggct gtttctgcac cgccgctgtt ccgttactcc ggtattctgg   2820
gtcgtcgtct gaacgacctg atgacccaca agcagagca ggaacgtaaa cactcttcct   2880
cctctctgga atcctacatg aaggaatata cgttaacga ggagtacgca cagactctga   2940
tctataaaga agttgaagac gtatggaaag acatcaaccg tgaataccctg actactaaaa   3000 acatcccgcg cccgctgctg atggcagtaa tctacctgtg ccagttcctg gaagtacagt   3060
acgctggtaa agataacttc actcgcatgg gcgacgaata caaacacctg atcaaatccc   3120
tgctggttta cccgatgtcc atctgatccc ggggatcctc tagagtcgac ctgcaggcat   3180
gcaagcttgg ctgttttggc ggatgagaga agattttcag cctgatacag attaaatcag   3240
aacgcagaag cggtctgata aaacagaatt tgcctggcgg cagtagcgcg gtggtcccac   3300
ctgaccccat gccgaactca gaagtgaaac gccgtagcgc cgatggtagt gtggggtctc   3360
cccatgcgag agtagggaac tgccaggcat caaataaaac gaaaggctca gtcgaaagac   3420
tgggcctttc gttttatctg ttgtttgtcg gtgaacgctc tcctgagtag acaaatccg   3480 ccgggagcgg atttgaacgt tgcgaagcaa cggcccggag ggtggcgggc aggacgcccg   3540
ccataaactg ccaggcatca aattaagcag aaggccatcc tgacggatgg cctttttgcg   3600
tttctacaaa ctctttttgt ttatttttct aaatacattc aaatatgtat ccgctcatga   3660
gacaataacc ctgataaatg cttcaataat attgaaaaag gaagagtatg agtattcaac   3720
atttccgtgt cgcccttatt cccttttttg cggcattttg ccttcctgtt tttgctcacc   3780
cagaaacgct ggtgaaagta aaagatgctg aagatcagtt gggtgcacga gtgggttaca   3840
tcgaactgga tctcaacagc ggtaagatcc ttgagagttt cgccccgaa gaacgttttc   3900 caatgatgag cacttttaaa gttctgctat gtggcgcggt attatcccgt gttgacgccg   3960
ggcaagagca actcggtcgc cgcatacact attctcagaa tgacttggtt gagtactcac   4020
cagtcacaga aaagcatctt acggatggca tgacagtaag agaattatgc agtgctgcca   4080
taaccatgag tgataacact gcggccaact tacttctgac aacgatcgga ggaccgaagg   4140
agctaaccgc ttttttgcac aacatggggg atcatgtaac tcgccttgat cgttgggaac   4200
cggagctgaa tgaagccata ccaaacgacg agcgtgacac cacgatgcct acagcaatgg   4260
caacaacgtt gcgcaaacta ttaactggcg aactacttac tctagcttcc cggcaacaat   4320
taatagactg gatggaggcg gataaagttg caggaccact tctgcgctcg gcccttccgg   4380
ctggctggtt tattgctgat aaatctggag ccggtgagcg tgggtctcgc ggtatcattg   4440
```

```
cagcactggg gccagatggt aagccctccc gtatcgtagt tatctacacg acggggagtc    4500
aggcaactat ggatgaacga aatagacaga tcgctgagat aggtgcctca ctgattaagc    4560
attggtaact gtcagaccaa gtttactcat atatacttta gattgattta aaacttcatt    4620
tttaatttaa aaggatctag gtgaagatcc ttttgataa tctcatgacc aaaatccctt     4680
aacgtgagtt tcgttccac tgagcgtcag accccgtaga aaagatcaaa ggatcttctt     4740
gagatccttt ttttctgcgc gtaatctgct gcttgcaaac aaaaaaacca ccgctaccag    4800
cggtggtttg tttgccggat caagagctac caactctttt tccgaaggta actggcttca    4860
gcagagcgca gataccaaat actgtccttc tagtgtagcc gtagttaggc caccacttca    4920
agaactctgt agcaccgcct acatacccg ctctgctaat cctgttacca gtggctgctg     4980
ccagtggcga taagtcgtgt cttaccgggt tggactcaag acgatagtta ccggataagg    5040
cgcagcggtc gggctgaacg gggggttcgt gcacacagcc cagcttggag cgaacgacct    5100
acaccgaact gagatacccta cagcgtgagc tatgagaaag cgccacgctt cccgaaggga   5160
gaaaggcgga caggtatccg gtaagcggca gggtcggaac aggagagcgc acgagggagc    5220
ttccaggggg aaacgcctgg tatctttata gtcctgtcgg gtttcgccac ctctgacttg    5280
agcgtcgatt tttgtgatgc tcgtcagggg gcggagcct atggaaaaac gccagcaacg     5340
cggccttttt acggttcctg gccttttgct ggccttttgc tcacatgttc tttcctgcgt    5400
tatcccctga ttctgtggat aaccgtatta ccgcctttga gtgagctgat accgctcgcc    5460
gcagccgaac gaccgagcgc agcgagtcag tgagcgagga agcggaagag cgcctgatgc    5520
ggtattttct ccttacgcat ctgtgcggta tttcacaccg catatggtgc actctcagta    5580
caatctgctc tgatgccgca tagttaagcc agtatacact ccgctatcgc tacgtgactg    5640
ggtcatggct gcgccccgac acccgccaac acccgctgac gcgccctgac gggcttgtct    5700
gctcccggca tccgcttaca gacaagctgt gaccgtctcc gggagctgca tgtgtcagag    5760
gttttcaccg tcatcaccga aacgcgcgag gcagcagat                           5799

<210> SEQ ID NO 6
<211> LENGTH: 6545
<212> TYPE: DNA
<213> ORGANISM: Artificial Sequence
<220> FEATURE:
<223> OTHER INFORMATION: pAtoB plasmid

<400> SEQUENCE: 6
atcgatgcat aatgtgcctg tcaaatggac gaagcaggga ttctgcaaac cctatgctac      60
tccgtcaagc cgtcaattgt ctgattcgtt accaattatg acaacttgac ggctacatca     120 ttcactttt cttcacaacc ggcacggaac tcgctcgggc tggccccggt gcatttttta     180
aatacccgcg agaaatagag ttgatcgtca aaaccaacat tgcgaccgac ggtggcgata    240
ggcatccggg tggtgctcaa aagcagcttc gcctggctga tacgttggtc ctcgcgccag    300
cttaagacgc taatccctaa ctgctggcgg aaaagatgtg acagacgcga cggcgacaag    360
caaacatgct gtgcgacgct ggcgatatca aaattgctgt ctgccaggtg atcgctgatg    420
tactgacaag cctcgcgtac ccgattatcc atcggtggat ggagcgactc gttaatcgct    480
tccatgcgcc gcagtaacaa ttgctcaagc agatttatcg ccagcagctc cgaatagcgc    540 ccttccccctt gcccggcgtt aatgatttgc ccaaacaggt cgctgaaatg cggctggtgc    600
gcttcatccg ggcgaaagaa cccgtattg caaatattg acggcagtt aagccattca       660
```

```
tgccagtagg cgcgcggacg aaagtaaacc cactggtgat accattcgcg agcctccgga    720
tgacgaccgt agtgatgaat ctctcctggc gggaacagca aaatatcacc cggtcggcaa    780
acaaattctc gtccctgatt tttcaccacc ccctgaccgc gaatggtgag attgagaata    840
taacctttca ttcccagcgg tcggtcgata aaaaaatcga gataaccgtt ggcctcaatc    900
ggcgttaaac ccgccaccag atgggcatta acgagtatc ccggcagcag gggatcattt     960
tgcgcttcag ccatactttt catactcccg ccattcagag aagaaaccaa ttgtccatat   1020
tgcatcagac attgccgtca ctgcgtcttt tactggctct ctcgctaac caaaccggta    1080 accccgctta ttaaaagcat tctgtaacaa agcgggacca agccatgac aaaaacgcgt    1140 aacaaaagtg tctataatca cggcagaaaa gtccacattg attatttgca cggcgtcaca   1200
ctttgctatg ccatagcatt tttatccata agattagcgg atcctacctg acgctttta    1260 tcgcaactct ctactgtttc tccatacccg tttttttggg ctagcgaatt cgagctcggt   1320
acccgggtag gaggaatata aaatgaaaaa ttgtgtcatc gtcagtgcgg tacgtactgc   1380
tatcggtagt tttaacggtt cactcgcttc caccagcgcc atcgacctgg gggcgacagt   1440
aattaaagcc gccattgaac gtgcaaaaat cgattcacaa cacgttgatg aagtgattat   1500
gggtaacgtg ttacaagccg ggctggggca aaatccggcg cgtcaggcac tgttaaaaag   1560
cgggctggca gaaacggtgt gcggattcac ggtcaataaa gtatgtggtt cgggtcttaa   1620
aagtgtggcg cttgccgccc aggccattca ggcaggtcag gcgcagagca ttgtggcggg   1680
gggtatggaa aatatgagtt tagcccccta cttactcgat gcaaaagcac gctctggtta   1740
tcgtcttgga gacggacagg tttatgacgt aatcctgcgc gatggcctga tgtgcgccac   1800
ccatggttat catatgggga ttaccgccga aaacgtggct aaagagtacg gaattacccg   1860
tgaaatgcag gatgaactgg cgctacattc acagcgtaaa gcggcagccg caattgagtc   1920
cggtgctttt acagccgaaa tcgtcccggt aaatgttgtc actcgaaaga aaaccttcgt   1980
cttcagtcaa gacgaattcc cgaaagcgaa ttcaacggct gaagcgttag gtgcattgcg   2040
cccggccttc gataaagcag gaacagtcac cgctgggaac cgtctggta ttaacgacgg    2100 tgctgccgct ctggtgatta tggaagaatc tgcggcgctg gcagcaggcc ttaccccct    2160 ggctcgcatt aaaagttatg ccagcggtgg cgtgccccc gcattgatgg gtatggggcc    2220
agtacctgcc acgcaaaaag cgttacaact ggcggggctg caactggcgg atattgatct   2280
cattgaggct aatgaagcat tgctgcaca gttccttgcc gttgggaaaa acctgggctt    2340
tgattctgag aaagtgaatg tcaacggcgg ggccatcgcc ctcgggcatc ctatcggtgc   2400
cagtggtgct cgtattctgg tcacactatt acatgccatg caggcacgcg ataaaacgct   2460
ggggctggca acactgtgca ttggcggcgg tcagggaatt gcgatggtga ttgaacggtt   2520
gaattaagtc gacctgcagg catgcaagct tggctgtttt ggcggatgag agaagatttt   2580
cagcctgata cagattaaat cagaacgcag aagcggtctg ataaaacaga atttgcctgg   2640
cggcagtagc gcggtggtcc cacctgaccc catgccgaac tcagaagtga acgccgtag    2700 cgccgatggt agtgtgggt ctccccatgc gagagtaggg aactgccagg catcaaataa    2760
aacgaaaggc tcagtcgaaa gactgggcct ttcgttttat ctgttgtttg tcggtgaacg   2820
ctctcctgag taggacaaat ccgccgggag cggatttgaa cgttgcgaag caacggcccg   2880
gagggtggcg gcaggacgc ccgccataaa ctgccaggca tcaaattaag cagaaggcca    2940
tcctgacgga tggcctttt gcgtttctac aaactctttt gtttatttt ctaaatacat     3000 tcaaatatgt atccgctcat gagacaataa ccctgataaa tgcttcaata atattgaaaa   3060
```

```
aggaagagta tgagtattca acatttccgt gtcgcccttg ttcccttttt tgcggcattt    3120
tgccttcctg ttttgctca cccagaaacg ctggtgaaag taaaagatgc tgaagatcag     3180
ttgggtgcag caaactatta actggcgaac tacttactct agcttcccgg caacaattaa    3240
tagactggat ggaggcggat aaagttgcag gaccacttct gcgctcggcc cttccggctg    3300
gctggtttat tgctgataaa tctggagccg gtgagcgtgg gtctcgcggt atcattgcag    3360
cactggggcc agatggtaag ccctcccgta tcgtagttat ctacacgacg gggagtcagg    3420
caactatgga tgaacgaaat agacagatcg ctgagatagg tgcctcactg attaagcatt    3480
ggtaactgtc agaccaagtt tactcatata ctttagat tgatttacgc gccctgtagc      3540
ggcgcattaa gcgcggcggg tgtggtggtt acgcgcagcg tgaccgctac acttgccagc    3600
gccctagcgc ccgctccttt cgctttcttc ccttcctttc tcgccacgtt cgccggcttt    3660
ccccgtcaag ctctaaatcg ggggctccct ttagggttcc gatttagtgc tttacggcac    3720
ctcgacccca aaaaacttga tttgggtgat ggttcacgta gtgggccatc gccctgatag    3780 acggttttc gcccttgac gttggagtcc acgttcttta atagtggact cttgttccaa      3840
acttgaacaa cactcaaccc tatctcgggc tattcttttg atttataagg gattttgccg    3900
atttcggcct attggttaaa aaatgagctg atttaacaaa aatttaacgc gaattttaac    3960
aaaatattaa cgtttacaat ttaaaaggat ctaggtgaag atcctttttg ataatctcat    4020
gaccaaaatc ccttaacgtg agttttcgtt ccactgagcg tcagacccg tagaaaagat     4080 caaaggatct tcttgagatc ctttttttct gcgcgtaatc tgctgcttgc aaacaaaaaa    4140
accaccgcta ccagcggtgg tttgtttgcc ggatcaagag ctaccaactc ttttttccgaa   4200 ggtaactggc ttcagcagag cgcagatacc aaatactgtc cttctagtgt agccgtagtt    4260
aggccaccac ttcaagaact ctgtagcacc gcctacatac ctcgctctgc taatcctgtt    4320
accagtgggg catttgagaa gcacacggtc acactgcttc cggtagtcaa taaaccggta    4380
aaccagcaat agacataagc ggctatttaa cgaccctgcc ctgaaccgac gaccgggtcg    4440
aatttgcttt cgaatttctg ccattcatcc gcttattatc acttattcag gcgtagcacc    4500
aggcgtttaa gggcaccaat aactgcctta aaaaaattac gccccgccct gccactcatc    4560
gcagtactgt tgtaattcat taagcattct gccgacatgg aagccatcac agacggcatg    4620
atgaacctga atcgccagcg gcatcagcac cttgtcgcct gcgtataat atttgcccat     4680 ggtgaaaacg ggggcgaaga agttgtccat attggccacg tttaaatcaa aactggtgaa    4740
actcacccag ggattggctg agacgaaaaa catattctca ataaacccctt agggaaata   4800 ggccaggttt tcaccgtaac acgccacatc ttgcgaatat atgtgtagaa actgccggaa    4860
atcgtcgtgg tattcactcc agagcgatga aaacgtttca gtttgctcat ggaaaacggt    4920
gtaacaaggg tgaacactat cccatatcac cagctcaccg tctttcattg ccatacggaa    4980
ttccggatga gcattcatca ggcgggcaag aatgtgaata aaggccggat aaaacttgtg    5040 cttattttc tttacggtct ttaaaaaggc cgtaatatcc agctgaacgg tctggttata    5100
ggtacattga gcaactgact gaaatgcctc aaaatgttct ttacgatgcc attgggatat    5160
atcaacggtg gtatatccag tgatttttt ctccatttta gcttccttag ctcctgaaaa     5220
tctcgataac tcaaaaaata cgcccggtag tgatcttatt tcattatggt gaaagttgga    5280
acctcttacg tgccgatcaa cgtctcattt tcgccaaaag ttggcccagg cttcccggt     5340 atcaacaggg acaccaggat ttatttattc tgcgaagtga tcttccgtca caggtattta    5400
```

-continued

| | |
|---|---|
| ttcggcgcaa agtgcgtcgg gtgatgctgc caacttactg atttagtgta tgatggtgtt | 5460 |
| tttgaggtgc tccagtggct tctgtttcta tcagctgtcc ctcctgttca gctactgacg | 5520 |
| gggtggtgcg taacggcaaa agcaccgccg gacatcagcg ctagcggagt gtatactggc | 5580 |
| ttactatgtt ggcactgatg agggtgtcag tgaagtgctt catgtggcag agaaaaaag | 5640 |
| gctgcaccgg tgcgtcagca gaatatgtga tacaggatat attccgcttc ctcgctcact | 5700 |
| gactcgctac gctcggtcgt tcgactgcgg cgagcggaaa tggcttacga acggggcgga | 5760 |
| gatttcctgg aagatgccag gaagatactt aacagggaag tgagagggcc gcggcaaagc | 5820 |
| cgttttccca taggctccgc cccctgaca agcatcacga aatctgacgc tcaaatcagt | 5880 |
| ggtggcgaaa cccgacagga ctataaagat accaggcgtt tccccctggc ggctccctcg | 5940 |
| tgcgctctcc tgttcctgcc tttcggttta ccggtgtcat tccgctgtta tggccgcgtt | 6000 |
| tgtctcattc cacgcctgac actcagttcc gggtaggcag ttcgctccaa gctggactgt | 6060 |
| atgcacgaac cccccgttca gtccgaccgc tgcgccttat ccggtaacta tcgtcttgag | 6120 |
| tccaacccgg aaagacatgc aaaagcacca ctggcagcag ccactggtaa ttgatttaga | 6180 |
| ggagttagtc ttgaagtcat gcgccggtta aggctaaact gaaaggacaa gttttggtga | 6240 |
| ctgcgctcct ccaagccagt tacctcggtt caaagagttg gtagctcaga gaaccttcga | 6300 |
| aaaaccgccc tgcaaggcgg ttttttcgtt ttcagagcaa gagattacgc gcagaccaaa | 6360 |
| acgatctcaa gaagatcatc ttattaatca gataaaatat ttgctcatga gcccgaagtg | 6420 |
| gcgagcccga tcttccccat cggtgatgtc ggcgatatag gcgccagcaa ccgcacctgt | 6480 |
| ggcgccggtg atgccggcca cgatgcgtcc ggcgtagagg atctgctcat gtttgacagc | 6540 |
| ttatc | 6545 |

<210> SEQ ID NO 7
<211> LENGTH: 6835
<212> TYPE: DNA
<213> ORGANISM: Artificial Sequence
<220> FEATURE:
<223> OTHER INFORMATION: pHMGS plasmid

<400> SEQUENCE: 7

| | |
|---|---|
| atcgatgcat aatgtgcctg tcaaatggac gaagcaggga ttctgcaaac cctatgctac | 60 |
| tccgtcaagc cgtcaattgt ctgattcgtt accaattatg acaacttgac ggctacatca | 120 |
| ttcactttt cttcacaacc ggcacggaac tcgctcgggc tggccccggt gcattttta | 180 |
| aatacccgcg agaaatagag ttgatcgtca aaaccaacat tgcgaccgac ggtggcgata | 240 |
| ggcatccggg tggtgctcaa aagcagcttc gcctggctga tacgttggtc ctcgcgccag | 300 |
| cttaagacgc taatccctaa ctgctggcgg aaaagatgtg acagacgcga cggcgacaag | 360 |
| caaacatgct gtgcgacgct ggcgatatca aaattgctgt ctgccaggtg atcgctgatg | 420 |
| tactgacaag cctcgcgtac ccgattatcc atcggtggat ggagcgactc gttaatcgct | 480 |
| tccatgcgcc gcagtaacaa ttgctcaagc agatttatcg ccagcagctc gaatagcgc | 540 |
| ccttcccctt gccggcgtt aatgatttgc ccaaacaggt cgctgaaatg cggctggtgc | 600 |
| gcttcatccg ggcgaaagaa ccccgtattg gcaaatattg acggccagtt aagccattca | 660 |
| tgccagtagg cgcgcggacg aaagtaaacc cactggtgat accattgcg agcctccgga | 720 |
| tgacgaccgt agtgatgaat ctctcctggc gggaacagca aaatatcacc cggtcggcaa | 780 |
| acaaattctc gtccctgatt tttcaccacc ccctgaccgc gaatggtgag attgagaata | 840 |
| taaccttca ttcccagcgg tcggtcgata aaaaaatcga gataaccgtt ggcctcaatc | 900 |

-continued

```
ggcgttaaac ccgccaccag atgggcatta aacgagtatc ccggcagcag gggatcattt    960
tgcgcttcag ccatactttt catactcccg ccattcagag aagaaaccaa ttgtccatat   1020
tgcatcagac attgccgtca ctgcgtcttt tactggctct tctcgctaac caaaccggta   1080
accccgctta ttaaaagcat tctgtaacaa agcgggacca aagccatgac aaaaacgcgt   1140
aacaaaagtg tctataatca cggcagaaaa gtccacattg attatttgca cggcgtcaca   1200
ctttgctatg ccatagcatt tttatccata agattagcgg atcctacctg acgcttttta   1260
tcgcaactct ctactgtttc tccatacccg tttttttggg ctagcgaatt cgagctcggt   1320
acccgggagg aggacagcta atgaaactc tcaactaaac tttgttggtg tggtattaaa    1380
ggaagactta ggccgcaaaa gcaacaacaa ttacacaata caaacttgca aatgactgaa   1440
ctaaaaaaac aaaagaccgc tgaacaaaaa accagacctc aaaatgtcgg tattaaaggt   1500
atccaaattt acatcccaac tcaatgtgtc aaccaatctg agctagagaa atttgatggc   1560
gtttctcaag gtaaatacac aattggtctg ggccaaacca acatgtcttt tgtcaatgac   1620
agagaagata tctactcgat gtccctaact gttttgtcta agttgatcaa gagttacaac   1680
atcgacacca acaaaattgg tagattagaa gtcggtactg aaactctgat tgacaagtcc   1740
aagtctgtca agtctgtctt gatgcaattg tttggtgaaa acactgacgt cgaaggtatt   1800
gacacgctta atgcctgtta cggtggtacc aacgcgttgt tcaactcttt gaactggatt   1860
gaatctaacg catgggatgg tagagacgcc attgtagttt gcggtgatat tgccatctac   1920
gataagggtg ccgcaagacc aaccggtggt gccggtactg ttgctatgtg gatcggtcct   1980
gatgctccaa ttgtatttga ctctgtaaga gcttcttaca tggaacacgc ctacgatttt   2040
tacaagccaa atttccaccag cgaatatcct tacgtcgatg gtcattttc attaacttgt   2100
tacgtcaagg ctcttgatca agtttacaag agttattcca agaaggctat ttctaaaggg   2160
ttggttagcg atcccgctgg ttcggatgct ttgaacgttt tgaaatattt cgactacaac   2220
gttttccatg ttccaacctg taaattggtc acaaaatcat acggtagatt actatataac   2280
gatttcagag ccaatcctca attgttccca gaagttgacg ccgaattagc tactcgcgat   2340
tatgacgaat cttaaccga taagaacatt gaaaaaactt ttgttaatgt tgctaagcca   2400
ttccacaaag agagagttgc ccaatctttg attgttccaa caaacacagg taacatgtac   2460
accgcatctg tttatgccgc ctttgcatct ctattaaact atgttggatc tgacgactta   2520
caaggcaagc gtgttggttt attttcttac ggttccggtt tagctgcatc tctatattct   2580
tgcaaaattg ttggtgacgt ccaacatatt atcaaggaat tagatattac taacaaatta   2640
gccaagagaa tcaccgaaac tccaaaggat tacgaagctg ccatcgaatt gagagaaaat   2700
gcccatttga agaagaactt caaacctcaa ggttccattg agcatttgca aagtggtgtt   2760
tactacttga ccaacatcga tgacaaattt agaagatctt acgatgttaa aaaataagtc   2820
gacctgcagg catgcaagct tggctgtttt ggcggatgag agaagatttt cagcctgata   2880
cagattaaat cagaacgcag aagcggtctg ataaaacaga atttgcctgg cggcagtagc   2940
gcggtggtcc cacctgaccc catgccgaac tcagaagtga acgccgtag cgccgatggt   3000
agtgtggggt ctccccatgc gagagtaggg aactgccagg catcaaataa acgaaaggc    3060
tcagtcgaaa gactgggcct ttcgttttat ctgttgtttg tcggtgaacg ctctcctgag   3120
taggacaaat ccgccgggag cggatttgaa cgttgcgaag caacggcccg gagggtggcg   3180
ggcaggacgc ccgccataaa ctgccaggca tcaaattaag cagaaggcca tcctgacgga   3240
```

```
tggccttttt gcgtttctac aaactctttt gtttatttttt ctaaatacat tcaaatatgt    3300
atccgctcat gagacaataa ccctgataaa tgcttcaata atattgaaaa aggaagagta    3360
tgagtattca acatttccgt gtcgcccttta ttccctttt tgcggcattt tgccttcctg    3420
tttttgctca cccagaaacg ctggtgaaag taaaagatgc tgaagatcag ttgggtgcag    3480
caaactatta actggcgaac tacttactct agcttcccgg caacaattaa tagactggat    3540
ggaggcggat aaagttgcag gaccacttct gcgctcggcc cttccggctg gctggtttat    3600
tgctgataaa tctggagccg gtgagcgtgg gtctcgcggt atcattgcag cactggggcc    3660
agatggtaag ccctcccgta tcgtagttat ctacacgacg gggagtcagg caactatgga    3720
tgaacgaaat agacagatcg ctgagatagg tgcctcactg attaagcatt ggtaactgtc    3780
agaccaagtt tactcatata ctttagat tgatttacgc ccctgtagc ggcgcattaa    3840
gcgcggcggg tgtggtggtt acgcgcagcg tgaccgctac acttgccagc gccctagcgc    3900
ccgctccttt cgctttcttc ccttcctttc tcgccacgtt cgccggcttt cccgtcaag    3960
ctctaaatcg ggggctccct ttagggttcc gatttagtgc tttacggcac ctcgacccca    4020
aaaaacttga tttgggtgat ggttcacgta gtgggccatc gccctgatag acggttttc    4080
gccctttgac gttggagtcc acgttcttta atagtggact cttgttccaa acttgaacaa    4140
cactcaaccc tatctcgggc tattcttttg atttataagg gattttgccg atttcggcct    4200
attggttaaa aaatgagctg atttaacaaa aatttaacgc gaattttaac aaaatattaa    4260
cgtttacaat ttaaaaggat ctaggtgaag atccttttg ataatctcat gaccaaaatc    4320
ccttaacgtg agtttcgtt ccactgagcg tcagaccccg tagaaaagat caaaggatct    4380
tcttgagatc cttttttct gcgcgtaatc tgctgcttgc aaacaaaaaa accaccgcta    4440
ccagcggtgg tttgtttgcc ggatcaagag ctaccaactc ttttccgaa ggtaactggc    4500
ttcagcagag cgcagatacc aaatactgtc cttctagtgt agccgtagtt aggccaccac    4560
ttcaagaact ctgtagcacc gcctacatac ctcgctctgc taatcctgtt accagtgggg    4620
catttgagaa gcacacggtc acactgcttc cggtagtcaa taaaccggta aaccagcaat    4680
agacataagc ggctatttaa cgaccctgcc ctgaaccgac gaccgggtcg aatttgcttt    4740
cgaatttctg ccattcatcc gcttattatc acttattcag gcgtagcacc aggcgtttaa    4800
gggcaccaat aactgcctta aaaaaattac gccccgccct gccactcatc gcagtactgt    4860
tgtaattcat taagcattct gccgacatgg aagccatcac agacggcatg atgaacctga    4920
atcgccagcg gcatcagcac cttgtcgcct tgcgtataat atttgcccat ggtgaaaacg    4980
ggggcgaaga agttgtccat attggccacg tttaaatcaa aactggtgaa actcacccag    5040
ggattggctg agacgaaaaa catattctca ataaacccctt tagggaaata ggccaggttt    5100
tcaccgtaac acgccacatc ttgcgaatat atgtgtagaa actgccggaa atcgtcgtgg    5160
tattcactcc agagcgatga aaacgtttca gtttgctcat ggaaaacggt gtaacaaggg    5220
tgaacactat cccatatcac cagctcaccg tctttcattg ccatacggaa ttccggatga    5280
gcattcatca ggcgggcaag aatgtgaata aaggccggat aaaacttgtg cttatttttc    5340
tttacggtct ttaaaaaggc cgtaatatcc agctgaacgg tctggttata ggtacattga    5400
gcaactgact gaaatgcctc aaaatgttct ttacgatgcc attgggatat atcaacggtg    5460
gtatatccag tgatttttt ctccatttta gcttccttag ctcctgaaaa tctcgataac    5520
tcaaaaaata cgcccggtag tgatcttatt tcattatggt gaaagttgga acctcttacg    5580
tgccgatcaa cgtctcattt tcgccaaaag ttggcccagg gcttcccggt atcaacaggg    5640
```

-continued

| | |
|---|---|
| acaccaggat ttatttattc tgcgaagtga tcttccgtca caggtattta ttcggcgcaa | 5700 |
| agtgcgtcgg gtgatgctgc caacttactg atttagtgta tgatggtgtt tttgaggtgc | 5760 |
| tccagtggct tctgtttcta tcagctgtcc ctcctgttca gctactgacg gggtggtgcg | 5820 |
| taacggcaaa agcaccgccg gacatcagcg ctagcggagt gtatactggc ttactatgtt | 5880 |
| ggcactgatg agggtgtcag tgaagtgctt catgtggcag gagaaaaaag gctgcaccgg | 5940 |
| tgcgtcagca gaatatgtga tacaggatat attccgcttc ctcgctcact gactcgctac | 6000 |
| gctcggtcgt tcgactgcgg cgagcggaaa tggcttacga acggggcgga gatttcctgg | 6060 |
| aagatgccag gaagatactt aacagggaag tgagagggcc gcggcaaagc cgttttttcca | 6120 |
| taggctccgc cccctgaca agcatcacga aatctgacgc tcaaatcagt ggtggcgaaa | 6180 |
| cccgacagga ctataaagat accaggcgtt tccccctggc ggctccctcg tgcgctctcc | 6240 |
| tgttcctgcc tttcggttta ccggtgtcat tccgctgtta tggccgcgtt tgtctcattc | 6300 |
| cacgcctgac actcagttcc gggtaggcag ttcgctccaa gctggactgt atgcacgaac | 6360 |
| cccccgttca gtccgaccgc tgcgccttat ccggtaacta tcgtcttgag tccaacccgg | 6420 |
| aaagacatgc aaaagcacca ctggcagcag ccactggtaa ttgatttaga ggagttagtc | 6480 |
| ttgaagtcat gcgccggtta aggctaaact gaaaggacaa gttttggtga ctgcgctcct | 6540 |
| ccaagccagt tacctcggtt caaagagttg gtagctcaga gaaccttcga aaaaccgccc | 6600 |
| tgcaaggcgg ttttttcgtt ttcagagcaa gagattacgc gcagaccaaa acgatctcaa | 6660 |
| gaagatcatc ttattaatca gataaaatat ttgctcatga gcccgaagtg gcgagcccga | 6720 |
| tcttccccat cggtgatgtc ggcgatatag gcgccagcaa ccgcacctgt ggcgccggtg | 6780 |
| atgccggcca cgatgcgtcc ggcgtagagg atctgctcat gtttgacagc ttatc | 6835 |

<210> SEQ ID NO 8
<211> LENGTH: 6868
<212> TYPE: DNA
<213> ORGANISM: Artificial Sequence
<220> FEATURE:
<223> OTHER INFORMATION: pHMGR plasmid

<400> SEQUENCE: 8

| | |
|---|---|
| atcgatgcat aatgtgcctg tcaaatggac gaagcaggga ttctgcaaac cctatgctac | 60 |
| tccgtcaagc cgtcaattgt ctgattcgtt accaattatg caacttgac ggctacatca | 120 |
| ttcactttt cttcacaacc ggcacggaac tcgctcgggc tggccccggt gcatttttta | 180 |
| aatacccgcg agaaatagag ttgatcgtca aaaccaacat tgcgaccgac ggtggcgata | 240 |
| ggcatccggg tggtgctcaa aagcagcttc gcctggctga tacgttggtc ctcgcgccag | 300 |
| cttaagacgc taatccctaa ctgctggcgg aaaagatgtg acagacgcga cggcgacaag | 360 |
| caaacatgct gtgcgacgct ggcgatatca aaattgctgt ctgccaggtg atcgctgatg | 420 |
| tactgacaag cctcgcgtac ccgattatcc atcggtggat ggagcgactc gttaatcgct | 480 |
| tccatgcgcc gcagtaacaa ttgctcaagc agatttatcg ccagcagctc cgaatagcgc | 540 |
| ccttcccctt gcccggcgtt aatgatttgc ccaaacaggt cgctgaaatg cggctggtgc | 600 |
| gcttcatccg ggcgaaagaa ccccgtattg gcaaatattg acggcagtt aagccattca | 660 |
| tgccagtagg cgcgcggacg aaagtaaacc cactggtgat accattcgcg agcctccgga | 720 |
| tgacgaccgt agtgatgaat ctctcctggc gggaacagca aaatatcacc cggtcggcaa | 780 |
| acaaattctc gtccctgatt tttcaccacc ccctgaccgc gaatggtgag attgagaata | 840 |

-continued

| | |
|---|---|
| taaccttttca ttcccagcgg tcggtcgata aaaaaatcga gataaccgtt ggcctcaatc | 900 |
| ggcgttaaac ccgccaccag atgggcatta acgagtatc ccggcagcag gggatcattt | 960 |
| tgcgcttcag ccatactttt catactcccg ccattcagag aagaaaccaa ttgtccatat | 1020 |
| tgcatcagac attgccgtca ctgcgtcttt tactggctct tctcgctaac caaaccggta | 1080 |
| acccccgctta ttaaaagcat tctgtaacaa agcgggacca aagccatgac aaaaacgcgt | 1140 |
| aacaaaagtg tctataatca cggcagaaaa gtccacattg attatttgca cggcgtcaca | 1200 |
| ctttgctatg ccatagcatt tttatccata agattagcgg atcctacctg acgcttttta | 1260 |
| tcgcaactct ctactgtttc tccatacccg ttttttttggg ctagcgaatt cgagctcggt | 1320 |
| acccggagg aggattacac tatggtttta accaataaaa cagtcatttc tggatcgaaa | 1380 |
| gtcaaaagtt tatcatctgc gcaatcgagc tcatcggacc cttcatcatc tagtgaggaa | 1440 |
| gatgattccc gcgatattga aagcttggat aagaaaatac gtcctttaga agaattagaa | 1500 |
| gcattattaa gtagtggaaa tacaaaacaa ttgaagaaca aagaggtcgc tgccttggtt | 1560 |
| attcacggta agttaccttt gtacgctttg gagaaaaaat taggtgatac tacgagagcg | 1620 |
| gttgcggtac gtaggaaggc tcttttcaatt ttggcagaag ctcctgtatt agcatctgat | 1680 |
| cgtttaccat ataaaaatta tgactacgac cgcgtatttg gcgcttgttg tgaaaatgtt | 1740 |
| ataggttaca tgcctttgcc cgttggtgtt ataggcccct tggttatcga tggtacatct | 1800 |
| tatcatatac caatggcaac tacagagggt tgtttggtag cttctgccat gcgtggctgt | 1860 |
| aaggcaatca atgctggcgg tggtgcaaca actgttttaa ctaaggatgg tatgacaaga | 1920 |
| ggcccagtag tccgtttccc aactttgaaa agatctggtg cctgtaagat atggttagac | 1980 |
| tcagaagagg gacaaaacgc aattaaaaaa gcttttaact ctacatcaag atttgcacgt | 2040 |
| ctgcaacata ttcaaacttg tctagcagga gatttactct tcatgagatt tagaacaact | 2100 |
| actggtgacg caatgggtat gaatatgatt tctaaaggtg tcgaatactc attaaagcaa | 2160 |
| atggtagaag agtatggctg ggaagatatg gaggttgtct ccgtttctgg taactactgt | 2220 |
| accgacaaaa aaccagctgc catcaactgg atcgaaggtc gtggtaagag tgtcgtcgca | 2280 |
| gaagctacta ttcctggtga tgttgtcaga aaagtgttaa aaagtgatgt ttccgcattg | 2340 |
| gttgagttga acattgctaa gaatttggtt ggatctgcaa tggctgggtc tgttggtgga | 2400 |
| tttaacgcac atgcagctaa tttagtgaca gctgttttct tggcattagg acaagatcct | 2460 |
| gcacaaaatg ttgaaagttc caactgtata acattgatga agaagtggga cggtgatttg | 2520 |
| agaatttccg tatccatgcc atccatcgaa gtaggtacca tcggtggtgg tactgttcta | 2580 |
| gaaccacaag gtgccatgtt ggacttatta ggtgtaagag gcccgcatgc taccgctcct | 2640 |
| ggtaccaacg cacgtcaatt agcaagaata gttgcctgtg ccgtcttggc aggtgaatta | 2700 |
| tccttatgtg ctgccctagc agccggccat ttggttcaaa gtcatatgac ccacaacagg | 2760 |
| aaacctgctg aaccaacaaa acctaacaat ttggacgcca ctgatataaa tcgtttgaaa | 2820 |
| gatgggtccg tcacctgcat taaatcctaa gtcgacctgc aggcatgcaa gcttggctgt | 2880 |
| tttggcggat gagagaagat tttcagcctg atacagatta aatcagaacg cagaagcggt | 2940 |
| ctgataaaac agaatttgcc tggcggcagt agcgcggtgg tcccacctga ccccatgccg | 3000 |
| aactcagaag tgaaacgccg tagcgccgat ggtagtgtgg ggtctcccca tgcgagagta | 3060 |
| gggaactgcc aggcatcaaa taaaacgaaa ggctcagtcg aaagactggg cctttcgttt | 3120 |
| tatctgttgt ttgtcggtga acgctctcct gagtaggaca aatccgccgg gagcggattt | 3180 |
| gaacgttgcg aagcaacggc ccggagggtg gcgggcagga cgcccgccat aaactgccag | 3240 |

-continued

```
gcatcaaatt aagcagaagg ccatcctgac ggatggcctt tttgcgtttc tacaaactct    3300
tttgtttatt tttctaaata cattcaaata tgtatccgct catgagacaa taaccctgat    3360
aaatgcttca ataatattga aaaggaaga gtatgagtat tcaacatttc cgtgtcgccc    3420
ttattccctt ttttgcggca ttttgccttc ctgtttttgc tcacccagaa acgctggtga    3480
aagtaaaaga tgctgaagat cagttgggtg cagcaaacta ttaactggcg aactacttac    3540
tctagcttcc cggcaacaat taatagactg gatggaggcg gataaagttg caggaccact    3600
tctgcgctcg gcccttccgg ctggctggtt tattgctgat aaatctggag ccggtgagcg    3660
tgggtctcgc ggtatcattg cagcactggg gccagatggt aagccctccc gtatcgtagt    3720
tatctacacg acggggagtc aggcaactat ggatgaacga atagacaga tcgctgagat    3780 aggtgcctca ctgattaagc attggtaact gtcagaccaa gtttactcat atatacttta    3840
gattgattta cgcgcccgt agcggcgcat aagcgcggc gggtgtggtg gttacgcgca    3900
gcgtgaccgc tacacttgcc agcgccctag cgcccgctcc tttcgctttc ttcccttcct    3960
ttctcgccac gttcgccggc tttccccgtc aagctctaaa tcgggggctc ccttagggt    4020 tccgatttag tgctttacgg cacctcgacc ccaaaaaact tgatttgggt gatggttcac    4080
gtagtgggcc atcgccctga tagacggttt ttcgcccttt gacgttggag tccacgttct    4140
ttaatagtgg actcttgttc caaacttgaa caacactcaa ccctatctcg gctattctt    4200 ttgatttata agggattttg ccgatttcgg cctattggtt aaaaaatgag ctgatttaac    4260
aaaaatttaa cgcgaatttt aacaaaatat taacgtttac aatttaaaag gatctaggtg    4320
aagatccttt ttgataatct catgaccaaa atcccttaac gtgagttttc gttccactga    4380
gcgtcagacc ccgtagaaaa gatcaaagga tcttcttgag atcctttttt tctgcgcgta    4440
atctgctgct tgcaaacaaa aaaccaccg ctaccagcgg tggtttgttt gccggatcaa    4500
gagctaccaa ctcttttcc gaaggtaact ggcttcagca gagcgcagat accaaatact    4560
gtccttctag tgtagccgta gttaggccac cacttcaaga actctgtagc accgcctaca    4620
tacctcgctc tgctaatcct gttaccagtg ggcatttga gaagcacacg gtcacactgc    4680
ttccggtagt caataaaccg gtaaaccagc aatagacata gcggctatt taacgaccct    4740 gccctgaacc gacgaccggg tcgaatttgc tttcgaattt ctgccattca tccgcttatt    4800
atcacttatt caggcgtagc accaggcgtt taagggcacc aataactgcc ttaaaaaaat    4860
tacgccccgc cctgccactc atcgcagtac tgttgtaatt cattaagcat tctgccgaca    4920
tggaagccat cacagacggc atgatgaacc tgaatcgcca gcggcatcag caccttgtcg    4980
ccttgcgtat aatatttgcc catggtgaaa acggggggcga agaagttgtc catattggcc    5040
acgtttaaat caaaactggt gaaactcacc cagggattgg ctgagacgaa aaacatattc    5100
tcaataaacc cttagggaa ataggccagg ttttcaccgt aacacgccac atcttgcgaa    5160
tatatgtgta gaaactgccg gaaatcgtcg tggtattcac tccagagcga tgaaaacgtt    5220
tcagtttgct catggaaaac ggtgtaacaa gggtgaacac tatcccatat caccagctca    5280
ccgtctttca ttgccatacg gaattccgga tgagcattca tcaggcgggc aagaatgtga    5340
ataaaggccg gataaaactt gtgcttattt tctttacgg tctttaaaaa ggccgtaata    5400
tccagctgaa cggtctggtt ataggtacat tgagcaactg actgaaatgc ctcaaaatgt    5460
tctttacgat gccattggga tatatcaacg gtggtatatc cagtgatttt ttctccatt    5520 ttagcttcct tagctcctga aaatctcgat aactcaaaaa atacgcccgg tagtgatctt    5580
```

| | |
|---|---|
| atttcattat ggtgaaagtt ggaacctctt acgtgccgat caacgtctca ttttcgccaa | 5640 |
| aagttggccc agggcttccc ggtatcaaca gggacaccag gatttattta ttctgcgaag | 5700 |
| tgatcttccg tcacaggtat ttattcggcg caaagtgcgt cgggtgatgc tgccaactta | 5760 |
| ctgatttagt gtatgatggt gtttttgagg tgctccagtg gcttctgttt ctatcagctg | 5820 |
| tccctcctgt tcagctactg acggggtggt gcgtaacggc aaaagcaccg ccggacatca | 5880 |
| gcgctagcgg agtgtatact ggcttactat gttggcactg atgagggtgt cagtgaagtg | 5940 |
| cttcatgtgg caggagaaaa aaggctgcac cggtgcgtca gcagaatatg tgatacagga | 6000 |
| tatattccgc ttcctcgctc actgactcgc tacgctcggt cgttcgactg cggcgagcgg | 6060 |
| aaatggctta cgaacggggc ggagatttcc tggaagatgc caggaagata cttaacaggg | 6120 |
| aagtgagagg gccgcggcaa agccgttttt ccataggctc cgcccccctg acaagcatca | 6180 |
| cgaaatctga cgctcaaatc agtggtggcg aaacccgaca ggactataaa gataccaggc | 6240 |
| gtttccccct ggcggctccc tcgtgcgctc tcctgttcct gcctttcggt ttaccggtgt | 6300 |
| cattccgctg ttatggccgc gtttgtctca ttccacgcct gacactcagt tccgggtagg | 6360 |
| cagttcgctc caagctggac tgtatgcacg aaccccccgt tcagtccgac cgctgcgcct | 6420 |
| tatccggtaa ctatcgtctt gagtccaacc cggaaagaca tgcaaaagca ccactggcag | 6480 |
| cagccactgg taattgattt agaggagtta gtcttgaagt catgcgccgg ttaaggctaa | 6540 |
| actgaaagga caagttttgg tgactgcgct cctccaagcc agttacctcg gttcaaagag | 6600 |
| ttggtagctc agagaacctt cgaaaaaccg ccctgcaagg cggttttttc gttttcagag | 6660 |
| caagagatta cgcgcagacc aaaacgatct caagaagatc atcttattaa tcagataaaa | 6720 |
| tatttgctca tgagcccgaa gtggcgagcc cgatcttccc catcggtgat gtcggcgata | 6780 |
| taggcgccag caaccgcacc tgtggcgccg gtgatgccgg ccacgatgcg tccggcgtag | 6840 |
| aggatctgct catgtttgac agcttatc | 6868 |

<210> SEQ ID NO 9
<211> LENGTH: 6125
<212> TYPE: DNA
<213> ORGANISM: Artificial Sequence
<220> FEATURE:
<223> OTHER INFORMATION: pBAD18HMGR plasmid

<400> SEQUENCE: 9

| | |
|---|---|
| atcgatgcat aatgtgcctg tcaaatggac gaagcaggga ttctgcaaac cctatgctac | 60 |
| tccgtcaagc cgtcaattgt ctgattcgtt accaattatg acaacttgac ggctacatca | 120 |
| ttcactttt cttcacaacc ggcacggaac tcgctcgggc tggccccggt gcatttttta | 180 |
| aatacccgcg agaaatagag ttgatcgtca aaaccaacat tgcgaccgac ggtggcgata | 240 |
| ggcatccggg tggtgctcaa aagcagcttc gcctggctga tacgttggtc ctcgcgccag | 300 |
| cttaagacgc taatccctaa ctgctggcgg aaaagatgtg acagacgcga cggcgacaag | 360 |
| caaacatgct gtgcgacgct ggcgatatca aaattgctgt ctgccaggtg atcgctgatg | 420 |
| tactgacaag cctcgcgtac ccgattatcc atcggtggat ggagcgactc gttaatcgct | 480 |
| tccatgcgcc gcagtaacaa ttgctcaagc agatttatcg ccagcagctc gaatagcgc | 540 |
| ccttcccctt gcccggcgtt aatgatttgc ccaaacaggt cgctgaaatg cggctggtgc | 600 |
| gcttcatccg ggcgaaagaa ccccgtattg gcaaatattg acggccagtt aagccattca | 660 |
| tgccagtagg cgcgcggacg aaagtaaacc cactggtgat accattcgcg agcctccgga | 720 |
| tgacgaccgt agtgatgaat ctctcctggc gggaacagca aatatcacc cggtcggcaa | 780 |

```
acaaattctc gtccctgatt tttcaccacc ccctgaccgc gaatggtgag attgagaata    840
taacctttca ttcccagcgg tcggtcgata aaaaaatcga gataaccgtt ggcctcaatc    900
ggcgttaaac ccgccaccag atgggcatta acgagtatc ccggcagcag gggatcattt    960
tgcgcttcag ccatactttt catactcccg ccattcagag aagaaaccaa ttgtccatat   1020
tgcatcagac attgccgtca ctgcgtcttt tactggctct tctcgctaac caaaccggta   1080
accccgctta ttaaaagcat tctgtaacaa agcgggacca aagccatgac aaaaacgcgt   1140
aacaaaagtg tctataatca cggcagaaaa gtccacattg attatttgca cggcgtcaca   1200
ctttgctatg ccatagcatt tttatccata agattagcgg atcctacctg acgctttta    1260
tcgcaactct ctactgtttc tccatacccg ttttttggg ctagcgaatt cgagctcggt    1320
acccggagg aggattacac tatggtttta accaataaaa cagtcatttc tggatcgaaa    1380
gtcaaaagtt tatcatctgc gcaatcgagc tcatcaggac cttcatcatc tagtgaggaa   1440
gatgattccc gcgatattga agcttggat aagaaatac gtcctttaga agaattagaa     1500
gcattattaa gtagtggaaa tacaaaacaa ttgaagaaca agaggtcgc tgccttggtt    1560
attcacggta agttaccttt gtacgctttg gagaaaaaat taggtgatac tacgagagcg   1620
gttgcggtac gtaggaaggc tctttcaatt ttggcagaag ctcctgtatt agcatctgat   1680
cgtttaccat ataaaaatta tgactacgac cgcgtatttg gcgcttgttg tgaaaatgtt   1740
ataggttaca tgccttttgcc cgttggtgtt ataggcccct tggttatcga tggtacatct   1800
tatcatatac caatggcaac tacagagggt tgtttggtag cttctgccat gcgtggctgt   1860
aaggcaatca atgctggcgg tgtgcaaca actgttttaa ctaaggatgg tatgacaaga   1920
ggcccagtag tccgtttccc aactttgaaa agatctggtg cctgtaagat atggttagac   1980
tcagaagagg gacaaaacgc aattaaaaaa gcttttaact ctacatcaag atttgcacgt   2040
ctgcaacata ttcaaacttg tctagcagga gatttactct tcatgagatt tagaacaact   2100
actggtgacg caatgggtat gaatatgatt tctaaaggtg tcgaatactc attaaagcaa   2160
atggtagaag agtatggctg ggaagatatg gaggttgtct ccgtttctgg taactactgt   2220
accgacaaaa aaccagctgc catcaactgg atcgaaggtc gtggtaagag tgtcgtcgca   2280
gaagctacta ttcctggtga tgttgtcaga aaagtgttaa aaagtgatgt tccgcattg    2340
gttgagttga acattgctaa gaatttggtt ggatctgcaa tggctgggtc tgttggtgga   2400
tttaacgcac atgcagctaa tttagtgaca gctgttttct tggcattagg acaagatcct   2460
gcacaaaatg ttgaaagttc caactgtata acattgatga agaagtgga cggtgatttg    2520
agaatttccg tatccatgcc atccatcgaa gtaggtacca tcggtggtgg tactgttcta   2580
gaaccacaag gtgccatgtt ggacttatta ggtgtaagag gcccgcatgc taccgctcct   2640
ggtaccaacg cacgtcaatt agcaagaata gttgcctgtg ccgtcttggc aggtgaatta   2700
tccttatgtg ctgccctagc agccggccat ttggttcaaa gtcatatgac ccacaacagg   2760
aaacctgctg aaccaacaaa acctaacaat ttggacgcca ctgatataaa tcgtttgaaa   2820
gatgggtccg tcacctgcat taaatcctaa gtcgacctgc aggcatgcaa gcttggctgt   2880
tttggcggat gagagaagat tttcagcctg atacagatta aatcgaacg cagaagcggt    2940
ctgataaaac agaatttgcc tggcggcagt agcgcggtgg tcccacctga ccccatgccg   3000
aactcagaag tgaaacgccg tagcgccgat ggtagtgtgg ggtctcccca tgcgagagta   3060
gggaactgcc aggcatcaaa taaaacgaaa ggctcagtcg aaagactggg cctttcgttt   3120
```

```
tatctgttgt tgtcggtga acgctctcct gagtaggaca atccgccgg gagcggattt      3180
gaacgttgcg aagcaacggc ccggagggtg gcgggcagga cgcccgccat aaactgccag    3240
gcatcaaatt aagcagaagg ccatcctgac ggatggcctt tttgcgtttc tacaaactct    3300
tttgtttatt tttctaaata cattcaaata tgtatccgct catgagacaa taaccctgat    3360
aaatgcttca ataatattga aaaggaaga gtatgagtat tcaacatttc cgtgtcgccc     3420
ttattcccct ttttgcggca ttttgccttc ctgtttttgc tcacccagaa acgctggtga    3480
aagtaaaaga tgctgaagat cagttgggtg cacgagtggg ttacatcgaa ctggatctca    3540
acagcggtaa gatccttgag agttttcgcc ccgaagaacg ttttccaatg atgagcactt    3600
ttaaagttct gctatgtggc gcggtattat cccgtgttga cgccgggcaa gagcaactcg    3660
gtcgccgcat acactattct cagaatgact tggttgagta ctcaccagtc acagaaaagc    3720
atcttacgga tggcatgaca gtaagagaat tatgcagtgc tgccataacc atgagtgata    3780
acactgcggc caacttactt ctgacaacga tcggaggacc gaaggagcta accgcttttt    3840
tgcacaacat gggggatcat gtaactcgcc ttgatcgttg ggaaccggag ctgaatgaag    3900
ccataccaaa cgacgagcgt gacaccacga tgcctgcagc aatggcaaca acgttgcgca    3960
aactattaac tggcgaacta cttactctag cttcccggca acaattaata gactggatgg    4020
aggcggataa agttgcagga ccacttctgc gctcggccct tccggctggc tggtttattg    4080
ctgataaatc tggagccggt gagcgtgggt ctcgcggtat cattgcagca ctggggccag    4140
atggtaagcc ctcccgtatc gtagttatct acacgacggg gagtcaggca actatggatg    4200
aacgaaatag acagatcgct gagataggtg cctcactgat taagcattgg taactgtcag    4260
accaagttta ctcatatata ctttagattg atttacgcgc cctgtagcgg cgcattaagc    4320
gcggcgggtg tggtggttac gcgcagcgtg accgctacac ttgccagcgc cctagcgccc    4380
gctcctttcg ctttcttccc ttcctttctc gccacgttcg ccggctttcc ccgtcaagct    4440
ctaaatcggg ggctcccttt agggttccga tttagtgctt tacggcacct cgaccccaaa    4500
aaacttgatt tgggtgatgg ttcacgtagt gggccatcgc cctgatagac ggttttcgc    4560
cctttgacgt tggagtccac gttctttaat agtggactct tgttccaaac ttgaacaaca    4620
ctcaacccta tctcgggcta ttcttttgat ttataaggga ttttgccgat ttcggcctat    4680
tggttaaaaa atgagctgat ttaacaaaaa tttaacgcga attttaacaa aatattaacg    4740
tttacaattt aaaaggatct aggtgaagat ccttttttgat aatctcatga ccaaaatccc    4800
ttaacgtgag ttttcgttcc actgagcgtc agacccccgta gaaaagatca aggatcttc    4860
ttgagatcct tttttttctgc gcgtaatctg ctgcttgcaa acaaaaaaac caccgctacc    4920
agcggtggtt tgtttgccgg atcaagagct accaactctt tttccgaagg taactggctt    4980
cagcagagcg cagataccaa atactgtcct tctagtgtag ccgtagttag gccaccactt    5040
caagaactct gtagcaccgc ctacatacct cgctctgcta atcctgttac cagtggctgc    5100
tgccagtggc gataagtcgt gtcttaccgg gttggactca agacgatagt taccggataa    5160
ggcgcagcgg tcgggctgaa cggggggttc gtgcacacag cccagcttgg agcgaacgac    5220
ctacaccgaa ctgagatacc tacagcgtga gctatgagaa agcgccacgc ttcccgaagg    5280
gagaaaggcg gacaggtatc cggtaagcgg cagggtcgga acaggagagc gcacgaggga    5340
gcttccaggg ggaaacgcct ggtatcttta tagtcctgtc gggtttcgcc acctctgact    5400
tgagcgtcga tttttgtgat gctcgtcagg gggcggagc ctatggaaaa acgccagcaa    5460
cgcggccttt ttacggttcc tggccttttg ctggcctttt gctcacatgt tctttcctgc    5520
```

-continued

```
gttatcccct gattctgtgg ataaccgtat taccgccttt gagtgagctg ataccgctcg    5580
ccgcagccga acgaccgagc gcagcgagtc agtgagcgag gaagcggaag agcgcctgat    5640
gcggtatttt ctccttacgc atctgtgcgg tatttcacac cgcatatggt gcactctcag    5700
tacaatctgc tctgatgccg catagttaag ccagtataca ctccgctatc gctacgtgac    5760
tgggtcatgg ctgcgccccg acacccgcca acacccgctg acgcgccctg acgggcttgt    5820
ctgctcccgg catccgctta cagacaagct gtgaccgtct ccgggagctg catgtgtcag    5880
aggttttcac cgtcatcacc gaaacgcgcg aggcagcaag gagatggcgc ccaacagtcc    5940
cccggccacg gggcctgcca ccatacccac gccgaaacaa gcgctcatga gcccgaagtg    6000
gcgagcccga tcttccccat cggtgatgtc ggcgatatag gcgccagcaa ccgcacctgt    6060
ggcgccggtg atgccggcca cgatgcgtcc ggcgtagagg atctgctcat gtttgacagc    6120
ttatc                                                                6125
```

<210> SEQ ID NO 10
<211> LENGTH: 8374
<212> TYPE: DNA
<213> ORGANISM: Artificial Sequence
<220> FEATURE:
<223> OTHER INFORMATION: pHMGSR plasmid

<400> SEQUENCE: 10

```
atcgatgcat aatgtgcctg tcaaatggac gaagcaggga ttctgcaaac cctatgctac      60
tccgtcaagc cgtcaattgt ctgattcgtt accaattatg acaacttgac ggctacatca     120
ttcactttt cttcacaacc ggcacggaac tcgctcgggc tggccccggt gcattttta     180
aatacccgcg agaaatagag ttgatcgtca aaaccaacat tgcgaccgac ggtggcgata     240
ggcatccggg tggtgctcaa aagcagcttc gcctggctga tacgttggtc ctcgcgccag     300
cttaagacgc taatccctaa ctgctggcgg aaaagatgtg acagacgcga cggcgacaag     360
caaacatgct gtgcgacgct ggcgatatca aaattgctgt ctgccaggtg atcgctgatg     420
tactgacaag cctcgcgtac ccgattatcc atcggtggat ggagcgactc gttaatcgct     480
tccatgcgcc gcagtaacaa ttgctcaagc agatttatcg ccagcagctc gaatagcgc     540
ccttccccctt gccggcgtt aatgatttgc ccaaacaggt cgctgaaatg cggctggtgc     600
gcttcatccg ggcgaaagaa ccccgtattg gcaaatattg acggccagtt aagccattca     660
tgccagtagg cgcgcggacg aaagtaaacc cactggtgat accattcgcg agcctccgga     720
tgacgaccgt agtgatgaat ctctcctggc gggaacagca aaatatcacc cggtcggcaa     780
acaaattctc gtccctgatt tttcaccacc ccctgaccgc gaatggtgag attgagaata     840
taaccttca ttcccagcgg tcggtcgata aaaaaatcga gataaccgtt ggcctcaatc     900
ggcgttaaac ccgccaccag atgggcatta acgagtatc ccggcagcag gggatcattt     960
tgcgcttcag ccatactttt catactcccg ccattcagag aagaaaccaa ttgtccatat    1020
tgcatcagac attgccgtca ctgcgtcttt tactggctct ctcgctaac caaaccggta    1080
accccgctta ttaaaagcat tctgtaacaa gcgggacca aagccatgac aaaaacgcgt    1140
aacaaaagtg tctataatca cggcagaaaa gtccacattg attatttgca cggcgtcaca    1200
ctttgctatg ccatagcatt tttatccata agattagcgg atcctacctg acgcttttta    1260
tcgcaactct ctactgtttc tccatacccg tttttttggg ctagcgaatt cgagctcggt    1320
acccggggat cctctagagt cgacaggagg acagctaaat gaaactctca actaaacttt    1380
```

```
gttggtgtgg tattaaagga agacttaggc cgcaaaagca acaacaatta cacaatacaa   1440
acttgcaaat gactgaacta aaaaaacaaa agaccgctga acaaaaaacc agacctcaaa   1500
atgtcggtat taaaggtatc caaatttaca tcccaactca atgtgtcaac caatctgagc   1560
tagagaaatt tgatggcgtt tctcaaggta aatacacaat tggtctgggc caaaccaaca   1620
tgtcttttgt caatgacaga gaagatatct actcgatgtc cctaactgtt ttgtctaagt   1680
tgatcaagag ttacaacatc gacaccaaca aaattggtag attagaagtc ggtactgaaa   1740
ctctgattga caagtccaag tctgtcaagt ctgtcttgat gcaattgttt ggtgaaaaca   1800
ctgacgtcga aggtattgac acgcttaatg cctgttacgg tggtaccaac gcgttgttca   1860
actctttgaa ctggattgaa tctaacgcat gggatggtag agacgccatt gtagtttgcg   1920
gtgatattgc catctacgat aagggtgccg caagaccaac cggtggtgcc ggtactgttg   1980
ctatgtggat cggtcctgat gctccaattg tatttgactc tgtaagagct tcttacatgg   2040
aacacgccta cgattttac aagccagatt tcaccagcga atatccttac gtcgatggtc   2100
atttttcatt aacttgttac gtcaaggctc ttgatcaagt ttacaagagt tattccaaga   2160
aggctatttc taaaggggttg gttagcgatc ccgctggttc ggatgctttg aacgttttga   2220
aatatttcga ctacaacgtt ttccatgttc caacctgtaa attggtcaca aaatcatacg   2280
gtagattact atataacgat ttcagagcca atcctcaatt gttcccagaa gttgacgccg   2340
aattagctac tcgcgattat gacgaatctt taaccgataa gaacattgaa aaacttttg    2400 ttaatgttgc taagccattc cacaaagaga gagttgccca atctttgatt gttccaacaa   2460
acacaggtaa catgtacacc gcatctgttt atgccgcctt tgcatctcta ttaaactatg   2520
ttggatctga cgacttacaa ggcaagcgtg ttggttttatt ttcttacggt tccggtttag   2580
ctgcatctct atattcttgc aaaattgttg gtgacgtcca acatattatc aaggaattag   2640
atattactaa caaattagcc aagagaatca ccgaaactcc aaaggattac gaagctgcca   2700
tcgaattgag agaaaatgcc catttgaaga agaacttcaa acctcaaggt tccattgagc   2760
atttgcaaag tggtgtttac tacttgacca acatcgatga caaatttaga agatcttacg   2820
atgttaaaaa ataaggagga ttacactatg gtttttaacca ataaaacagt catttctgga   2880
tcgaaagtca aaagtttatc atctgcgcaa tcgagctcat caggaccttc atcatctagt   2940
gaggaagatg attcccgcga tattgaaagc ttggataaga aaatacgtcc tttagaagaa   3000
ttagaagcat tattaagtag tggaaataca aacaattga agaacaaaga ggtcgctgcc   3060
ttggttattc acggtaagtt acctttgtac gctttggaga aaaaattagg tgatactacg   3120
agagcggttg cggtacgtag gaaggctctt tcaattttgg cagaagctcc tgtattagca   3180
tctgatcgtt taccatataa aaattatgac tacgaccgcg tatttggcgc ttgttgtgaa   3240
aatgttatag gttacatgcc tttgcccgtt ggtgttatag gccccttggt tatcgatggt   3300
acatcttatc atataccaat ggcaactaca gagggttgtt tggtagcttc tgccatgcgt   3360
ggctgtaagg caatcaatgc tggcggtggt gcaacaactg ttttaactaa ggatggtatg   3420
acaagaggcc cagtagtccg tttcccaact ttgaaaagat ctggtgcctg taagatatgg   3480
ttagactcag aagagggaca aaacgcaatt aaaaaagctt ttaactctac atcaagattt   3540
gcacgtctgc aacatattca aacttgtcta gcaggagatt tactcttcat gagatttaga   3600
acaactactg gtgacgcaat gggtatgaat atgatttcta aggtgtcga atactcatta   3660 aagcaaatgg tagaagagta tggctgggaa gatatgagg ttgtctccgt ttctggtaac   3720
tactgtaccg acaaaaaacc agctgccatc aactggatcg aaggtcgtgg taagagtgtc   3780
```

-continued

```
gtcgcagaag ctactattcc tggtgatgtt gtcagaaaag tgttaaaaag tgatgtttcc    3840
gcattggttg agttgaacat tgctaagaat ttggttggat ctgcaatggc tgggtctgtt    3900
ggtggattta acgcacatgc agctaattta gtgacagctg ttttcttggc attaggacaa    3960
gatcctgcac aaaatgttga aagttccaac tgtataacat tgatgaaaga agtggacggt    4020
gatttgagaa tttccgtatc catgccatcc atcgaagtag gtaccatcgg tggtggtact    4080
gttctagaac cacaaggtgc catgttggac ttattaggtg taagaggccc gcatgctacc    4140
gctcctggta ccaacgcacg tcaattagca agaatagttg cctgtgccgt cttggcaggt    4200
gaattatcct tatgtgctgc cctagcagcc ggccatttgg ttcaaagtca tatgacccac    4260
aacaggaaac ctgctgaacc aacaaaacct aacaatttgg acgccactga tataaatcgt    4320
ttgaaagatg ggtccgtcac ctgcattaaa tcctaagtcg acctgcaggc atgcaagctt    4380
ggctgttttg gcggatgaga agagattttc agcctgatac agattaaatc agaacgcaga    4440
agcggtctga taaaacagaa tttgcctggc ggcagtagcg cggtggtccc acctgacccc    4500
atgccgaact cagaagtgaa acgccgtagc gccgatggta gtgtgggtc tccccatgcg    4560 agagtaggga actgccaggc atcaaataaa acgaaaggct cagtcgaaag actgggcctt    4620
tcgttttatc tgttgtttgt cggtgaacgc tctcctgagt aggacaaatc cgccgggagc    4680
ggatttgaac gttgcgaagc aacggcccgg agggtggcgg gcaggacgcc cgccataaac    4740
tgccaggcat caaattaagc agaaggccca cctgacggat ggcctttttg cgtttctaca    4800
aactcttttg tttattttc taaatacatt caaatatgta tccgctcatg agacaataac    4860
cctgataaat gcttcaataa tattgaaaaa ggaagagtat gagtattcaa catttccgtg    4920
tcgcccttat tcccttttt gcggcatttt gccttcctgt tttgctcac ccagaaacgc    4980 tggtgaaagt aaaagatgct gaagatcagt tgggtgcagc aaactattaa ctggcgaact    5040
acttactcta gcttcccggc aacaattaat agactggatg gaggcggata agttgcagg    5100 accacttctg cgctcggccc ttccggctgg ctggtttatt gctgataaat ctggagccgg    5160
tgagcgtggg tctcgcggta tcattgcagc actggggcca gatggtaagc cctcccgtat    5220
cgtagttatc tacacgacgg ggagtcaggc aactatggat gaacgaaata gacagatcgc    5280
tgagataggt gcctcactga ttaagcattg gtaactgtca gaccaagttt actcatatat    5340
actttagatt gatttacgcg ccctgtagcg gcgcattaag cgcggcgggt gtggtggtta    5400
cgcgcagcgt gaccgctaca cttgccacgc cctagcgcc cgctcctttc gctttcttcc    5460
cttcctttct cgccacgttc gccggctttc cccgtcaagc tctaaatcgg gggctccctt    5520
tagggttccg atttagtgct ttacggcacc tcgaccccaa aaaacttgat tagggtgatg    5580
gttcacgtag tgggccatcg ccctgataga cggtttttcg ccctttgacg ttggagtcca    5640
cgttctttaa tagtggactc ttgttccaaa cttgaacaac actcaaccct atctcgggct    5700
attcttttga tttataaggg attttgccga tttcggccta ttggttaaaa aatgagctga    5760
tttaacaaaa atttaacgcg aattttaaca aaatattaac gtttacaatt taaaaggatc    5820
taggtgaaga tccttttga taatctcatg accaaaatcc cttaacgtga gttttcgttc    5880
cactgagcgt cagacccccgt agaaaagatc aaaggatctt cttgagatcc ttttttctg    5940 cgcgtaatct gctgcttgca acaaaaaaa ccaccgctac cagcggtggt ttgtttgccg    6000
gatcaagagc taccaactct ttttccgaag gtaactggct tcagcagagc gcagatacca    6060
aatactgtcc ttctagtgta gccgtagtta ggccaccact tcaagaactc tgtagcaccg    6120
```

-continued

```
cctacatacc tcgctctgct aatcctgtta ccagtggggc atttgagaag cacacggtca      6180
cactgcttcc ggtagtcaat aaaccggtaa accagcaata gacataagcg gctatttaac      6240
gaccctgccc tgaaccgacg accgggtcga atttgctttc gaatttctgc cattcatccg      6300
cttattatca cttattcagg cgtagcacca ggcgtttaag ggcaccaata actgccttaa      6360
aaaaattacg ccccgccctg ccactcatcg cagtactgtt gtaattcatt aagcattctg      6420
ccgacatgga agccatcaca gacggcatga tgaacctgaa tcgccagcgg catcagcacc      6480
ttgtcgcctt gcgtataata tttgcccatg gtgaaaacgg gggcgaagaa gttgtccata      6540
ttggccacgt ttaaatcaaa actggtgaaa ctcacccagg gattggctga gacgaaaaac      6600
atattctcaa taaacccttt agggaaatag gccaggtttt caccgtaaca cgccacatct      6660
tgcgaatata tgtgtagaaa ctgccggaaa tcgtcgtggc attcactcca gagcgatgaa      6720
aacgtttcag tttgctcatg gaaaacggtg taacaagggt gaacactatc ccatatcacc      6780
agctcaccgt ctttcattgc catacggaat tccggatgag cattcatcag gcgggcaaga      6840
atgtgaataa aggccggata aaacttgtgc ttattttttct ttacggtctt taaaaaggcc      6900
gtaatatcca gctgaacggt ctggttatag gtacattgag caactgactg aaatgcctca      6960
aaatgttctt tacgatgcca ttgggatata tcaacggtgg tatatccagt gatttttttc      7020
tccatttttag cttccttagc tcctgaaaat ctcgataact caaaaaatac gcccggtagt      7080
gatcttattt cattatggtg aaagttggaa cctcttacgt gccgatcaac gtctcatttt      7140
cgccaaaagt tggcccaggg cttcccggta tcaacaggga caccaggatt tatttattct      7200
gcgaagtgat cttccgtcac aggtatttat tcggcgcaaa gtgcgtcggg tgatgctgcc      7260
aacttactga tttagtgtat gatggtgttt ttgaggtgct ccagtggctt ctgtttctat      7320
cagctgtccc tcctgttcag ctactgacgg ggtggtgcgt aacggcaaaa gcaccgccgg      7380
acatcagcgc tagcggagtg tatactggct tactatgttg gcactgatga gggtgtcagt      7440
gaagtgcttc atgtggcagg agaaaaaagg ctgcaccggt gcgtcagcag aatatgtgat      7500
acaggatata ttccgcttcc tcgctcactg actcgctacg ctcggtcgtt cgactgcggc      7560
gagcggaaat ggcttacgaa cggggcggag atttcctgga agatgccagg aagatactta      7620
acagggaagt gagagggccg cggcaaagcc gttttttccat aggctccgcc ccctgacaa      7680
gcatcacgaa atctgacgct caaatcagtg gtggcgaaac ccgacaggac tataaagata      7740
ccaggcgttt cccctggcg ctccctcgt gcgctctcct gttcctgcct ttcggtttac      7800
cggtgtcatt ccgctgttat ggccgcgttt gtctcattcc acgcctgaca ctcagttccg      7860
ggtaggcagt tcgctccaag ctggactgta tgcacgaacc ccccgttcag tccgaccgct      7920
gcgccttatc cggtaactat cgtcttgagt ccaacccgga aagacatgca aaagcaccac      7980
tggcagcagc cactggtaat tgatttagag gagttagtct tgaagtcatg cgccggttaa      8040
ggctaaactg aaaggacaag ttttggtgac tgcgctcctc caagccagtt acctcggttc      8100
aaagagttgg tagctcagag aaccttcgaa aaaccgccct gcaaggcggt tttttcgttt      8160
tcagagcaag agattacgcg cagaccaaaa cgatctcaag aagatcatct tattaatcag      8220
ataaaatatt tgctcatgag cccgaagtgg cgagcccgat cttccccatc ggtgatgtcg      8280
gcgatatagg cgccagcaac cgcacctgtg gcgccggtga tgccggccac gatgcgtccg      8340
gcgtagagga tctgctcatg tttgacagct tatc                                 8374
```

<210> SEQ ID NO 11
<211> LENGTH: 9573

<212> TYPE: DNA
<213> ORGANISM: Artificial Sequence
<220> FEATURE:
<223> OTHER INFORMATION: pBAD33MevT(C159A) plasmid

<400> SEQUENCE: 11

```
atcgatgcat aatgtgcctg tcaaatggac gaagcaggga ttctgcaaac cctatgctac      60
tccgtcaagc cgtcaattgt ctgattcgtt accaattatg acaacttgac ggctacatca     120
ttcactttt cttcacaacc ggcacggaac tcgctcgggc tggccccggt gcattttta      180
aatacccgcg agaaatagag ttgatcgtca aaccaacat tgcgaccgac ggtggcgata     240
ggcatccggg tggtgctcaa aagcagcttc gcctggctga tacgttggtc ctcgcgccag     300
cttaagacgc taatccctaa ctgctggcgg aaaagatgtg acagacgcga cggcgacaag     360
caaacatgct gtgcgacgct ggcgatatca aaattgctgt ctgccaggtg atcgctgatg     420
tactgacaag cctcgcgtac ccgattatcc atcggtggat ggagcgactc gttaatcgct     480
tccatgcgcc gcagtaacaa ttgctcaagc agatttatcg ccagcagctc cgaatagcgc     540
ccttcccctt gcccggcgtt aatgatttgc ccaaacaggt cgctgaaatg cggctggtgc     600
gcttcatccg ggcgaaagaa ccccgtattg gcaaatattg acggccagtt aagccattca     660
tgccagtagg cgcgcggacg aaagtaaacc cactggtgat accattcgcg agcctccgga     720
tgacgaccgt agtgatgaat ctctcctggc gggaacagca aaatatcacc cggtcggcaa     780
acaaattctc gtccctgatt tttcaccacc ccctgaccgc gaatggtgag attgagaata     840
taacctttca ttcccagcgg tcggtcgata aaaaaatcga gataaccgtt ggcctcaatc     900
ggcgttaaac ccgccaccag atgggcatta acgagtatc ccggcagcag gggatcattt     960
tgcgcttcag ccatactttt catactcccg ccattcagaa agaaaccaa ttgtccatat    1020
tgcatcagac attgccgtca ctgcgtcttt tactggctct ctcgctaac caaaccggta    1080
accccgctta ttaaaagcat tctgtaacaa agcgggacca aagccatgac aaaaacgcgt    1140
aacaaaagtg tctataatca cggcagaaaa gtccacattg attatttgca cggcgtcaca    1200
ctttgctatg ccatagcatt tttatccata agattagcgg atcctacctg acgctttta    1260
tcgcaactct ctactgtttc tccataccg ttttttggg ctagcgaatt cgagctcggt    1320
acccggggat cctctagagt cgactaggag gaatataaaa tgaaaaattg tgtcatcgtc    1380
agtgcggtac gtactgctat cggtagtttt aacggttcac tcgcttccac cagcgccatc    1440
gacctggggg cgacagtaat taagccgcc attgaacgtg caaaaatcga ttcacaacac    1500
gttgatgaag tgattatggg taacgtgtta caagccgggc tggggcaaaa tccggcgcgt    1560
caggcactgt taaaagcgg gctggcagaa acggtgtgcg gattcacggt caataaagta    1620
tgtggttcgg gtcttaaag tgtggcgctt gccgcccagg ccattcaggc aggtcaggcg    1680
cagagcattg tggcgggggg tatggaaaat atgagtttag cccctactt actcgatgca    1740
aaagcacgct ctggttatcg tcttggagac ggacaggttt atgacgtaat cctgcgcgat    1800
ggcctgatgt gcgccaccca tggttatcat atgggatta ccgccgaaaa cgtggctaaa    1860
gagtacggaa ttacccgtga atgcaggat gaactggcgc tacattcaca gcgtaaagcg    1920
gcagccgcaa ttgagtccgg tgcttttaca gccgaaatcg tcccggtaaa tgttgtcact    1980
cgaaagaaaa ccttcgtctt cagtcaagac gaattcccga aagcgaattc aacggctgaa    2040
gcgttaggtg cattgcgccc ggccttcgat aaagcaggaa cagtcaccgc tgggaacgcg    2100
tctggtatta acgacggtgc tgccgctctg gtgattatgg aagaatctgc ggcgctggca    2160
```

```
gcaggcctta ccccctggc tcgcattaaa agttatgcca gcggtggcgt gcccccgca      2220 ttgatgggta tggggccagt acctgccacg caaaaagcgt tacaactggc ggggctgcaa    2280 ctggcgata ttgatctcat tgaggctaat gaagcatttg ctgcacagtt ccttgccgtt    2340
gggaaaaacc tgggctttga ttctgagaaa gtgaatgtca acggcgggc catcgcgctc    2400 ggcatccta tcggtgccag tggtgctcgt attctggtca cactattaca tgccatgcag    2460
gcacgcgata aaacgctggg gctggcaaca ctgtgcattg gcggcggtca gggaattgcg    2520
atggtgattg aacggttgaa ttaaggagga cagctaaatg aaactctcaa ctaaactttg    2580
ttggtgtggt attaaaggaa gacttaggcc gcaaagcaa caacaattac acaatacaaa    2640
cttgcaaatg actgaactaa aaaacaaaa gaccgctgaa caaaaaacca gacctcaaaa    2700
tgtcggtatt aaaggtatcc aaatttacat cccaactcaa tgtgtcaacc aatctgagct    2760
agagaaattt gatggcgttt ctcaaggtaa atacacaatt ggtctgggcc aaaccaacat    2820 gtctttgtc aatgacagag aagatatcta ctcgatgtcc ctaactgttt tgtctaagtt    2880
gatcaagagt tacaacatcg acaccaacaa aattggtaga ttagaagtcg gtactgaaac    2940
tctgattgac aagtccaagt ctgtcaagtc tgtcttgatg caattgtttg gtgaaaacac    3000
tgacgtcgaa ggtattgaca cgcttaatgc cgcgtacggt ggtaccaacg cgttgttcaa    3060
ctctttgaac tggattgaat ctaacgcatg ggatggtaga gacgccattg tagtttgcgg    3120
tgatattgcc atctacgata agggtgccgc aagaccaacc ggtggtgccg gtactgttgc    3180
tatgtggatc ggtcctgatg ctccaattgt atttgactct gtaagagctt cttacatgga    3240
acacgcctac gattttttaca agccagattt caccagcgaa tatccttacg tcgatggtca    3300
tttttcatta acttgttacg tcaaggctct tgatcaagtt tacaagagtt attccaagaa    3360
ggctatttct aaagggttgg ttagcgatcc cgctggttcg gatgctttga acgttttgaa    3420
atatttcgac tacaacgttt tccatgttcc aacctgtaaa ttggtcacaa aatcatacgg    3480
tagattacta tataacgatt tcagagccaa tcctcaattg ttcccagaag ttgacgccga    3540
attagctact cgcgattatg acgaatcttt aaccgataag aacattgaaa aaactttttgt    3600 taatgttgct aagccattcc acaaagagag agttgcccaa tctttgattg ttccaacaaa    3660
cacaggtaac atgtacaccg catctgttta tgccgccttt gcatctctat aaaactatgt    3720
tggatctgac gacttacaag gcaagcgtgt tggtttattt tcttacggtt ccggtttagc    3780
tgcatctcta tattcttgca aaattgttgg tgacgtccaa catattatca aggaattaga    3840
tattactaac aaaattagcca agagaatcac cgaaactcca aaggattacg aagctgccat    3900
cgaattgaga gaaaatgccc atttgaagaa gaacttcaaa cctcaaggtt ccattgagca    3960
tttgcaaagt ggtgtttact acttgaccaa catcgatgac aaatttagaa gatcttacga    4020
tgttaaaaaa taaggaggat tacactatgg ttttaaccaa taaaacagtc atttctggat    4080
cgaaagtcaa aagtttatca tctgcgcaat cgagctcatc aggaccttca tcatctagtg    4140
aggaagatga ttcccgcgat attgaaagct tggataagaa aatacgtcct ttagaagaat    4200
tagaagcatt attaagtagt ggaaatacaa acaattgaa gaacaaagag gtcgctgcct    4260
tggttattca cggtaagtta ccttttgtacg ctttggagaa aaaattaggt gatactacga    4320
gagcggttgc ggtacgtagg aaggctcttt caatttttggc agaagctcct gtattagcat    4380
ctgatcgttt accatataaa aattatgact acgaccgcgt atttggcgct tgttgtgaaa    4440
atgttatagg ttcatgcct ttgcccgttg gtgtttatagg cccctttggtt atcgatggta    4500 catcttatca tataccaatg gcaactacag agggttgttt ggtagcttct gccatgcgtg    4560
```

```
gctgtaaggc aatcaatgct ggcggtggtg caacaactgt tttaactaag gatggtatga    4620
caagaggccc agtagtccgt ttcccaactt tgaaaagatc tggtgcctgt aagatatggt    4680
tagactcaga agagggacaa aacgcaatta aaaaagcttt taactctaca tcaagatttg    4740
cacgtctgca acatattcaa acttgtctag caggagattt actcttcatg agatttagaa    4800
caactactgg tgacgcaatg ggtatgaata tgatttctaa aggtgtcgaa tactcattaa    4860
agcaaatggt agaagagtat ggctgggaag atatggaggt tgtctccgtt tctggtaact    4920
actgtaccga caaaaaacca gctgccatca actggatcga aggtcgtggt aagagtgtcg    4980
tcgcagaagc tactattcct ggtgatgttg tcagaaaagt gttaaaaagt gatgtttccg    5040
cattggttga gttgaacatt gctaagaatt tggttggatc tgcaatggct gggtctgttg    5100
gtggatttaa cgcacatgca gctaatttag tgacagctgt tttcttggca ttaggacaag    5160
atcctgcaca aaatgttgaa agttccaact gtataacatt gatgaaagaa gtggacggtg    5220
atttgagaat tccgtatcc atgccatcca tcgaagtagg taccatcggt ggtggtactg    5280
ttctagaacc acaaggtgcc atgttggact tattaggtgt aagaggcccg catgctaccg    5340
ctcctggtac caacgcacgt caattagcaa gaatagttgc ctgtgccgtc ttggcaggtg    5400
aattatcctt atgtgctgcc ctagcagccg gccatttggt tcaaagtcat atgacccaca    5460
acaggaaacc tgctgaacca acaaaaccta acaatttgga cgccactgat ataaatcgtt    5520
tgaaagatgg gtccgtcacc tgcattaaat cctaagtcga cctgcaggca tgcaagcttg    5580
gctgttttgg cggatgagag aagattttca gcctgataca gattaaatca gaacgcagaa    5640
gcggtctgat aaaacagaat ttgcctggcg gcagtagcgc ggtggtccca cctgacccca    5700
tgccgaactc agaagtgaaa cgccgtagcg ccgatggtag tgtggggtct ccccatgcga    5760
gagtagggaa ctgccaggca tcaaataaaa cgaaaggctc agtcgaaaga ctgggccttt    5820
cgttttatct gttgtttgtc ggtgaacgct ctcctgagta ggacaaatcc gccgggagcg    5880
gatttgaacg ttgcgaagca acggcccgga gggtggcggg caggacgccc gccataaact    5940
gccaggcatc aaattaagca gaaggccatc ctgacggatg ccttttttgc gtttctacaa    6000
actcttttgt ttatttttct aaatacattc aaatatgtat ccgctcatga gacaataacc    6060
ctgataaatg cttcaataat attgaaaaag gaagagtatg agtattcaac atttccgtgt    6120
cgcccttatt cccttttttg cggcattttg ccttcctgtt tttgctcacc cagaaacgct    6180
ggtgaaagta aaagatgctg aagatcagtt gggtgcagca actattaac tggcgaacta    6240 cttactctag cttcccggca acaattaata gactggatgg aggcggataa agttgcagga    6300
ccacttctgc gctcggccct tccggctggc tggtttattg ctgataaatc tggagccggt    6360
gagcgtgggt ctcgcggtat cattgcagca ctggggccag atggtaagcc ctcccgtatc    6420
gtagttatct acacgacggg gagtcaggca actatggatg aacgaaatag acagatcgct    6480
gagataggtg cctcactgat taagcattgg taactgtcag accaagttta ctcatatata    6540
ctttagattg atttacgcgc cctgtagcgg cgcattaagc gcggcgggtg tggtggttac    6600
gcgcagcgtg accgctacac ttgccagcgc cctagcgccc gctcctttcg ctttcttccc    6660
ttcctttctc gccacgttcg ccggctttcc ccgtcaagct ctaaatcggg ggctcccttt    6720
agggttccga tttagtgctt tacggcacct cgaccccaaa aaacttgatt tgggtgatgg    6780
ttcacgtagt gggccatcgc cctgatagac ggtttttcgc cctttgacgt tggagtccac    6840
gttctttaat agtggactct tgttccaaac ttgaacaaca ctcaaccta tctcgggcta    6900
```

```
ttcttttgat ttataaggga ttttgccgat ttcggcctat tggttaaaaa atgagctgat    6960
ttaacaaaaa tttaacgcga attttaacaa aatattaacg tttacaattt aaaaggatct    7020
aggtgaagat cctttttgat aatctcatga ccaaaatccc ttaacgtgag ttttcgttcc    7080
actgagcgtc agacccgta gaaaagatca aaggatcttc ttgagatcct tttttctgc     7140
gcgtaatctg ctgcttgcaa acaaaaaaac caccgctacc agcggtggtt tgtttgccgg    7200
atcaagagct accaactctt tttccgaagg taactggctt cagcagagcg cagataccaa    7260
atactgtcct tctagtgtag ccgtagttag gccaccactt caagaactct gtagcaccgc    7320
ctacatacct cgctctgcta atcctgttac cagtggggca tttgagaagc acacggtcac    7380
actgcttccg gtagtcaata aaccggtaaa ccagcaatag acataagcgg ctatttaacg    7440
accctgccct gaaccgacga ccgggtcgaa tttgctttcg aatttctgcc attcatccgc    7500
ttattatcac ttattcaggc gtagcaccag gcgtttaagg gcaccaataa ctgccttaaa    7560
aaaattacgc cccgccctgc cactcatcgc agtactgttg taattcatta agcattctgc    7620
cgacatggaa gccatcacag acggcatgat gaacctgaat cgccagcggc atcagcacct    7680
tgtcgccttg cgtataatat ttgcccatgt gaaaacgggg gcgaagaag ttgtccatat    7740
tggccacgtt taaatcaaaa ctggtgaaac tcacccaggg attggctgag acgaaaaaca    7800
tattctcaat aaacccttta gggaaatagg ccaggttttc accgtaacac gccacatctt    7860
gcgaatatat gtgtagaaac tgccggaaat cgtcgtggta ttcactccag agcgatgaaa    7920
acgtttcagt ttgctcatgg aaaacggtgt aacaagggtg aacactatcc catatcacca    7980
gctcaccgtc tttcattgcc atacggaatt ccggatgagc attcatcagg cgggcaagaa    8040
tgtgaataaa ggccggataa aacttgtgct tattttttctt tacggtcttt aaaaaggccg    8100
taatatccag ctgaacggtc tggttatagg tacattgagc aactgactga atgcctcaa    8160
aatgttcttt acgatgccat tgggatatat caacggtggt atatccagtg atttttttct    8220
ccatttagc ttccttagct cctgaaaatc tcgataactc aaaaaatacg cccggtagtg    8280
atcttatttc attatggtga agttggaac ctcttacgtg ccgatcaacg tctcattttc    8340
gccaaaagtt ggcccagggc ttcccggtat caacagggac accaggattt atttattctg    8400
cgaagtgatc ttccgtcaca ggtatttatt cggcgcaaag tgcgtcgggt gatgctgcca    8460
acttactgat ttagtgtatg atggtgtttt tgaggtgctc cagtggcttc tgtttctatc    8520
agctgtccct cctgttcagc tactgacggg gtggtgcgta acggcaaaag caccgccgga    8580
catcagcgct agcggagtgt atactggctt actatgttgg cactgatgag ggtgtcagtg    8640
aagtgcttca tgtggcagga gaaaaaaggc tgcaccggtg cgtcagcaga atatgtgata    8700
caggatatat tccgcttcct cgctcactga ctcgctacgc tcggtcgttc gactgcggcg    8760
agcggaaatg gcttacgaac ggggcggaga tttcctggaa gatgccagga agatacttaa    8820
cagggaagtg agagggccgc ggcaaagccg ttttttccata ggctccgccc ccctgacaag    8880
catcacgaaa tctgacgctc aaatcagtgg tggcgaaacc cgacaggact ataaagatac    8940
caggcgtttc cccctggcgg ctccctcgtg cgctctcctg ttcctgcctt tcggtttacc    9000
ggtgtcattc cgctgttatg gccgcgtttg tctcattcca cgcctgacac tcagttccgg    9060
gtaggcagtt cgctccaagc tggactgtat gcacgaaccc ccgttcagt ccgaccgctg    9120
cgccttatcc ggtaactatc gtcttgagtc aacccggaa agacatgcaa aagcaccact    9180
ggcagcagcc actggtaatt gatttagagg agttagtctt gaagtcatgc gccggttaag    9240
gctaaactga aaggacaagt tttggtgact gcgctcctcc aagccagtta cctcggttca    9300
```

-continued

| | |
|---|---|
| aagagttggt agctcagaga accttcgaaa aaccgccctg caaggcggtt ttttcgtttt | 9360 |
| cagagcaaga gattacgcgc agaccaaaac gatctcaaga agatcatctt attaatcaga | 9420 |
| taaaatattt gctcatgagc ccgaagtggc gagcccgatc ttccccatcg gtgatgtcgg | 9480 |
| cgatataggc gccagcaacc gcacctgtgg cgccggtgat gccggccacg atgcgtccgg | 9540 |
| cgtagaggat ctgctcatgt ttgacagctt atc | 9573 |

<210> SEQ ID NO 12
<211> LENGTH: 6835
<212> TYPE: DNA
<213> ORGANISM: Artificial Sequence
<220> FEATURE:
<223> OTHER INFORMATION: pHMGS(C159A) plasmid

<400> SEQUENCE: 12

| | |
|---|---|
| atcgatgcat aatgtgcctg tcaaatggac gaagcaggga ttctgcaaac cctatgctac | 60 |
| tccgtcaagc cgtcaattgt ctgattcgtt accaattatg acaacttgac ggctacatca | 120 |
| ttcactttt cttcacaacc ggcacggaac tcgctcgggc tggccccggt gcatttttta | 180 |
| aatacccgcg agaaatagag ttgatcgtca aaaccaacat tgcgaccgac ggtggcgata | 240 |
| ggcatccggg tggtgctcaa aagcagcttc gcctggctga tacgttggtc ctcgcgccag | 300 |
| cttaagacgc taatccctaa ctgctggcgg aaaagatgtg acagacgcga cggcgacaag | 360 |
| caaacatgct gtgcgacgct ggcgatatca aaattgctgt ctgccaggtg atcgctgatg | 420 |
| tactgacaag cctcgcgtac ccgattatcc atcggtggat ggagcgactc gttaatcgct | 480 |
| tccatgcgcc gcagtaacaa ttgctcaagc agatttatcg ccagcagctc cgaatagcgc | 540 |
| ccttcccctt gcccggcgtt aatgatttgc ccaaacaggt cgctgaaatg cggctggtgc | 600 |
| gcttcatccg ggcgaaagaa ccccgtattg gcaaatattg acggccagtt aagccattca | 660 |
| tgccagtagg cgcgcggacg aaagtaaacc cactggtgat accattcgcg agcctccgga | 720 |
| tgacgaccgt agtgatgaat ctctcctggc gggaacagca aaatatcacc cggtcggcaa | 780 |
| acaaattctc gtccctgatt tttcaccacc ccctgaccgc gaatggtgag attgagaata | 840 |
| taacctttca ttcccagcgg tcggtcgata aaaaaatcga gataaccgtt ggcctcaatc | 900 |
| ggcgttaaac ccgccaccag atgggcatta acgagtatc ccggcagcag gggatcattt | 960 |
| tgcgcttcag ccatactttt catactcccg ccattcagag aagaaaccaa ttgtccatat | 1020 |
| tgcatcagac attgccgtca ctgcgtcttt tactggctct ctcgctaac caaaccggta | 1080 |
| accccgctta ttaaaagcat tctgtaacaa agcgggacca aagccatgac aaaaacgcgt | 1140 |
| aacaaaagtg tctataatca cggcagaaaa gtccacattg attatttgca cggcgtcaca | 1200 |
| ctttgctatg ccatagcatt tttatccata agattagcgg atcctacctg acgcttttta | 1260 |
| tcgcaactct ctactgtttc tccatacccg tttttttggg ctagcgaatt cgagctcggt | 1320 |
| acccggagg aggacagcta atgaaactc tcaactaaac tttgttggtg tggtattaaa | 1380 |
| ggaagactta ggccgcaaaa gcaacaacaa ttacacaata caaacttgca aatgactgaa | 1440 |
| ctaaaaaaac aaaagaccgc tgaacaaaaa accagacctc aaaatgtcgg tattaaaggt | 1500 |
| atccaaattt acatcccaac tcaatgtgtc aaccatctg agctagagaa atttgatggc | 1560 |
| gtttctcaag gtaaatacac aattggtctg gccaaaacca acatgtcttt tgtcaatgac | 1620 |
| agagaagata tctactcgat gtccctaact gttttgtcta agttgatcaa gagttacaac | 1680 |
| atcgacacca acaaaattgg tagattagaa gtcggtactg aaactctgat tgacaagtcc | 1740 |

-continued

```
aagtctgtca agtctgtctt gatgcaattg tttggtgaaa acactgacgt cgaaggtatt    1800
gacacgctta atgccgcgta cggtggtacc aacgcgttgt tcaactcttt gaactggatt    1860
gaatctaacg catgggatgg tagagacgcc attgtagttt gcggtgatat tgccatctac    1920
gataagggtg ccgcaagacc aaccggtggt gccggtactg ttgctatgtg gatcggtcct    1980
gatgctccaa ttgtatttga ctctgtaaga gcttcttaca tggaacacgc ctacgatttt    2040
tacaagccag atttcaccag cgaatatcct tacgtcgatg gtcatttttc attaacttgt    2100
tacgtcaagg ctcttgatca agtttacaag agttattcca agaaggctat ttctaaaggg    2160
ttggttagcg atcccgctgg ttcggatgct ttgaacgttt tgaaatattt cgactacaac    2220
gttttccatg ttccaacctg taaattggtc acaaaatcat acggtagatt actatataac    2280
gatttcagag ccaatcctca attgttccca gaagttgacg ccgaattagc tactcgcgat    2340
tatgacgaat ctttaaccga taagaacatt gaaaaaactt ttgttaatgt tgctaagcca    2400
ttccacaaag agagagttgc ccaatctttg attgttccaa caaacacagg taacatgtac    2460
accgcatctg tttatgccgc cttttgcatct ctattaaact atgttggatc tgacgactta    2520
caaggcaagc gtgttggttt attttcttac ggttccggtt tagctgcatc tctatattct    2580
tgcaaaattg ttggtgacgt ccaacatatt atcaaggaat tagatattac taacaaatta    2640
gccaagagaa tcaccgaaac tccaaaggat tacgaagctg ccatcgaatt gagagaaaat    2700
gcccatttga agaagaactt caaacctcaa ggttccattg agcatttgca aagtggtgtt    2760
tactacttga ccaacatcga tgacaaattt agaagatctt acgatgttaa aaataagtc    2820
gacctgcagg catgcaagct tggctgtttt ggcggatgag agaagatttt cagcctgata    2880
cagattaaat cagaacgcag aagcggtctg ataaaacaga atttgcctgg cggcagtagc    2940
gcggtggtcc cacctgaccc catgccgaac tcagaagtga acgccgtag cgccgatggt    3000
agtgtgggt ctcccatgc gagagtaggg aactgccagg catcaaataa aacgaaaggc    3060
tcagtcgaaa gactgggcct ttcgttttat ctgttgtttg tcggtgaacg ctctcctgag    3120
taggacaaat ccgccgggag cggatttgaa cgttgcgaag caacggcccg gagggtggcg    3180
ggcaggacgc ccgccataaa ctgccaggca tcaaattaag cagaaggcca tcctgacgga    3240
tggccttttt gcgtttctac aaactctttt gtttattttt ctaaatacat tcaaatatgt    3300
atccgctcat gagacaataa ccctgataaa tgcttcaata atattgaaaa aggaagagta    3360
tgagtattca aatttccgt gtcgccctta ttccctttttt gcggcattt tgccttcctg    3420
tttttgctca cccagaaacg ctggtgaaag taaaagatgc tgaagatcag ttgggtgcag    3480
caaactatta actggcgaac tacttactct agcttcccgg caacaattaa tagactggat    3540
ggaggcggat aaagttgcag gaccacttct gcgctcggcc cttccggctg ctggttat    3600
tgctgataaa tctggagccg gtgagcgtgg gtctcgcggt atcattgcag cactggggcc    3660
agatggtaag ccctcccgta tcgtagttat ctacacgacg gggagtcagg caactatgga    3720
tgaacgaaat agacagatcg ctgagatagg tgcctcactg attaagcatt ggtaactgtc    3780
agaccaagtt tactcatata ctttttagat tgatttacgc gccctgtagc ggcgcattaa    3840
gcgcggcggg tgtggtggtt acgcgcagcg tgaccgctac acttgccagc gccctagcgc    3900
ccgctccttt cgctttcttc ccttcctttc tcgccacgtt cgccggcttt ccccgtcaag    3960
ctctaaatcg ggggctccct ttagggttcc gatttagtgc tttacggcac ctcgacccca    4020
aaaaacttga tttgggtgat ggttcacgta gtgggccatc gccctgatag acggttttc    4080
gccctttgac gttggagtcc acgttcttta atagtggact cttgttccaa acttgaacaa    4140
```

-continued

```
cactcaaccc tatctcgggc tattcttttg atttataagg gattttgccg atttcggcct      4200
attggttaaa aaatgagctg atttaacaaa aatttaacgc gaattttaac aaaatattaa      4260
cgtttacaat ttaaaaggat ctaggtgaag atccttttg ataatctcat gaccaaaatc       4320
ccttaacgtg agttttcgtt ccactgagcg tcagaccccg tagaaaagat caaaggatct      4380
tcttgagatc cttttttct gcgcgtaatc tgctgcttgc aaacaaaaaa accaccgcta       4440
ccagcggtgg tttgtttgcc ggatcaagag ctaccaactc ttttccgaa ggtaactggc       4500
ttcagcagag cgcagatacc aaatactgtc cttctagtgt agccgtagtt aggccaccac      4560
ttcaagaact ctgtagcacc gcctacatac ctcgctctgc taatcctgtt accagtgggg      4620
catttgagaa gcacacggtc acactgcttc cggtagtcaa taaaccggta aaccagcaat      4680
agacataagc ggctatttaa cgaccctgcc ctgaaccgac gaccgggtcg aatttgcttt      4740
cgaatttctg ccattcatcc gcttattatc acttattcag gcgtagcacc aggcgtttaa      4800
gggcaccaat aactgcctta aaaaaattac gccccgccct gccactcatc gcagtactgt      4860
tgtaattcat taagcattct gccgacatgg aagccatcac agacggcatg atgaacctga      4920
atcgccagcg gcatcagcac cttgtcgcct tgcgtataat atttgcccat ggtgaaaacg      4980
ggggcgaaga gttgtccat attggccacg tttaaatcaa aactggtgaa actcacccag       5040
ggattggctg agacgaaaaa catattctca ataaacccctt tagggaaata ggccaggttt    5100
tcaccgtaac acgccacatc ttgcgaatat atgtgtagaa actgccggaa atcgtcgtgg      5160
tattcactcc agagcgatga aaacgtttca gtttgctcat ggaaaacggt gtaacaaggg     5220
tgaacactat cccatatcac cagctcaccg tctttcattg ccatacgaa ttccggatga     5280
gcattcatca ggcgggcaag aatgtgaata aaggccggat aaaacttgtg cttattttc      5340
tttacggtct ttaaaaaggc cgtaatatcc agctgaacgg tctggttata ggtacattga     5400
gcaactgact gaaatgcctc aaaatgttct ttacgatgcc attgggatat atcaacggtg      5460
gtatatccag tgattttttt ctccatttta gcttccttag ctcctgaaaa tctcgataac      5520
tcaaaaaata cgcccggtag tgatcttatt tcattatggt gaaagttgga acctcttacg     5580
tgccgatcaa cgtctcattt tcgccaaaag ttgggccagg gcttccccggt atcaacaggg    5640
acaccaggat ttatttattc tgcgaagtga tcttccgtca caggtattta ttcggcgcaa     5700
agtgcgtcgg gtgatgctgc caacttactg atttagtgta tgatggtgtt tttgaggtgc     5760
tccagtggct tctgtttcta tcagctgtcc ctcctgttca gctactgacg ggtggtgcg     5820
taacggcaaa agcaccgccg gacatcagcg ctagcggagt gtatactggc ttactatgtt     5880
ggcactgatg agggtgtcag tgaagtgctt catgtggcag agaaaaaag gctgcaccgg     5940
tgcgtcagca gaatatgtga tacaggatat attccgcttc ctcgctcact gactcgctac     6000
gctcggtcgt tcgactgcgg cgagcggaaa tggcttacga acgggggcgga gatttcctgg    6060
aagatgccag gaagatactt aacagggaag tgagagggcc gcggcaaagc cgttttccca    6120
taggctccgc cccctgaca agcatcacga aatctgacgc tcaaatcagt ggtggcgaaa     6180
cccgacagga ctataaagat accaggcgtt tccccctggc ggctccctcg tgcgctctcc     6240
tgttcctgcc tttcggttta ccggtgtcat tccgctgtta ggccgcgtt tgtctcattc       6300
cacgcctgac actcagttcc gggtaggcag ttcgctccaa gctggactgt atgcacgaac     6360
cccccgttca gtccgaccgc tgcgccttat ccggtaacta tcgtcttgag tccaacccgg    6420
aaagacatgc aaaagcacca ctggcagcag ccactggtaa ttgatttaga ggagttagtc    6480
```

-continued

| | |
|---|---|
| ttgaagtcat gcgccggtta aggctaaact gaaaggacaa gttttggtga ctgcgctcct | 6540 |
| ccaagccagt tacctcggtt caaagagttg gtagctcaga gaaccttcga aaaaccgccc | 6600 |
| tgcaaggcgg ttttttcgtt ttcagagcaa gagattacgc gcagaccaaa acgatctcaa | 6660 |
| gaagatcatc ttattaatca gataaaatat ttgctcatga gcccgaagtg gcgagcccga | 6720 |
| tcttccccat cggtgatgtc ggcgatatag gcgccagcaa ccgcacctgt ggcgccggtg | 6780 |
| atgccggcca cgatgcgtcc ggcgtagagg atctgctcat gtttgacagc ttatc | 6835 |

<210> SEQ ID NO 13
<211> LENGTH: 1509
<212> TYPE: DNA
<213> ORGANISM: Artificial Sequence
<220> FEATURE:
<223> OTHER INFORMATION: truncated HMGR coding sequence

<400> SEQUENCE: 13

| | |
|---|---|
| atggttttaa ccaataaaac agtcatttct ggatcgaaag tcaaaagttt atcatctgcg | 60 |
| caatcgagct catcaggacc ttcatcatct agtgaggaag atgattcccg cgatattgaa | 120 |
| agcttggata gaaaaatacg tcctttagaa gaattagaag cattattaag tagtggaaat | 180 |
| acaaacaat tgaagaacaa agaggtcgct gccttggtta ttcacggtaa gttacctttg | 240 |
| tacgctttgg agaaaaaatt aggtgatact acgagagcgg ttgcggtacg taggaaggct | 300 |
| cttttcaattt tggcagaagc tcctgtatta gcatctgatc gtttaccata taaaaattat | 360 |
| gactacgacc gcgtatttgg cgcttgttgt gaaaatgtta taggttacat gcctttgccc | 420 |
| gttggtgtta taggcccctt ggttatcgat ggtacatctt atcatatacc aatggcaact | 480 |
| acagagggtt gtttggtagc ttctgccatg cgtggctgta aggcaatcaa tgctggcggt | 540 |
| ggtgcaacaa ctgttttaac taaggatggt atgacaagag gcccagtagt ccgtttccca | 600 |
| actttgaaaa gatctggtgc ctgtaagata tggttagact cagaagaggg acaaaacgca | 660 |
| attaaaaaag cttttaactc tacatcaaga tttgcacgtc tgcaacatat tcaaacttgt | 720 |
| ctagcaggag atttactctt catgagattt agaacaacta ctggtgacgc aatgggtatg | 780 |
| aatatgattt ctaaaggtgt cgaatactca ttaaagcaaa tggtagaaga gtatggctgg | 840 |
| gaagatatgg aggttgtctc cgtttctggt aactactgta ccgacaaaaa accagctgcc | 900 |
| atcaactgga tcgaaggtcg tggtaagagt gtcgtcgcag aagctactat tcctggtgat | 960 |
| gttgtcagaa aagtgttaaa aagtgatgtt tccgcattgg ttgagttgaa cattgctaag | 1020 |
| aatttggttg gatctgcaat ggctgggtct gttggtggat ttaacgcaca tgcagctaat | 1080 |
| ttagtgacag ctgttttctt ggcattagga caagatcctg cacaaaatgt tgaaagttcc | 1140 |
| aactgtataa cattgatgaa agaagtggac ggtgatttga gaatttccgt atccatgcca | 1200 |
| tccatcgaag taggtaccat cggtggtggt actgttctag aaccacaagg tgccatgttg | 1260 |
| gacttattag gtgtaagagg cccgcatgct accgctcctg gtaccaacgc acgtcaatta | 1320 |
| gcaagaatag ttgcctgtgc cgtcttggca ggtgaattat ccttatgtgc tgccctagca | 1380 |
| gccggccatt tggttcaaag tcatatgacc cacaacagga aacctgctga accaacaaaa | 1440 |
| cctaacaatt tggacgccac tgatataaat cgtttgaaag atgggtccgt cacctgcatt | 1500 |
| aaatcctaa | 1509 |